(12) United States Patent
Thelen et al.

(10) Patent No.: US 7,488,329 B2
(45) Date of Patent: Feb. 10, 2009

(54) METHOD AND APPARATUS FOR REDUCING FEMORAL FRACTURES

(75) Inventors: Sarah L Thelen, North Manchester, IN (US); Antony J Lozier, Warsaw, IN (US); Nicolas J Pacelli, Culver, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 384 days.

(21) Appl. No.: 11/061,898

(22) Filed: Feb. 18, 2005

(65) Prior Publication Data

US 2005/0203508 A1    Sep. 15, 2005

Related U.S. Application Data

(63) Continuation-in-part of application No. 10/358,009, filed on Feb. 4, 2003, now abandoned, which is a continuation-in-part of application No. 10/266,313, filed on Oct. 8, 2002, now Pat. No. 6,814,787, which is a continuation-in-part of application No. 10/155,683, filed on May 23, 2002, now Pat. No. 7,258,692, which is a continuation-in-part of application No. 09/520,351, filed on Mar. 7, 2000, now Pat. No. 6,447,514.

(51) Int. Cl.
  *A61B 17/58* (2006.01)
  *A61F 2/00* (2006.01)
(52) U.S. Cl. ...................................................... 606/99
(58) Field of Classification Search ............... 606/53, 606/86, 96–98
See application file for complete search history.

(56) References Cited

U.S. PATENT DOCUMENTS

| | | | |
|---|---|---|---|
| 3,128,768 | A | 4/1964 | Mikelis |
| 3,991,600 | A | 11/1976 | Del Fabro |
| 4,285,618 | A | 8/1981 | Shanley |
| 4,313,434 | A | 2/1982 | Segal |
| 4,438,762 | A | 3/1984 | Kyle |
| 4,459,978 | A | 7/1984 | Kotsanis |
| 4,653,489 | A | 3/1987 | Tronzo |

(Continued)

FOREIGN PATENT DOCUMENTS

AU    200128554    6/2001

(Continued)

OTHER PUBLICATIONS

Pat. Abs. of Japan, vol. 1999, No. 12, Oct. 29, 1999, Whole Document.

*Primary Examiner*—Anu Ramana
(74) *Attorney, Agent, or Firm*—Baker & Daniels

(57) ABSTRACT

An improved apparatus for reducing a hip fracture utilizing a minimally invasive procedure which does not require incision of the quadriceps. A femoral implant in accordance with the present invention achieves intramedullary fixation as well as fixation into the femoral head to allow for the compression needed for a femoral fracture to heal. An alignment guide in accordance with the present invention is provided to facilitate alignment of instruments used to create a cavity in the bone for reception of the femoral implant and to facilitate size selection of the femoral implant. The alignment guide of the present invention includes a reference element and pattern arms having geometries which track an anatomical structure.

11 Claims, 82 Drawing Sheets

U.S. PATENT DOCUMENTS

| | | | |
|---|---|---|---|
| 4,714,478 A | 12/1987 | Fischer | |
| 4,777,942 A | 10/1988 | Frey et al. | |
| 4,969,888 A | 11/1990 | Scholten et al. | 606/94 |
| 5,102,413 A | 4/1992 | Poddar | |
| 5,108,404 A | 4/1992 | Scholten et al. | 606/94 |
| 5,312,408 A | 5/1994 | Brown | |
| 5,342,363 A | 8/1994 | Richelsoph | |
| 5,376,123 A | 12/1994 | Klaue et al. | |
| 5,403,320 A | 4/1995 | Luman et al. | |
| 5,462,547 A | 10/1995 | Weigum | |
| 5,514,137 A | 5/1996 | Coutts | |
| 5,527,316 A | 6/1996 | Stone et al. | |
| 5,531,792 A | 7/1996 | Huene | |
| 5,540,694 A | 7/1996 | DeCarlo, Jr. et al. | |
| 5,549,679 A | 8/1996 | Kuslich | 623/17 |
| 5,558,134 A | 9/1996 | Miyazaki | |
| 5,571,189 A | 11/1996 | Kuslich | 623/17 |
| 5,591,168 A | 1/1997 | Judet et al. | |
| 5,649,930 A | 7/1997 | Kertzner | |
| 5,690,671 A | 11/1997 | McGurk et al. | |
| 5,695,518 A | 12/1997 | Laerum | |
| 5,827,289 A | 10/1998 | Reiley et al. | |
| 5,976,139 A | 11/1999 | Bramlet | |
| 5,997,582 A | 12/1999 | Weiss | |
| 6,011,211 A | 1/2000 | Abrams | |
| 6,036,696 A * | 3/2000 | Lambrecht et al. | 606/97 |
| 6,053,922 A | 4/2000 | Krause et al. | |
| 6,066,154 A | 5/2000 | Reiley et al. | |
| 6,096,042 A | 8/2000 | Herbert | |
| 6,132,468 A | 10/2000 | Mansmann | |
| 6,156,069 A | 12/2000 | Amstutz | |
| 6,228,091 B1 | 5/2001 | Lombardo et al. | |
| 6,235,043 B1 | 5/2001 | Reiley et al. | 606/192 |
| 6,241,734 B1 | 6/2001 | Scribner et al. | 606/93 |
| 6,248,110 B1 | 6/2001 | Reiley et al. | 606/93 |
| 6,358,251 B1 | 3/2002 | Mirza | |
| 6,425,923 B1 | 7/2002 | Stalcup et al. | |
| 6,447,514 B1 | 9/2002 | Stalcup et al. | |
| 6,520,969 B2 * | 2/2003 | Lambrecht et al. | 606/130 |
| 6,613,054 B2 | 9/2003 | Scribner et al. | 606/93 |
| 6,755,862 B2 | 6/2004 | Keynan | |
| 7,083,624 B2 * | 8/2006 | Irving | 606/87 |
| 2001/0034526 A1 | 10/2001 | Kuslich et al. | |
| 2002/0010472 A1 | 1/2002 | Kuslich et al. | |
| 2002/0022847 A1 | 2/2002 | Ray et al. | |
| 2002/0193799 A1 | 12/2002 | Chappuis et al. | |
| 2004/0059317 A1 | 3/2004 | Harmann | |
| 2005/0113836 A1 | 5/2005 | Lozier | |

FOREIGN PATENT DOCUMENTS

| | | |
|---|---|---|
| EP | 0496636 | 1/1992 |
| EP | 0617927 | 10/1994 |
| EP | 1 132 051 A2 | 9/2001 |
| EP | 1132051 | 9/2001 |
| EP | 1132053 | 9/2001 |
| EP | 1149562 | 10/2001 |
| EP | 1201191 | 5/2002 |
| EP | 1 132 051 A3 | 6/2003 |
| EP | 1 348 384 | 10/2003 |
| FR | 2671006 | 7/1992 |
| FR | 2802080 | 6/2001 |
| JP | 11 188043 A | 7/1999 |
| NL | 9001858 | 3/1992 |
| WO | WO9820939 | 5/1998 |
| WO | WO 02/051319 A | 7/2002 |
| WO | WO02051319 | 7/2002 |

* cited by examiner

FIG._1

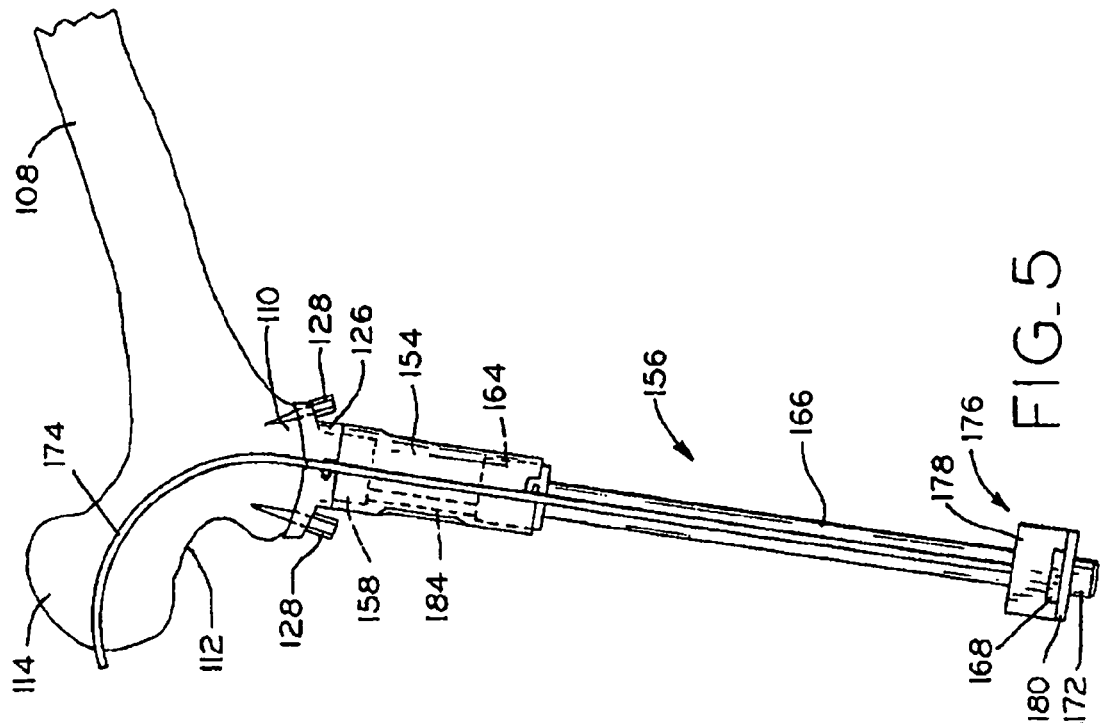
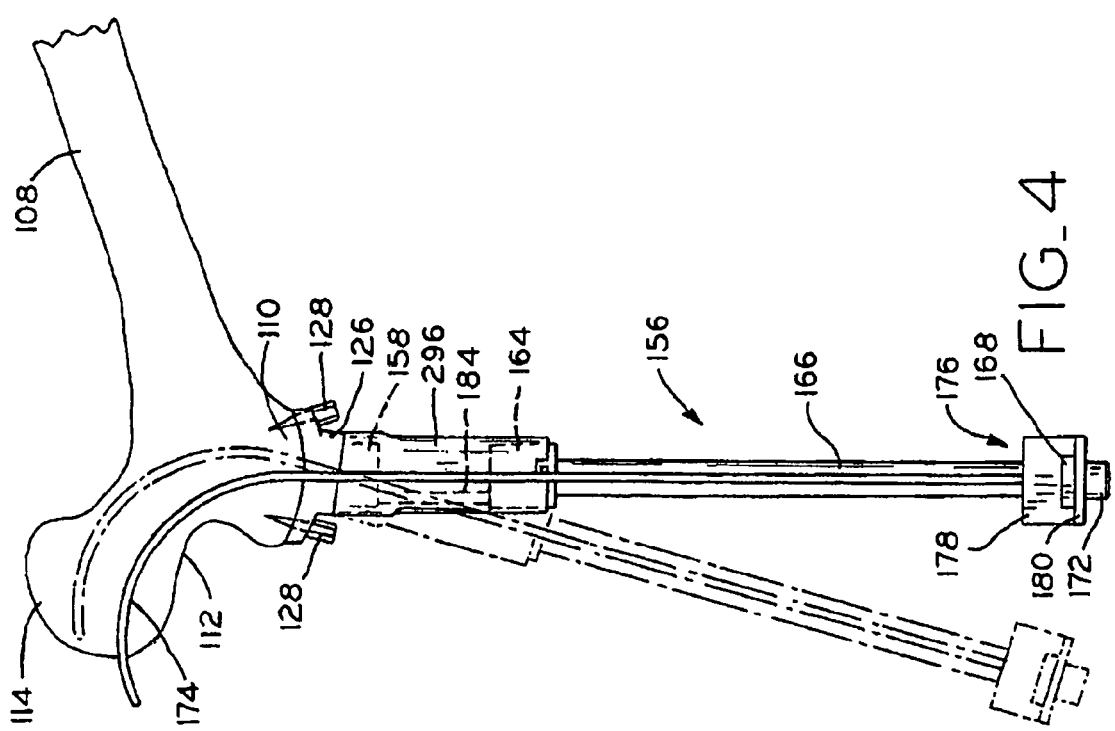

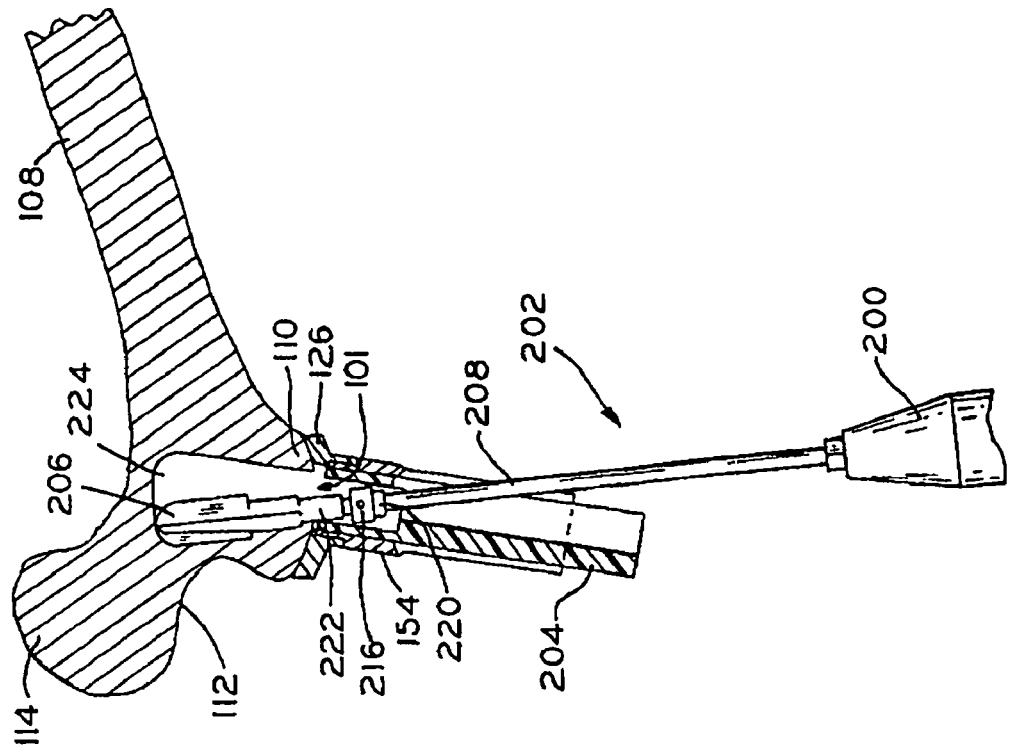
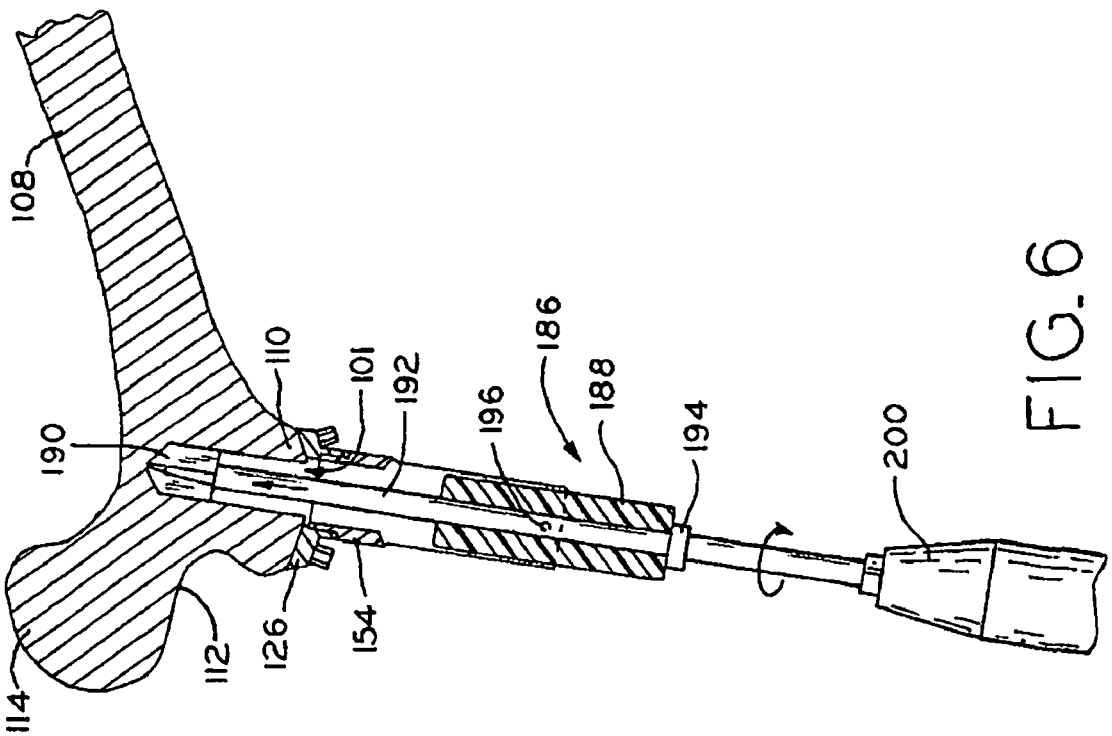

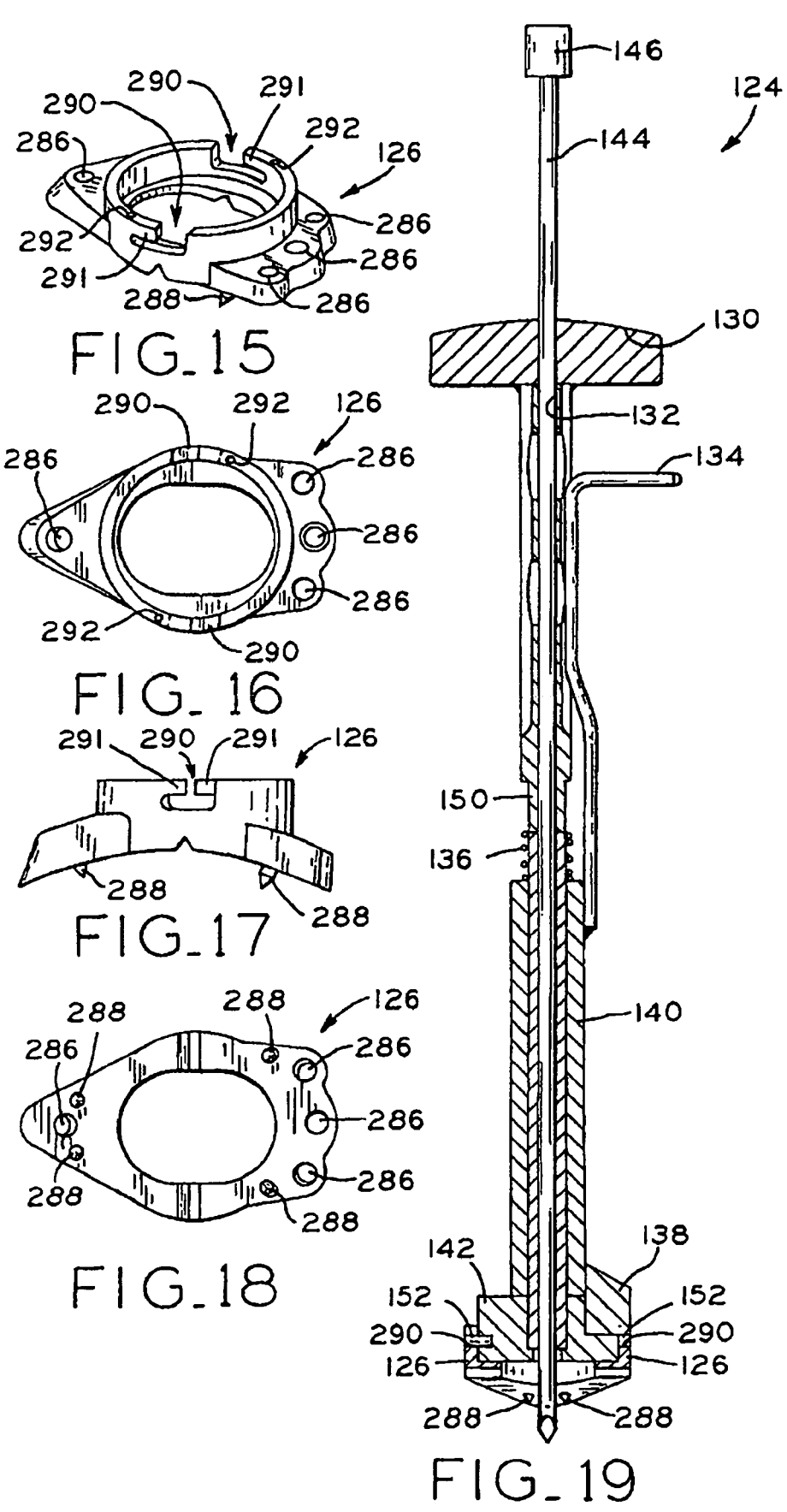

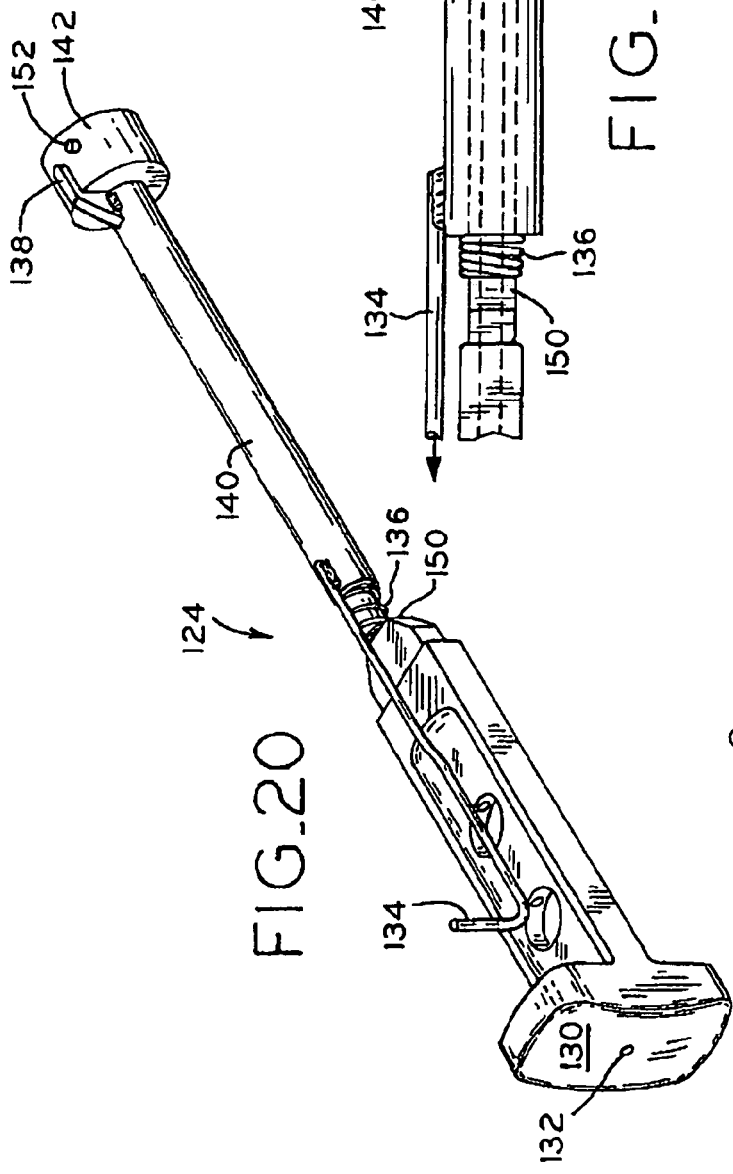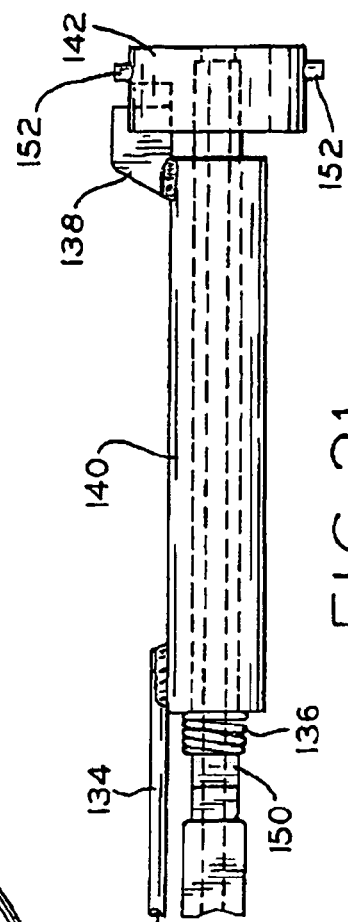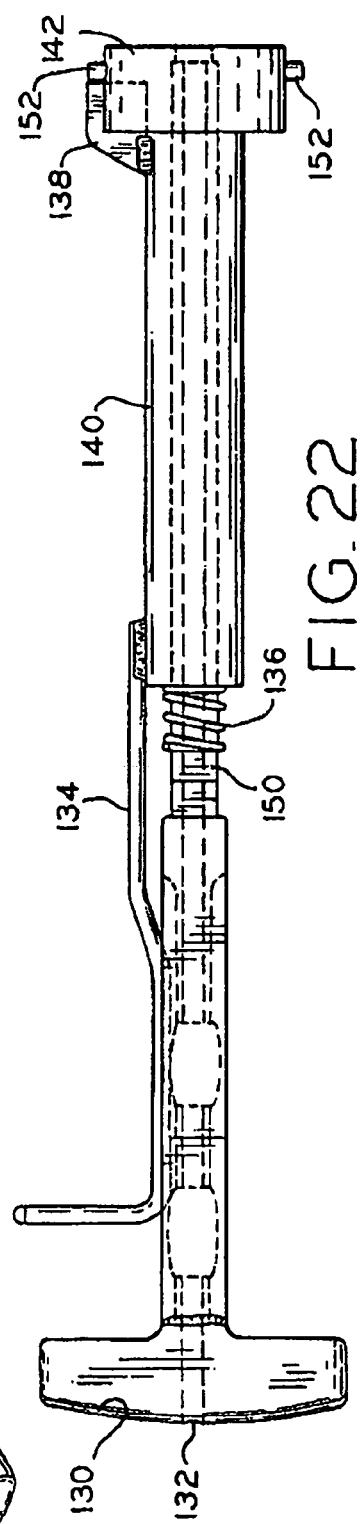

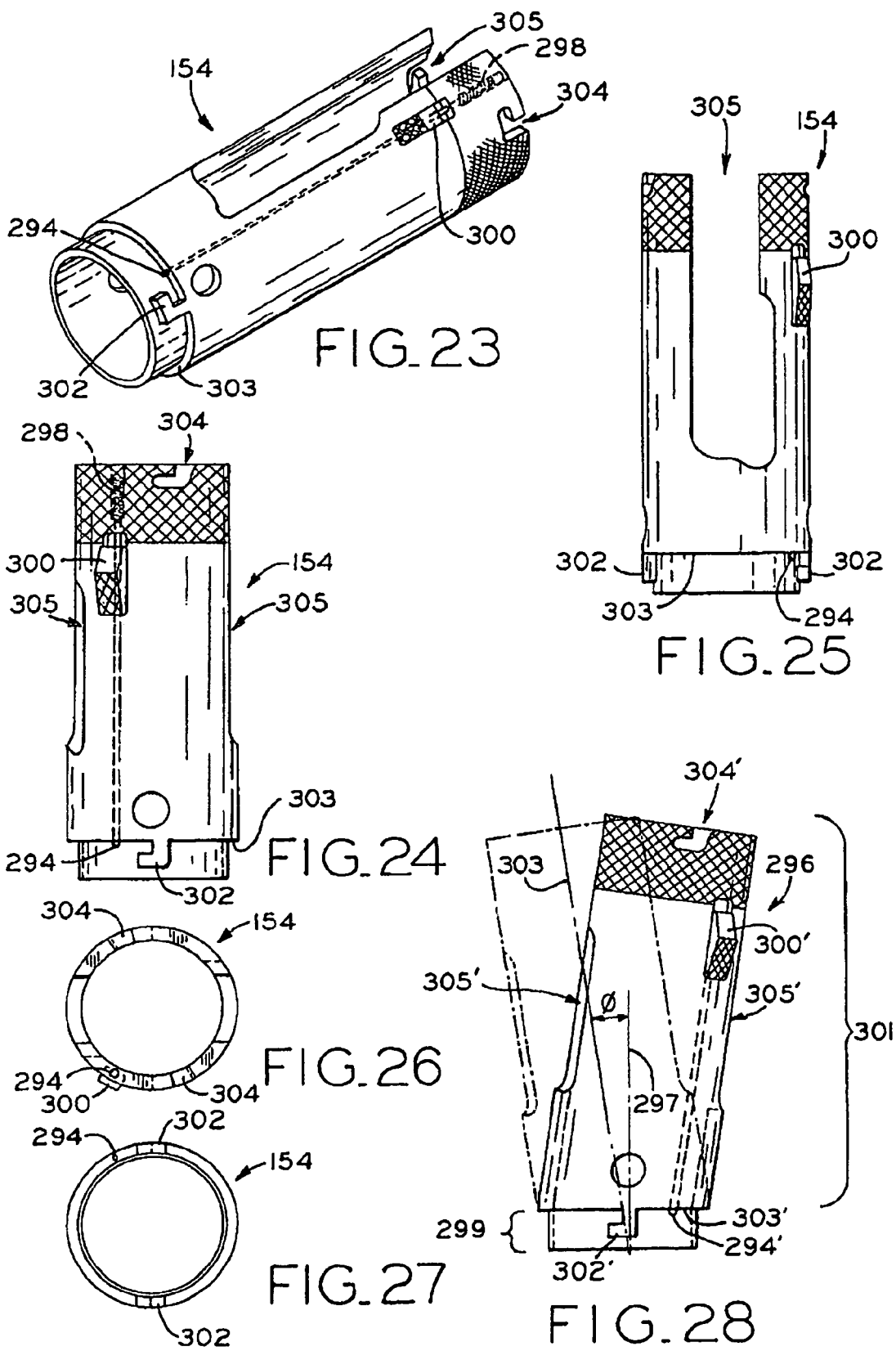

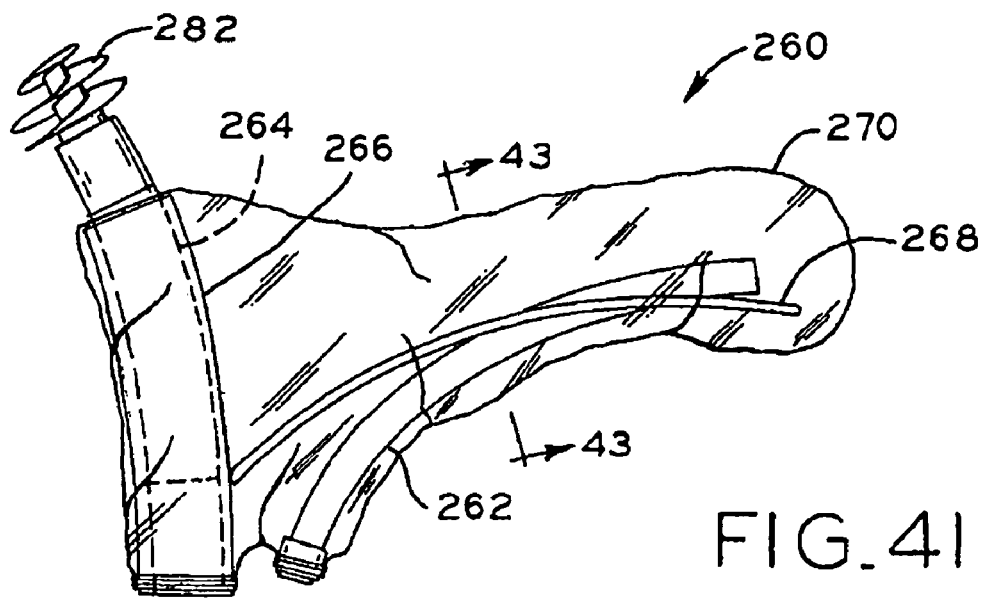
FIG_41
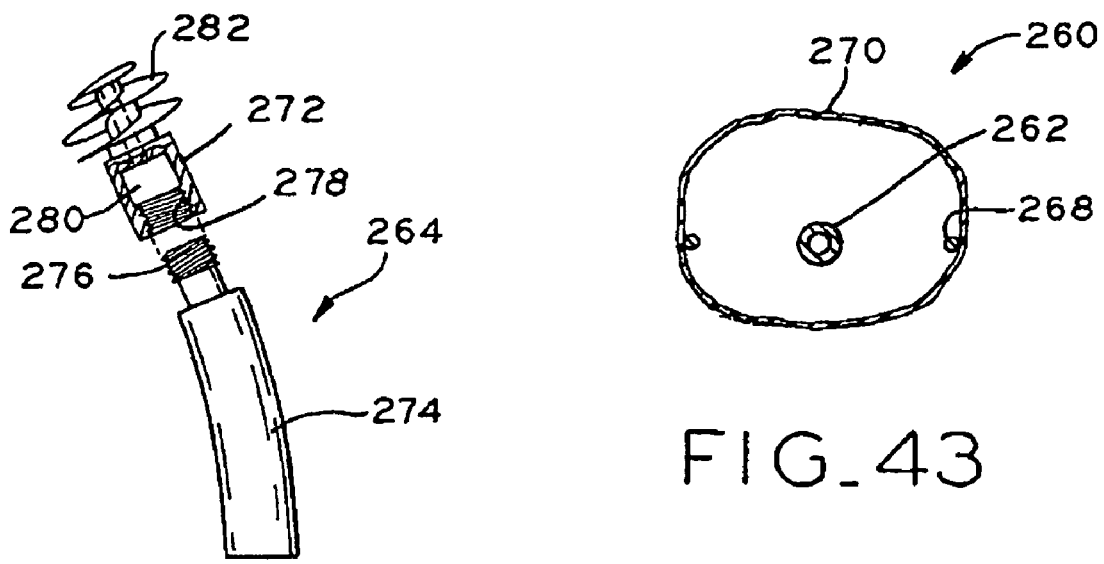
FIG_42
FIG_43

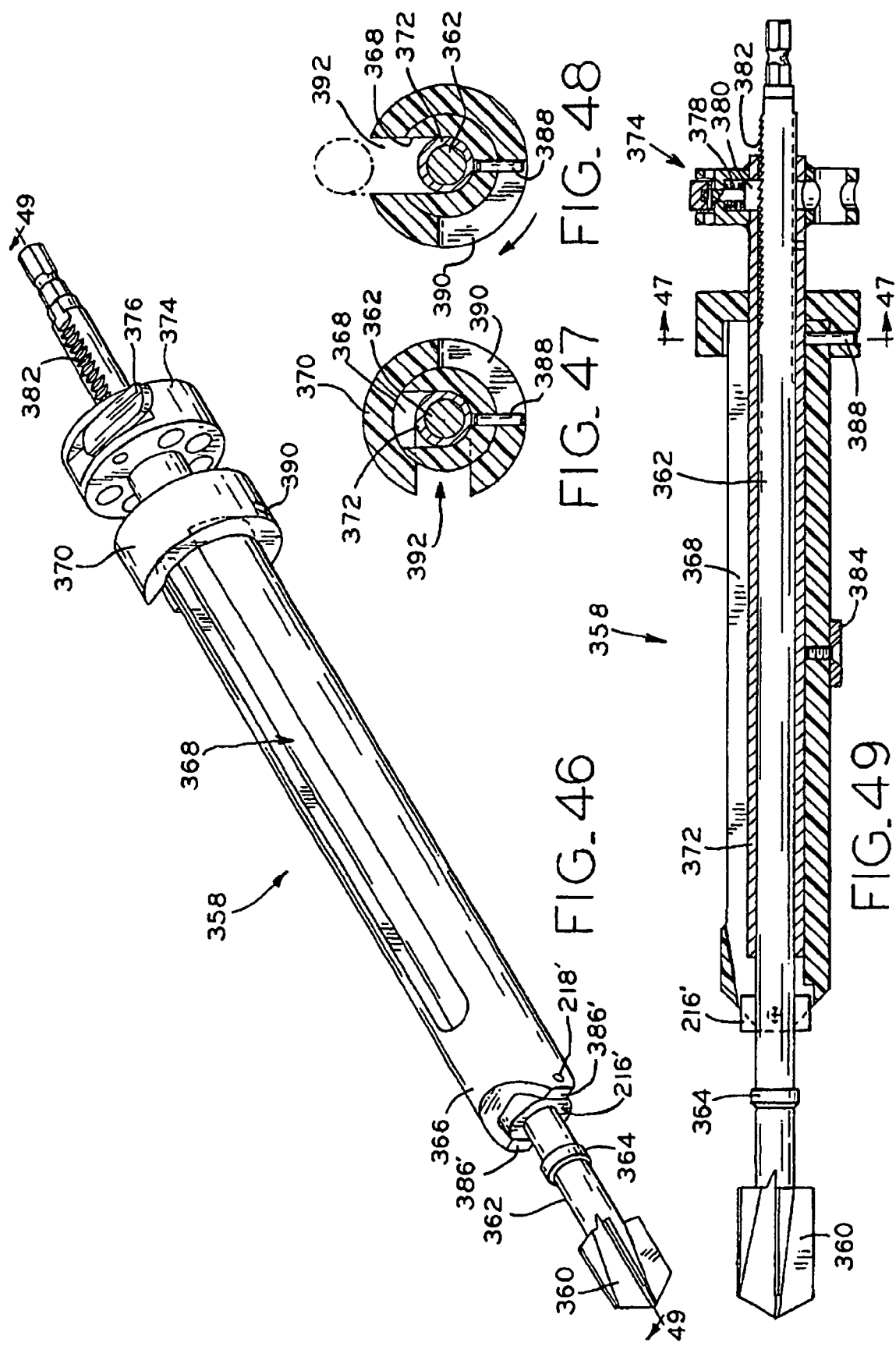

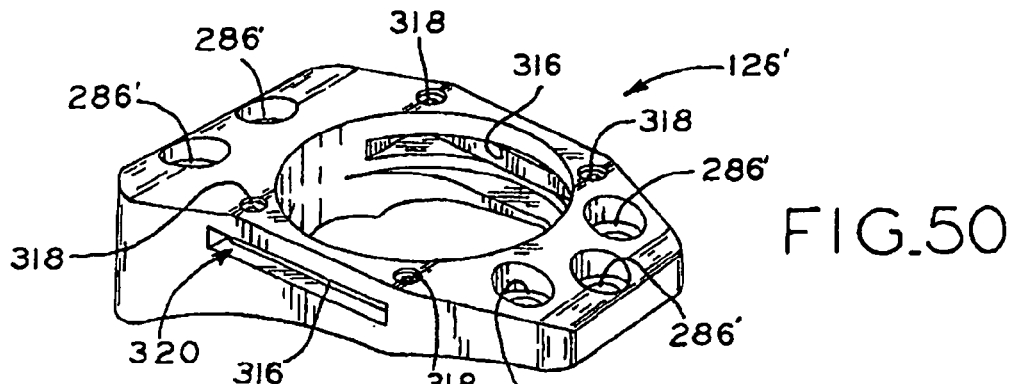
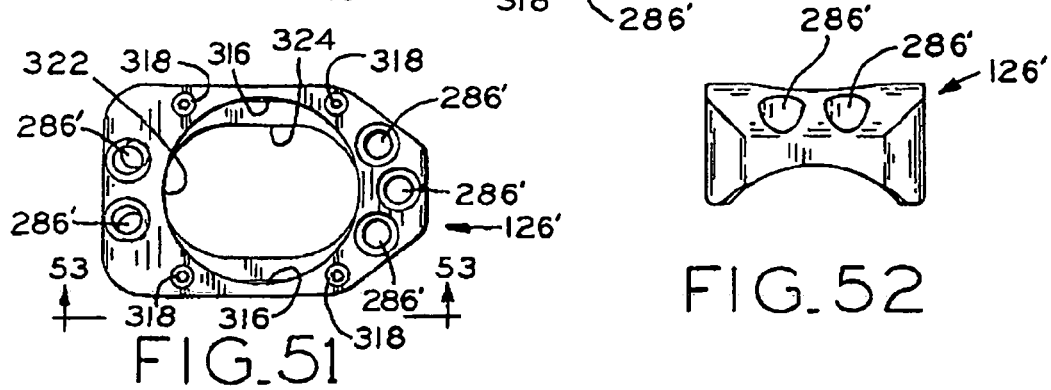
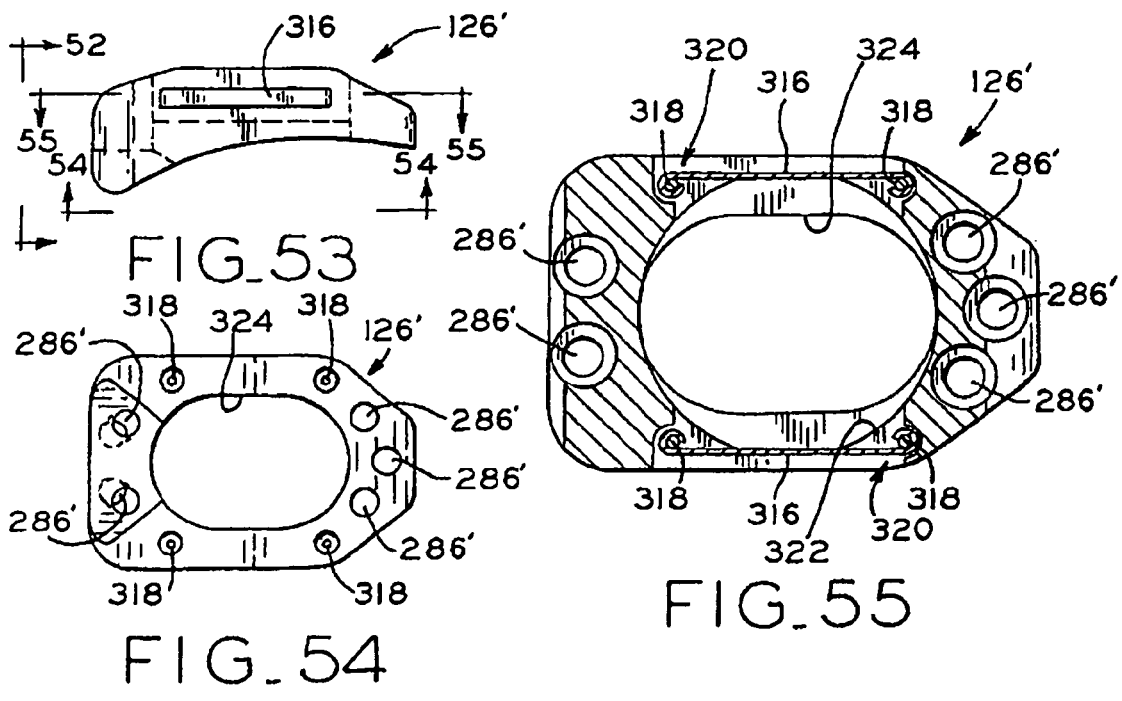

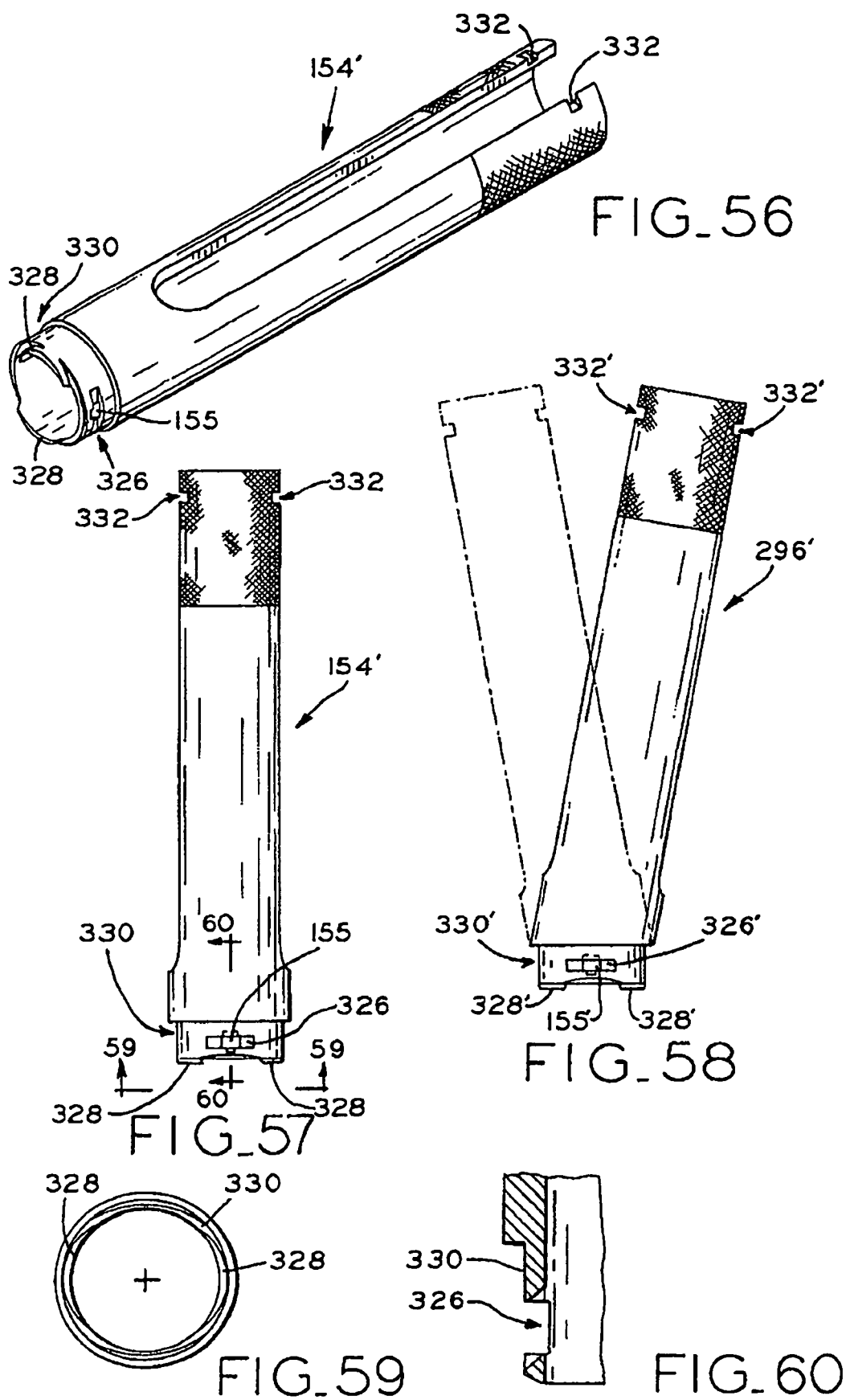

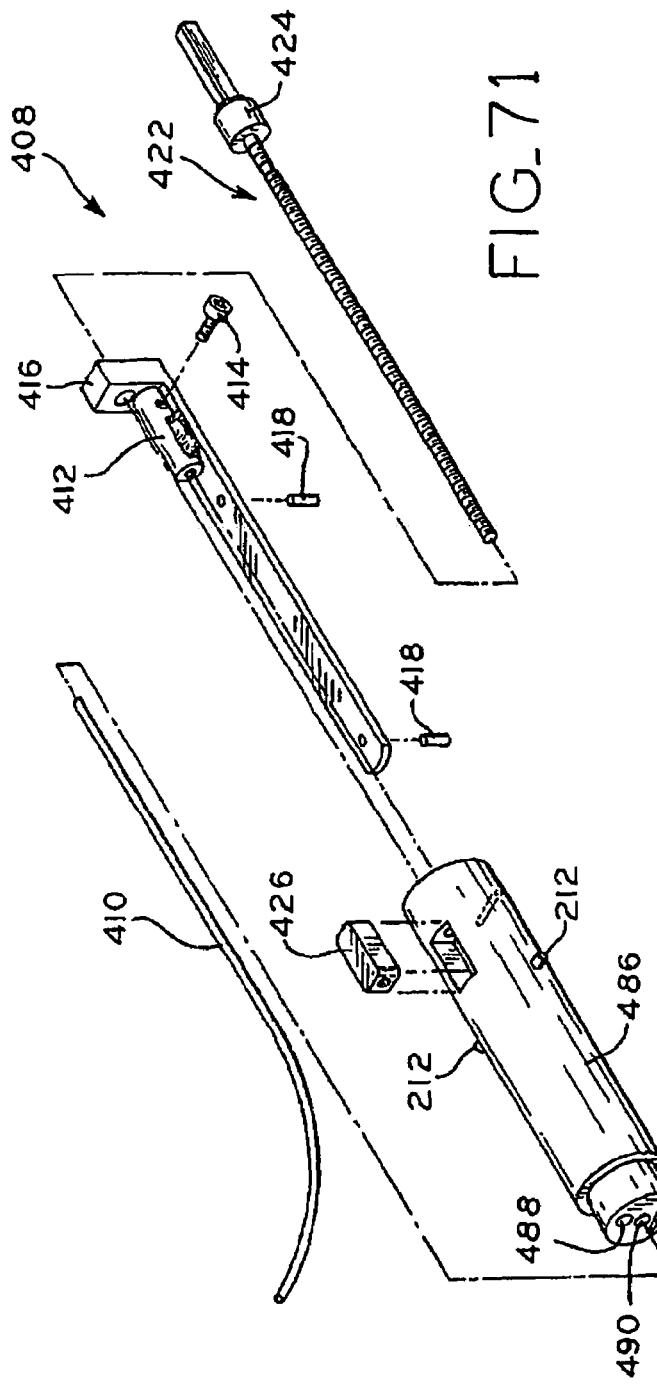
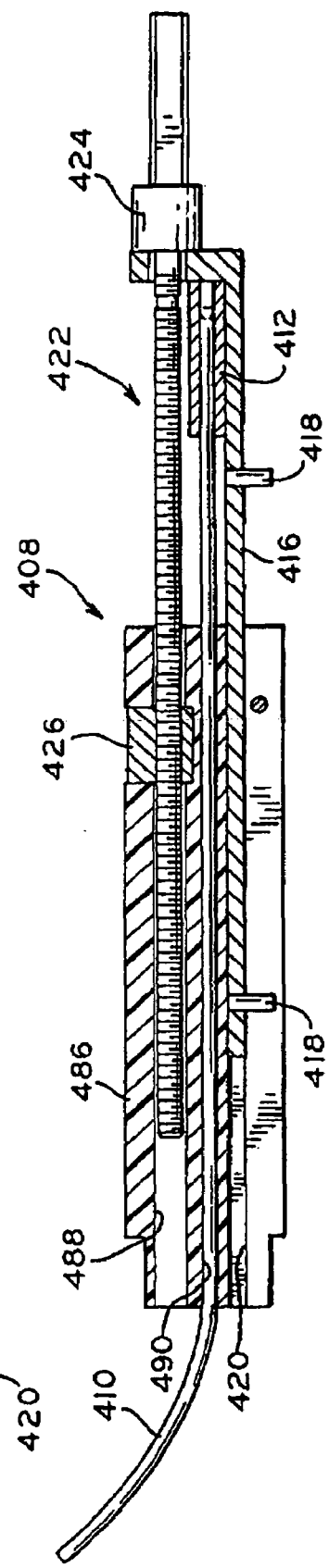
FIG_71
FIG_72

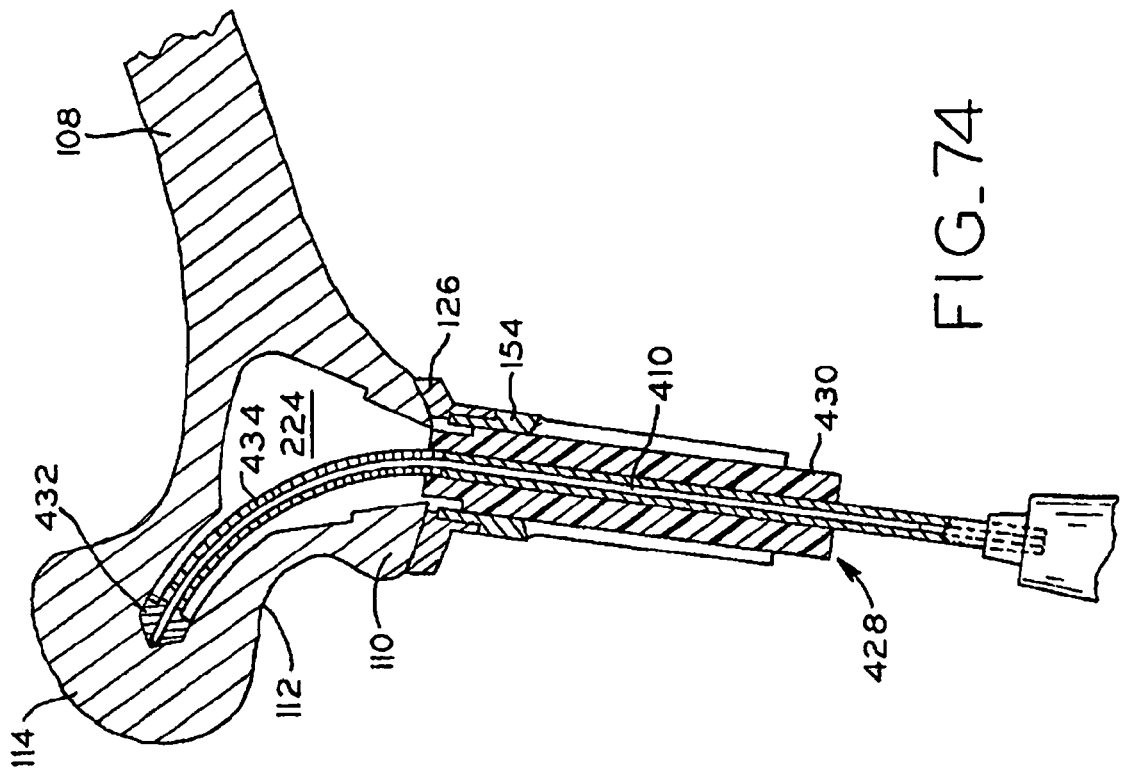
FIG_74
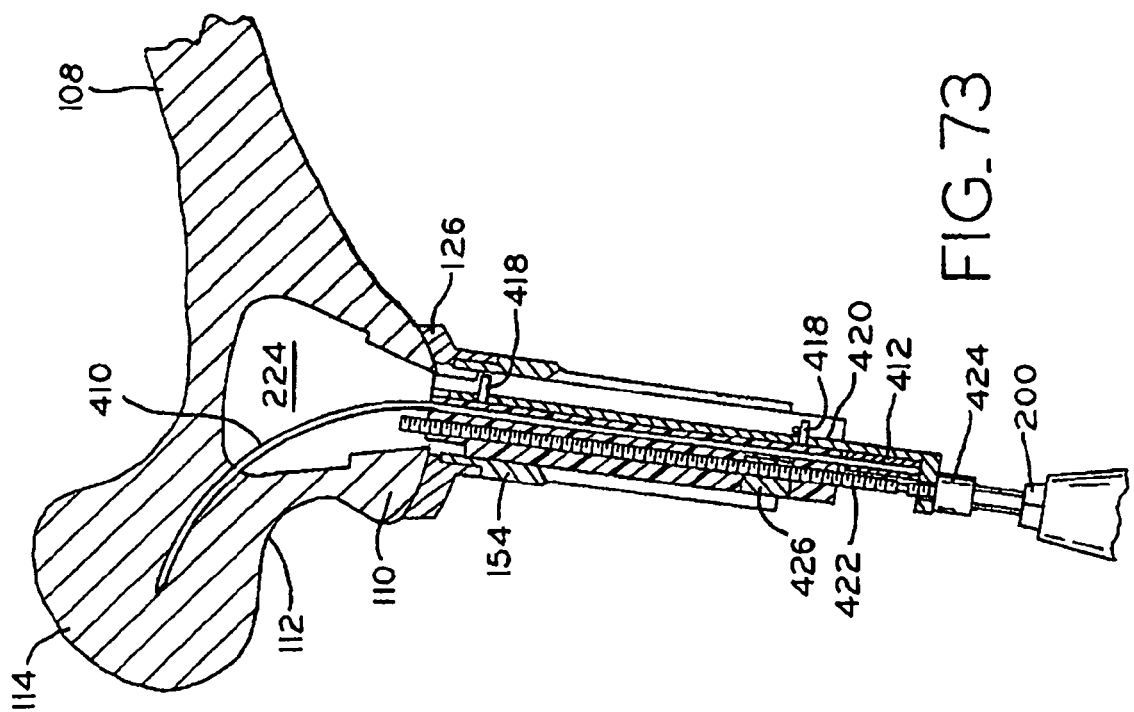
FIG_73

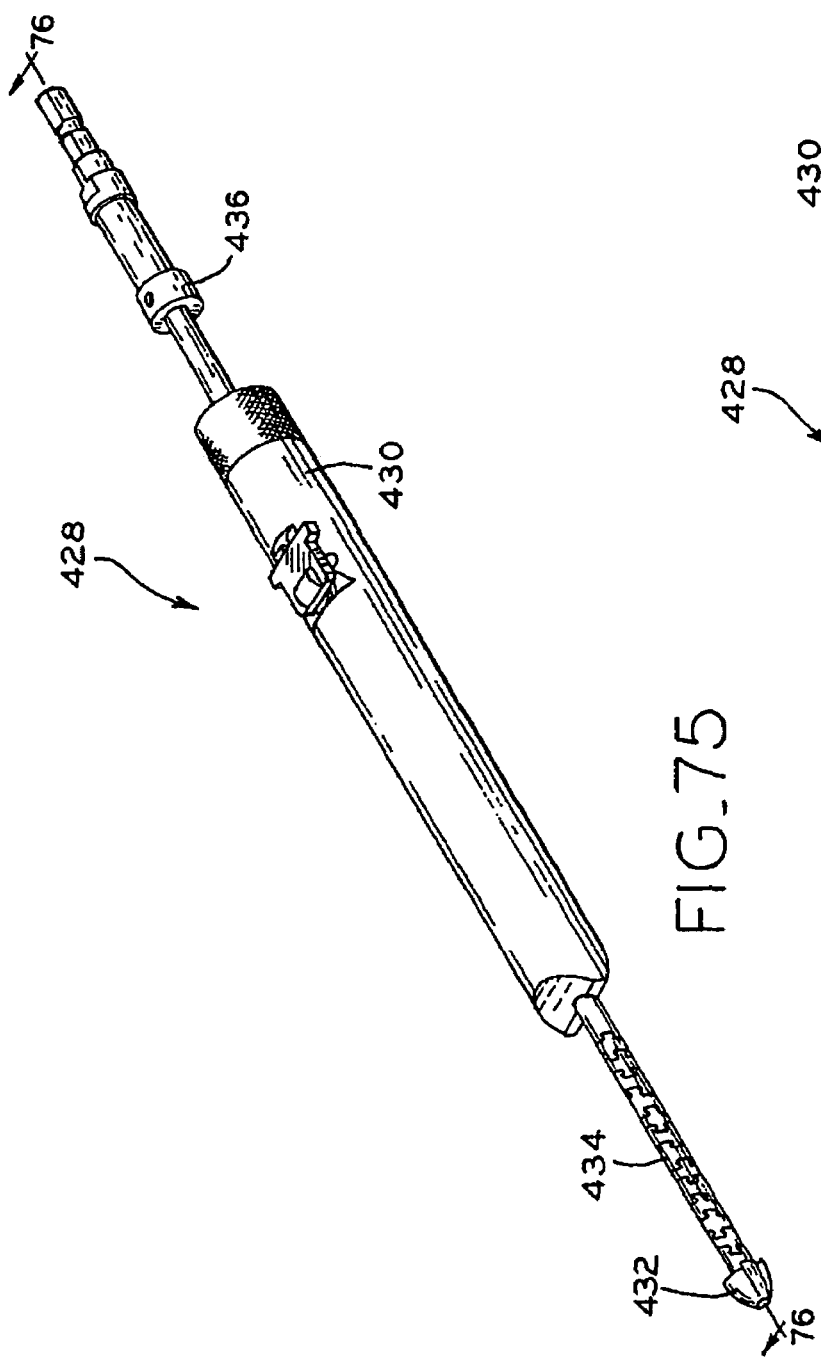
FIG._75
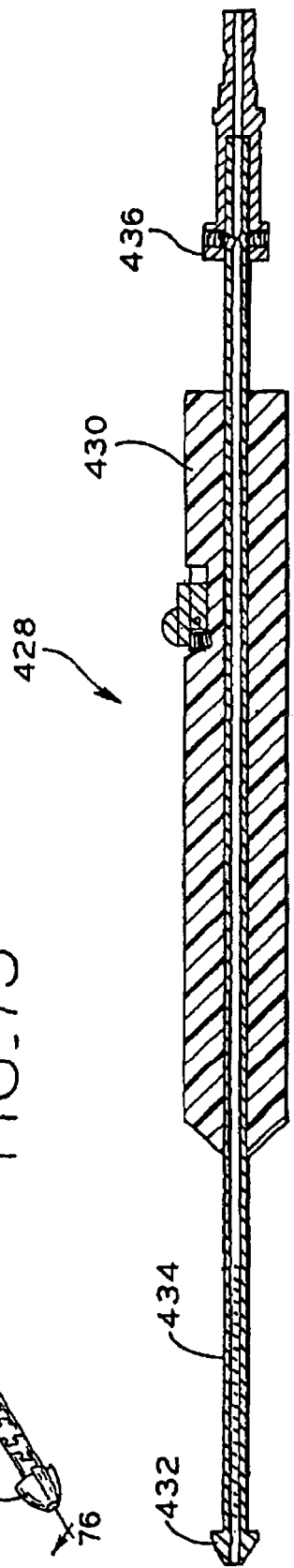
FIG._76

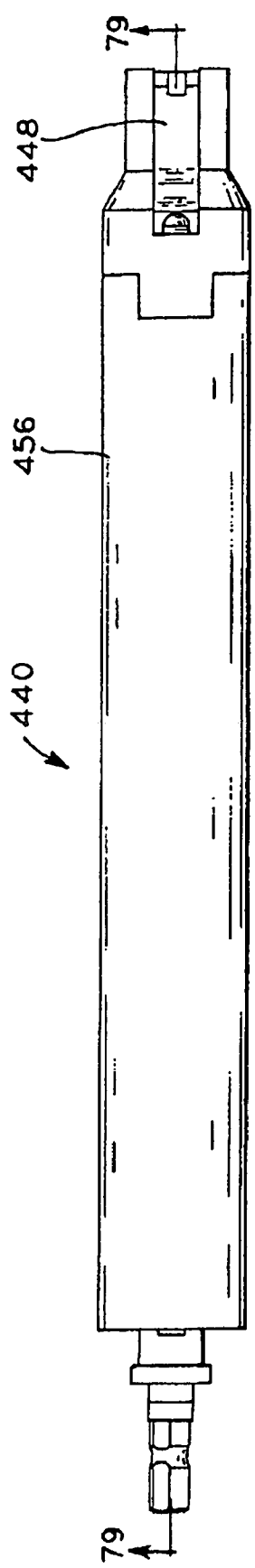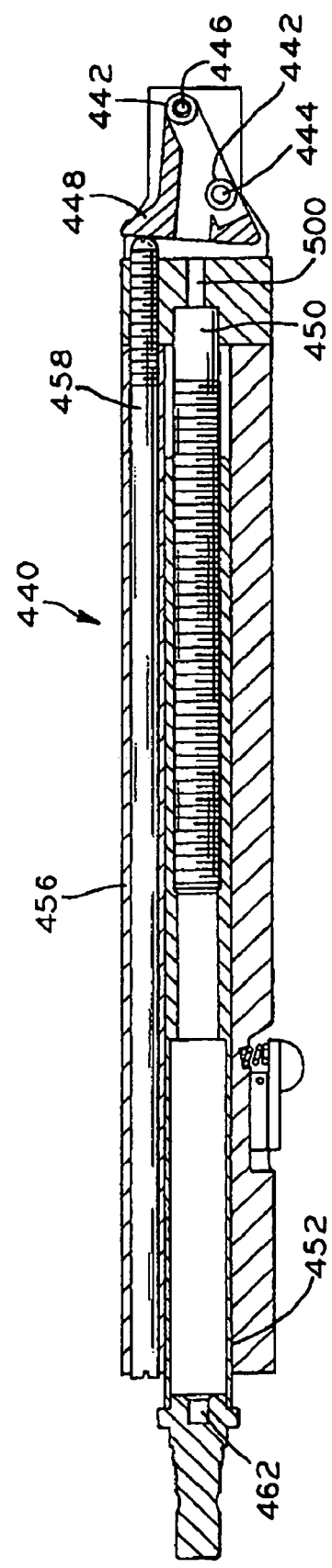

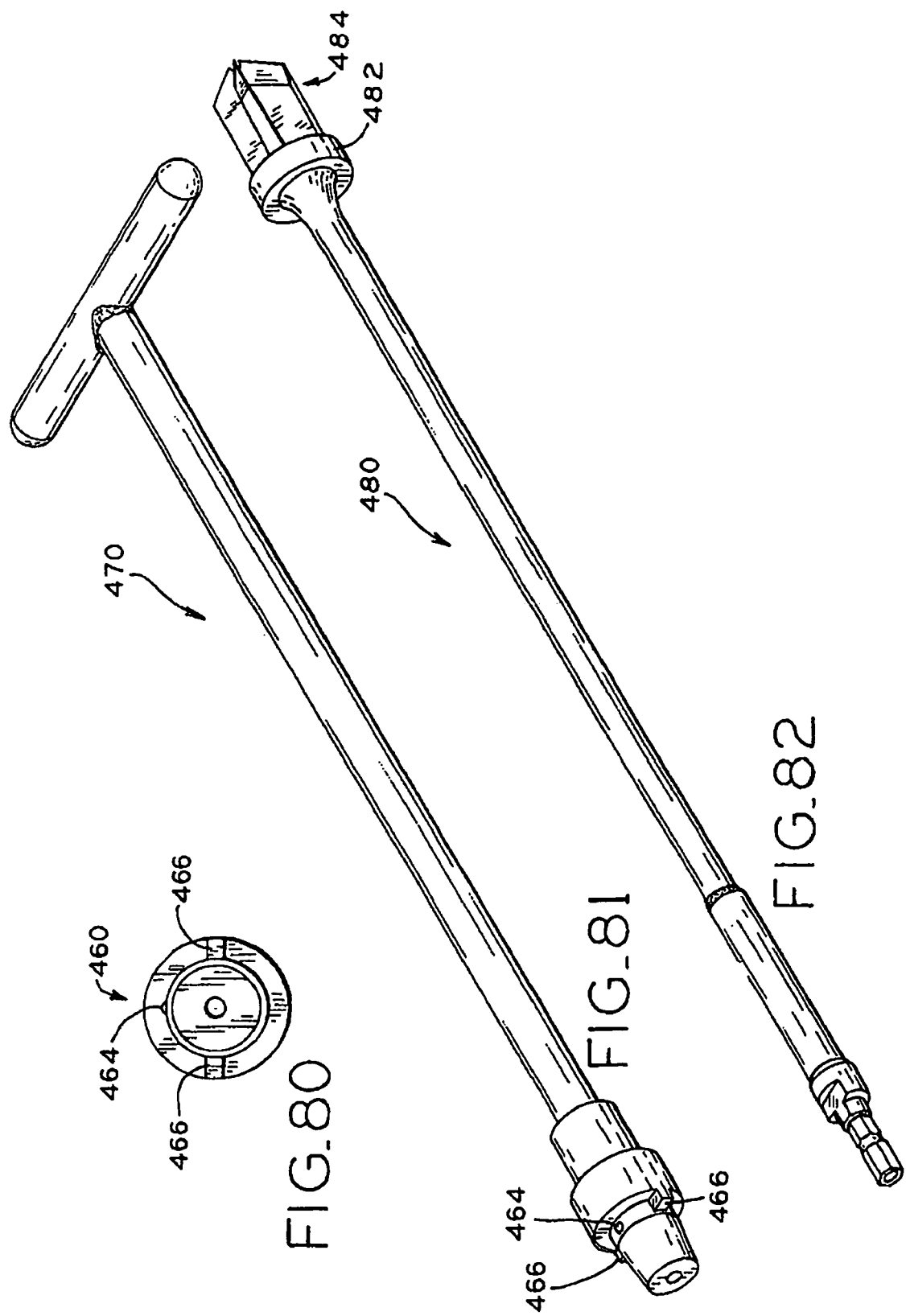

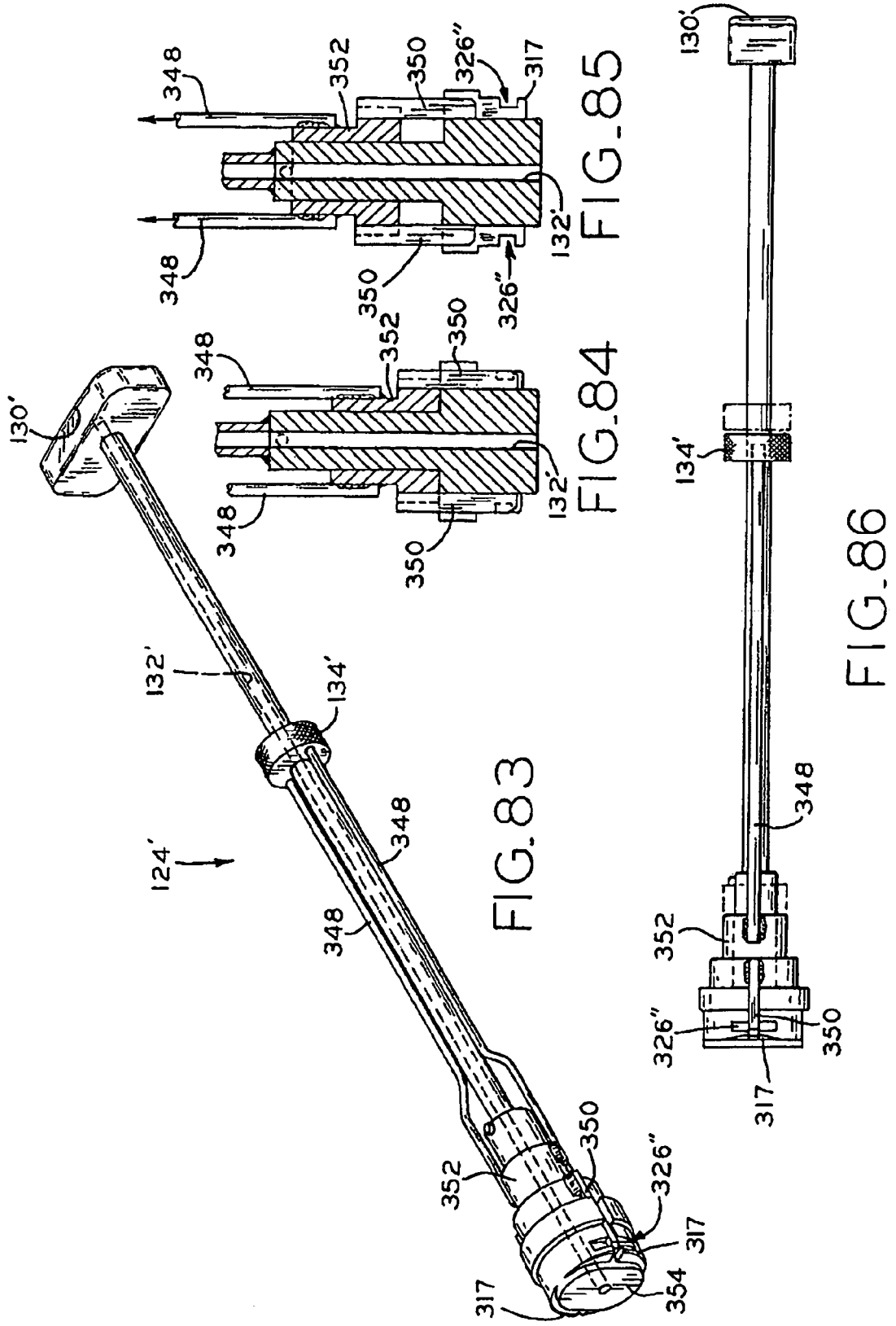

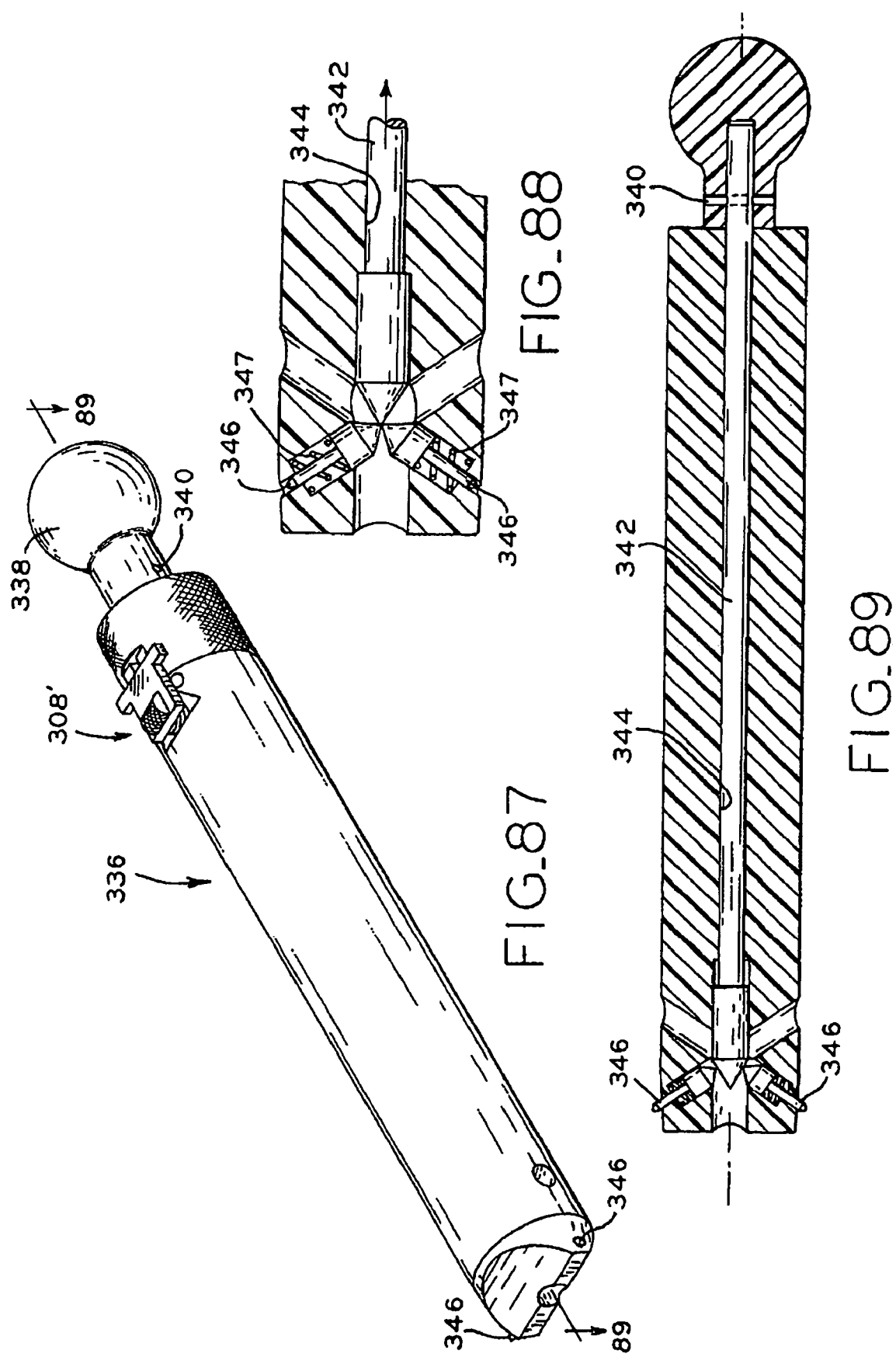

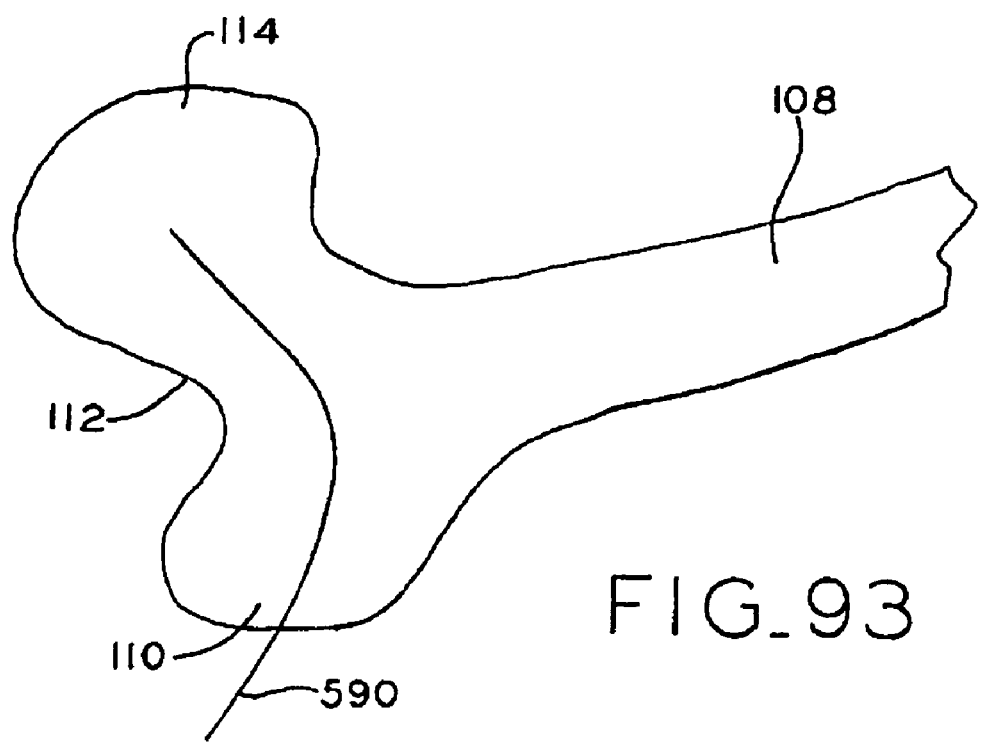
FIG_93
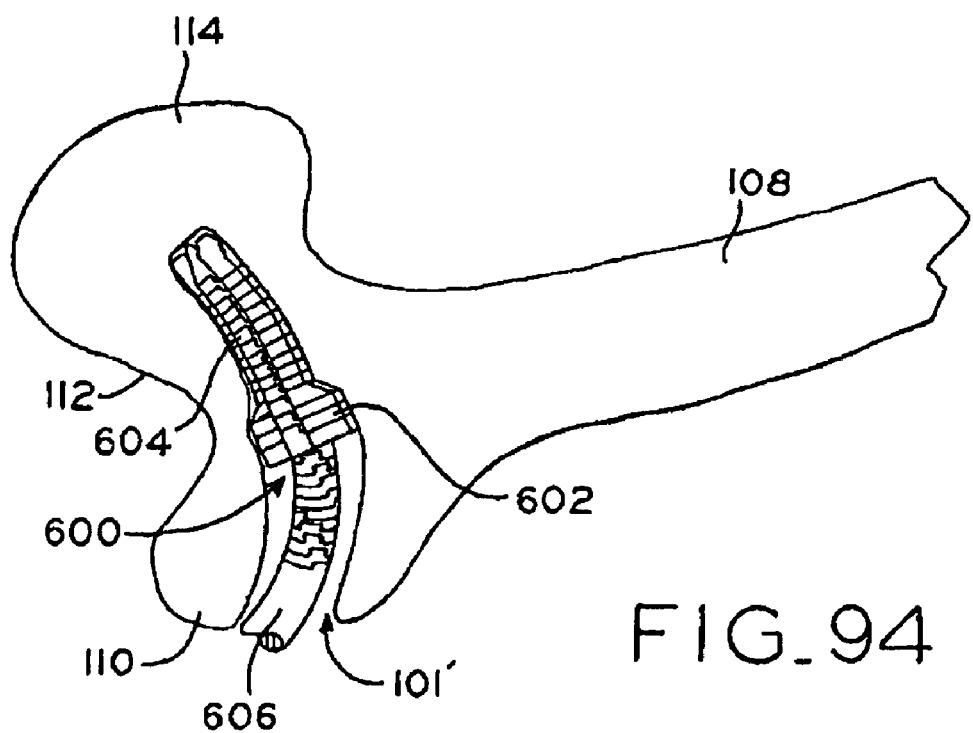
FIG_94

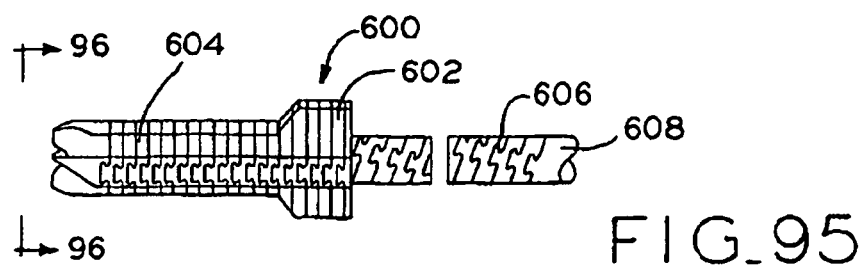
FIG_95
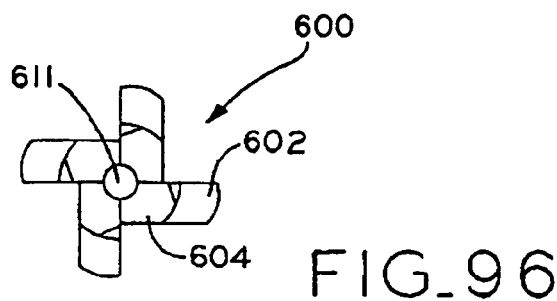
FIG_96
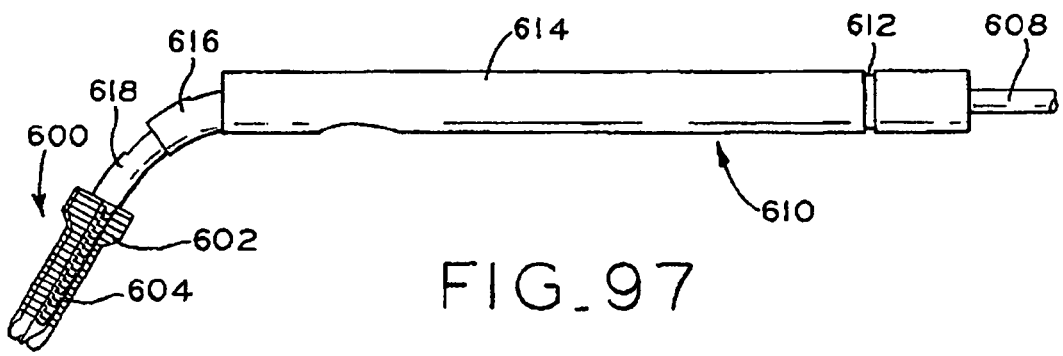
FIG_97
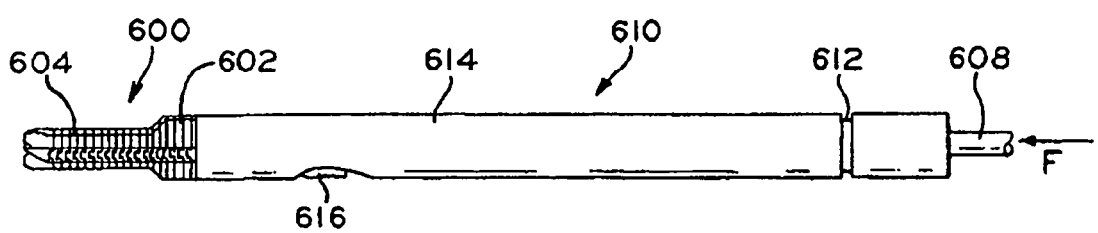
FIG_98

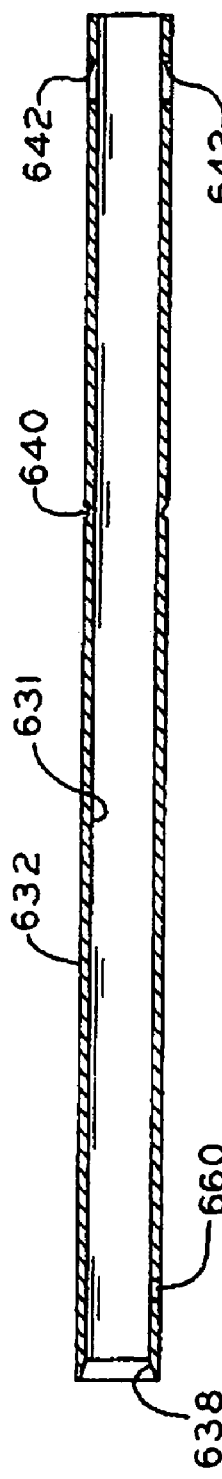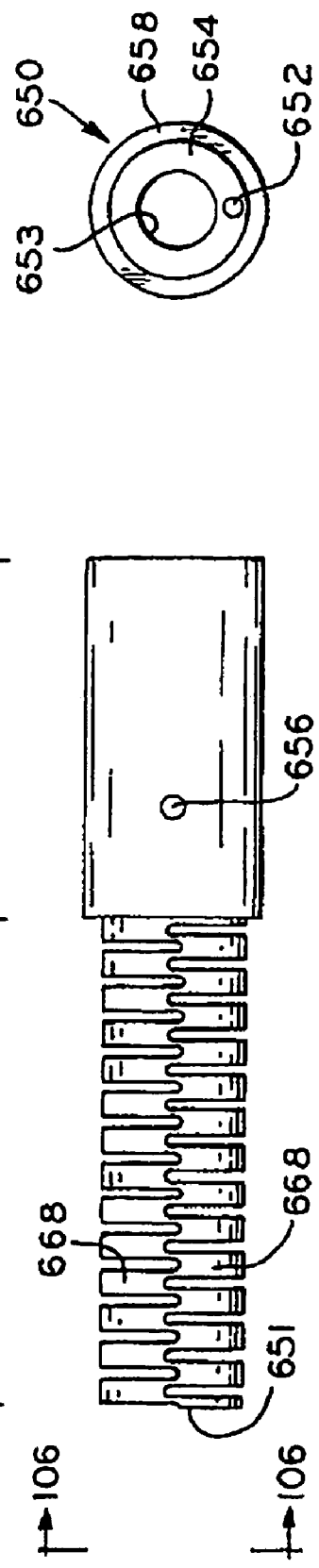

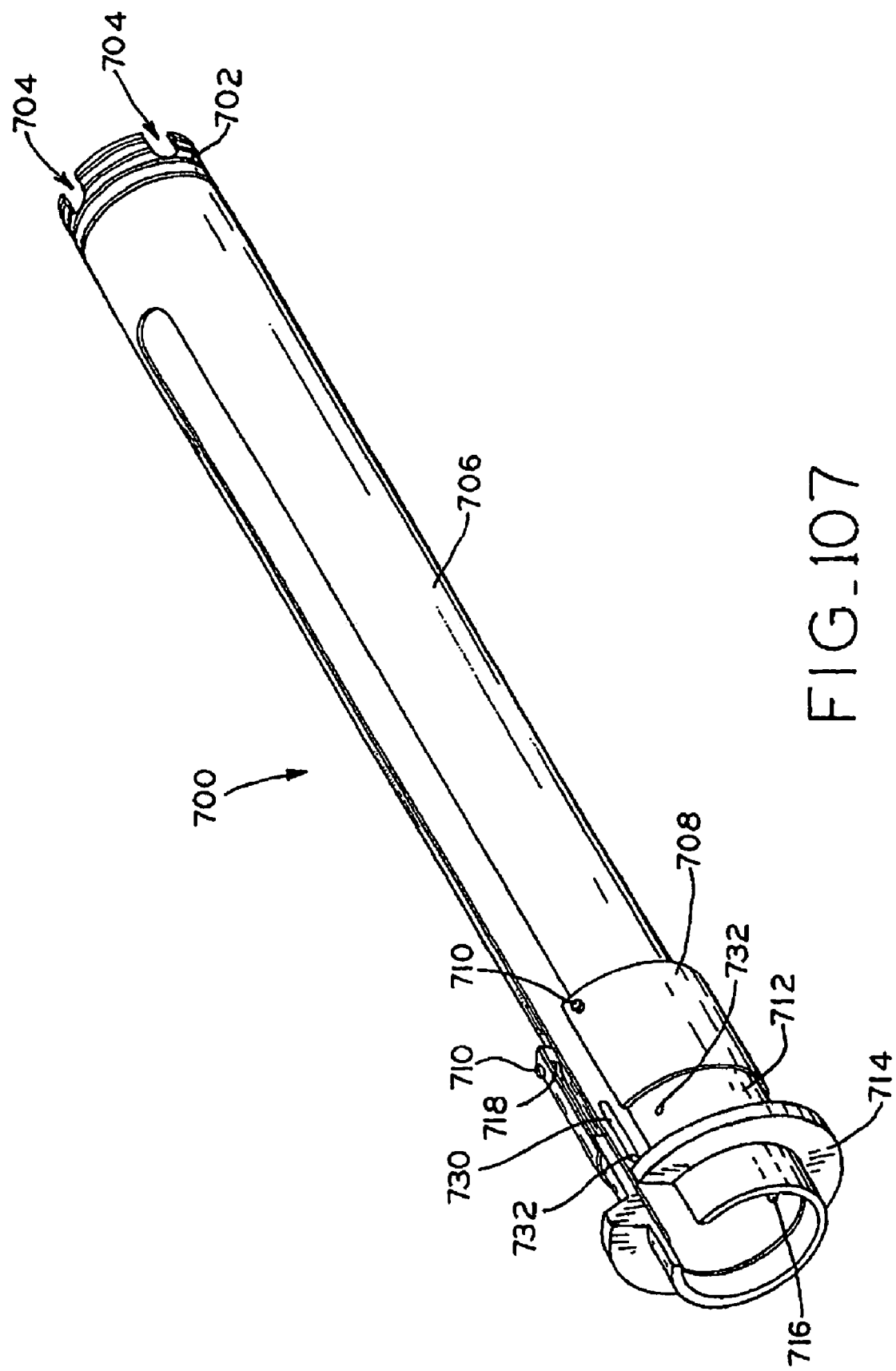
FIG._107

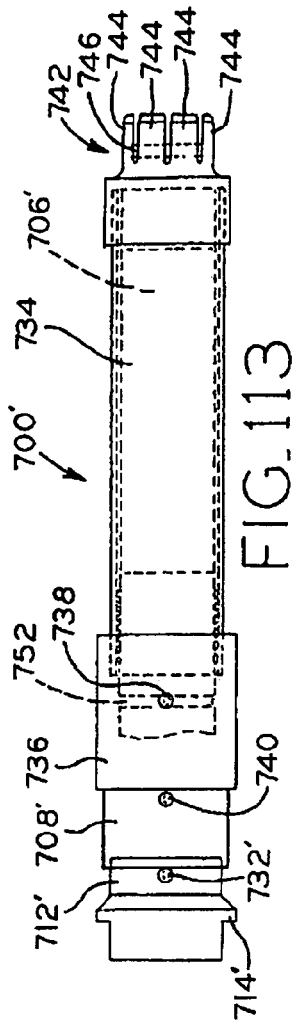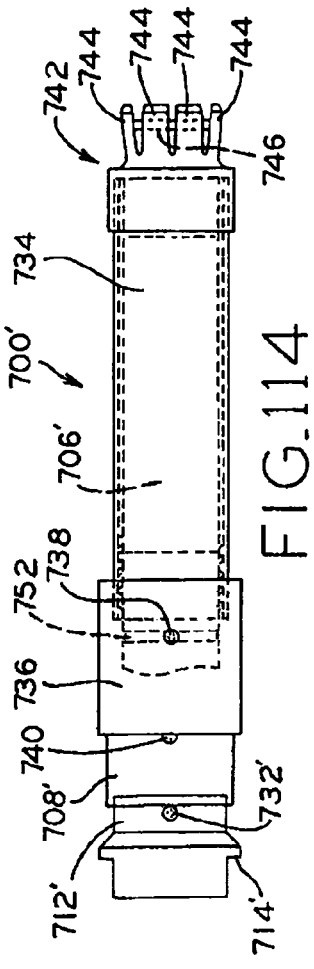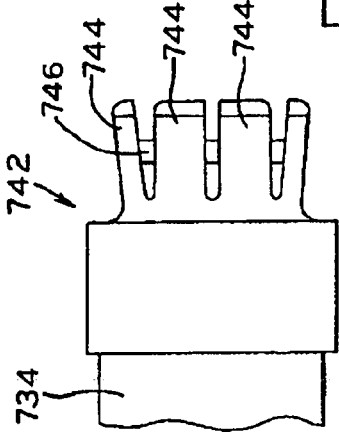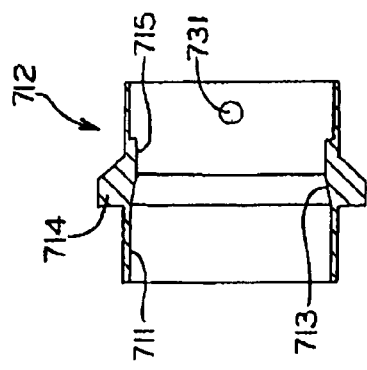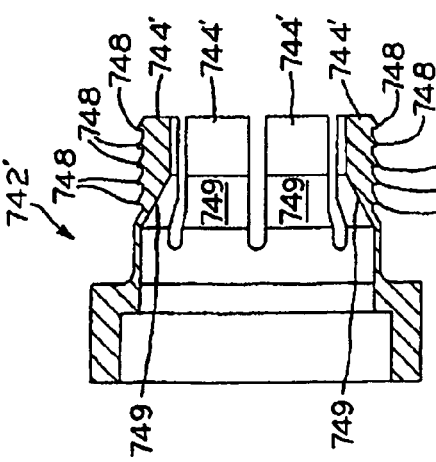

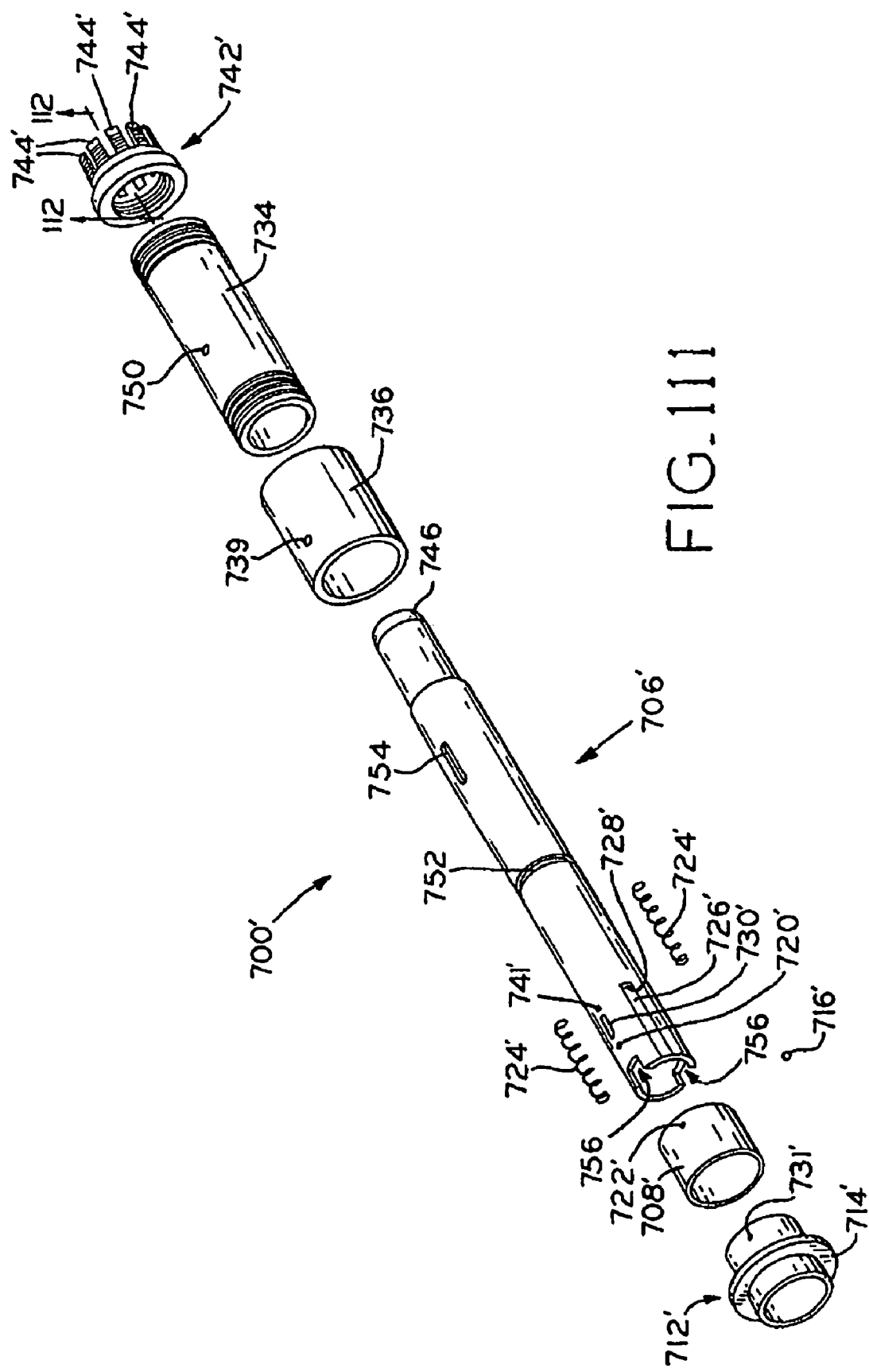
FIG_111

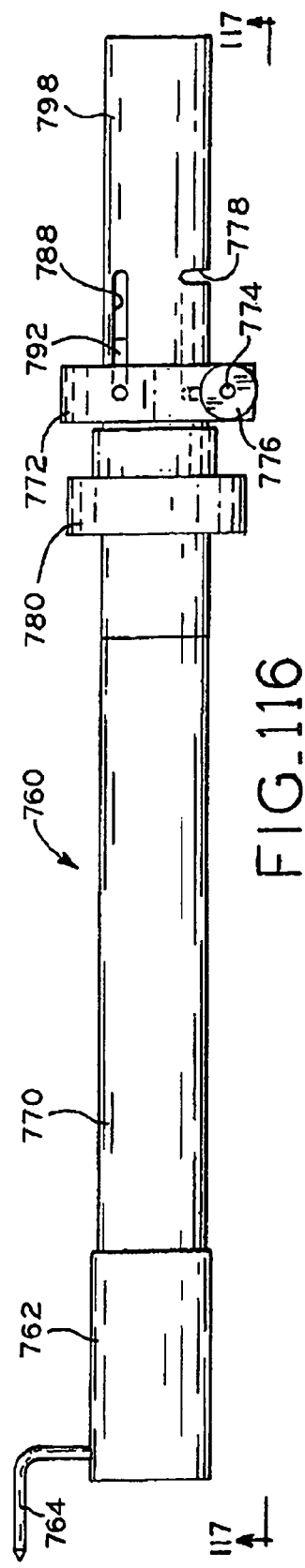
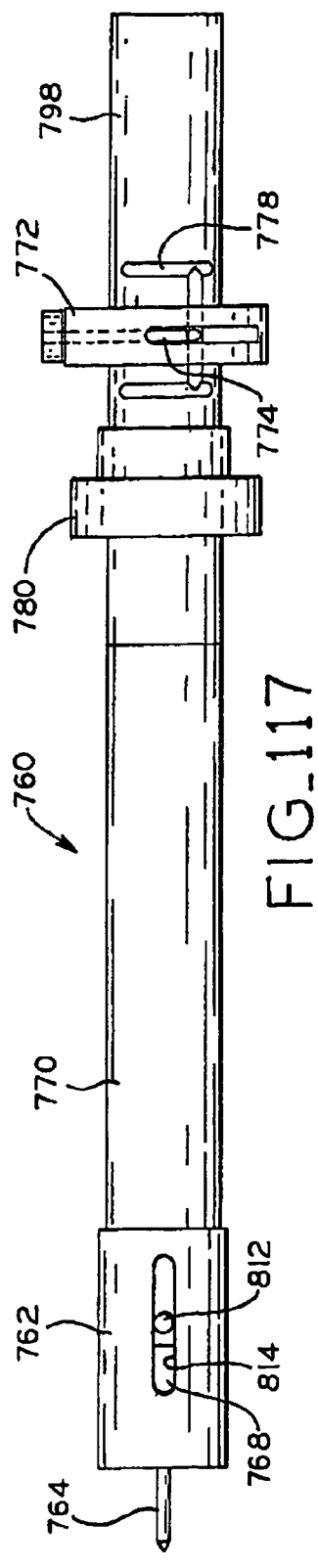
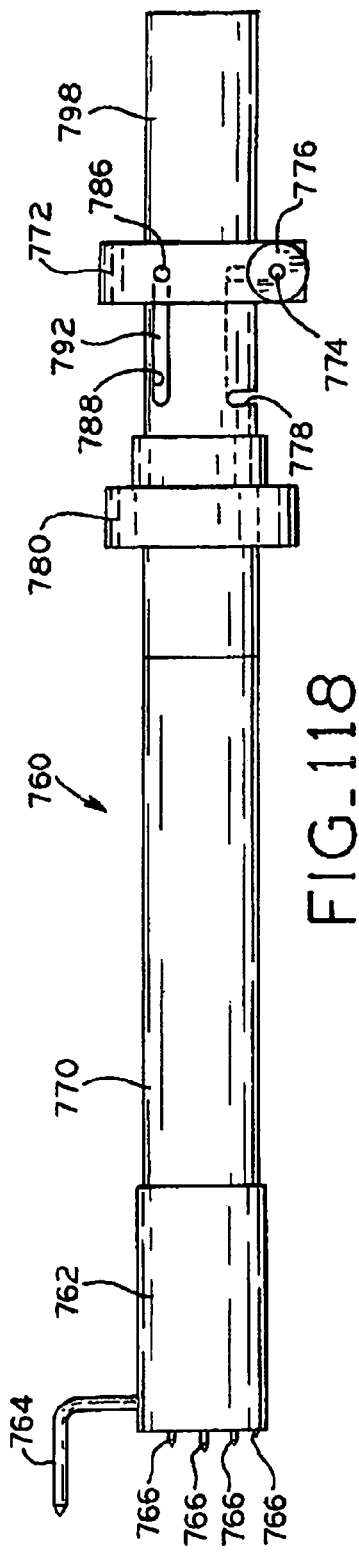

FIG._124

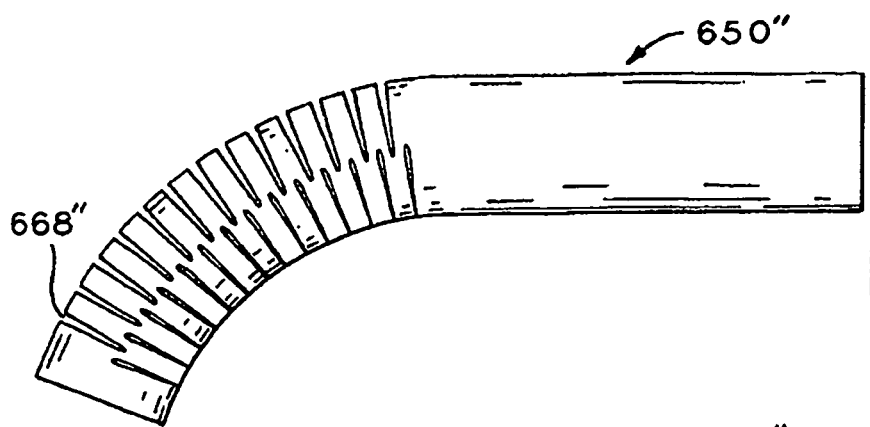
FIG.128
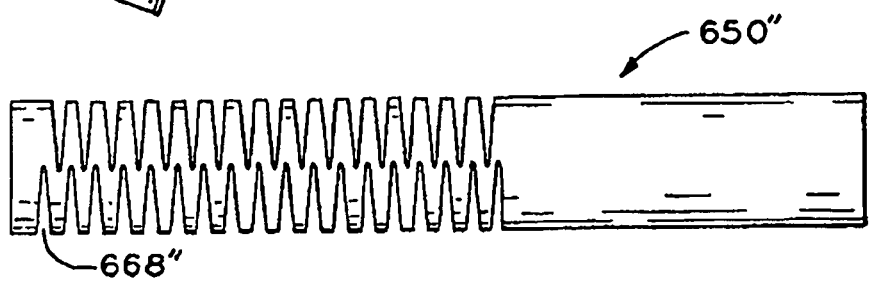
FIG.129
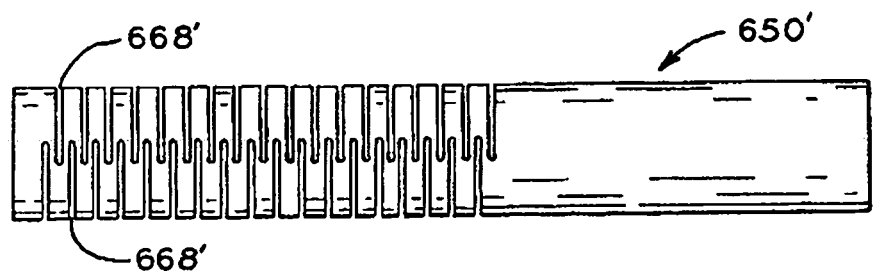
FIG.130
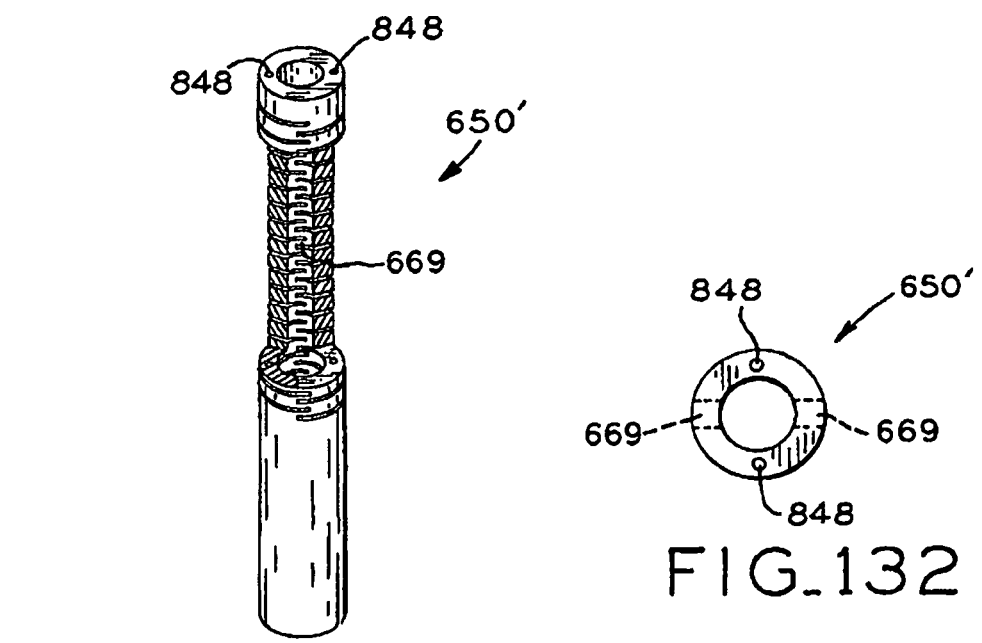
FIG.131
FIG.132

FIG_133

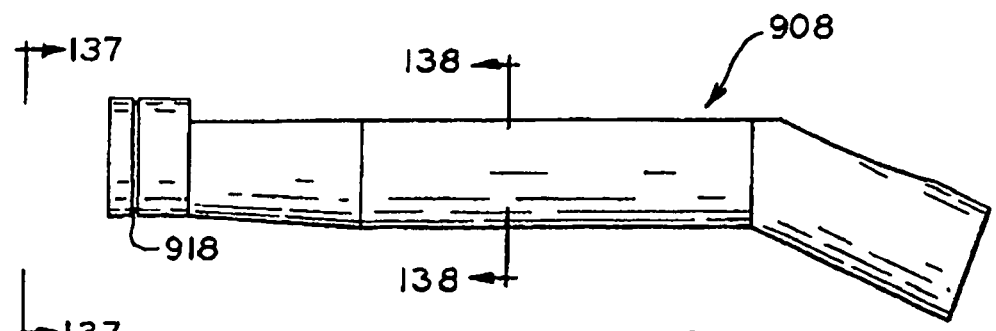
FIG_135
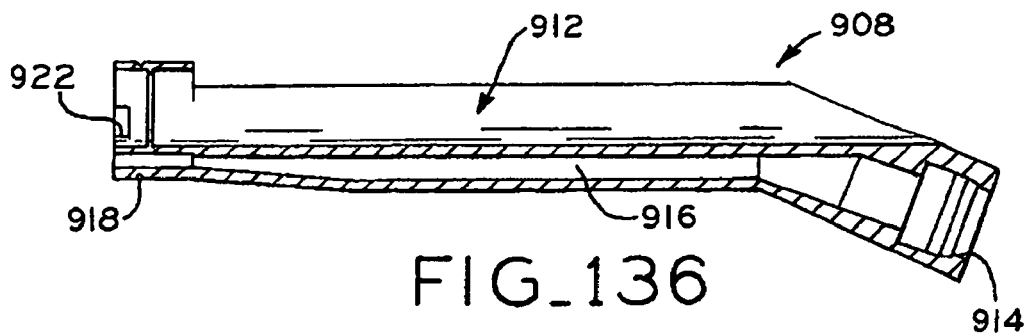
FIG_136
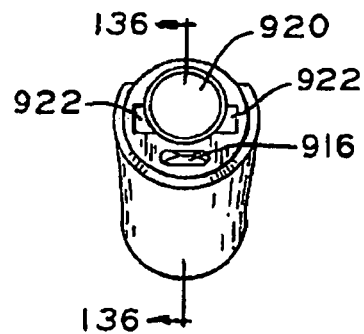
FIG_137
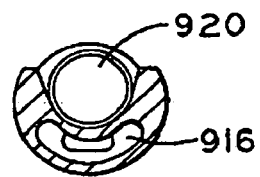
FIG_138
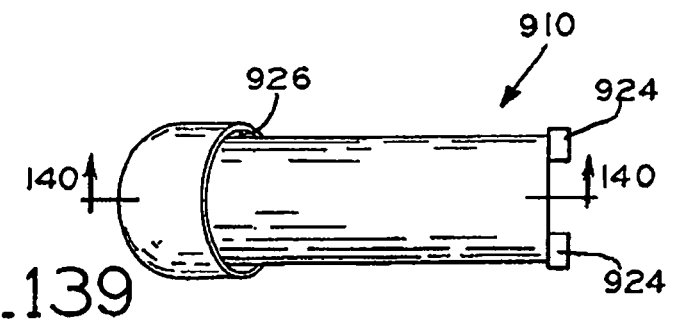
FIG_139
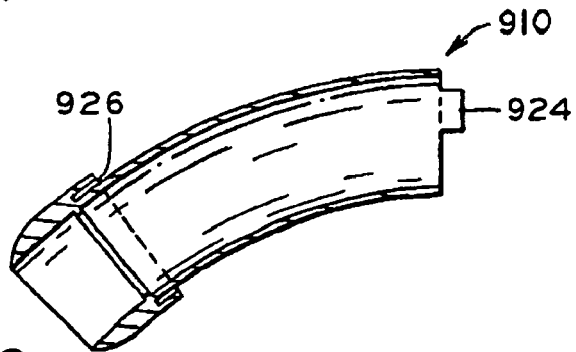
FIG_140

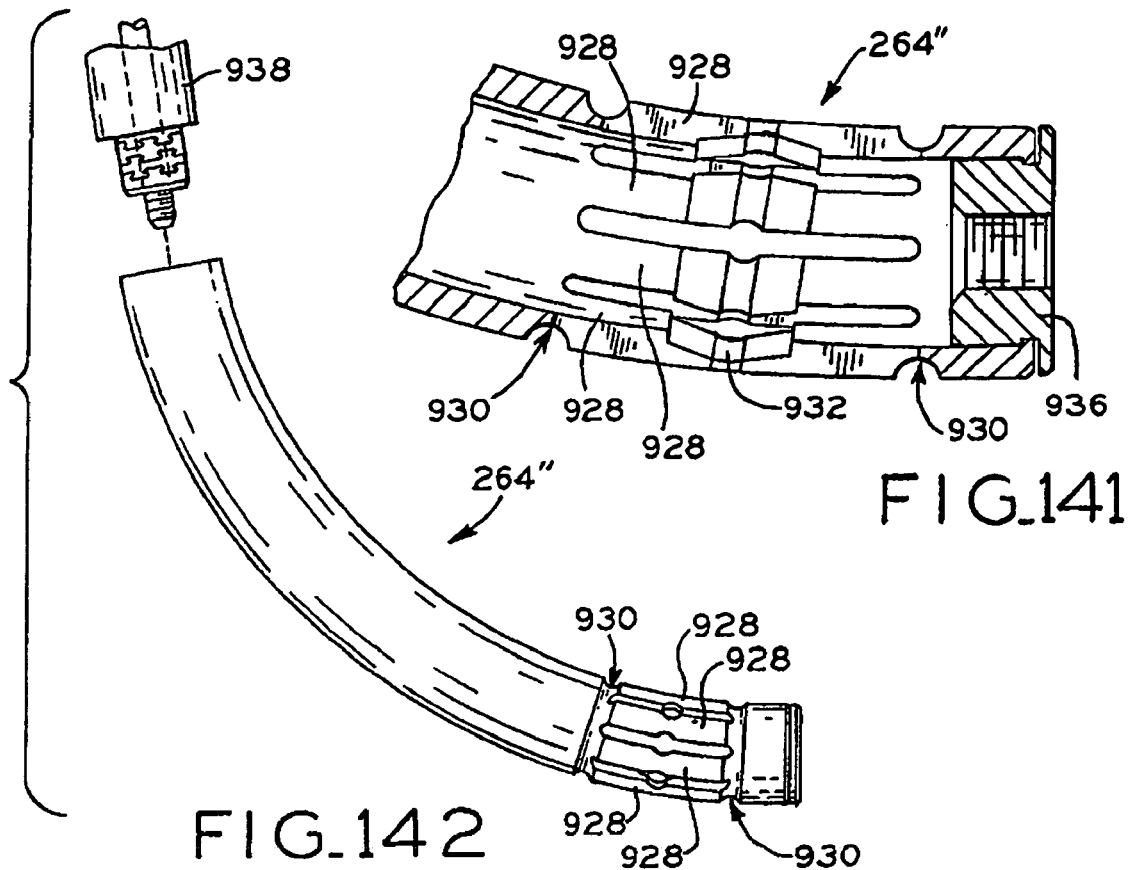
FIG_141
FIG_142
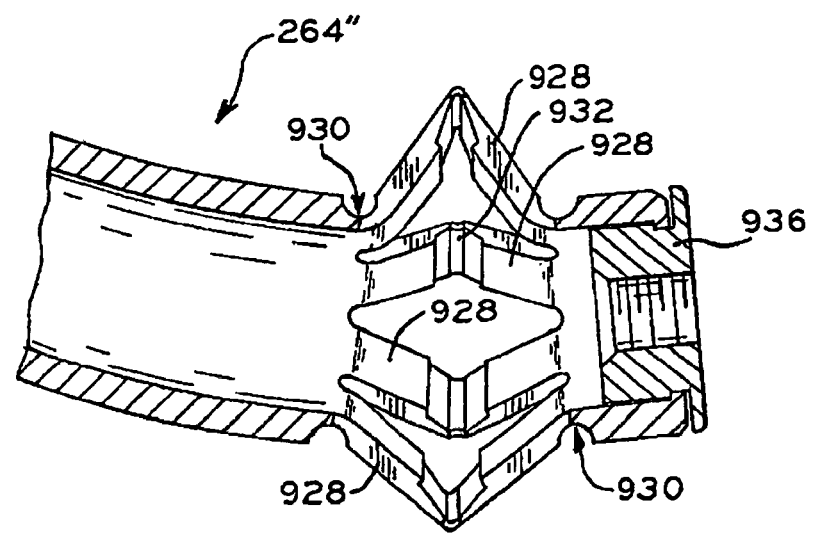
FIG_143

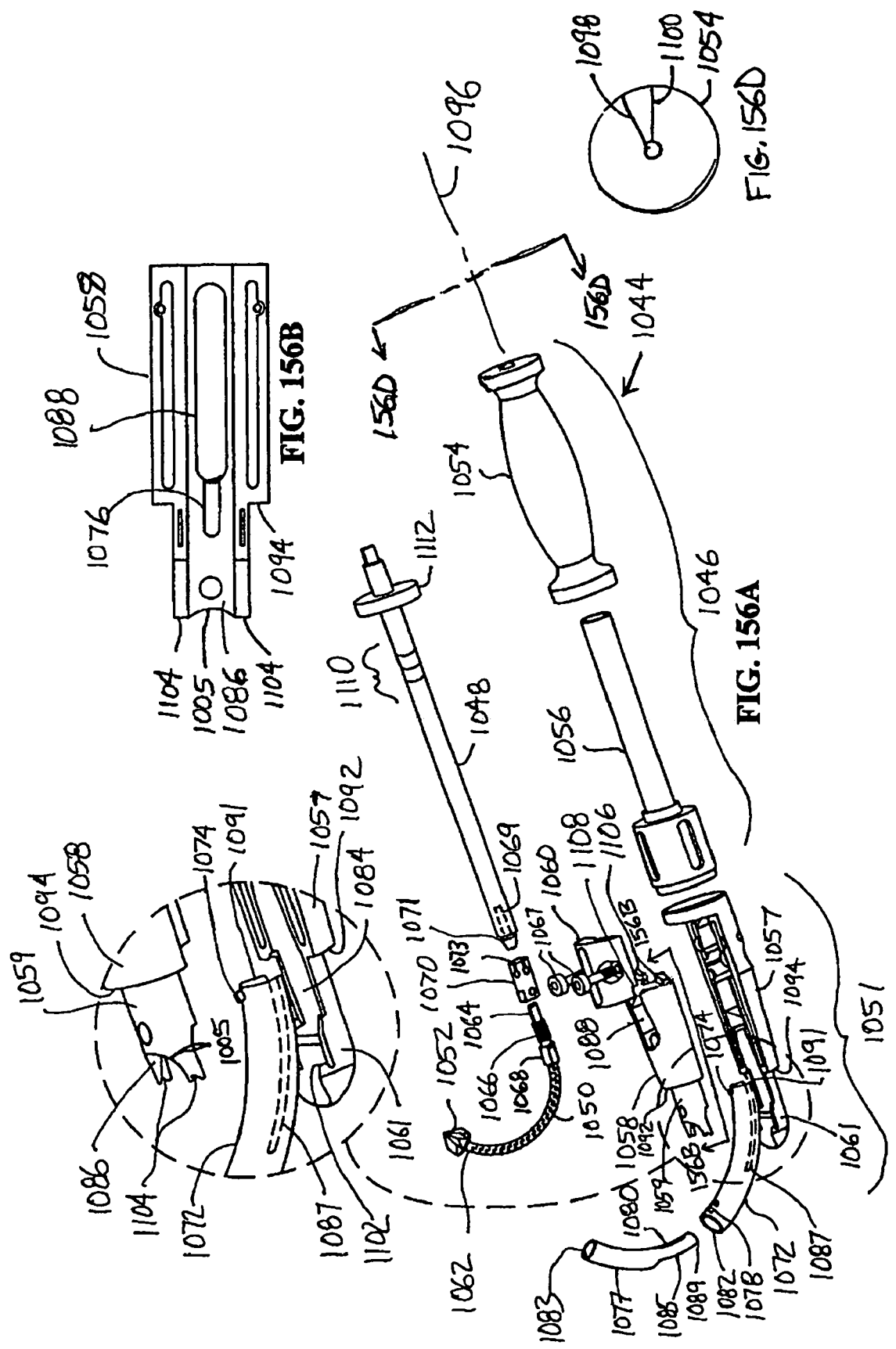

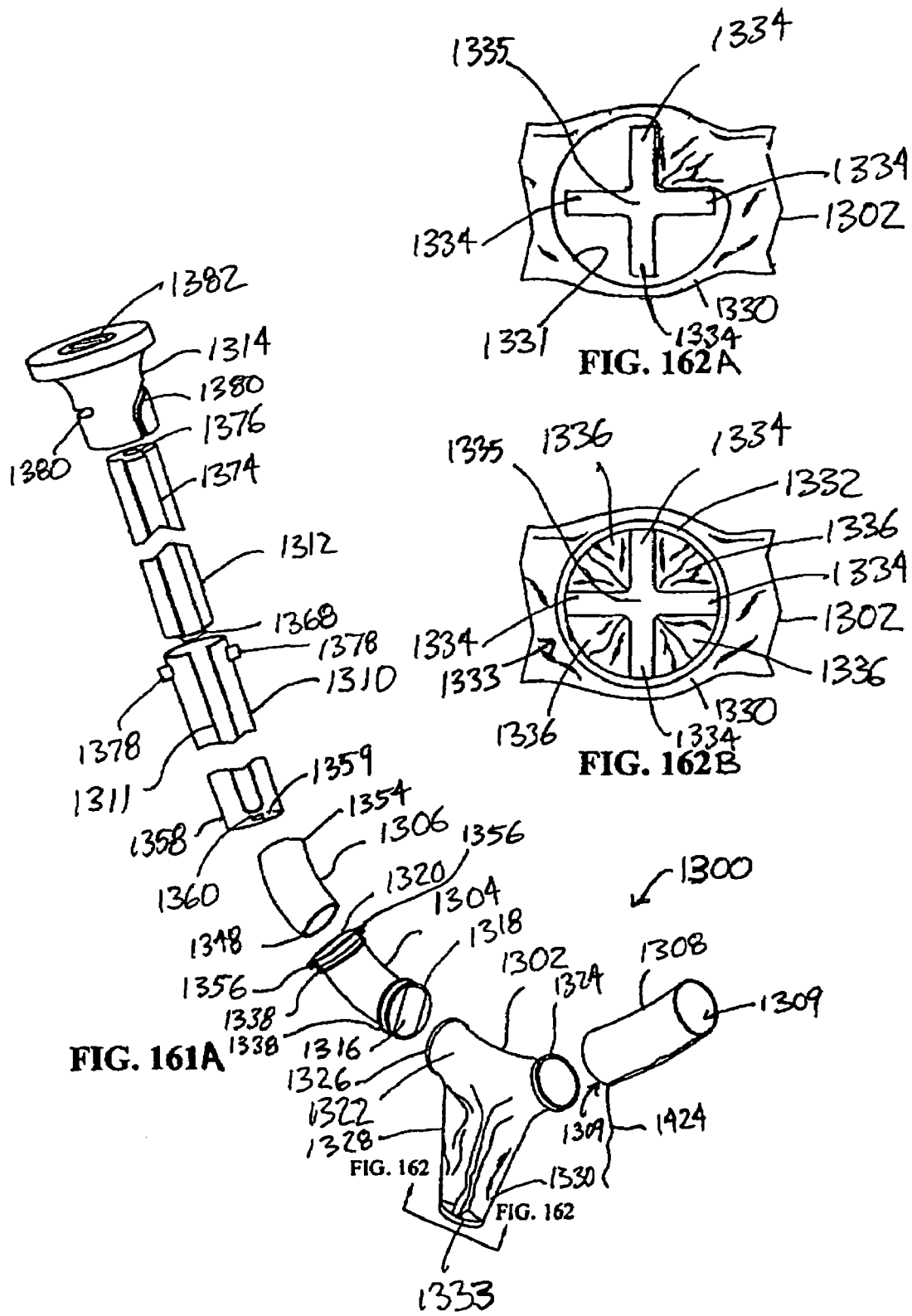

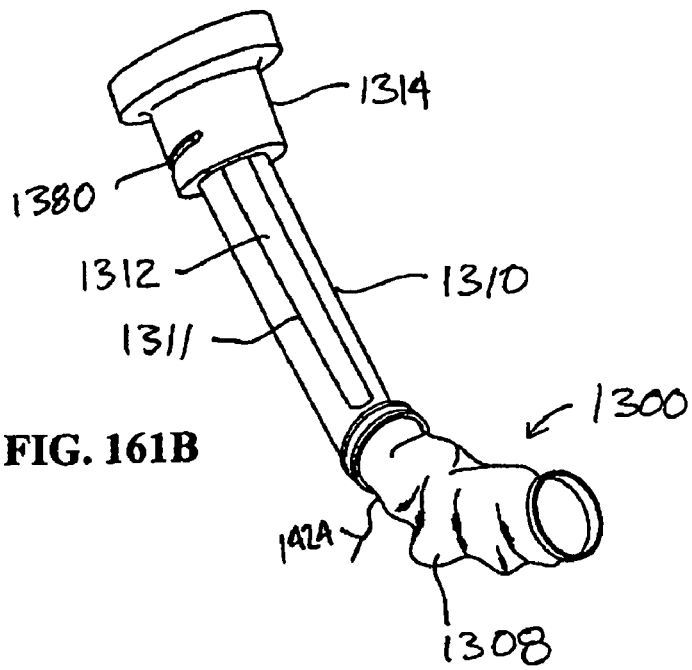
FIG. 161B
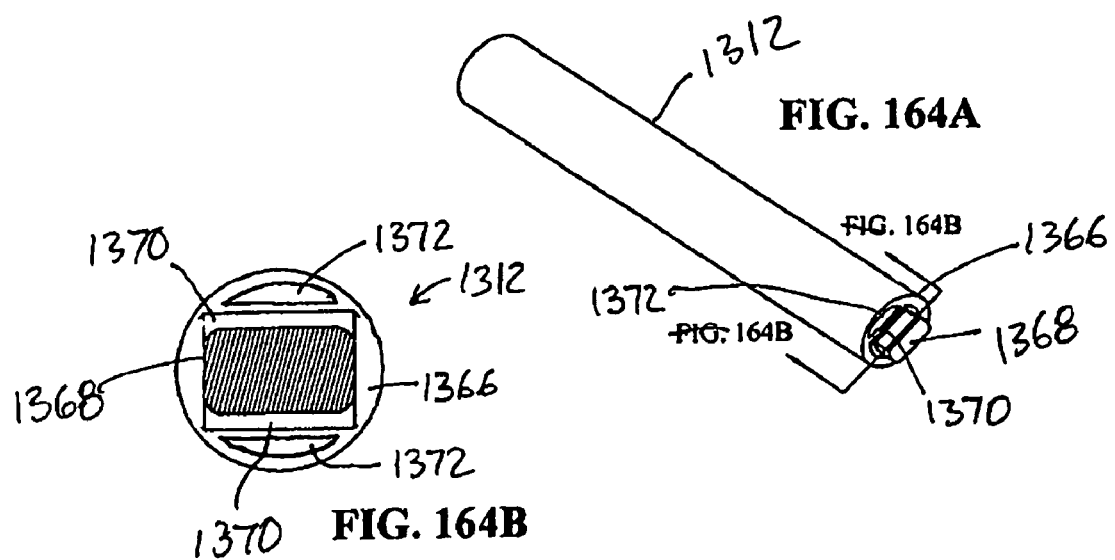
FIG. 164A
FIG. 164B

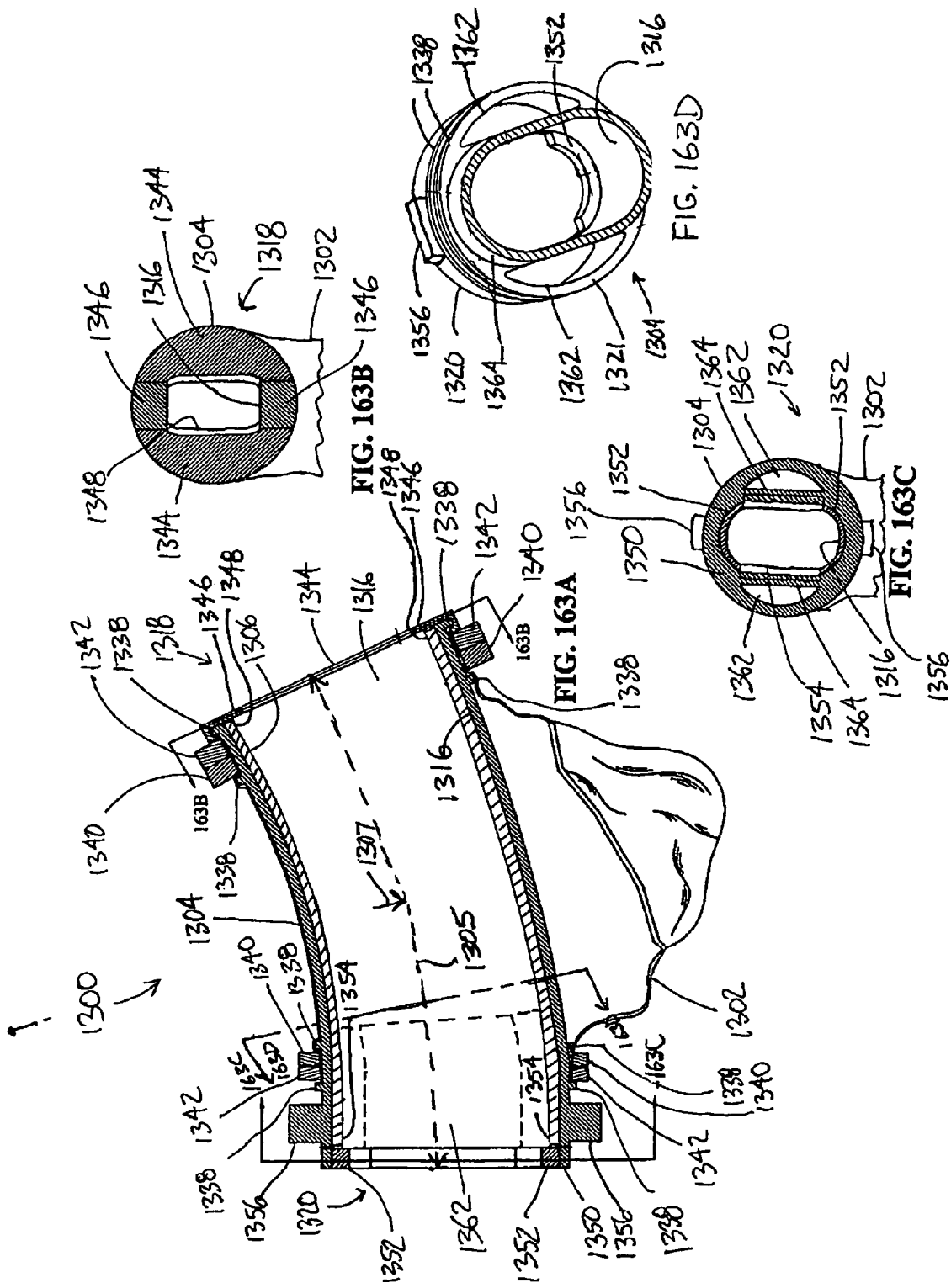

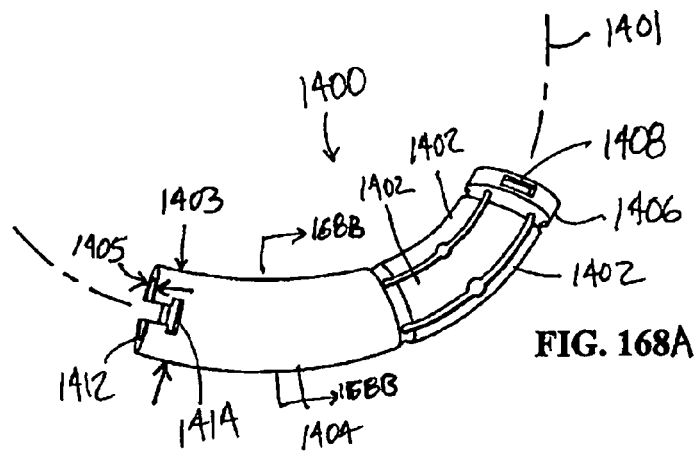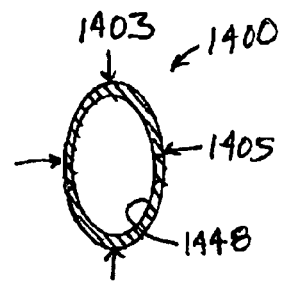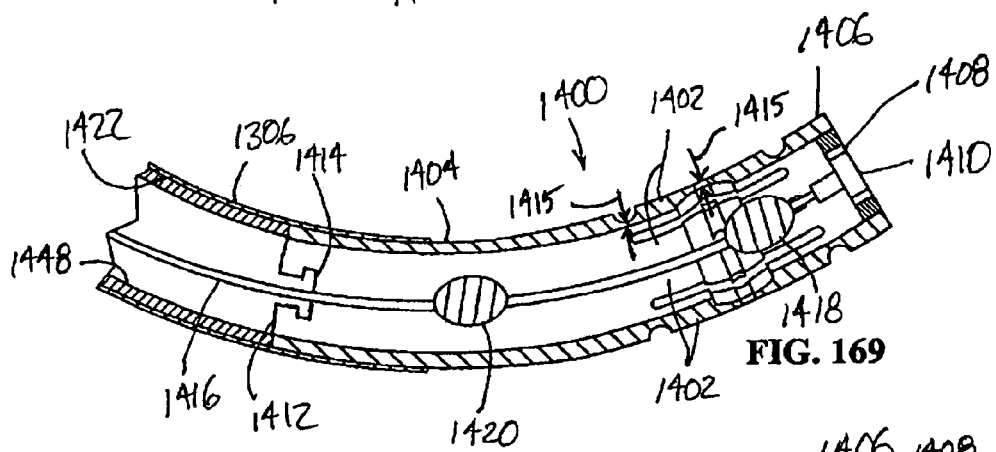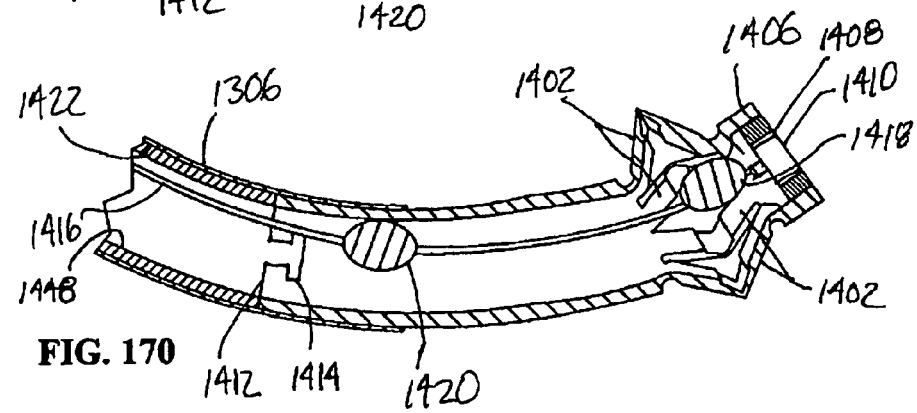

METHOD AND APPARATUS FOR REDUCING FEMORAL FRACTURES

CROSS-REFERENCE TO RELATED APPLICATION

This application is a continuation-in-part of prior U.S. patent application Ser. No. 10/358,009, filed Feb. 4, 2003, now abandoned which is a continuation-in-part of prior U.S. patent application Ser. No. 10/266,313, filed Oct. 8, 2002, now U.S. Pat. No. 6,814,787 which is a continuation-in-part of prior U.S. patent application Ser. No. 10/155,683, filed May 23, 2002, now U.S. Pat. No. 7,258,692 which is a continuation-in-part of prior U.S. patent application Ser. No. 09/520,351, filed Mar. 7, 2000, now U.S. Pat. No. 6,447,514.

This application is related to and claims the benefit under 35 U.S.C. § 119(e) of U.S. Provisional Patent Application Ser. No. 60/550,510, entitled METHOD AND APPARATUS FOR REDUCING FEMORAL FRACTURES, filed Mar. 5, 2004, the entire disclosure of which is hereby expressly incorporated by reference herein.

This utility patent application expressly incorporates by reference herein the entire disclosures of U.S. patent application Ser. No. 10/155,683, filed May 23, 2002; U.S. patent application Ser. No. 10/266,319, filed Oct. 8, 2002; U.S. patent application Ser. No. 10/358,009, filed Feb. 4, 2003; and U.S. Provisional Patent Application Ser. No. 60/621,487, filed Oct. 22, 2004.

BACKGROUND

1. Field of the Invention

The present invention relates to a method and apparatus for treating hip fractures, and, more particularly, to a method and apparatus for reducing femoral fractures utilizing a minimally invasive procedure.

2. Description of the Related Art

Current procedures utilized to reduce hip fractures generally utilize a side plate/hip screw combination, i.e., a bone plate affixed to a lateral aspect of the femur and having a hip screw operably connected thereto, with the hip screw extending into the femoral head. To properly implant a side plate hip screw, a surgeon must dissect an amount of muscle to expose the femur and operably attach the bone plate and hip screw. Typically, the side plate hip screw requires an incision of about 10-12 cm through the quadriceps to expose the femur. While this approach provides surgeons with an excellent view of the bone surface, the underlying damage to soft tissue, including muscle, e.g., the quadriceps can potentially lengthen a patient's rehabilitation time after surgery.

What is needed in the art is a method and apparatus for reducing a hip fracture which reduces or eliminates the need for an incision in soft tissue, including, e.g., the quadriceps.

SUMMARY

In one embodiment, the present invention provides an improved method and apparatus for reducing a hip fracture utilizing a minimally invasive procedure which avoids substantial dissection of muscle, e.g., the quadriceps, adductor, iliotibial band, and gluteus. A femoral implant in accordance with the present invention achieves intramedullary fixation as well as fixation into the femoral head to allow for the compression needed for a femoral fracture to heal. The femoral implant of the present invention allows for sliding compression of the femoral fracture.

To operably position a femoral implant of the present invention, an incision aligned with the greater trochanter is made and the wound is developed to expose the greater trochanter. The size of the wound developed on the surface is substantially constant throughout the depth of the wound. In one exemplary embodiment of the present invention, the incision through which the femur is prepared and the implant is inserted measures about 2.5 centimeters (1 inch). Because the greater trochanter is not substantially covered with muscle, the incision can be made and the wound developed through the skin and fascia to expose the greater trochanter, without incising muscle, including, e.g., the quadriceps. In one exemplary embodiment, the incision to expose the greater trochanter is made through soft tissue in an area bordered by the quadriceps, adductor, iliotibial band, and gluteus. However, in some cases muscle is found to overlay the greater trochanter. Any muscle over laying the greater trochanter can be moved from this position to expose the greater trochanter without cutting or otherwise damaging the muscle that is overlaying the greater trochanter.

An alignment guide having an alignment arm supporting implant pattern arms and an alignment pin is manually positioned relative to the femur for locating and orienting an access into the femur and for templating for implant size selection. Components of the alignment guide provide radiopaque features for orienting the alignment pin and implant pattern arms relative to the coronal femoral plane and other aspects of the femur. The alignment pin is subsequently driven into the femur, entering at the greater trochanter with the distal end of the guide pin disposed proximate, or resting against, the medial cortex. The alignment pin is then used to guide a reamer used to cut an access into the femur. The implant pattern arms are used to select the implant arc radius.

Novel instruments of the present invention are also utilized to prepare a cavity in the femur extending from the greater trochanter into the femoral head and further extending from the greater trochanter into the intramedullary canal of the femur. A telescoping reamer may be used to form a femoral head arm of the implant cavity extending from the access formed in the greater trochanter centrally through the femoral neck and in some cases into the central femoral head. Generally, some part of the implant cavity traverses the fracture line. In one exemplary embodiment, the telescoping reamer includes a flexible driveshaft for driving a cutting instrument that is guided through a predetermined arc by a telescoping guide. A flexible reamer is utilized to further enlarge the implant cavity adjacent the access formed in the greater trochanter, forming the femoral shaft arm of the implant cavity. The flexible reamer includes a flexible head driven by a flexible shaft which is guided by a swivel shaft which flexes up or down through only a single plane. In one exemplary embodiment, the flexible head may be formed to glance off the cortical wall while cutting cancellous bone, thereby removing as much soft bone as practical in the femoral shaft to provide a solid anchor for the implant in the hard cortical bone.

After exposing the greater trochanter, and preparing the femoral cavity, a femoral implant in accordance with the present invention is inserted into the aforementioned cavity in the femur. The femoral implant is thereafter secured in the femur, with portions of the implant extending into and being secured within the femoral neck or the femoral neck and head, and other portions of the implant extending into and being secured within the femoral shaft. To allow for sliding compression, in one embodiment the portion of the implant extending into the femoral head is slidable relative to the portion of the implant extending into the femoral shaft.

In one exemplary embodiment, the femoral implant of the present invention includes a sealed bag having a fill port with, in one embodiment, an implant tube positioned therein which provides access to the bag interior so that the implant bag can be filled with material, e.g., bone cement after implantation of the femoral implant within the cavity formed in the femur. The femoral implant of the present invention further includes a lag tube, placed within the bag of the femoral implant. In one embodiment, the implant tube of the femoral implant passes through two openings formed in the bag and each opening is tightly secured to the exterior of the implant tube to prevent material injected into the bag from escaping the bag at any point at which the bag contacts the implant tube. The implant tube is hollow and accommodates the lag tube therein and a lag or other fixation device to be advanced into and secured to the femoral head or neck, distally of the fracture. One embodiment of the inventive lag includes radially outwardly expanding fingers at a distal end for securing the lag in the femoral head or neck.

The bag of the femoral implant of the present invention can be, e.g., formed of various films and fabrics. In one exemplary embodiment the bag of the femoral implant of the present invention is formed from a biocompatible acrylic material, e.g., a woven acrylic material. Because bone cement is an acrylic, if the implant bag is formed of an acrylic material, the bag and the bone cement will achieve an intimate chemical bond.

The bag of the femoral implant of the present invention generally comprises a containment device and can be constructed of various materials including films such as, e.g., fiber or fabric reinforced films, or fabrics created by processes such as weaving, knitting, braiding, electrospinning, or hydrospinning. Alternative materials contemplated for the implant bag include various polymers including, e.g., polymethylmethacrylate (PMMA), polycarbonate, ultra-high molecular weight polyethylene (UHMWPE), low density polyethylene (LDPE), high density polyethylene (HDPE), polyamides, polypropylene, polyester, polyaryletherketone, polysulfone, or polyurethane. Further alternative materials contemplated for the implant bag include fabrics constructed of fibers formed of glass, ceramics, surgical grade stainless steel (e.g., 316L), titanium, or titanium alloys. Moreover, implant bag materials may be coated with, e.g., calcium phosphate, or a bioactive glass coating. Furthermore, the implant bag and filler may be utilized as a delivery mechanism for, e.g., drugs, or growth factors.

In a further embodiment of the present invention, the bag structure of the implant of the present invention comprises a nested bag structure in which an inner bag is filled with a high strength material relative to the material of an outer bag in which the inner bag is placed. The outer bag of this form of the present invention is formed from and filled with a more bioresorbable material relative to the material of construction and fill material of the inner bag.

The femoral implant of the present invention is, in one exemplary embodiment, inserted through an access aperture formed in the greater trochanter and placed within the femoral cavity described hereinabove. The lag or other fixation device is thereafter advanced through the lag tube and into the cavity formed in the femoral head, and is then secured to the femoral head, for example, by radially outwardly expandable fingers which secure the lag relative to the femoral head and/or neck. A lag actuator, for example, a tensioning device that tensions a cable releasably secured to the distal end of the lag, may be utilized to expand the fingers outwardly into the bone tissue after the lag is properly positioned.

A delivery device such as, e.g., a fill tube is utilized to fill the femoral implant with, e.g., bone cement to fill the femoral cavity and provide intramedullary fixation and stabilization of the lag. In an alternative embodiment of the present invention, bone cement is utilized in lieu of or in addition to the lag fingers to secure a lag shaft of an implant of the present invention to the femur. In a further alternative embodiment, the lag of the present invention includes an external thread at the distal end for securing the lag to the femur.

Several different guides and reamers may be utilized in accordance with the present invention to locate the position and orientation of, and to ream, the femoral cavity described above. These novel guides and reamers will be described in detail in the detailed description portion of this document. Generally, the guides and reamers of the present invention are designed to locate and form a femoral cavity extending from the greater trochanter proximally through the femoral neck and into the femoral head as well as from the greater trochanter distally into the intramedullary canal, with the femoral cavity having exposed access thereto only at the lateral surface of the greater trochanter.

The method and apparatus of the current invention advantageously allow for the treatment of a femoral hip fracture in a minimally invasive procedure which potentially hastens patient recovery.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 4 is an elevational view illustrating the use of an alignment device of the present invention to properly select the appropriate guide tube/retractor of the present invention;

FIG. 5 is an elevational view illustrating the alignment guide of FIG. 4 properly aligned from the greater trochanter along the femoral neck to the femoral head;

FIG. 6 is a sectional view of a femur illustrating a straight reamer utilized to begin making the femoral cavity of the present invention;

FIG. 7 is a sectional view illustrating the use of a swivel reamer in accordance with the present invention to further form the femoral cavity;

FIG. 15 is a perspective view of a guide plate in accordance with the present invention;

FIGS. 16, 17, and 18 are, respectively, top, side, and bottom elevational views thereof;

FIG. 19 is a sectional view of an insertion member of the present invention with the guide plate illustrated in FIGS. 15-18 affixed thereto;

FIG. 20 is a perspective view of an insertion member which is utilized to operably position a guide plate, e.g., the guide plate illustrated in FIGS. 15-18 atop the greater trochanter as illustrated in FIG. 2;

FIG. 21 is a partial elevational view illustrating deactuation of the latch utilized to temporarily fix the guide plate to the insertion member;

FIG. 22 is a side elevational view of the insertion member illustrated, e.g., in FIG. 20;

FIG. 23 is a perspective view of a guide tube/retractor of the present invention;

FIG. 24 is a radial elevational view thereof;

FIG. 25 is a further radial elevational view thereof, rotated approximately 90 degrees with respect to the radial elevational view of FIG. 24;

FIG. 26 is a proximal axial view thereof;

FIG. 27 is a distal axial view thereof;

FIG. 28 is a radial elevational view of an angled guide tube/retractor of the present invention;

FIG. 41 is an elevational view of a femoral implant of the present invention;

FIG. 42 is an exploded view of a lag screw of the present invention;

FIG. 43 is a sectional view of the femoral implant of the present invention taken along line 43-43 of FIG. 41;

FIG. 46 is a perspective view of a combination reamer in accordance with the present invention;

FIG. 47 is a sectional view thereof illustrating actuation of the swivel/plunge reaming selector into the plunge reaming position;

FIG. 48 is a sectional view thereof with the swivel/plunge reaming selector moved into position for swivel reaming;

FIG. 49 is a partial sectional view of the combination reamer of the present invention;

FIG. 50 is a perspective view of an alternative embodiment guide plate in accordance with the present invention;

FIGS. 51-54 are top, end, side, and bottom elevational views thereof, respectively;

FIG. 55 is a sectional view thereof taken along line 55-55 of FIG. 53;

FIG. 56 is a perspective view of an alternative embodiment guide tube/retractor of the present invention;

FIG. 57 is a radial elevational view thereof;

FIG. 58 is a radial elevational view of an alternative embodiment angled guide tube/retractor of the present invention;

FIG. 59 is a distal axial elevational view of the guide tube/retractor illustrated in FIG. 57;

FIG. 60 is a partial sectional view of the guide tube/retractor illustrated in FIG. 57 taken along line 60-60 thereof;

FIG. 71 is an exploded view of a flexible reamer guide in accordance with the present invention;

FIG. 72 is a sectional view thereof;

FIG. 73 is a sectional view illustrating the flexible reamer guide of FIGS. 71 and 72 operably positioned within a patient's femur to guide a flexible reamer into the femoral head;

FIG. 74 is a sectional view illustrating a flexible reamer positioned over a flexible reamer guide wire for reaming into the femoral head;

FIG. 75 is a perspective view of a flexible reamer in accordance with the present invention;

FIG. 76 is a sectional view thereof;

FIG. 78 is an elevational view thereof;

FIG. 79 is a sectional view thereof;

FIG. 80 is an axial elevational view of the distal end of a fixation screw placement instrument in accordance with the present invention;

FIG. 81 is a perspective view of the fixation screw placement instrument partially illustrated in FIG. 80;

FIG. 82 is a perspective view of a plunge reamer utilized to prepare the greater trochanter to receive the fixation screw illustrated in FIG. 61-64;

FIG. 83 is a perspective view of an alternative embodiment insertion member for inserting a guide plate of the present invention;

FIG. 84 is a partial sectional view thereof illustrating the release bars thereof actuated to effect release of the guide plate from locking engagement with the insertion member;

FIG. 85 is a partial sectional view illustrating the release bars of the insertion member illustrated in FIG. 83 positioned whereby the guide plate can be temporarily fixed to the insertion member;

FIG. 86 is an elevational view of the insertion member illustrated in FIG. 83;

FIG. 87 is a perspective view of a spring lock release instrument in accordance with the present invention;

FIG. 88 is a partial sectional view of the distal end thereof, illustrating the release pins in an unactuated position;

FIG. 89 is a sectional view of the spring lock release instrument of FIG. 87 actuated to force release pins 346 to protrude therefrom;

FIG. 93 is a partial elevational view of a femur illustrating insertion of a guide wire to guide reaming from the greater trochanter into the femoral head;

FIG. 94 is a partial elevational view of a femur illustrating use of a flexible reamer having two reaming diameters to ream a passage from the greater trochanter into the femoral head;

FIG. 95 is a partial radial elevational view of a flex up reamer for reaming a passage from the greater trochanter into the femoral head;

FIG. 96 is a distal axial elevational view thereof;

FIG. 97 is a radial elevational view of a telescoping reamer of the present invention illustrating extension of a reaming head therefrom;

FIG. 98 is a radial elevational view of the telescoping reamer of FIG. 97 shown in its retracted position;

FIG. 104 is a sectional view of the tool housing of the swivel/down reamer assembly depicted in FIGS. 100-102;

FIG. 105 is a radial elevational view of a flexible guide shaft of the swivel/down reamer assembly depicted in FIGS. 100-102;

FIG. 106 is an axial elevational view thereof;

FIG. 107 is a perspective view of a unitube retractor of the present invention with the ball detent retaining mechanism thereof illustrated in position to retain an instrument within the unitube retractor;

FIG. 110 is a sectional view of a plunger forming a part of the ball detent retaining mechanism depicted with the unitube retractor of FIGS. 107-109;

FIG. 111 is an exploded perspective view of an alternative embodiment unitube retractor in accordance with the present invention;

FIG. 112 is a sectional view of the lock ring of the unitube retractor depicted in FIG. 111;

FIG. 113 is a radial elevational view of the unitube retractor illustrated in FIG. 111 shown in unactuated position;

FIG. 114 is a radial elevational view illustrating the unitube retractor of FIGS. 111 and 113 in actuated position, with the fingers of the lock ring thereof radially expanded to lock the unitube retractor to the femur through the access formed therein;

FIG. 115 is a partial radial elevational view thereof;

FIG. 116 is a radial elevational view of an alignment guide of the present invention having its pin cover moved to cover the distal bone gripping pins thereof;

FIG. 117 is a radial elevational view of the alignment guide of FIG. 116 rotated 90° with respect to the radial elevational view of FIG. 116 illustrating actuation thereof to move the pin cover into position whereby the distal bone gripping pins are no longer covered;

FIG. 118 is a radial elevational view of an alignment guide of the present invention illustrating the pin cover thereof retained in position to expose the distal bone gripping pins thereof;

FIG. 124 is an exploded perspective view of the flexible reamer of FIGS. 120-123;

FIG. 125 is an end elevational view of a flexible guide shaft in accordance with the present invention;

FIG. 126 is an elevational view of a lock plate for use in the flexible reamer illustrated in FIGS. 120-124;

FIG. 127 is a plan view of a main body housing used in construction of the flexible reamer illustrated in FIGS. 120-124;

FIG. 128 is a radial elevational view of a flexible guide shaft of the present invention in flexed position;

FIG. 129 is a radial elevational view thereof in the straight position;

FIG. 130 is a radial elevational view of an alternative embodiment flexible guide tube of the present invention;

FIG. 131 is a partial sectional view thereof;

FIG. 132 is an axial elevational view thereof;

FIG. 133 is a perspective view of an alternative embodiment implant of the present invention;

FIG. 134 is an exploded perspective view thereof;

FIG. 135 is a radial plan view of an injection/insertion tube of a femoral implant of the present invention;

Figure 11:
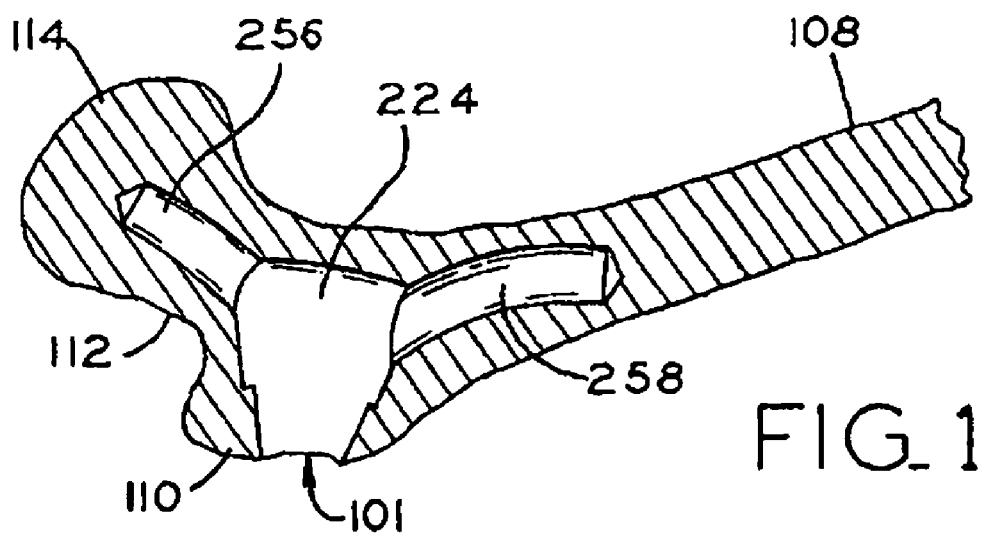
FIG. 11 is a sectional view illustrating a femoral cavity formed in accordance with the present invention.
Figure 133:
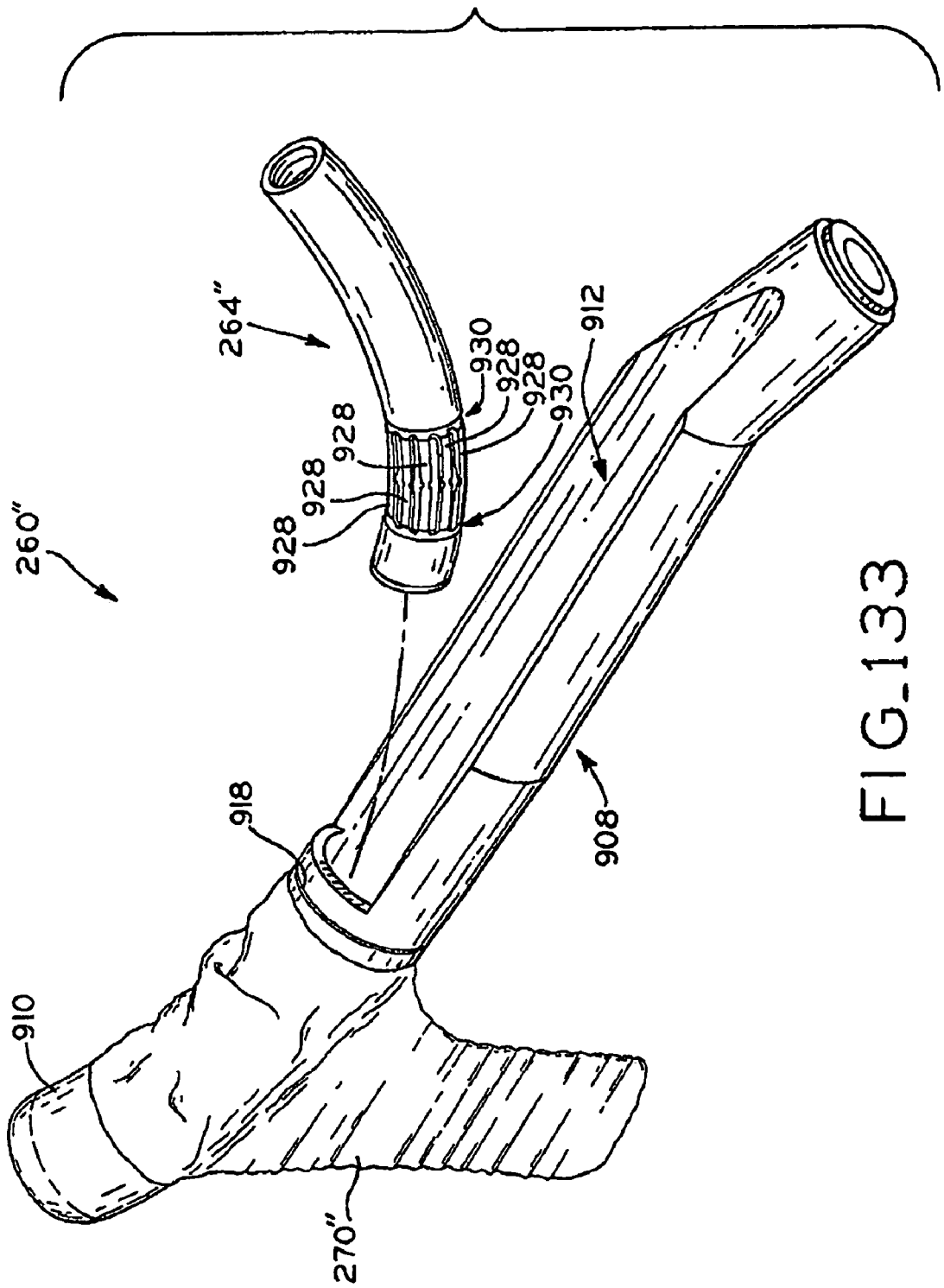
Figure 134:
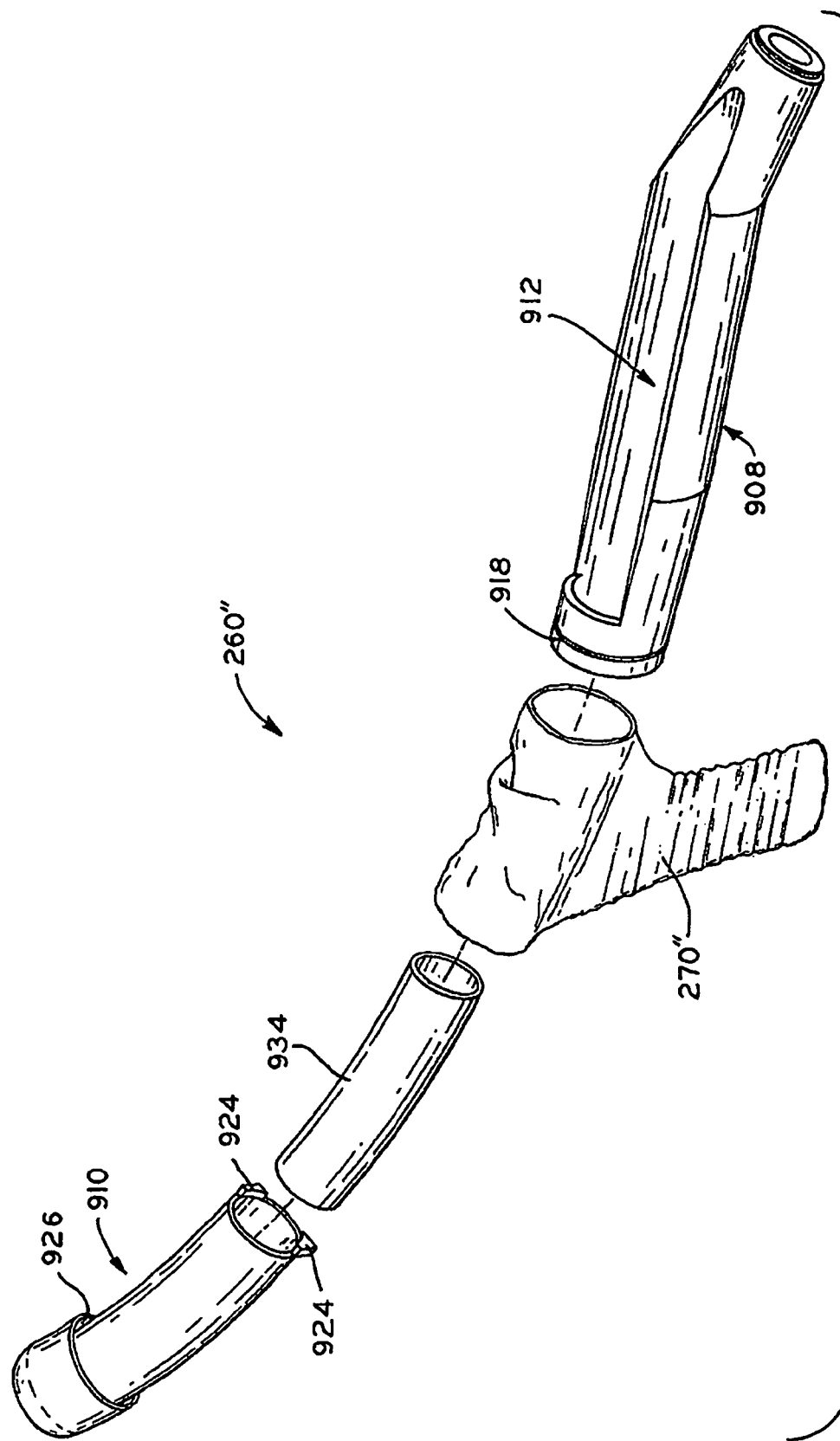
Figures 144, 145:
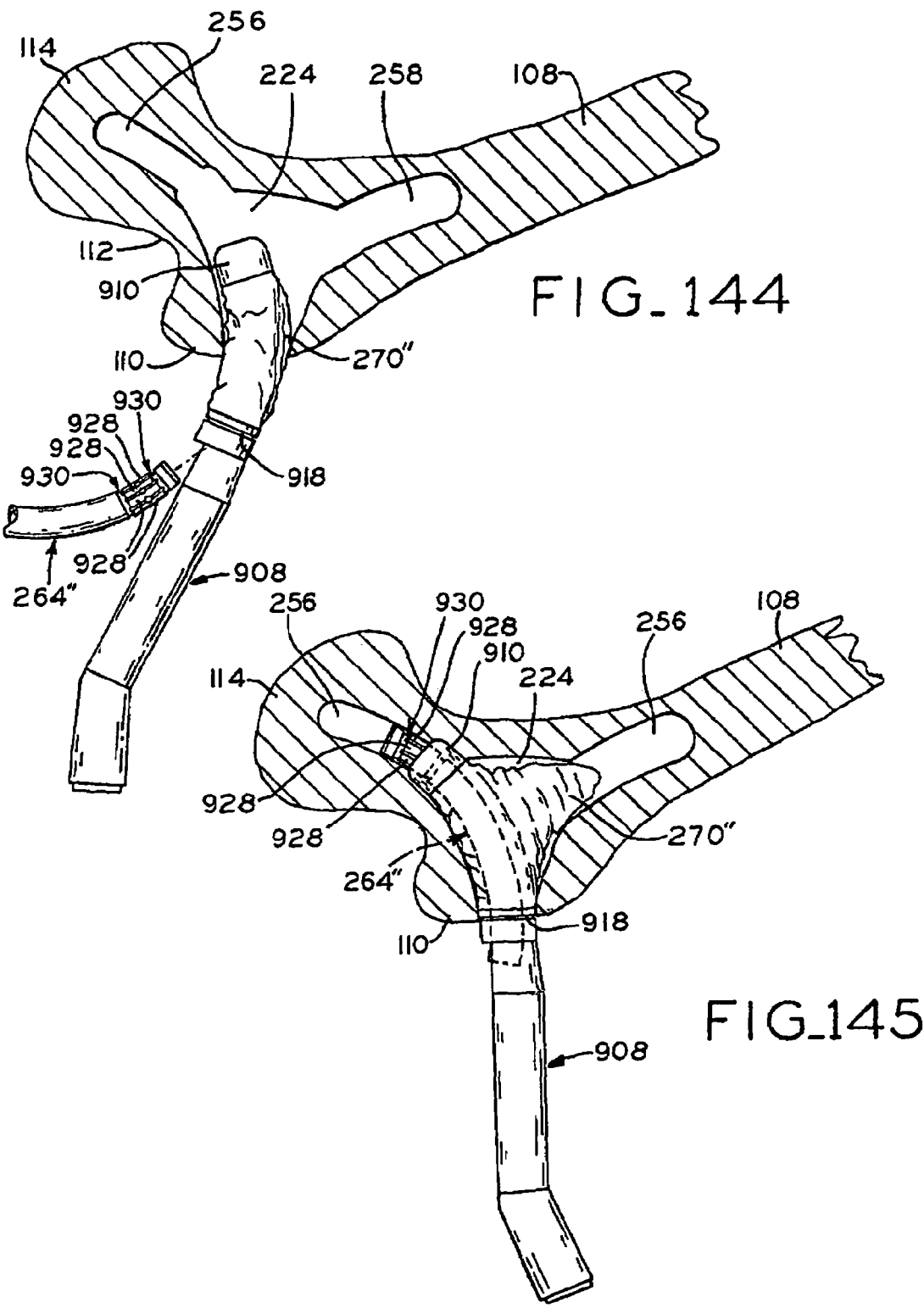
Figure 146:
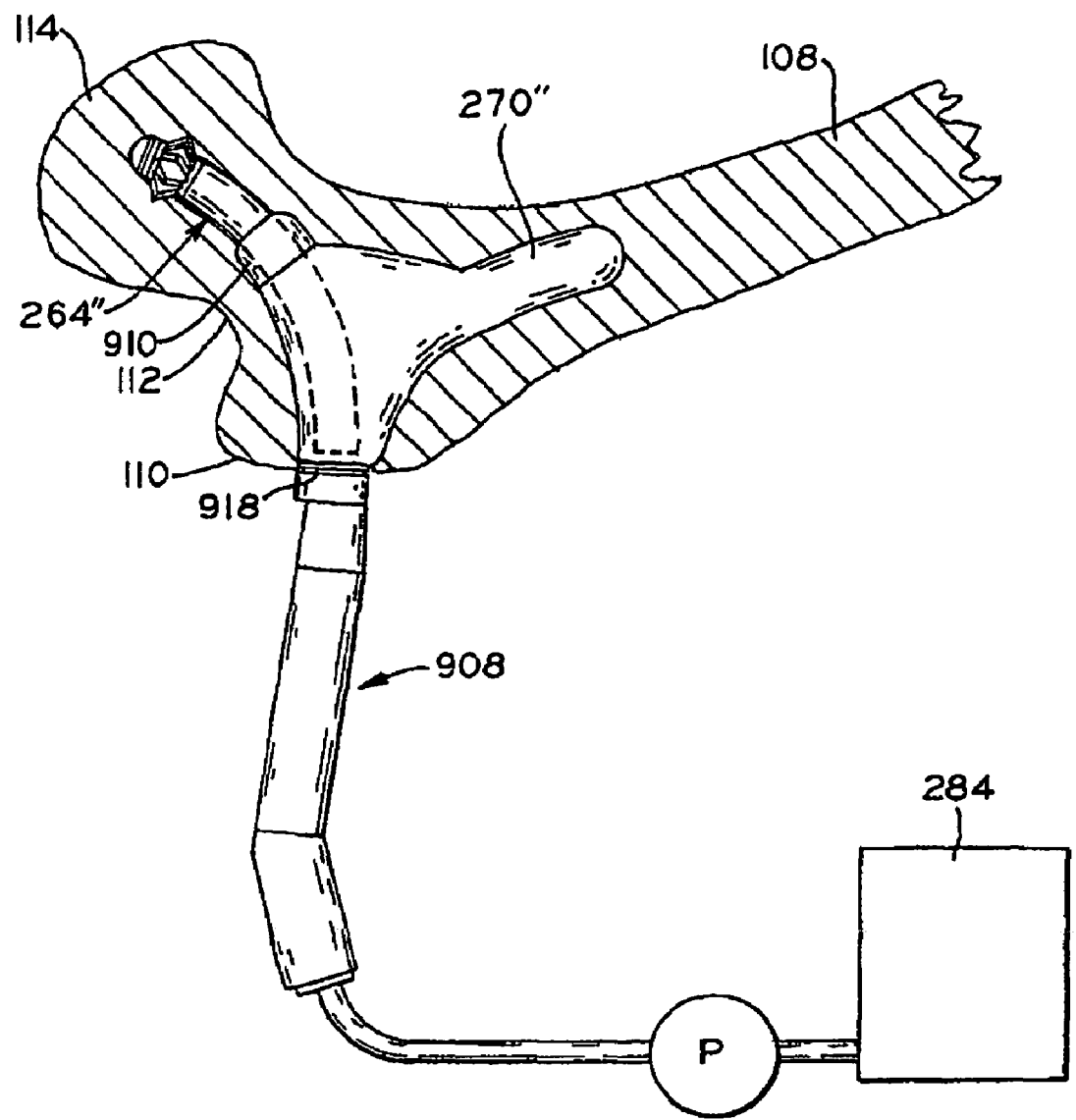
Figure 147:
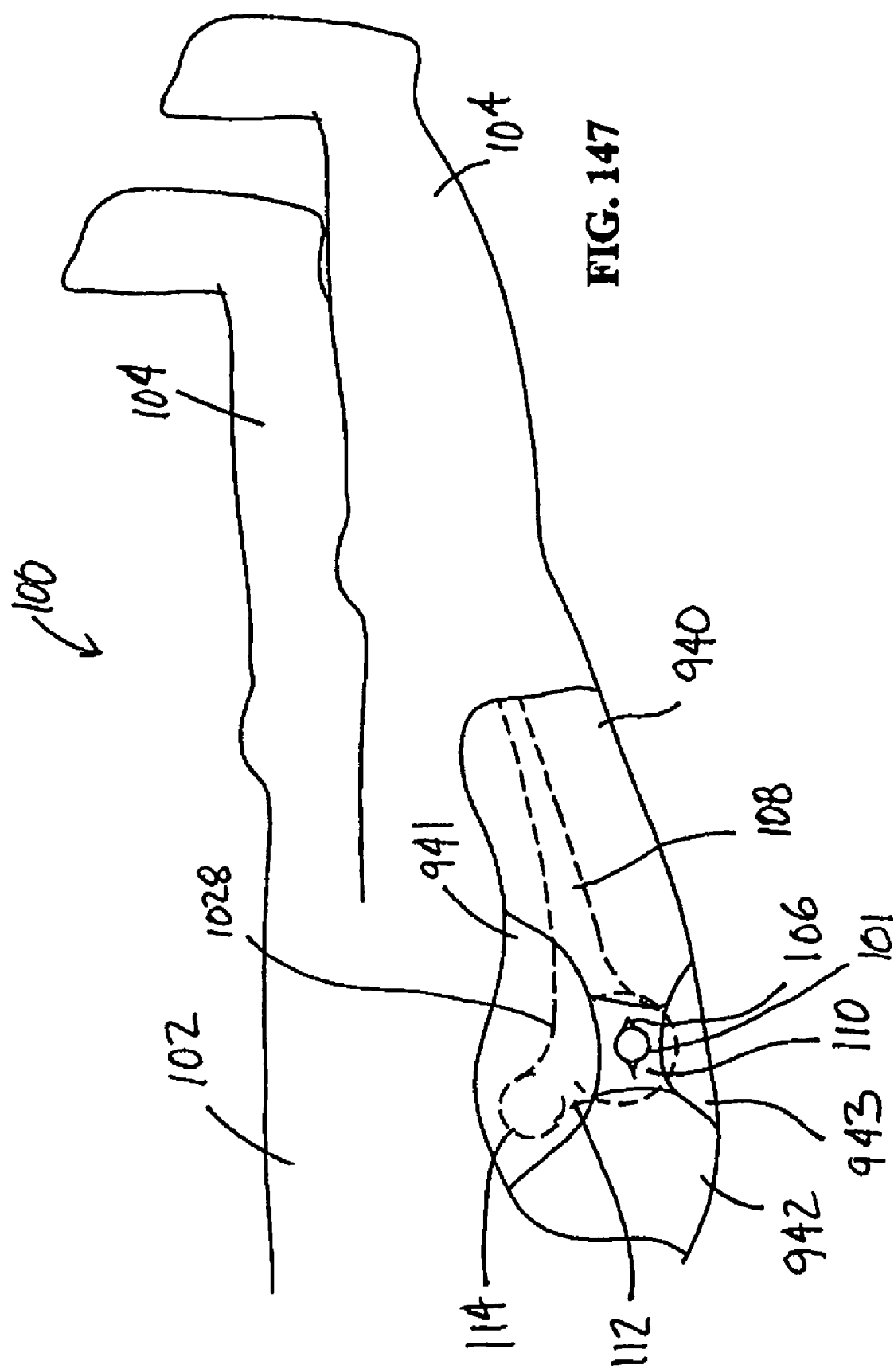
Figure 148:
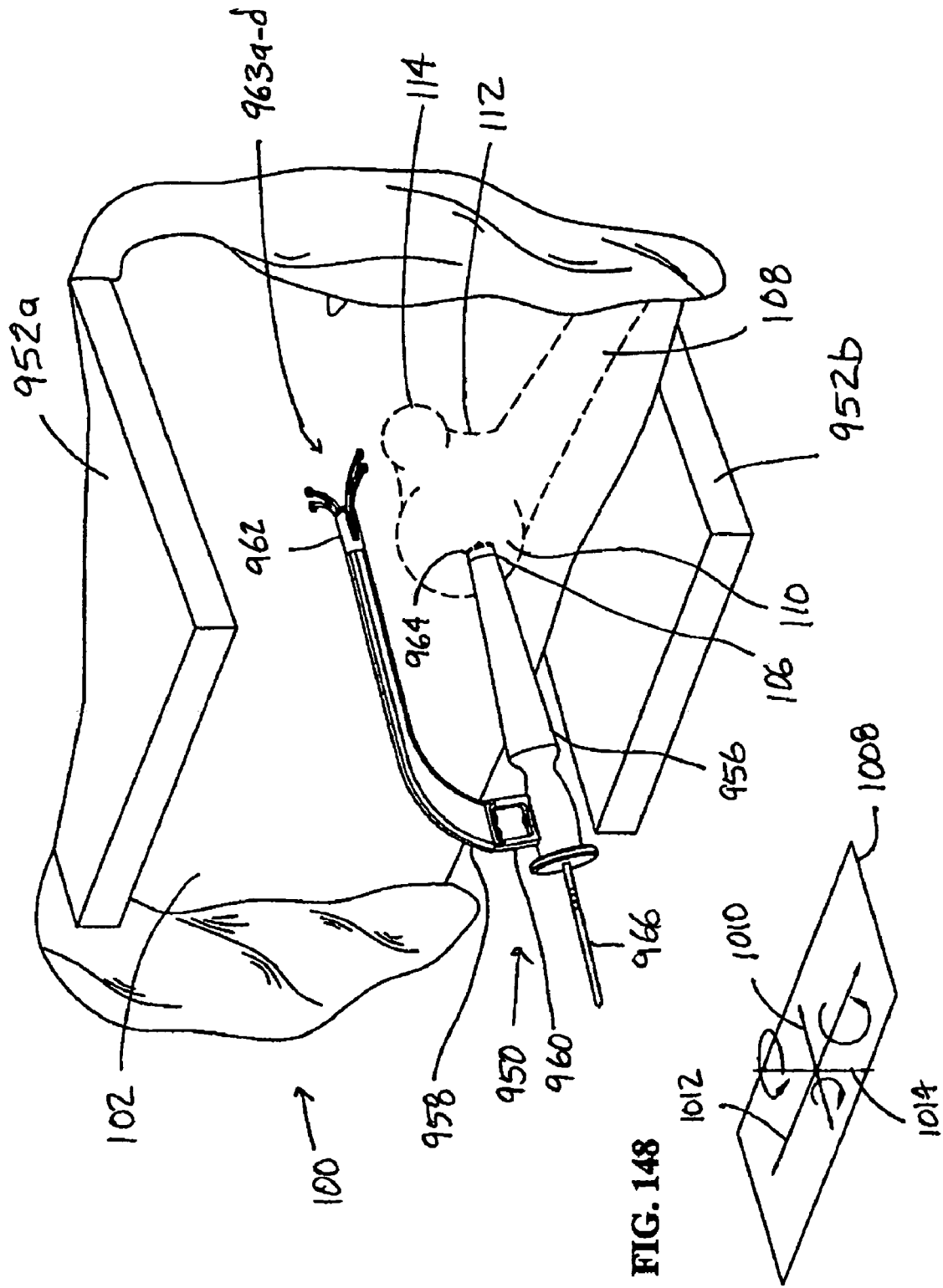
Figure 149:
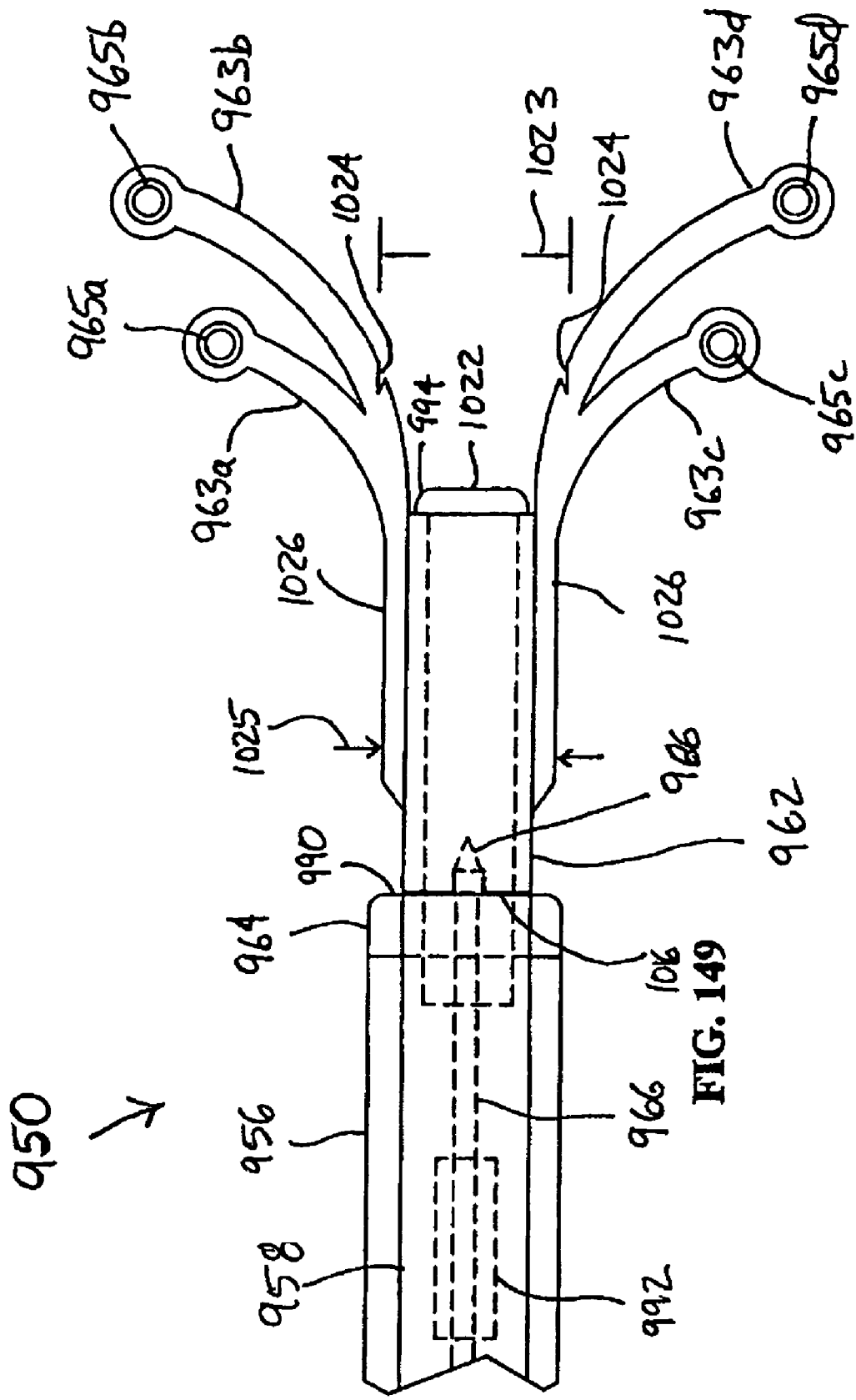
Figure 150:
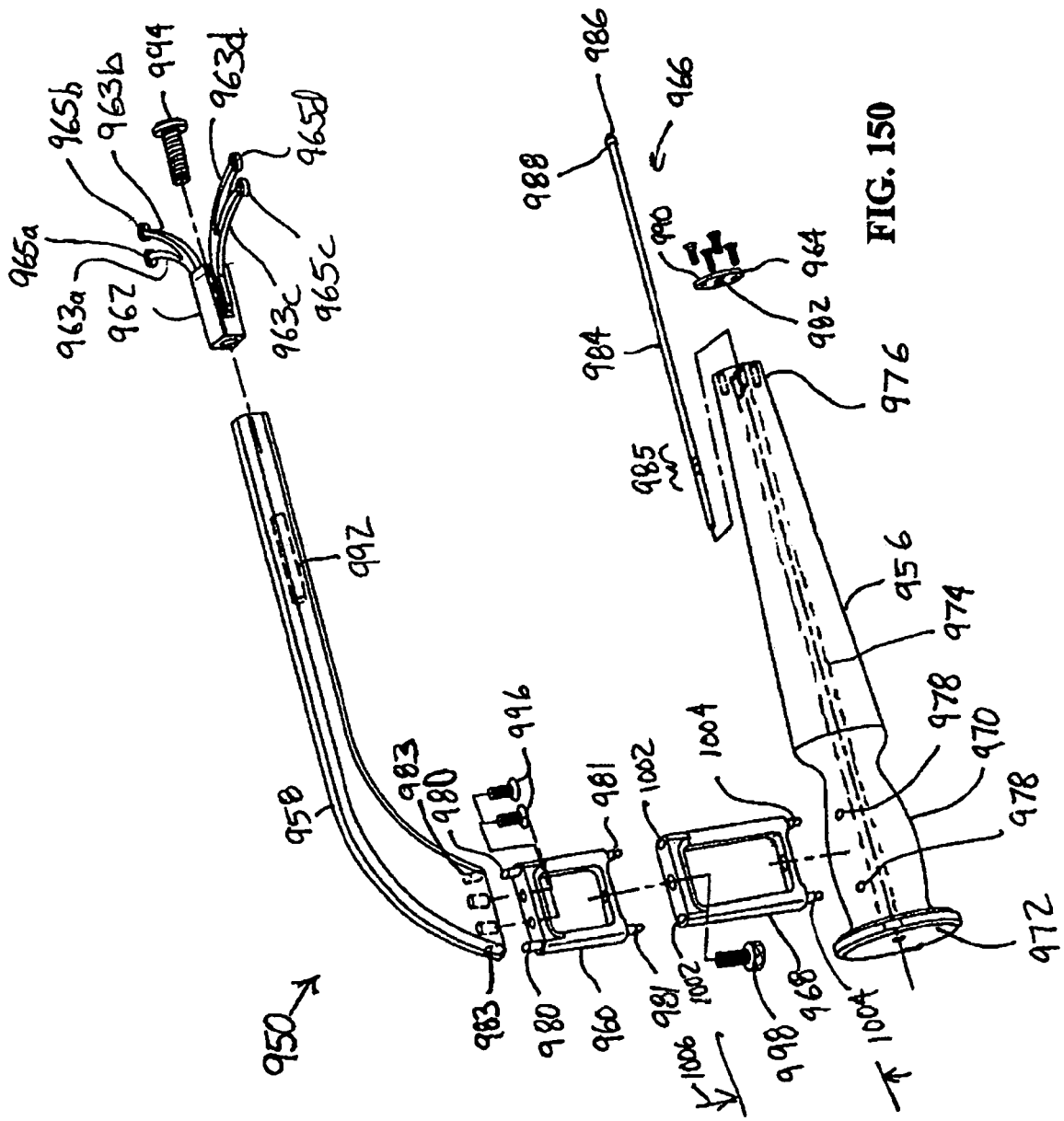
Figure 151A:
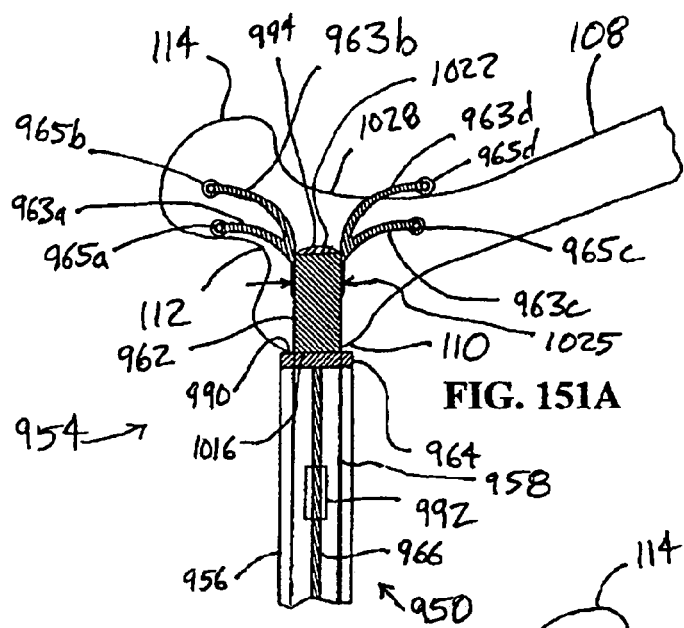
Figure 151B:
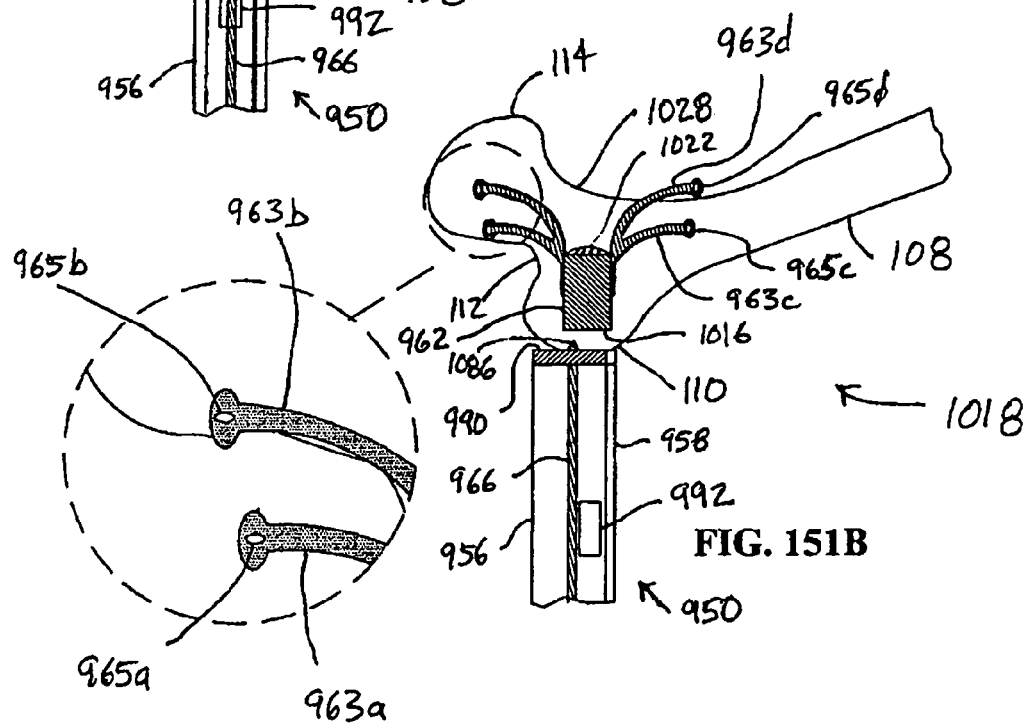
Figure 151C:
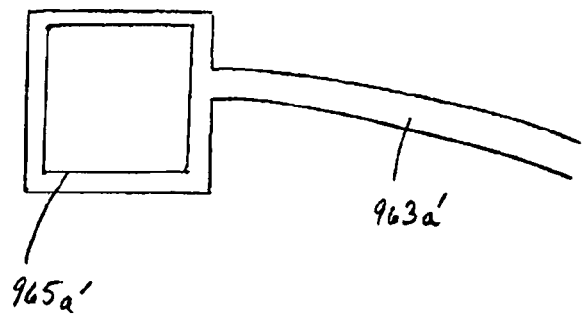
Figure 151D:
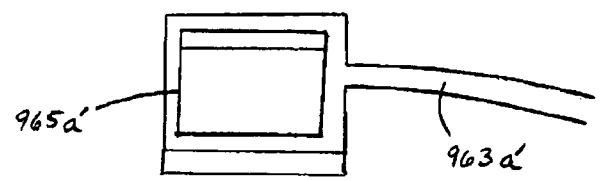
Figure 151E:
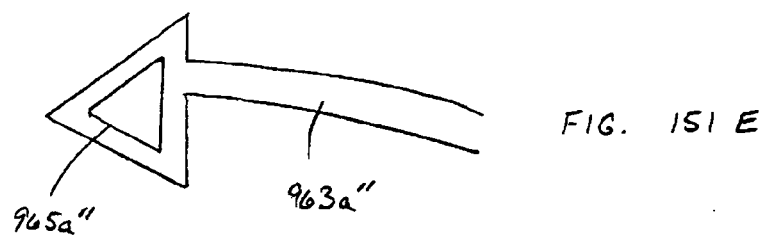
Figure 151F:
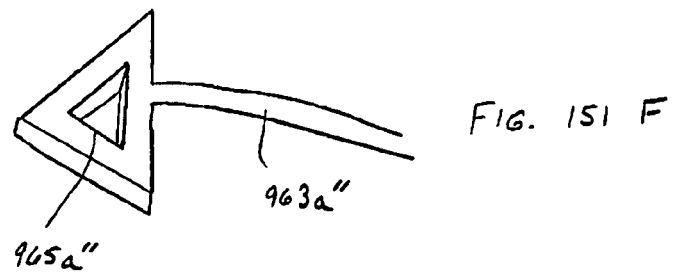
Figure 152:
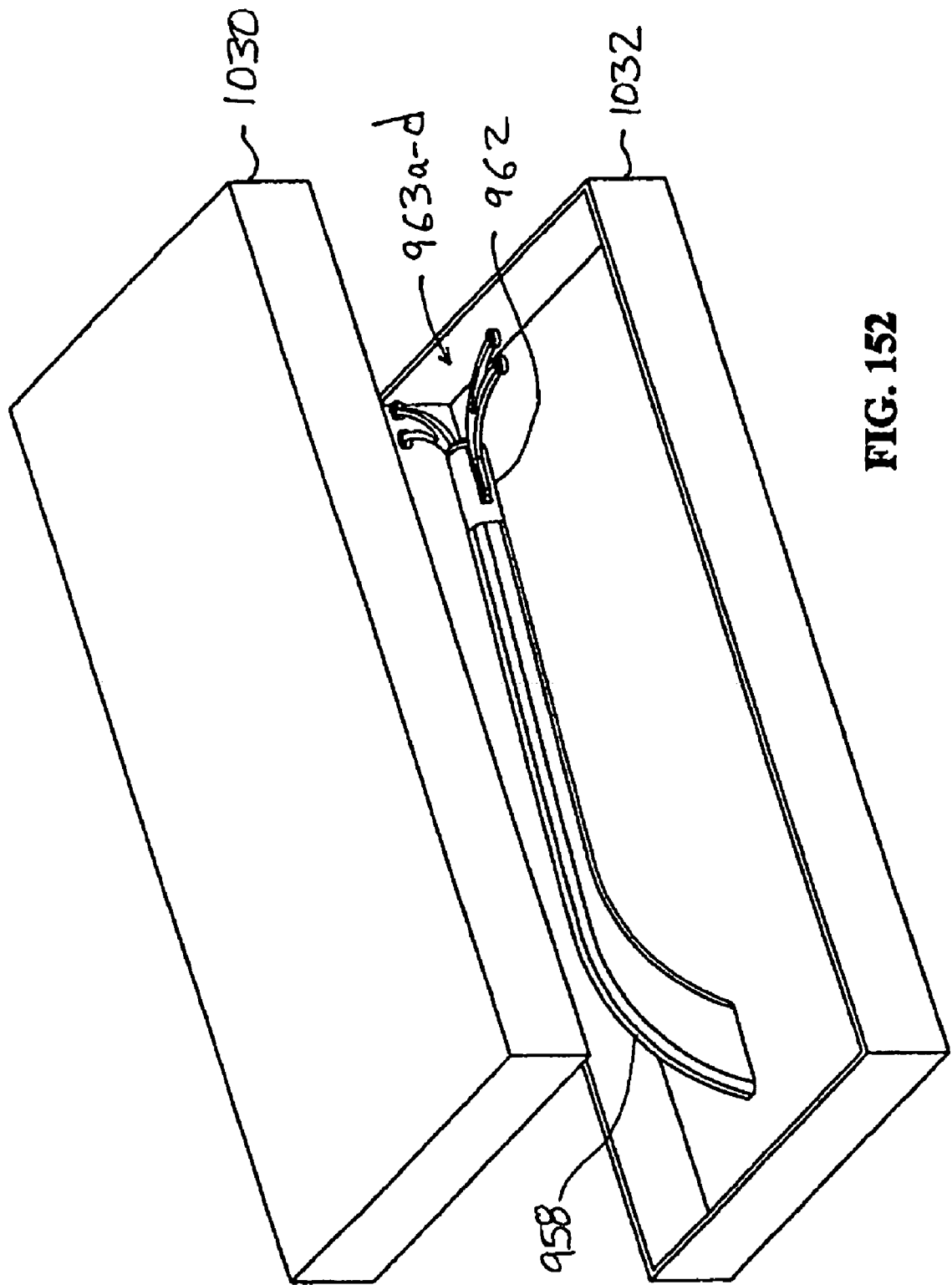
Figure 153:
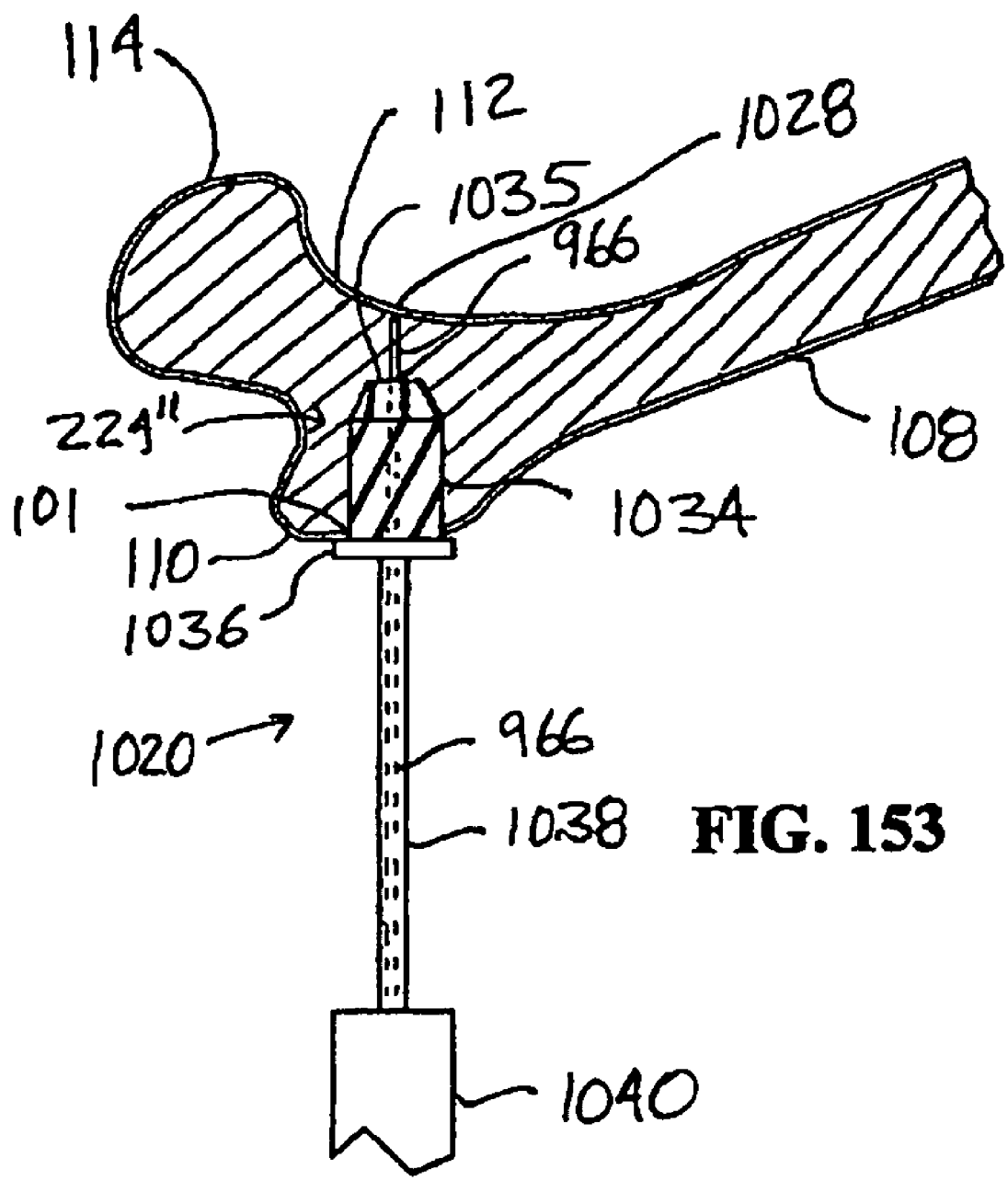
Figures 154, 155:
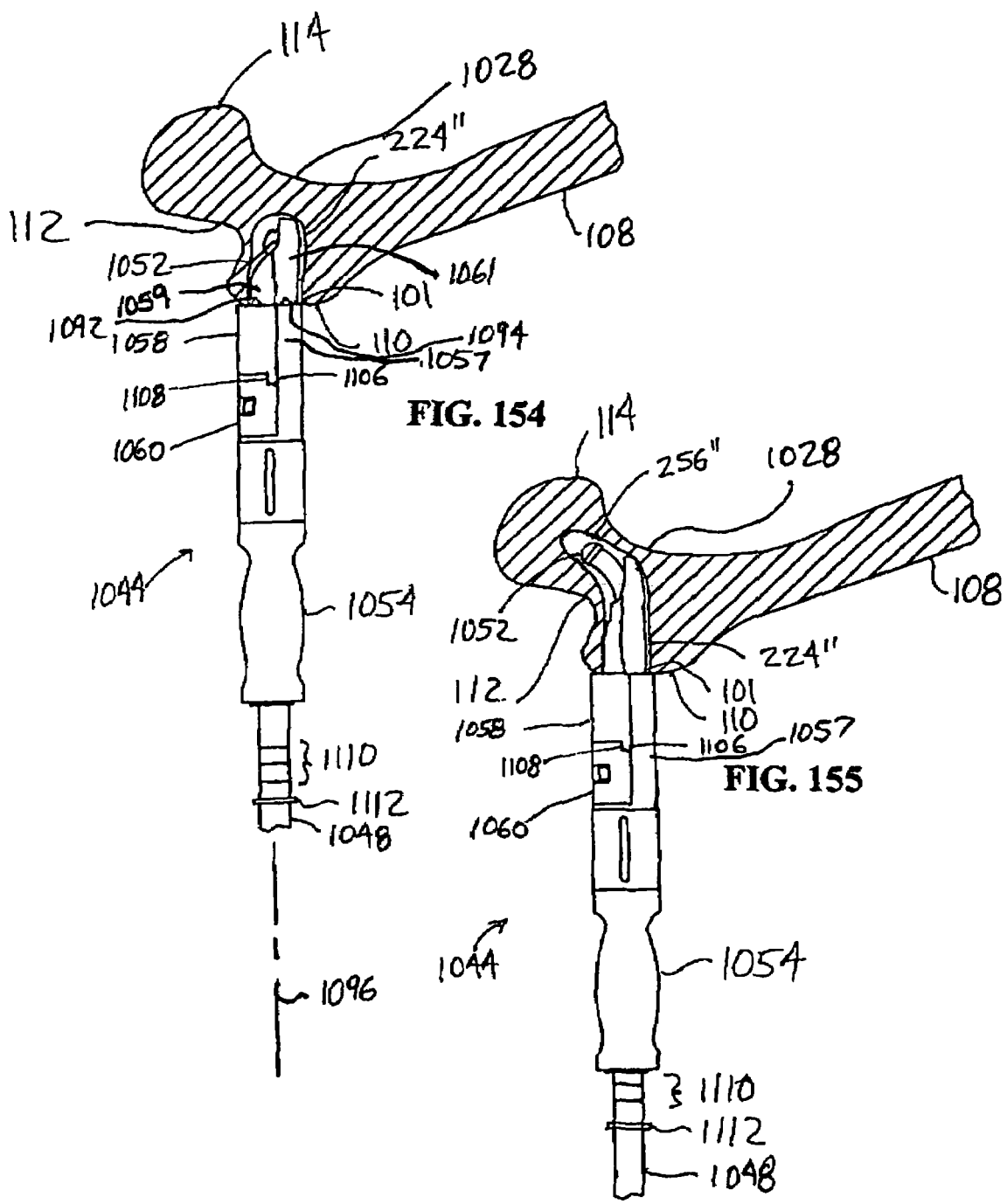
Figure 156C:
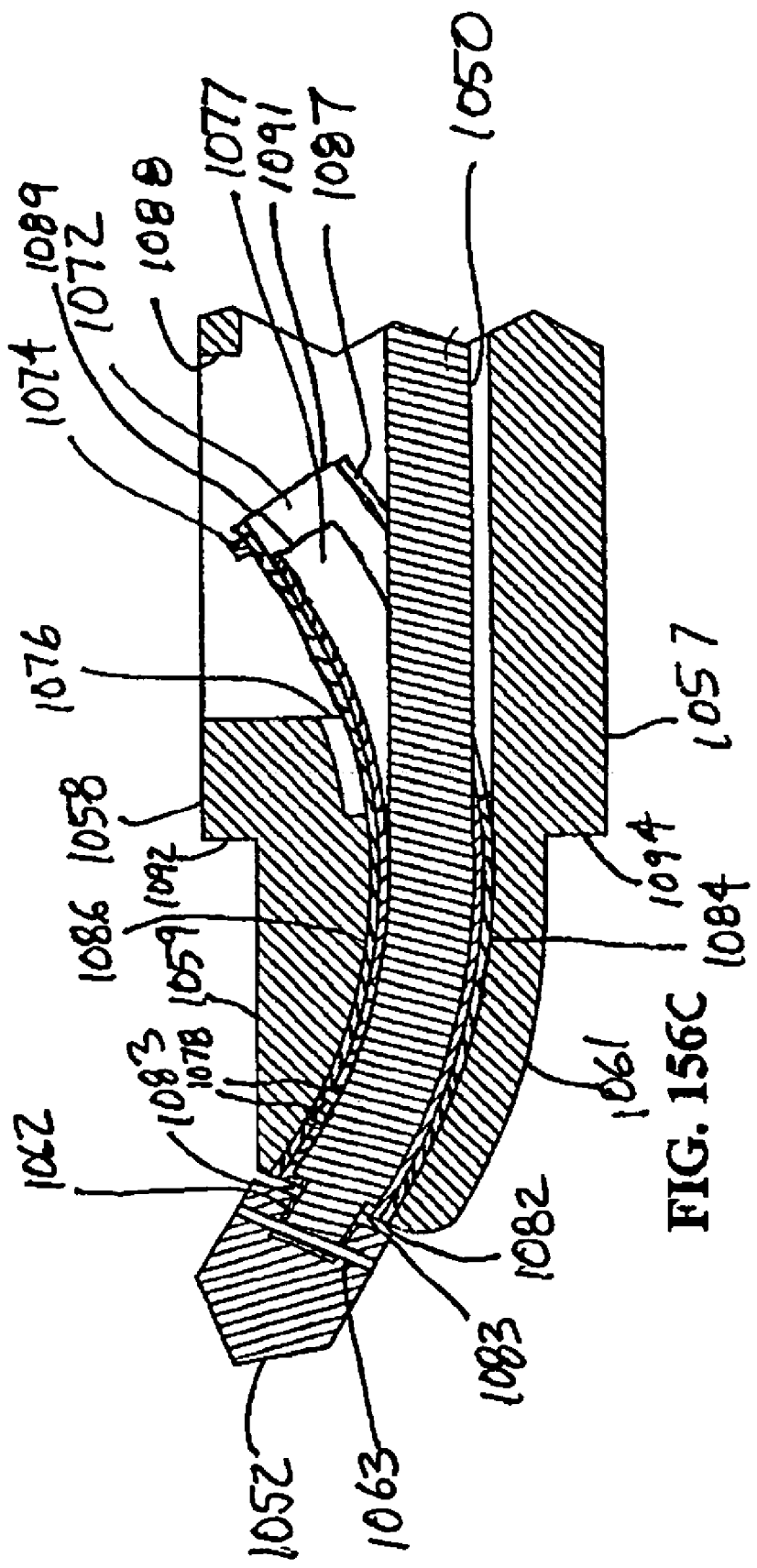
Figure 157:
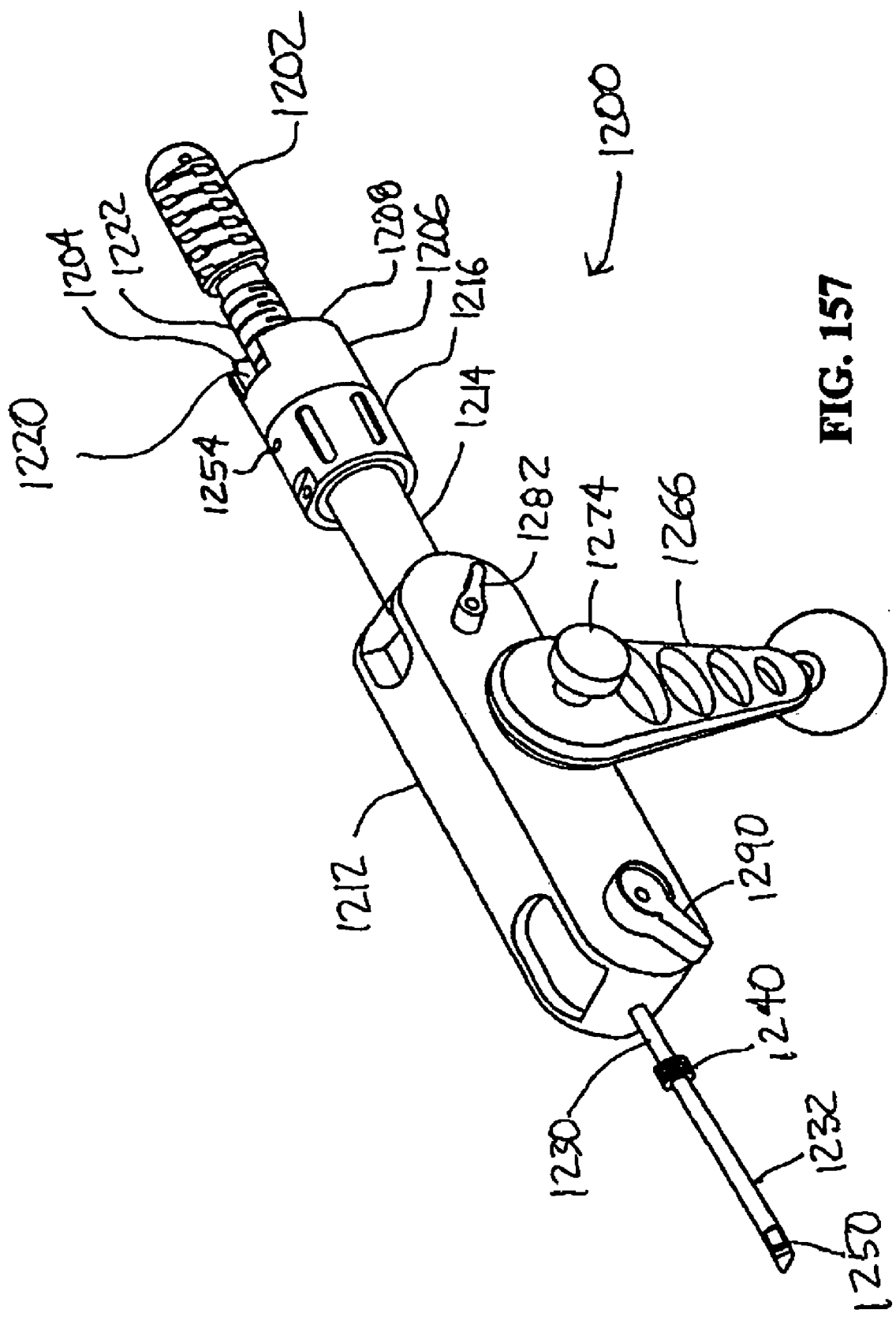
Figure 158:
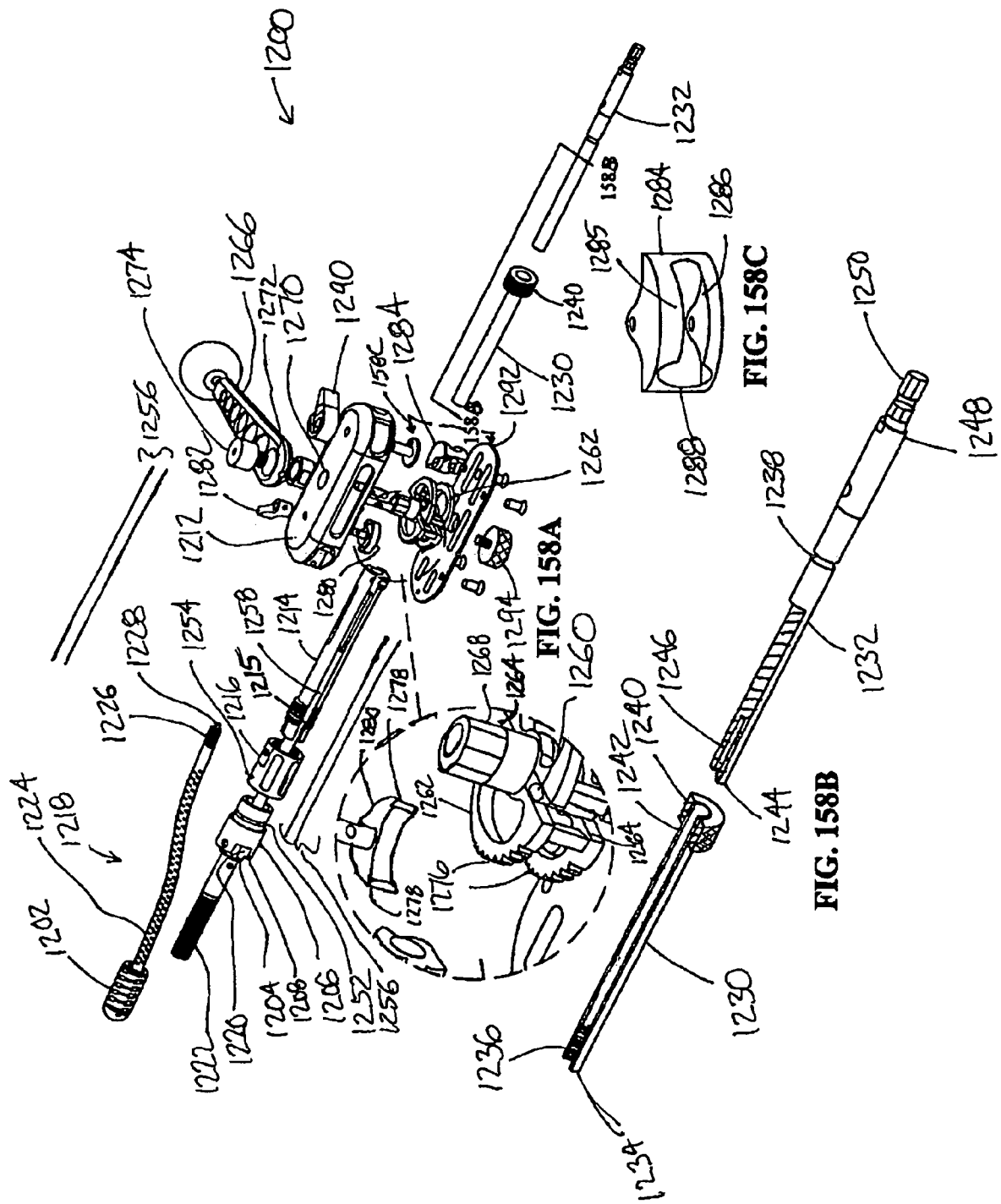
Figure 159:
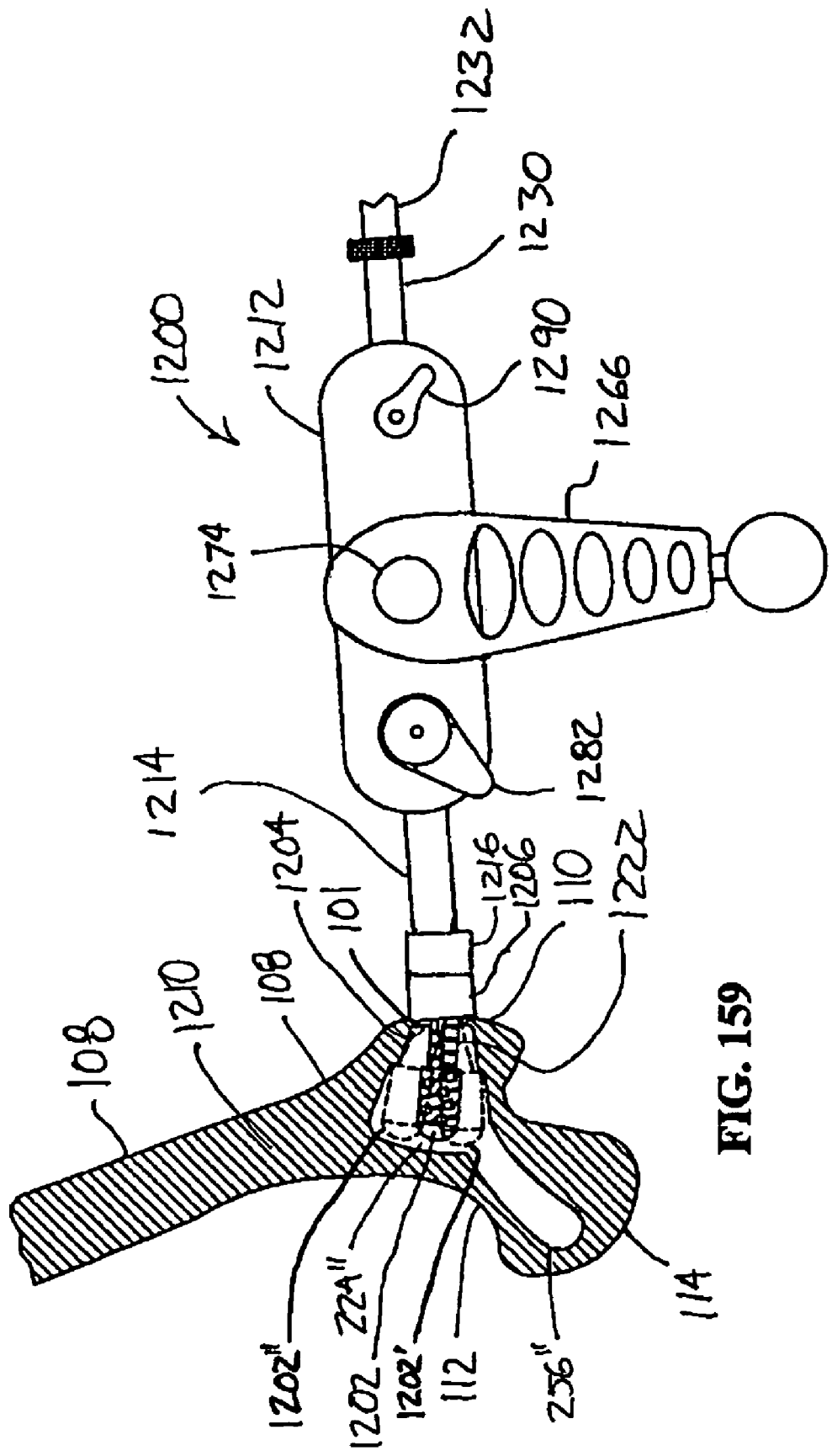
Figure 160:
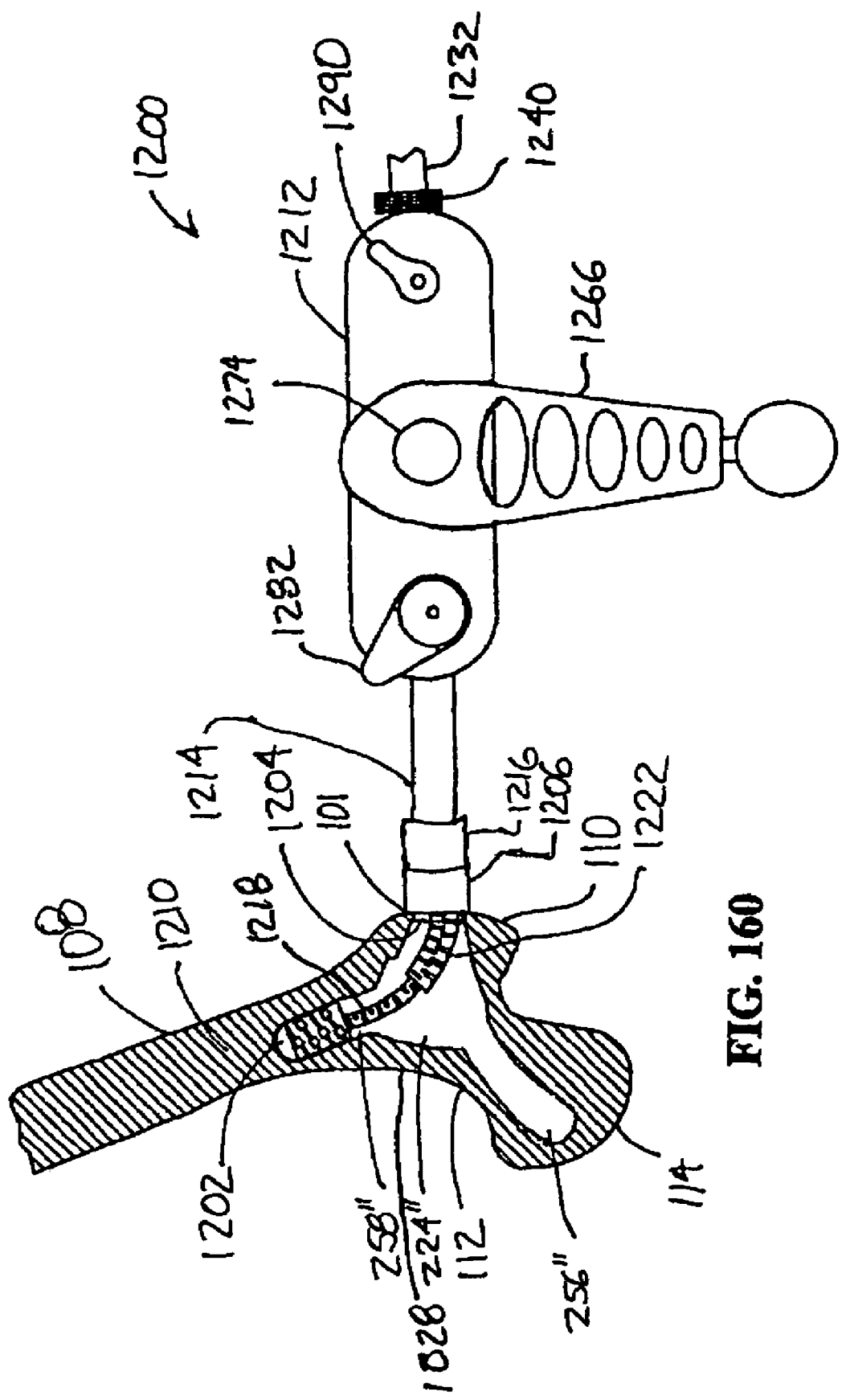
Figure 165:
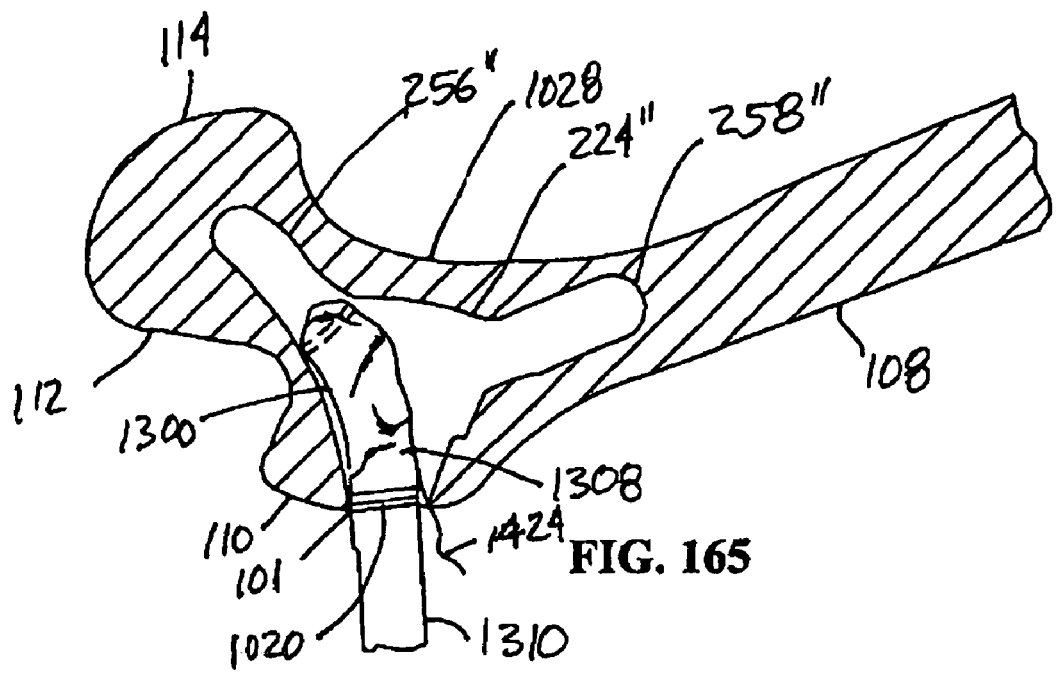
Figure 166:
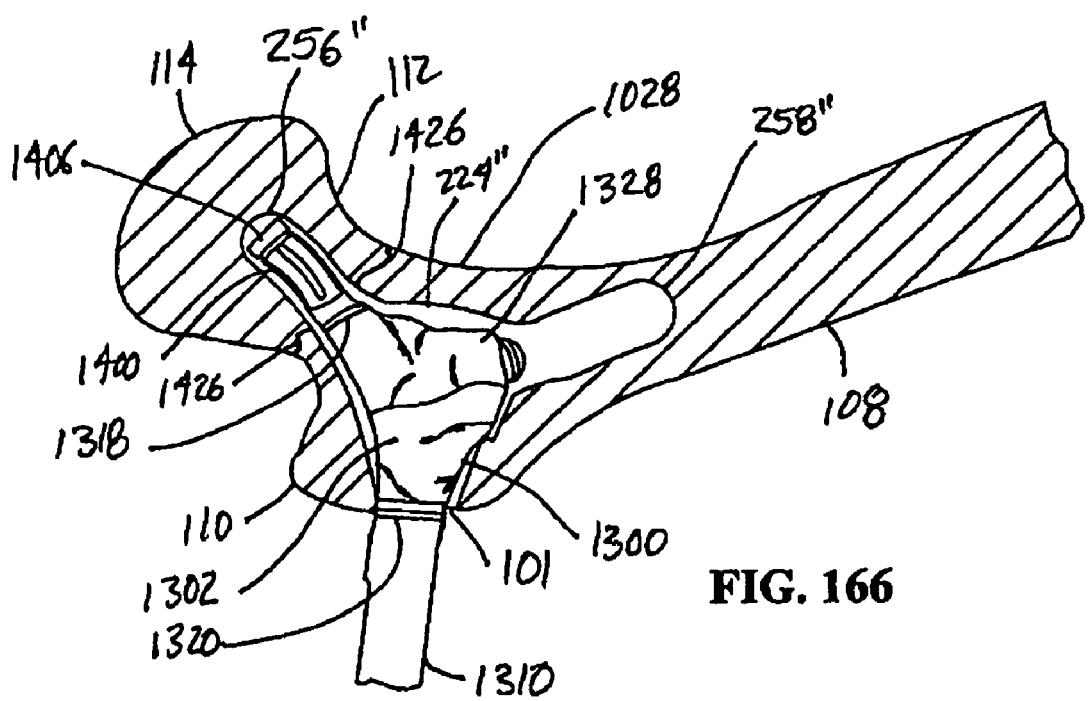
Figure 167:
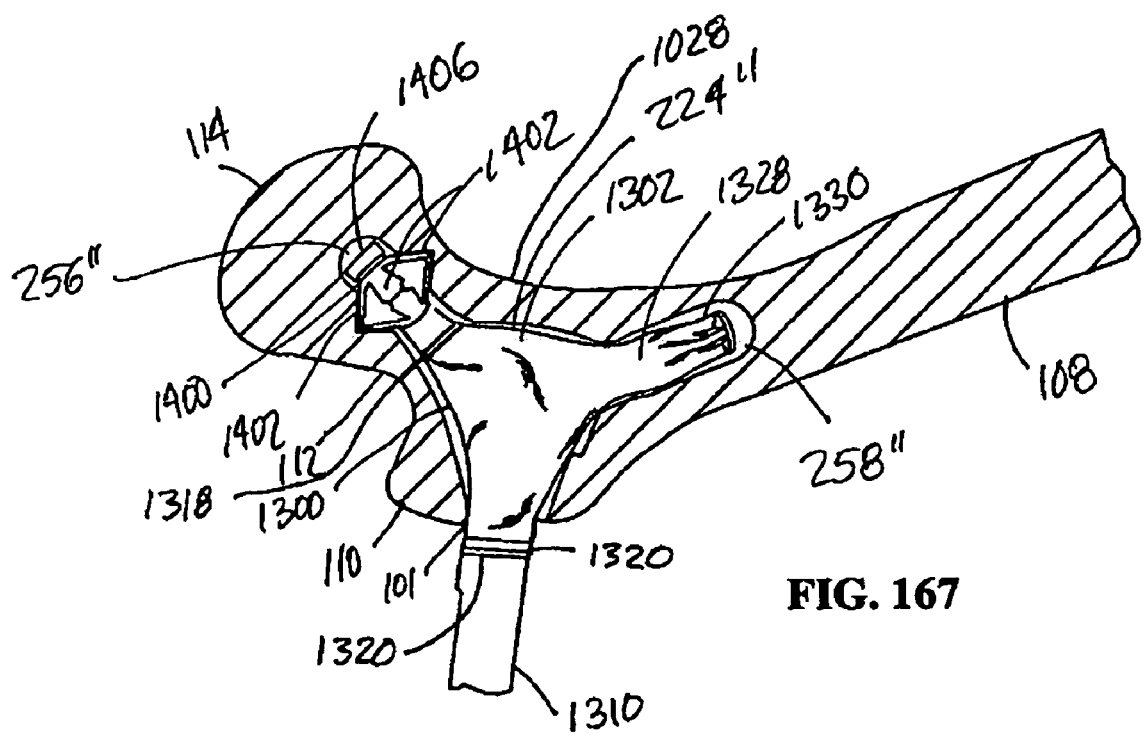
Figure 171:
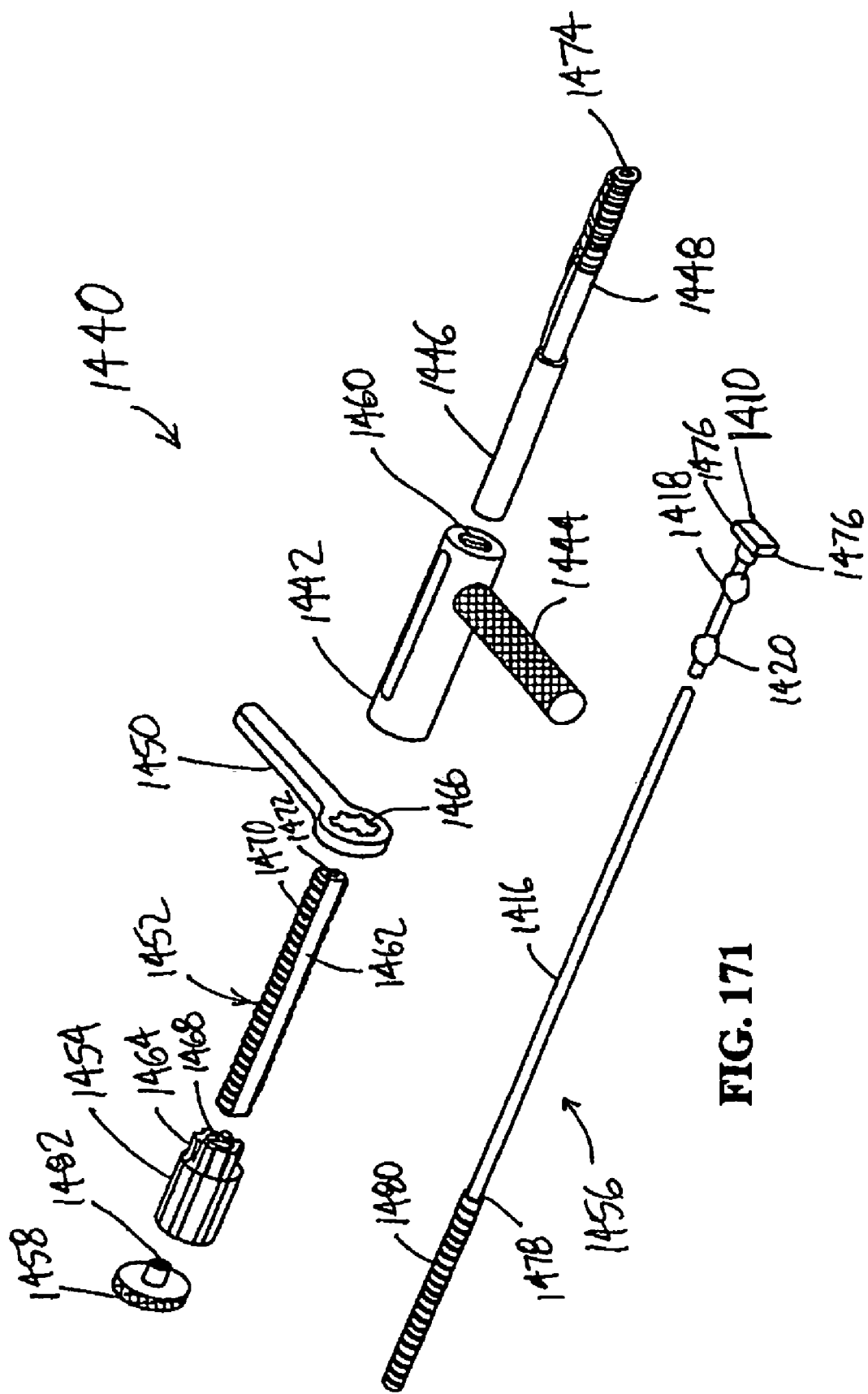
Figure 172:
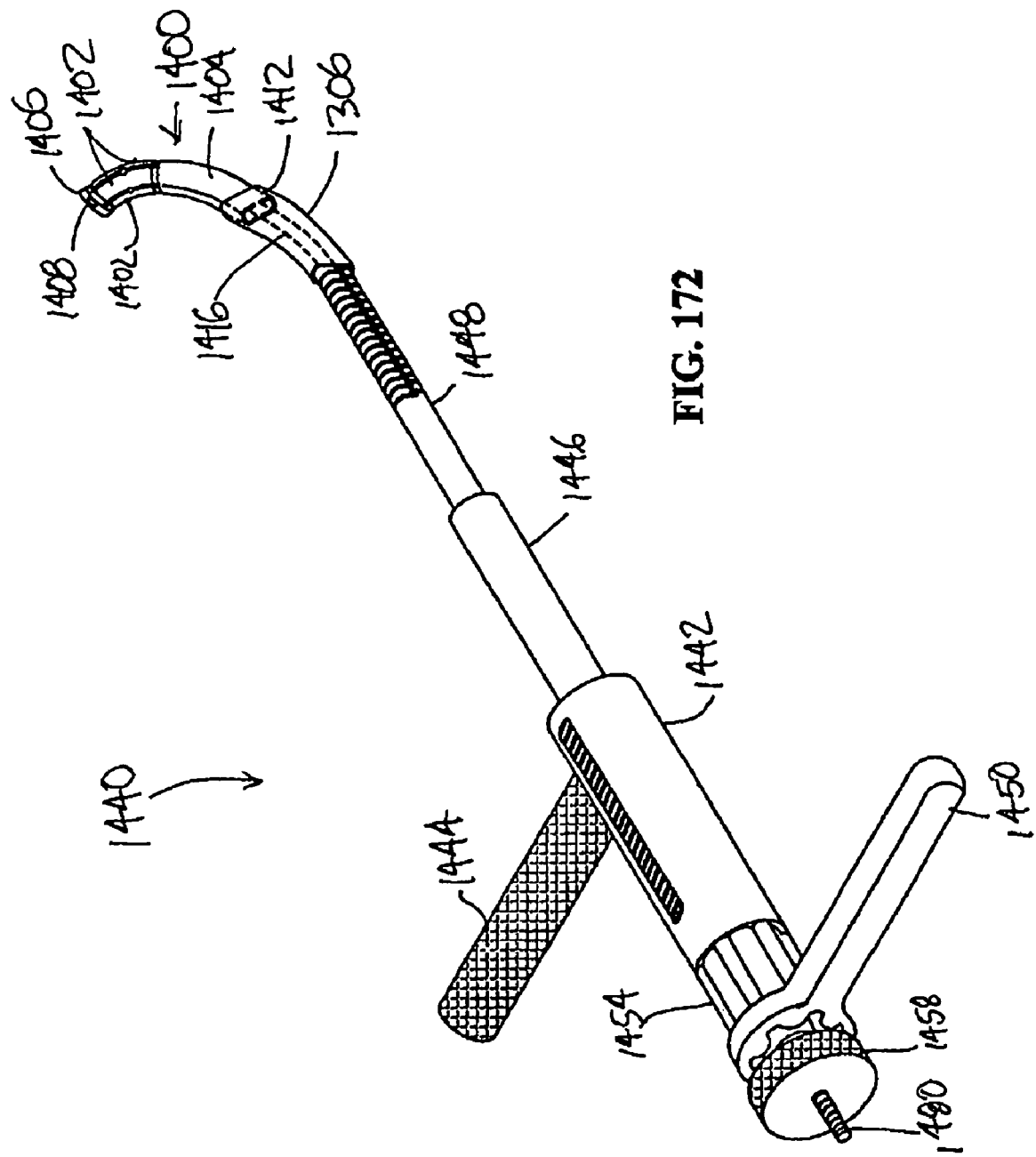
Figure 173:
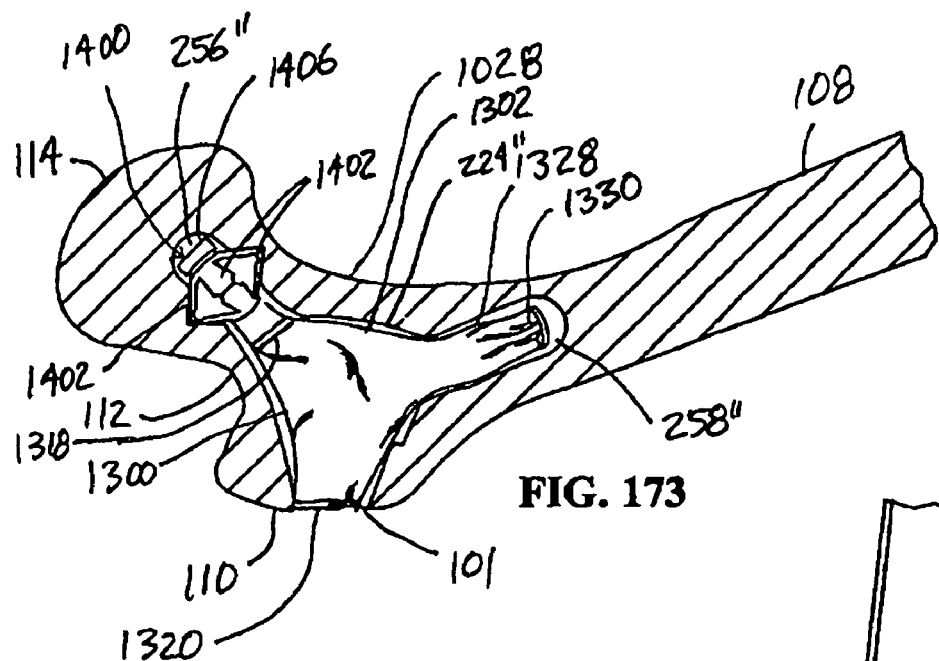
Figure 174:
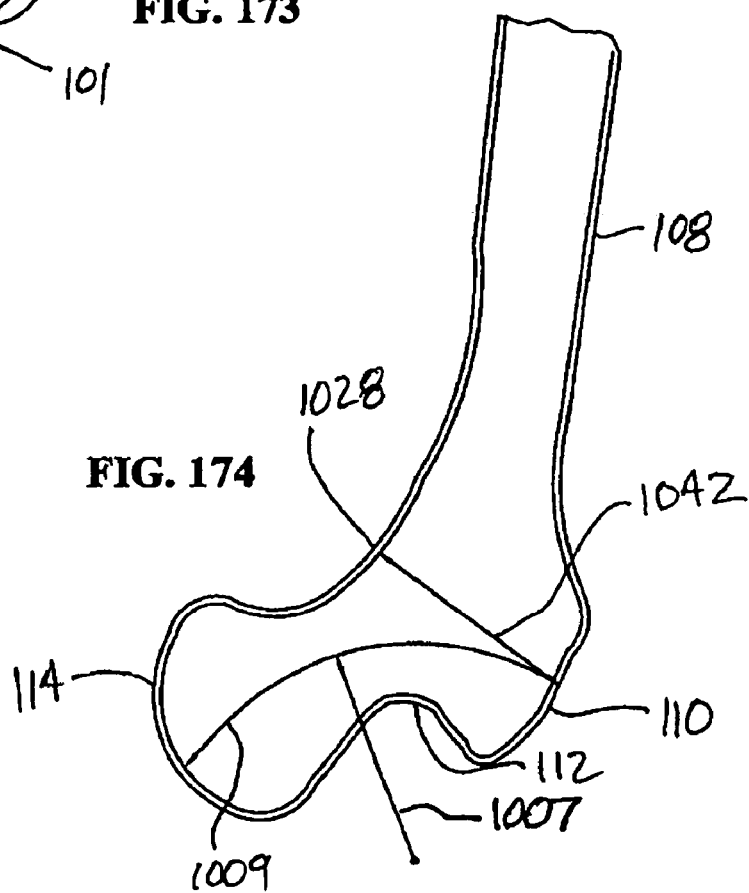
Figure 175A:
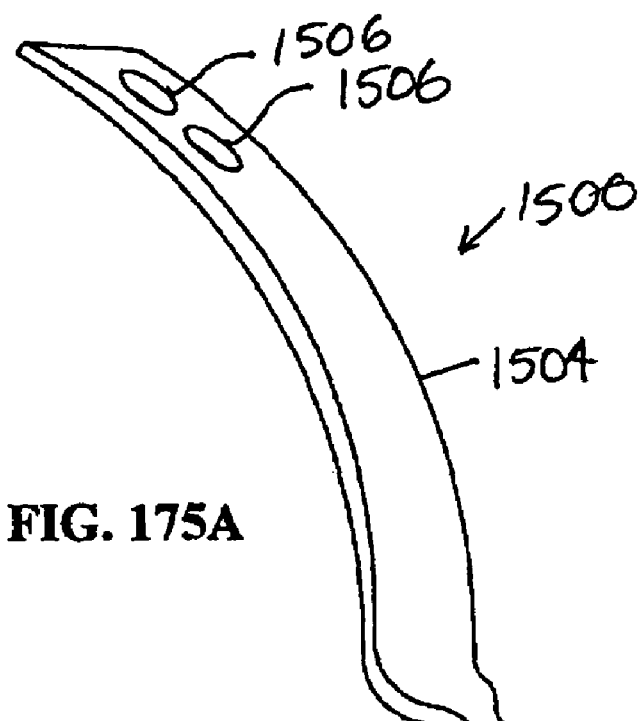
Figure 175B:
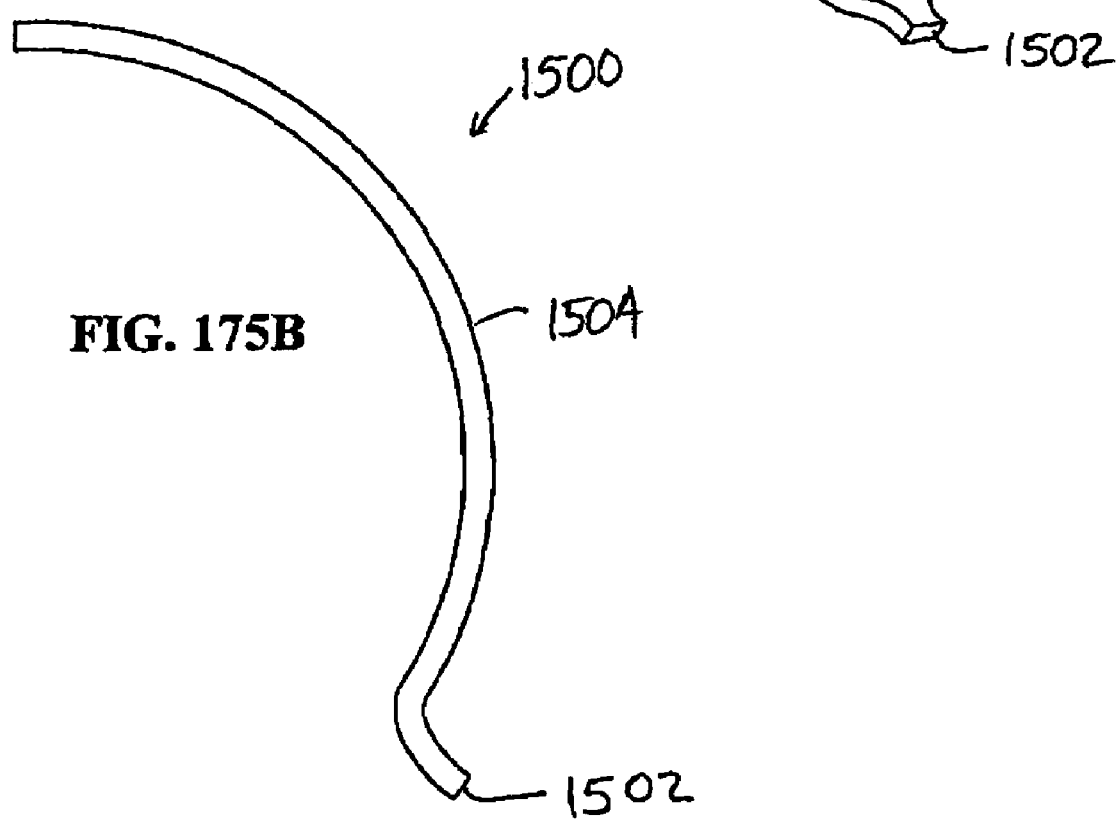

FIG. 136 is a sectional view of the injection/insertion tube illustrated in FIG. 135;

FIG. 137 is a distal end elevational view thereof;

FIG. 138 is a sectional view taken along line 138-138 of FIG. 135;

FIG. 139 is a radial elevational view of an outer lag screw tube of the present invention;

FIG. 140 is a sectional view thereof taken along line 140-140 of FIG. 139;

FIG. 141 is a partial sectional view of an alternative embodiment lag of the present invention;

FIG. 142 is a radial plan view of the lag of FIG. 141 together with an actuation instrument for securing the lag within the femur;

FIG. 143 is a partial sectional view of the lag depicted in FIGS. 141 and 142 actuated for engagement with the femur;

FIG. 144 is a sectional view illustrating insertion of the femoral implant of FIGS. 133 and 134 into the femoral cavity illustrated in FIG. 11;

FIG. 145 is a sectional view illustrating insertion of the lag depicted in FIGS. 141-143 through the injection/insertion tube depicted in FIGS. 135-137 and into the femoral cavity illustrated in FIG. 11;

FIG. 146 is a sectional view illustrating the final seated position of the implant illustrated in FIGS. 133 and 134 in the femur;

FIG. 147 is a partial perspective view of a portion of a patient having an incision along the greater trochanter to allow for implantation of a femoral implant of the present invention;

FIG. 148 is a partial perspective view illustrating the use of an alignment device of the present invention and a fluoroscope to position and orient a guide pin in or parallel to the coronal femoral plane and to select an implant size in accordance with the present invention;

FIG. 149 is an elevational view of the alignment guide of FIG. 148;

FIG. 150 is an exploded view of the alignment guide of FIG. 148;

FIG. 151A is a graphic depiction of a coronal femoral plane fluoroscopic image illustrating the use of the alignment guide of FIG. 148 to properly position and orient a guide pin in accordance with the present invention;

FIG. 151B is a graphic depiction of a coronal femoral plane fluoroscopic image showing the alignment guide of FIG. 148 misaligned with the femur;

FIG. 151C is a graphic depiction of an implant pattern arm of an aligned alignment guide having a square-shaped geometric reference bore;

FIG. 151D is a graphic depiction of the geometric reference bore of FIG. 151C where the alignment guide is misaligned;

FIG. 151E is a graphic depiction of an implant pattern arm of an aligned alignment guide having a triangle-shaped geometric reference bore;

FIG. 151F is a graphic depiction of the geometric reference bore of FIG. 151E where the alignment guide is misaligned;

FIG. 152 is an exploded view of a protective container for the alignment guide of FIG. 148;

FIG. 153 is a sectional view of a femur illustrating a plunge reamer utilized to form an access and to begin making the femoral cavity of the present invention;

FIG. 154 is a sectional view of a femur illustrating the use of an alternative embodiment curved telescoping reamer in accordance with the present invention to further form the femoral cavity;

FIG. 155 is a sectional view of a femur illustrating use of the telescoping reamer of FIG. 154 to extend the femoral cavity into the femoral neck and head;

FIG. 156A is an exploded view of the telescoping reamer of FIGS. 154 and 155;

FIG. 156B is an elevational view of an interior surface of a portion of the telescoping reamer taken along line 156B-156B of FIG. 156A;

FIG. 156C is a side cross-sectional view of a portion of the telescoping reamer of FIG. 156A;

FIG. 156D is a plan view of a proximal end portion of the telescoping reamer of FIG. 156A;

FIG. 157 is a perspective view illustrating an alternative embodiment swivel reamer in accordance with the present invention;

FIG. 158A is an exploded view of the swivel reamer of FIG. 157;

FIG. 158B is a partial cutaway view of a portion of the swivel reamer taken along line 158B-158B of FIG. 158A;

FIG. 158C is a perspective view of a portion of the swivel reamer of FIG. 157 and 158A;

FIG. 159 is a sectional view of a femur illustrating the use of the swivel reamer of FIG. 157 to further form the femoral cavity;

FIG. 160 is a sectional view of a femur illustrating the use of the swivel reamer of FIG. 157 to further form a femoral shaft arm of the femoral cavity;

FIG. 161A is an exploded view illustrating an alternative embodiment femoral implant of the present invention;

FIG. 161B is a perspective view illustrating the femoral implant of FIG. 161A assembled for implantation in a femur;

FIG. 162A and 162B is a bottom elevational view of the bag of the femoral implant illustrated in FIG. 161A;

FIG. 163A is a sectional view of the implant of FIG. 161A taken along a longitudinal axis of the implant;

FIG. 163B is an end view thereof taken along line 163B-163B of FIG. 163A;

FIG. 163C is an end view thereof taken along line 163C-163C of FIG. 163A;

FIG. 163D is an axial cross-section view thereof taken along line 163D-163D of FIG. 163A;

FIG. 164A is a perspective view of a bone cement insertion tube according to the present invention;

FIG. 164B is an end view thereof taken along line 164B-164B of FIG. 164A;

FIG. 165 is a sectional view of a femur illustrating insertion of the femoral implant of FIG. 161A in the femur;

FIG. 166 is a sectional view of a femur illustrating the further insertion of the femoral implant of FIG. 161A and the lag of FIG. 168A;

FIG. 167 is a sectional view of a femur illustrating the lag of FIG. 168A secured in the femoral head;

FIG. 168A illustrates an alternative exemplary lag in accordance with the present invention;

FIG. 168B is an axial sectional view of the lag of FIG. 168A;

FIG. 169 is a sectional view of the lag of FIG. 168A taken along the longitudinal axis thereof;

FIG. 170 is a sectional view of the lag of FIG. 168A, taken along the longitudinal axis of the lag after compression and showing the fingers expanded;

FIG. 171 is an exploded view illustrating a lag actuator of the present invention;

FIG. 172 is a perspective view of the lag actuator of FIG. 171 coupled to the lag of FIG. 168A and the lag tube of FIG. 161A;

FIG. 173 is a sectional view of a femur further illustrating securement of the femoral implant of FIG. 161B in the femoral shaft;

FIG. 174 is a sectional view of a femur illustrating landmarks for determining the selection of the femoral implant dimensions in accordance with the present invention;

FIG. 175A is a perspective view of a radiolucent retractor according to the present invention; and FIG. 175B is a side view of the radiolucent retractor of FIG. 175A.

Corresponding reference characters indicate corresponding parts throughout the several views. Although the drawings represent embodiments of the present invention, the drawings are not necessarily to scale and certain features may be exaggerated to better illustrate and explain the present invention. The exemplifications set out herein illustrate embodiments of the invention, and such exemplifications are not to be construed as limiting the scope of the invention in any manner.

Throughout this document, "proximal" and "distal" are used to refer to opposite ends of instruments described herein. When referring to the opposite ends of instruments, "proximal" and "distal" are used with reference to a user of the instrument. For example, the end of the instrument nearest to the user during use thereof is described as the proximal end, while the end of the instrument farthest from the user during use thereof is described as the distal end of the instrument.

DETAILED DESCRIPTION

Figure 1:
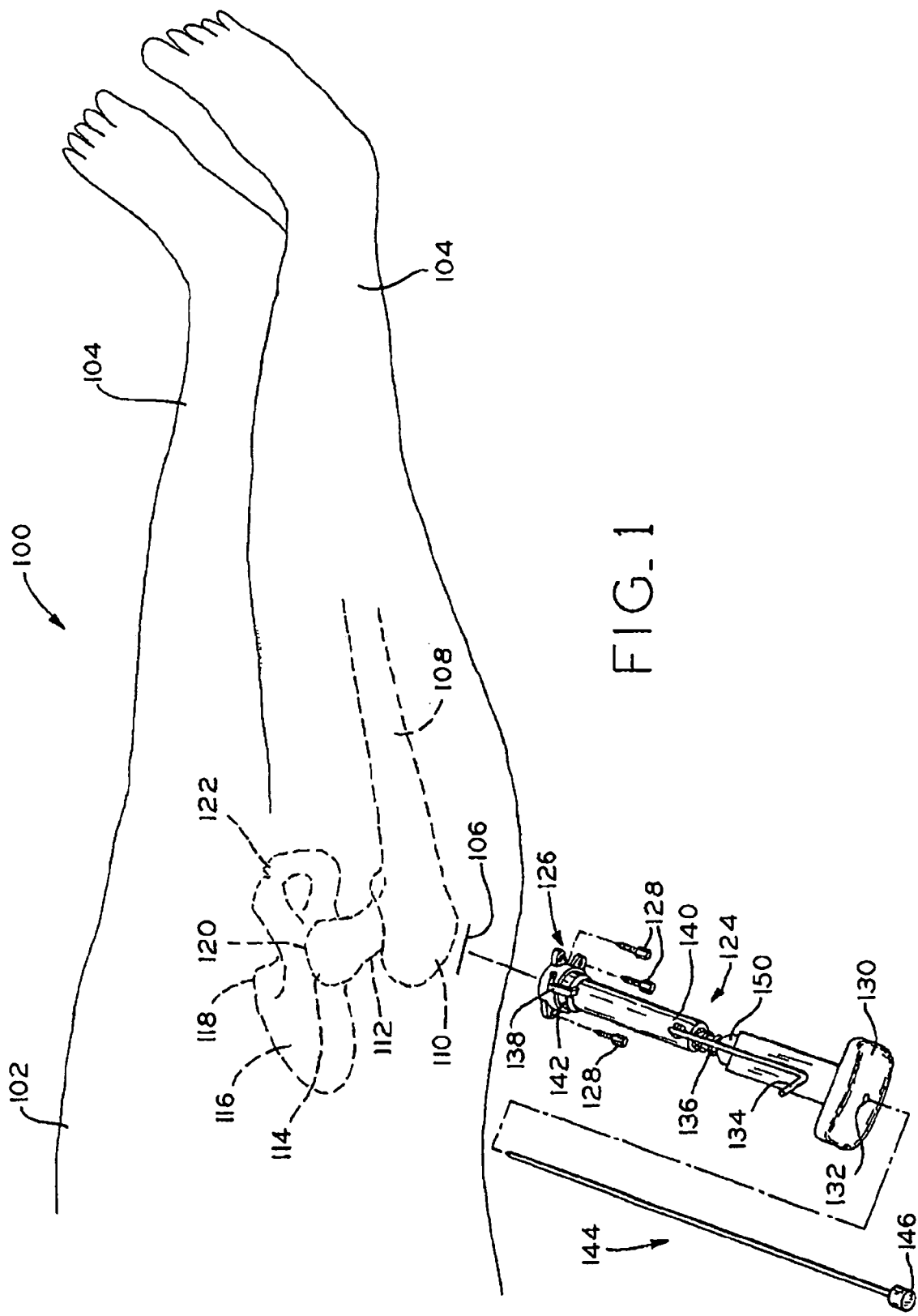
FIG. 1 is a partial perspective view of a portion of a patient, with an incision made along the greater trochanter to allow for implantation of a femoral implant of the present invention.

Implant 260 illustrated in FIG. 41 can be utilized to reduce a femoral fracture utilizing a method of implantation which does not require incision of muscle, e.g., the quadriceps, adductor, iliotibial band, and gluteus in the vicinity of the lateral femur. As illustrated in FIG. 1, incision 106 is aligned with greater trochanter 110, with femur 108 being prepared to receive implant 260 through incision 106. As described above, a portion of greater trochanter 110 is nude of muscle attachment and is generally not covered with muscle and therefore, incision 106 can be developed to expose greater trochanter 110 without requiring the incision of muscle. Incision 106 measures about 2.5 centimeters (1 inch). Referring now to FIG. 147, patient 100 is shown with incision 106 again aligned with greater trochanter 110 of femur 108. Incision 106 is located over a central, substantially planar portion of greater trochanter 110 that is not covered by muscle or which is covered by muscle which is not attached to the central portion of greater trochanter 110 and which can be easily retracted without substantial tissue damage. The central portion of greater trochanter 110 is generally bordered by quadriceps 940, iliotibial band 941, adductor 942, and gluteus 943.

Figure 12:
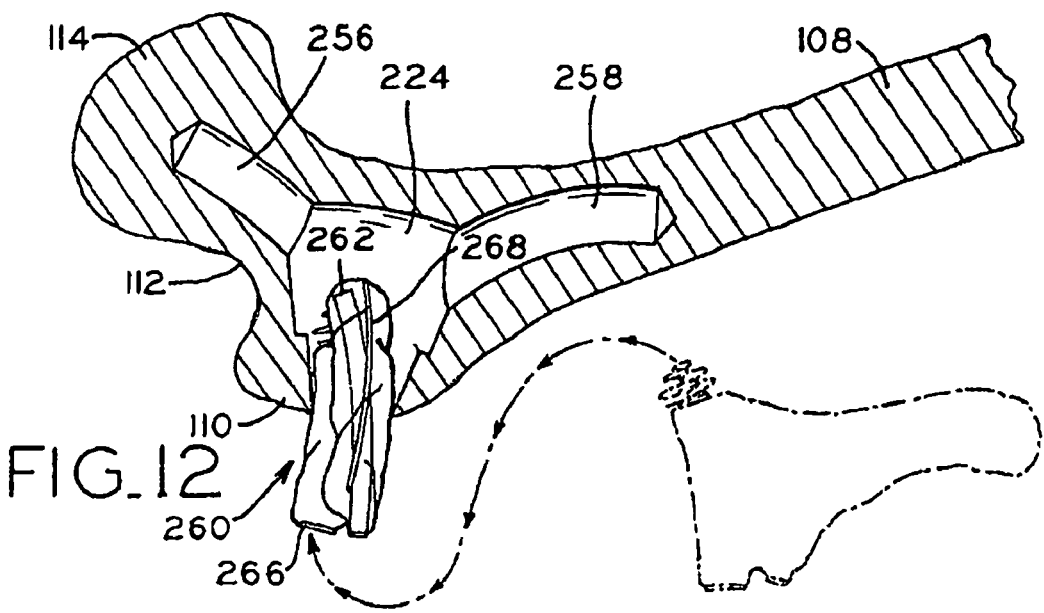
FIG. 12 is a sectional view illustrating insertion of a femoral implant of the present invention into the femoral cavity illustrated in FIG. 11.
Figure 13:
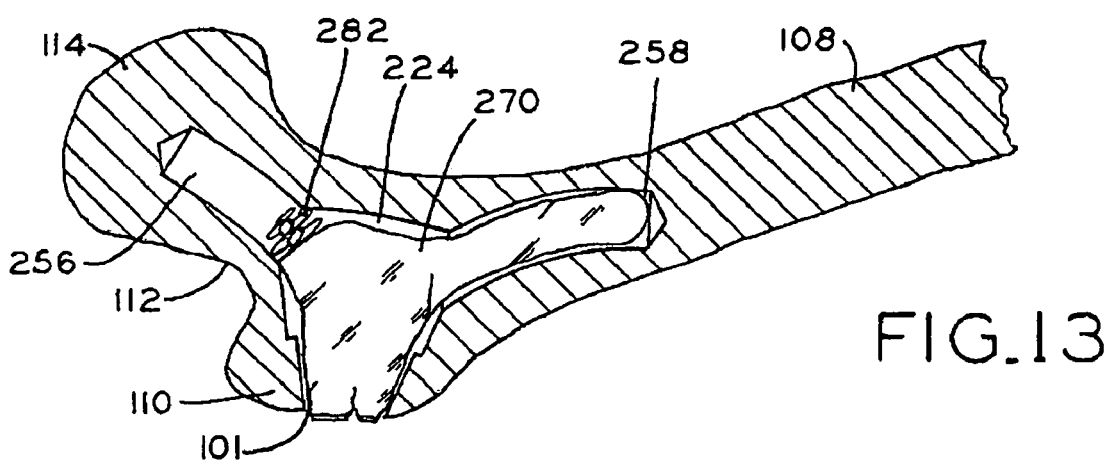
FIG. 13 is a sectional view illustrating extension of the bag of the femoral implant into the intramedullary canal.

FIGS. 6-10 illustrate use of various novel reamers of the present invention to form femoral cavity 224 (FIG. 11). Various instruments described below may be utilized in lieu of or in conjunction with the instruments illustrated in FIGS. 6-10. As illustrated in FIG. 12, in one exemplary embodiment, implant 260 (further illustrated in FIGS. 41-43) is inserted into femoral cavity 224 via access 101 (FIGS. 13 and 14) formed through greater trochanter 110. As illustrated in FIG. 13, lag screw 264 is advanced into femoral head 114 until lag screw threads 282 firmly engage femoral head 114 and lag screw 264 has achieved the position illustrated in FIG. 14. In one alternative embodiment of the present invention, as illustrated in FIG. 173, lag 1400 is firmly engaged in femoral head 114 with fingers 1406. Referring again to FIG. 13, bag 270 is thereafter filled with material, e.g., bone cement to fill femoral cavity 224 and provide intramedullary fixation of implant 260 and stabilization of lag screw 264. In this way, a femoral fracture including, e.g., an intertrochanteric fracture can be reduced. Generally, this document will refer to a femoral fracture and, specifically, to an intertrochanteric fracture.

However, the method and apparatus of the present invention is adaptable to various bone fractures including, e.g., supracondylar fractures of the femur.

FIG. 1 generally illustrates patient 100 including torso 102, and legs 104. FIG. 1 further illustrates the general bone structures comprising the hip joint including, pubis 122, anterior superior iliac spine 118, ilium 116, acetabulum 120, and femur 108. As illustrated in FIG. 1, femur 108 includes, e.g., greater trochanter 110, femoral neck 112, and femoral head 114. As described above, incision 106 is aligned with greater trochanter 110. Because greater trochanter 110 is not covered with muscle, incision 106 can be made and the wound developed through the skin and fascia to expose greater trochanter 110 without incising muscle, including, e.g., the quadriceps, iliotibial band, adductor, and gluteus.

Figure 2:
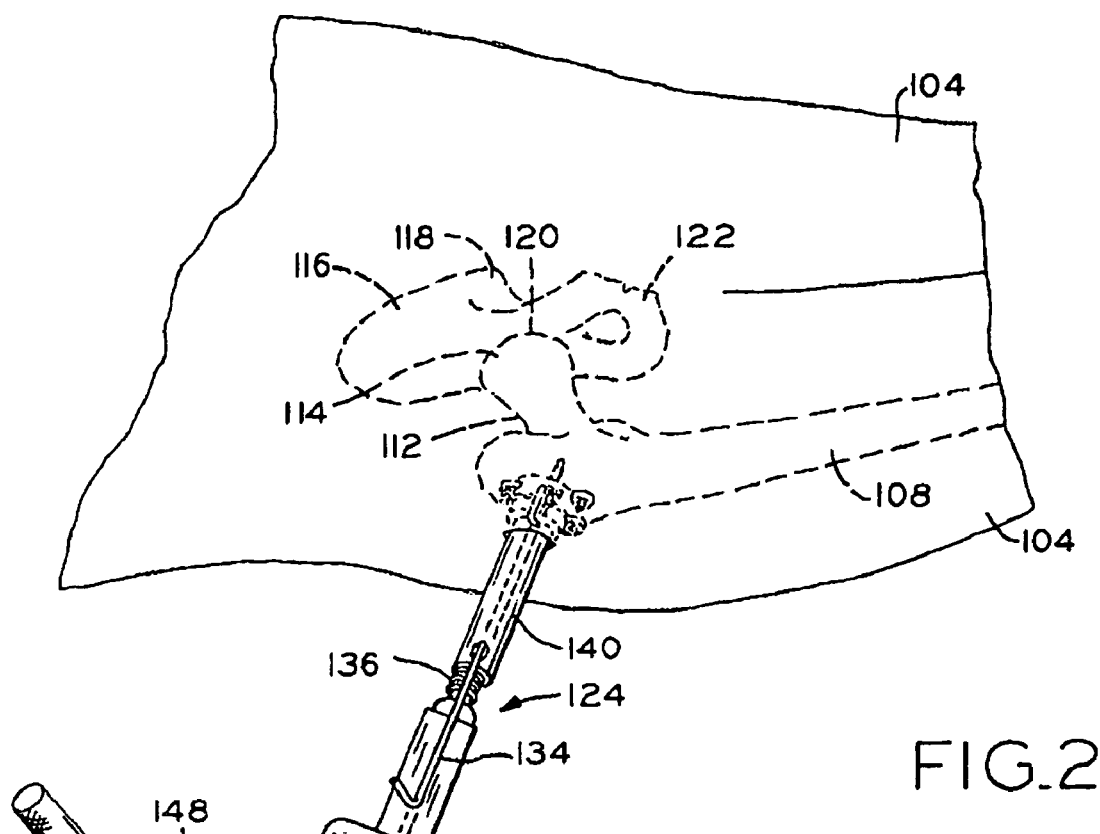
FIG. 2 is a partial perspective view illustrating insertion of a guide plate in accordance with the present invention.

In one embodiment of the present invention, cannulated insertion member 124 is utilized to insert guide plate 126 through incision 106 to be placed atop and secured to greater trochanter 110 as illustrated, e.g., in FIG. 2. After guide plate 126 traverses incision 106 and is placed atop greater trochanter 110, stabilization nail 144 is positioned through elongate aperture 132 (FIG. 19) of insertion member 124 and impaction instrument 148 (FIG. 2) is utilized to strike impaction surface 146 to drive stabilization nail 144 into femur 108 to provide initial stability to guide plate 126 prior to utilizing screws 128 (FIG. 1) to fix guide plate 126 to greater trochanter 110. In one exemplary embodiment, the surgeon implanting guide plate 126 will utilize a fluoroscope to verify proper placement of guide plate 126 atop greater trochanter 110. In alternative embodiments, the surgeon implanting guide plate 126 will utilize tactile feedback either alone or in conjunction with a fluoroscope image to determine proper placement of guide plate 126 atop greater trochanter 110. After guide plate 126 is properly positioned atop greater trochanter 110, screws 128 are driven through corresponding screw apertures 286 (FIG. 15) in guide plate 126 and into femur 108 to secure guide plate 126 to femur 108. Screw apertures 286 are, in one exemplary embodiment, formed in guide plate 126 to allow for oblique insertion of screws 128 relative to guide plate 126.

Insertion member 124 is illustrated in detail in FIGS. 19-22. As illustrated, insertion member 124 includes elongate aperture 132 accommodating stabilization nail 144 as described hereinabove. Insertion member 124 includes tubular latch connector 140 positioned about the distal end thereof. Intermediate the main body of insertion member 124 and tubular latch connector 140 is positioned spring 136. Spring 136 acts against spring stop 150 to bias tubular latch connector into the position illustrated in FIG. 22. Release member 134 is connected to tubular latch connector 140 and is operable to facilitate movement of tubular latch connector 140 against the biasing force of spring 136 into the position illustrated in FIG. 21. Insertion member 124 includes distal end 142 for engaging guide plate 126. Distal end 142 includes bosses 152 extending therefrom.

Guide plate 126 is temporarily affixed to insertion member 124 as described below. Bosses 152 of insertion member 124 enter attachment channels 290 of guide plate 126 (see, e.g., FIGS. 15 and 17). Concurrently, latch 138, connected to tubular latch connector 140, acts against the proximal surface of guide plate 126 to force tubular latch connector 140 against the biasing force of spring 136 and into the position illustrated in FIG. 21. Distal end 142 of insertion member 124 is then rotated until bosses 152 are positioned under lips 291 formed by attachment channels 290 and latch 138 can be positioned within one of attachment channels 290 and returned to its naturally biased position as illustrated in FIGS. 19 and 22. When guide plate 126 is attached to insertion member 124, one of bosses 152 and latch 138 abut opposing radial extremes of one attachment channel 290 to prevent relative rotation of guide plate 126 and insertion member 124. Moreover, when guide plate 126 is attached to insertion member 124, bosses 152 cooperate with lips 291 formed by attachment channels 290 to prevent relative axial displacement of guide plate 126 and insertion member 124. In this way, guide plate 126 is secured to insertion member 124 to facilitate positioning guide plate 126 atop greater trochanter 110 as described hereinabove.

After guide plate 126 is secured to greater trochanter 110, release member 134 may be actuated to position latch 138 in the position illustrated in FIG. 21 to allow for rotation of distal end 142 of insertion member 124 relative to guide plate 126. When latch 138 is positioned as illustrated in FIG. 21, it is no longer contained within attachment channel 290 and therefore allows relative rotation between guide plate 126 and insertion member 124. Distal end 142 of insertion member 124 is rotated to reposition bosses 152 out of axial alignment with lips 291 for removal from attachment channels 290. Insertion member 124 is thereafter removed from engagement with guide plate 126 and removed through incision 106.

Figure 3:
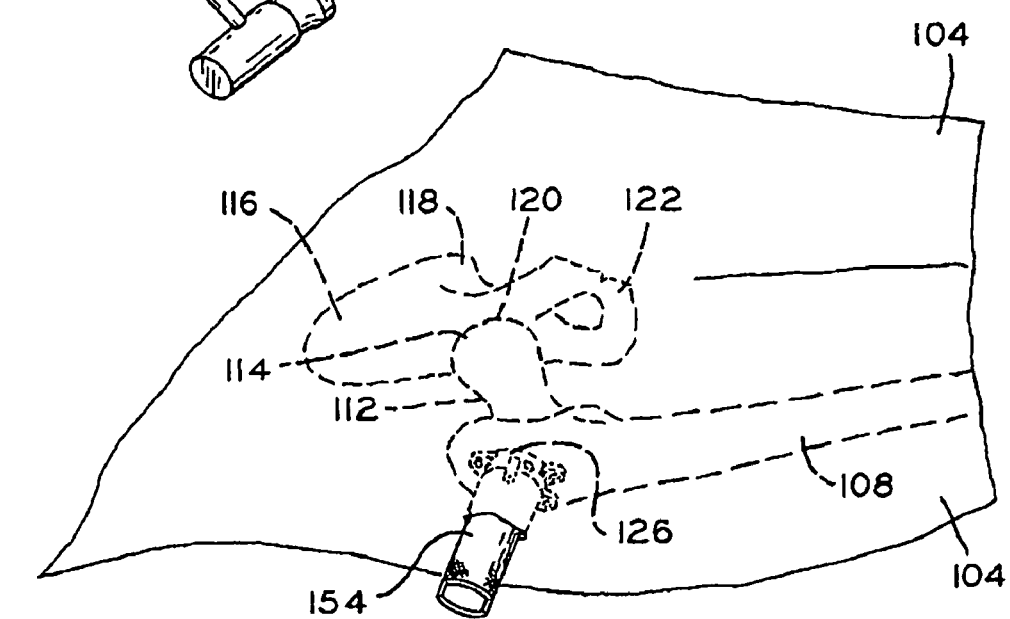
FIG. 3 is a partial perspective view illustrating a guide tube/retractor in accordance with the present invention inserted through the incision aligned with the greater trochanter and engaged with the guide plate.

After securement of guide plate 126 atop greater trochanter 110, guide tube/retractor 154 (FIGS. 23-27) is inserted through incision 106 and releasably fixed to guide plate 126 as illustrated in FIG. 3. Guide tube/retractor 154 is illustrated in detail in FIGS. 23-27, and guide plate 126 is illustrated in detail in FIGS. 15-18. With reference to FIGS. 23-27 and 15-18, the cooperating apparatus of guide tube/retractor 154 and guide plate 126 allowing for selective locking of guide tube/retractor 154 to guide plate 126 will now be described. Fixation of guide tube/retractor 154 to guide plate 126 is effected by first positioning attachment protrusions 302 of straight guide tube/retractor 154 into attachment channels 290 of guide plate 126. Guide tube/retractor 154 is then rotated clockwise to position the radially extending portion of attachment protrusions 302 under lips 291 formed by attachment channels 290 of guide plate 126. Once rotated into this position, spring biased locking pin 294 of guide tube/retractor 154 is positioned within lock detent 292 of guide plate 126 to prevent relative rotation of guide plate 126 and guide tube/retractor 154 and lock guide tube/retractor 154 to guide plate 126.

As illustrated in FIGS. 23 and 24, spring biased locking pin 294 extends substantially axially along guide tube/retractor 154 and is operably connected to actuation member 300 to provide for manual actuation of locking pin 294. Spring 298 is operatively associated with spring biased locking pin 294 and the interior of the cylindrical wall forming guide tube/retractor 154 to bias locking pin 294 into the position illustrated in FIG. 24. When distal shoulder 303 of guide tube/retractor 154 is initially positioned atop the proximal end of guide plate 126, with attachment protrusions 302 entering attachment channels 290, locking pin 294 is moved against the biasing force of spring 298 until guide tube/retractor 154 is rotated as described hereinabove to align locking pin 294 with detent 292 and lock guide tube/retractor 154 to guide plate 126.

While the engagement of a guide tube/retractor of the present invention with guide plate 126 has been described with respect to straight guide tube/retractor 154, angled guide tube/retractor 296 (illustrated in FIG. 28 and described below) is locked to guide plate 126 in the same manner utilizing the same structure as described above with respect to straight guide tube/retractor 154. The shared components of straight guide tube/retractor 154 and angled guide tube/retractor 296 are denoted with primed reference numerals. The mechanism for locking a guide tube/retractor of the present invention to guide plate 126 allows for locking of a guide tube/retractor to guide plate 126 in one of two positions separated by 180 degrees. This allows for angled guide tube/retractor 296 to provide for realignment in two directions as further described hereinbelow.

Guide tube/retractor 154 serves the dual purpose of maintaining an access from incision 106 to greater trochanter 110 and guiding various instruments utilized to prepare femoral cavity 224 (FIG. 11). Generally, either a straight or an angled guide tube/retractor will be utilized. FIGS. 24 and 28 respectively illustrate straight guide tube/retractor 154 and angled guide tube/retractor 296. As illustrated, e.g., in FIG. 28, angled guide tube/retractor 296 includes distal end 299 and retractor body 301. Longitudinal axis 297 of distal end 299 of angled guide tube/retractor 296 forms an angle Ø of about 10° with longitudinal axis 303 of retractor body 301. In this way, angled guide tube/retractor 296 allows for a 10° realignment with respect to straight guide tube/retractor 154. A surgeon can choose either straight guide tube/retractor 154 or angled guide tube/retractor 296 based upon the geometry of femur 108 into which implant 260 (FIG. 41) will be placed. In accordance with the present invention, an alignment device is provided to facilitate choice of straight guide tube/retractor 154 or angled guide tube/retractor 296 as well as the orientation of angled guide tube/retractor 296 as further described hereinbelow.

Figure 29:
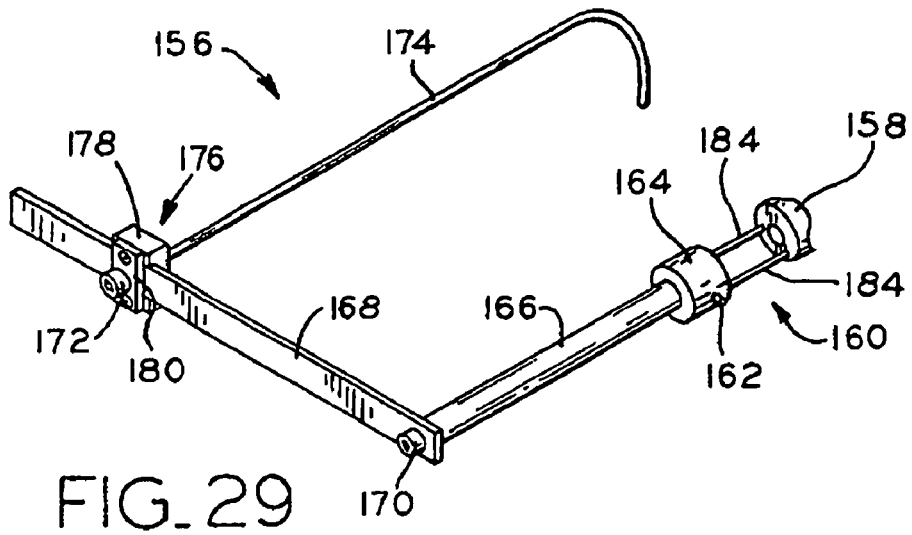
FIG. 29 is a perspective view of an alignment device of the present invention.

FIGS. 4 and 5 illustrate use of alignment device 156 to choose either straight guide tube/retractor 154 or angled guide tube/retractor 296. Alignment device 156 is illustrated in detail in FIGS. 29 and 30 and includes extension 166 connected to transverse bar 168, with alignment arm 174 slidably attached thereto. As illustrated in FIG. 29, extension 166 is connected to insertion member 160 at a distal end thereof. Insertion member 160 is sized for insertion into either straight guide tube/retractor 154 or angled guide tube/retractor 296 as illustrated in FIGS. 4 and 5.

Figure 30:
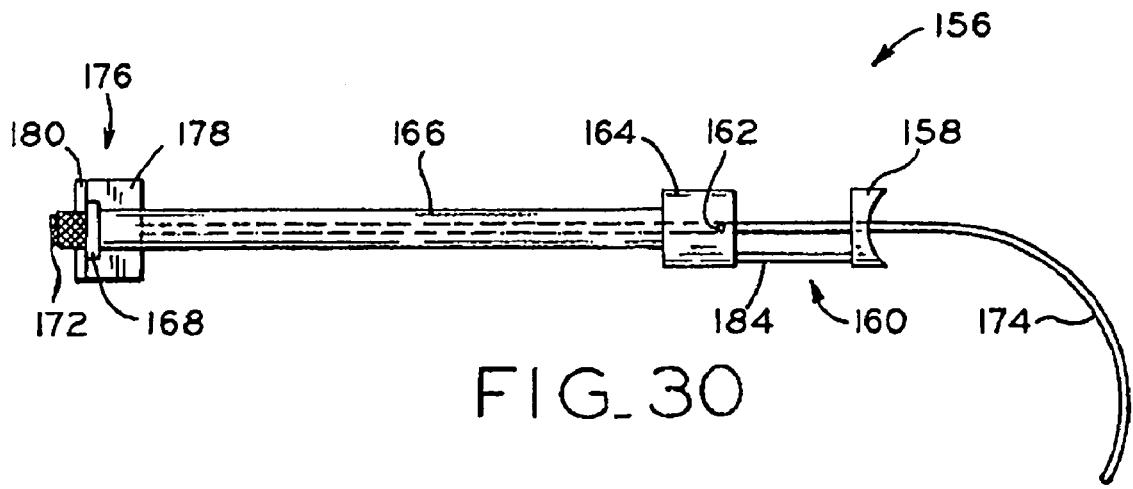
FIG. 30 is an elevational view thereof.

As illustrated in FIGS. 29 and 30, insertion portion 160 of alignment device 156 includes distal end 158 connected via connecting rods 184 to positioning cylinder 164. Positioning cylinder 164 includes a pair of opposing bosses 162, only one of which is depicted in FIGS. 29 and 30. Distal end 158 and positioning cylinder 164 have external geometries sized to cooperate with the hollow interior of the guide tube/retractors of the present invention to provide a stationary base for alignment device 156, as illustrated in FIGS. 4 and 5. Insertion portion 160 of alignment device 156 as illustrated in FIGS. 29 and 30 comprises merely one exemplary design for an insertion portion of alignment device 156 operable to stabilize alignment device 156 with the guide tube/retractors of the present invention. Generally, insertion portion 160 will include a portion thereof having an exterior geometry sized to cooperate with the interior of the guide tube/retractors of the present invention to provide a stationary base for alignment device 156. In an alternative embodiment, the insertion portion of alignment device 156 depicted in FIGS. 29 and 30 comprises a solid insertion member having a consistent cross sectional area along its length. In this embodiment, the exterior of the solid insertion member will cooperate with the interior of the guide tube/retractors of the present invention to provide a stable connection of alignment device 156 with a guide tube/retractor in accordance with the present invention.

Alignment device 156 includes transverse bar 168 fixed to extension 166 via screw 170. Positioning cylinder 164 and extension 166 provide a stable base for transverse bar 168. As illustrated in FIGS. 29 and 30, alignment arm 174 is slidably connected to transverse bar 168 via slidable attachment member 176. Slidable attachment member 176 includes attachment block 178 having a cutout therein accommodating transverse bar 168. Top plate 180 is mounted atop attachment block 178, with set screw 172 threaded therein. Set screw 172 traverses top plate 180 to selectively engage transverse bar 168 and lock alignment arm 174 in position along transverse bar 168.

As illustrated in FIGS. 4 and 5, alignment device 156 is utilized to facilitate selection of the appropriate guide tube/retractor. FIG. 5 illustrates alignment device 156 operably positioned within straight guide tube/retractor 154, which is locked to guide plate 126. In use, bosses 162 on positioning cylinder 164 are positioned within attachment channels 290 of guide plate 156 and positioning cylinder 164 is rotated until bosses 162 contact the terminal ends of channels 290 and are positioned under lips 291. After positioning alignment device 156 within guide tube/retractor 154, slidable attachment member 176 may be adjusted to accommodate the physiological characteristics of the patient and place alignment arm 174 adjacent the patient's skin. Alignment arm 174 of alignment device 156 includes a curved distal end having a curvature based on statistical data which follows a path from the central portion of greater trochanter 110, along the central axis of femoral neck 112, to the central region of femoral head 114. FIG. 5 illustrates an arrangement with the distal end of alignment arm 174 following the aforementioned path on femur 108. In the environment illustrated in FIG. 5, straight guide tube/retractor 154 is the appropriate guide tube/retractor to be utilized to effect the method of the present invention. In some cases, the distal end of alignment arm 174 will not coincide with the aforementioned path on the femur in question due to, e.g., the specific geometry of the bone in question. In this case, angled guide tube/retractor 296 may be utilized in an attempt to provide the appropriate alignment with the femur in question.

FIG. 4 illustrates alignment device 156 utilized with angled guide tube/retractor 296 on femur 108. As described above, femur 108, illustrated, e.g., in FIGS. 4 and 5, has a geometry accommodating the use of straight guide tube/retractor 154. With this in mind, FIG. 4 is useful in illustrating a situation in which the distal end of alignment arm 174 does not follow a path from the central portion of greater trochanter 110, along the central axis of femoral neck 112 to the central region of femoral head 114 and, therefore, use of the attached guide tube/retractor, i.e., angled guide tube/retractor 296 is contraindicated. Comparison of the distal end of alignment arm 174 to the aforementioned path from the central portion of the greater trochanter, along the central axis of the femoral neck to the central portion of the femoral head will be effected during surgery with the use of a fluoroscope.

Generally, straight guide tube/retractor 154 will first be locked to guide plate 126, and alignment device 156 will be operably positioned therein. A fluoroscope will then be utilized to compare the distal end of alignment arm 174 with the path from the central portion of the greater trochanter, along the central axis of the femoral neck to the central portion of the femoral head. If the distal end of alignment arm 174 does not follow the aforementioned path from the central portion of the greater trochanter to the central portion of the femoral head, then alignment device 156 and straight guide tube/retractor 154 will be removed and angled guide tube retractor 296 will be locked to guide plate 126. The angle Ø of about 10° formed between longitudinal axis 297 of distal end 299 of angled guide tube/retractor 296 and longitudinal axis 303 of retractor body 301 allows for an approximately 10 degree realignment on either side of the longitudinal axis of straight guide tube/retractor 154 in a plane substantially containing the central axis of femur 108. The inventors of the current invention have found that this 10 degree realignment in either direction typically accounts for the various bone geometries encountered. However, the inventors of the present invention further contemplate provision of additional angled guide tubes/retractors having an angle Ø as described hereinabove of other than 10 degrees. For example, Ø could measure 5°, 10°, or 15° to provide for increased versatility in performing the method of reducing a femoral fracture in accordance with the present invention.

Referring to FIG. 148, torso 102 of patient 100 is positioned between upper fluoroscopic component 952a and lower fluoroscopic component 952b of a C-arm fluoroscope or other device suitable for imaging femur 108. Fluoroscopic components 952a and 952b are positioned parallel to coronal femoral plane 1008 in order to provide imagery that aids proper positioning of instruments. Specifically, coronal femoral plane 1008 is defined as the plane which centrally intersects greater trochanter 110 and the shaft of femur 108 extends. Coronal femoral plane 1008 is selected as the reference plane for fluoroscopic imagery because the below-described implant cavity 224" (FIG. 154) in femur 108 is in part oriented relative to coronal femoral plane 1008, and the below-described instruments include radiopaque features designed to utilize fluoroscopic imagery which is oriented parallel to coronal femoral plane 1008.

After forming incision 106, a portion of alignment guide 950 is positioned through incision 106 and relative to greater trochanter 110 and femoral neck 112 and head 114 with the aid of a fluoroscopic image, for example image 954 shown in FIG. 151A. Specifically, components of alignment guide 950 provide radiopaque features for orienting alignment guide 950 relative to coronal femoral plane 1008 and other aspects of femur 108. Orienting alignment guide 950 may include rotation of the instrument about lateral/medial axis 1010, proximal/distal axis 1012, and anterior/posterior axis 1014.

Referring to FIGS. 149 and 150, alignment guide 950 generally includes pin insertion guide 956, alignment arm 958, arm coupler 960, distal arm portion 962, implant pattern arms 963a-d, distal insertion guide portion 964, alignment pin 966, and, optionally, radial arm extender 968. Pin insertion guide 956 may be a generally cylindrical shaft or body having handle portion 970 defined near proximate end 972 and longitudinal bore 974 extending from proximate end 972 to distal end 976. Longitudinal bore 974 is sized to receive pin shaft 984 of alignment pin 966 therethrough. Handle portion 970 is suitable for manually positioning alignment guide 950 relative to femur 108.

Radial bores 978 are defined in pin insertion guide 956 and are sized to alternatively receive coupler pins 981 and 1004 of arm coupler 960 and lateral arm extender 968, respectively. Pin insertion guide 956 may be constructed of a rigid substantially radiolucent material, e.g., polyphenylsulfone resin (Radel™, a registered trademark of Amoco Performance Products, Inc., available from Amoco Polymers, of Alpharetta, Ga.), or another polymer or other material that is rigid and is suitable for surgical use, e.g., autoclavable and chemically stable.

Distal insertion guide portion 964 is fixed to distal end 976 of pin insertion guide 956 and is constructed of a substantially radiopaque material, e.g., stainless steel, such as 316L SST or 17-4 PH SST, hereafter generically referred to as "SST." Bore 982 is defined through distal insertion guide portion 964, and in construction bore 982 is aligned with longitudinal bore 974. Bore 982 is sized to receive pin shaft 984 but not the enlarged diameter of pin head 986; therefore, pin shaft 984 of alignment pin 966 translates proximally through distal insertion guide portion 964 and pin insertion guide 956 until shoulder 988 of pin head 986 contacts reference surface 990 (FIG. 149) of distal insertion guide portion 964. Shoulder 988 contacting reference surface 990 prevents pin head 986 of alignment pin 966 from translating proximally through alignment guide 950, thereby providing pin head 986 slightly distally protruded from distal insertion guide portion 964, the advantage of which will be further described below.

Alignment arm 958 is coupled to pin insertion guide 956 by arm coupler 960 and optionally, radial arm extender 968. The function of alignment arm 958 and arm coupler 960 is to displace distal arm portion 962 radially outward (anteriorly relative to coronal femoral plane 1008 (FIG. 148)) from distal insertion guide portion 964; therefore, when portion 964 is positioned against greater trochanter 110, distal arm portion 962 and implant pattern arms 963a-b or 963c-d are positioned over torso 102 of patient 100 and, more specifically, over femoral neck 112 and head 114, as shown in FIG. 151A. Alignment arm 958 can also be constructed of polyphenylsufone resin or another suitable substantially radiolucent material that is rigid and is suitable for surgical use, e.g. autoclavable and chemically stable.

Alignment arm 958 includes radiopaque rotational reference pin 992, which may be embedded in or otherwise fixed relative to alignment arm 958. When alignment arm 958 and pin 966 are aligned in a plane perpendicular to coronal femoral plane 1008, reference pin 992 is aligned with pin 966 as shown in fluoroscopic image 954 of FIG. 151A. For example, reference pin 992 may be laterally centered in reference arm 958. Distal arm portion 962 is fixed to alignment arm 958, for example, by fastener 994 (FIG. 150) and both distal arm portion 962 and implant pattern arms 963a-d can be constructed of rigid radiopaque material, e.g., SST.

Referring still to FIG. 150, exemplary embodiments of arm coupler 960 and lateral arm extender 968 are rectangular hoops formed from SST or another rigid material. Arm coupler 960 may be accurately, releasably coupled to alignment arm 958 with coupler pins 980 engaging bores 983 located at a proximate end of reference arm 958. Coupler arm 960 can be fixed to alignment arm 958 by, for example, fasteners 996 such as screws. Coupler pins 981, fixed to arm coupler 960 at an end opposite coupler pins 980, provide accurate, releasable coupling of alignment arm 958 and pin insertion guide 956. In one embodiment, coupler pins 981 provide a slip fit with bores 978 in handle 970 of pin insertion guide 956. The slip fit of pins 981 and bores 978 generally retain alignment arm 958 with pin insertion guide 956. Additionally, when gripping handle 970, the user's thumb may extend through the opening formed in coupler arm 960, thereby further retaining alignment arm 958 relative to pin insertion guide 956.

Alternatively, in the case of a patient having a large torso 102, radial arm extender 968 receives coupler pins 981 in bores 1002 and coupler pins 1004, located on radial arm extender 968 at an end opposite bores 1002, are received by radial bores 978 of pin insertion guide 956. Arm coupler 960 and radial arm extender 968 accurately position alignment arm 958 relative to alignment pin 966 and with increased radial displacement of distal arm portion 962 relative to pin insertion guide 956. Thumbscrew 998, or another fastener may be used to secure arm coupler 960 to radial arm extender 968. Similar to coupler arm 960, when holding handle 970, the user's thumb may pass through the opening formed in radial arm extender 968, thereby retaining extender 968 to pin insertion guide 956. Advantageously, a plurality of radial arm extenders 968 may be provided, each having a different length 1006. Alternatively, radial arm extenders 968 may be coupled together, thus accommodating various sized patient torsos 102.

Referring generally to FIG. 148 and FIG. 151A (showing exemplary fluoroscopic image 954), alignment guide 950 facilitates selection of implant size and location as well as orientation of access 101 (FIG. 147) relative to femur 108. Implant pattern arms 963a and 963b are used to select implant arc radius 1007 (FIG. 174) for a right femur. Similarly, implant pattern arms 963c and 963d are used for selecting implant arc radius 1007 for a left femur, as described below.

Implant pattern arms 963a-b oppose implant pattern arms 963c-d, respectively, as shown in FIG. 151A. Pattern arms 963a-b overlie femoral head 114 and, in opposition thereto, pattern arms 963c-d overlie the intramedullary canal of femur 108.

Referring to FIGS. 148 and 149, radiopaque features of alignment guide 950 assist orienting alignment pin 966 relative to coronal femoral plane 1008. Specifically, alignment pin 966 is oriented parallel to coronal femoral plane 1008 (FIG. 148) by rotation of alignment guide 950 about proximal/distal axis 1012. Upon alignment pin 966 being parallel to coronal femoral plane 1008, distal end reference surface 990 (FIG. 149) of distal insertion guide portion 964 and proximal end surface 1016 of distal arm portion 962 will be aligned. Fluoroscopic image 954, shown in FIG. 151A, may be viewed to discern the alignment of distal end reference surface 990 with proximal end surface 1016. In the event that alignment pin 966 is not parallel to coronal plane 1008, as shown in misaligned fluoroscopic image 1018 in FIG. 151B, proximal end surface 1016 of distal arm portion 962 will not be aligned with distal end reference surface 990. Specifically, there will be a gap between proximal end surface 1016 and distal end reference surface 990 upon proximal end 972 of pin insertion guide 956 being located anteriorly. Alternatively, proximal end surface 1016 will appear on the fluoroscopic image (not shown) laterally of greater trochanter 110 and of distal end reference surface 990 upon proximal end 972 of pin insertion guide 956 being displaced excessively posteriorly. Additionally, geometric reference bores 965a-d provide an additional geometric reference which is discernible upon viewing a fluoroscopic image ("radio-discernable"), as shown in the detail of FIG. 151B.

Geometric reference bores 965a-d may be circular or another geometric shape suitable for a radio-discernable changing geometry upon rotation relative to coronal plane 1008. For example as shown in the detailed view of fluoroscopic image 1018 of FIG. 151B, geometric reference bores 965a-d, which are circular in the exemplary embodiment, are distorted to a radio-discernable ellipse having a major and minor axis because of rotation about lateral/medial axis 1010. Similarly, rotation about proximal/distal axis 1012 will distort the image of geometric reference bores 965a-d to radio-discernable ellipses each having a major and minor axis. Upon parallel alignment of implant pattern arms 963a-d with coronal femoral plane 1008, geometric reference bores 965a-d will provide a circular fluoroscopic image, as shown in FIG. 151A, or more clearly in FIG. 149. Rotational alignment of alignment arm 958, and thus implant pattern arms 963a-d, about lateral/medial axis 1010 is indicated on fluoroscopic image 952 shown in FIG. 151A by rotational reference pin 992 being aligned with alignment pin 966. Rotational misalignment about axis 1010 as indicated by rotational reference pin 992 being misaligned with alignment pin 966, i.e., viewed as non-colinear upon fluoroscopic imaging relative to coronal femoral plane 1008, and is also indicated by distortion of geometric references bores 965*a-d*, both as shown in fluoroscopic image 1018 of FIG. 151B.

Geometric reference bores 965*a-d* could be formed in a polygonal shape, e.g., a square, rectangle, or triangle. In operation, the use of the polygonal shape for geometric reference bores 965*a'-d'* and 965*a"-d"* would be substantially identical to the use of circular reference bores 965*a-d*. For example, if geometric reference bores 965*a'-d'* are square-shaped, as shown in FIG. 151C, reference bores 965*a'-d'* would appear as squares when alignment guide 950 is properly aligned with femur 108. Rotation about proximal/distal axis 1012 will misalign alignment guide 950, distort the image of geometric reference bores 965*a'-d'* to a radio-discernible shape such as a rectangle, and, additionally, change the view of geometric reference bores 965*a'-d'* from a top plan view to a perspective view, as shown in FIG. 151D. In another example, as shown in FIG. 151E, reference bores 965*a"-d"* would appear as equilateral triangles when alignment guide 950 is properly aligned with femur 108. Rotation about proximal/distal axis 1012 will misalign alignment guide 950, distort the image of geometric reference bores 965*a"-d"* to a radio-discernible shape such as an isosceles triangle, and, additionally, change the view of geometric reference bores 965*a"-d"* from a top plan view to a perspective view, as shown in FIG. 151F.

Referring now to FIG. 149, additional substantially radiopaque features of alignment guide 950 indicate the depth and diameter of the portion of implant cavity 224" which will be formed in the metaphysical region of femur 108 by plunge reamer 1020 (FIG. 153). Upon reference surface 990 contacting greater trochanter 110, distal end 1022 of fastener 994 indicates the medial depth of implant cavity 224" formed by the shortest of the exemplary plunge reamer 1020 lengths. Additionally, the breadth 1023 between notches 1024 and the largest dimension 1025 of proximal arm portions 1026 indicate the width of implant cavity 224" formed by plunge reamer 1020, which is approximately 18 mm (0.7 in.) for one embodiment. Indication of the width of implant cavity 224" allows verification that the selected position for cavity 224" will not result in perforation of the cortical wall of femur 108.

As can be comprehended from fluoroscopic image 954 (FIG. 151A), alignment guide 950 may be positioned relative to femur 108, i.e. rotated about anterior/posterior axis 1014 (FIG. 148) and translated parallel to coronal femoral plane 1008, so that implant cavity 224" will not cut through cortical bone of femoral neck 112 and so that the shortest plunge reamer 1020 will not cut through medial cortex 1028, located medial from greater trochanter 110. Additional radiopaque or visual references marks or structure(s) may be added to alignment guide 950 to aid in determining arc length 1009 (FIG. 174) from greater trochanter 110 to the cortex of femoral head 114 and in determining medial depth 1042 (FIG. 174) from greater trochanter 110 to the opposite femoral wall, medial cortex 1028, such as medial depth indicators 985 (FIG. 150) located on pin shaft 984, and to aid in selecting the appropriate length plunge reamer 1020 and implant size. Alternatively, medial depth 1042 and/or arc length 1009 may be determined pre- or intraoperatively based on X-ray or other anatomical images.

Positioning of alignment guide 950 is facilitated by holding alignment guide 950 at handle 970 such that pin head 986 presses against greater trochanter 110. Placement of pin head 986 firmly against greater trochanter 110 provides a pivot point about which alignment guide 950 may be rotated. To properly position implant pattern arms 963*a-b* or 963*c-d* relative to landmarks of femur 108, it may be necessary to select a revised point on greater trochanter 110 on which to stabilize pin head 986. Preferably, the selected one of pattern arms 963*a-d* is centrally located relative to neck 112 and head 114, as shown for pattern arm 963*b* in FIG. 151A. For the right femur, available arc radii 1307 of implants 1300 (FIG. 163A) are represented by pattern arms 963*a-b*. The best fit arc radii 1307, depending on the anatomy of femur 108, is selected with the aid of pattern arms 963*a-b* and fluoroscopic image 954. Fluoroscopic viewing and repositioning of alignment guide 950 provides for implant selection and location relative to landmarks of femur 108 as is further described below.

Each implant pattern arm 963*a-b* tracks a path from greater trochanter 110 through femoral neck 112 into femoral head 114. Each implant pattern arm 963*c-d* tracks a path from greater trochanter 110 through femoral neck 112 into the intramedullary canal of femur 108. More specifically, each implant pattern arm 963*a-b* tracks a central path from greater trochanter 110 through femoral neck 112 into femoral head 114 and each implant pattern arm 963*c-d* tracks a central path from greater trochanter 110 through femoral neck 112 into the intramedullary canal of femur 108, as shown in FIG. 151A.

Once the radiopaque references of alignment guide 950 are used to facilitate the desired selection and positioning of implant pattern arms 963*a-b* or 963*c-d* and distal arm portion 962, a mallet may be used to drive alignment pin 966 through the proximal cortical bone of greater trochanter 110 and through cancellous bone until pin head 986 contacts medial cortex 1028 across from greater trochanter 110. Contact of pin head 986 with medial cortex 1028 is generally audibly and tactilely indicated. The medial depth indicator 985 (FIG. 150) that is visible and closest to proximal end 972 of insertion guide 964 may be used as an indication of medial depth 1042 (FIG. 174) and is useful for selecting the length of cutting head 1034 (FIG. 153) of plunge reamer 1020. In one embodiment the length along the arc of lag tube 1306 and along the arc of implant tube 1304 (FIG. 161A) are selected based on medial depth 1042. In one embodiment, the length along the arc of lag tube 1306 and along the arc of implant tube 1304 are selected to be about equal to medial depth 1042.

After driving alignment pin 966 to medial cortex 1028, pin insertion guide 956 may then be slid distally off of alignment pin 966, with alignment pin 966 remaining in place, projecting from femur 108. Alignment pin 966 may then be used as a guide for reaming access 101, as described below. Alignment pin 966 is removed from femur 108 subsequent to reaming access 101. Advantageously, access 101 in greater trochanter 110 and the substantially planar surface of greater trochanter 110 provide a stable reference platform for positioning and orienting other instruments relative to femur 108. Additionally, access 101 in greater trochanter 110 provides access for other instruments used for forming features of implant cavity 224".

Referring to FIG. 152, portions of alignment guide 950 may be provided in a protective enclosure, for example, formed by enclosure top 1030 and enclosure bottom 1032, to ensure that components of alignment guide 950 have not been bent or otherwise damaged before use. For example, preassembled alignment guide arm 958, arm coupler 960, implant pattern arms 963*a-d*, and distal arm portion 962 may be encased in enclosure top 1030 and bottom 1032, the material of which may be brittle and subject to fracture, thus indicating rough handling and possible damage. For example, top 1030 and bottom 1032 can be less resilient than alignment guide 950 so that application of a force sufficient to cause plastic deformation of the enclosed components of alignment guide 950 will fracture enclosure top 1030 or bottom 1032. Enclosure top 1030 and/or bottom 1032 may also include a formed template which facilitates verification that all reference aspects of the contained components of alignment guide 950 are intact and not displaced or otherwise damaged from there original condition. Other embodiments of the enclosure may include other shapes, for example, cylindrical or a shape fitting the form of alignment guide 950. Alternatively, substantially all or at least a portion of the components of alignment guide 950 may be constructed of a memory material, such as nitinol, which returns to its preformed shape after unintended deformation.

With alignment pin 966 still protruding from greater trochanter 110, plunge reamer 1020, shown in FIG. 153, is used to form an initial implant cavity 224". Plunge reamer 1020 includes features of plunge reamer 480 shown in FIG. 82 and discussed below. Plunge reamer 1020 includes cutting head 1034, which may, for example, be a rigid fluted cutter, stop flange 1036, and shaft 1038, which may include a segment (not shown) for coupling with a chuck of rotary drive instrument 1040. Additionally, plunge reamer 1020 is cannulated so that alignment pin 966 may be received therein and guide cutting head 1034 as shown in FIG. 153. In one exemplary embodiment, a plurality of plunge reamers 1020 of different lengths are available, i.e., the dimension between distal end 1035 of cutting head 1034 and flange 1036 may be varied. The selection of the length is related to medial depth 1042 (FIG. 174) as determined according to the above described method. One embodiment of the invention includes plunge reamers 1020 for reaming to a depth of approximately 38 mm (1.5 in.), 48 mm (1.875 in.), and 58 mm (2.25 in.). Advantageously, plunge reamer 1020 will follow alignment pin 966, providing proper orientation of implant cavity 224", until stop flange 1036 contacts the surface of greater trochanter 110, providing the desired depth for implant cavity 224".

Figure 9:
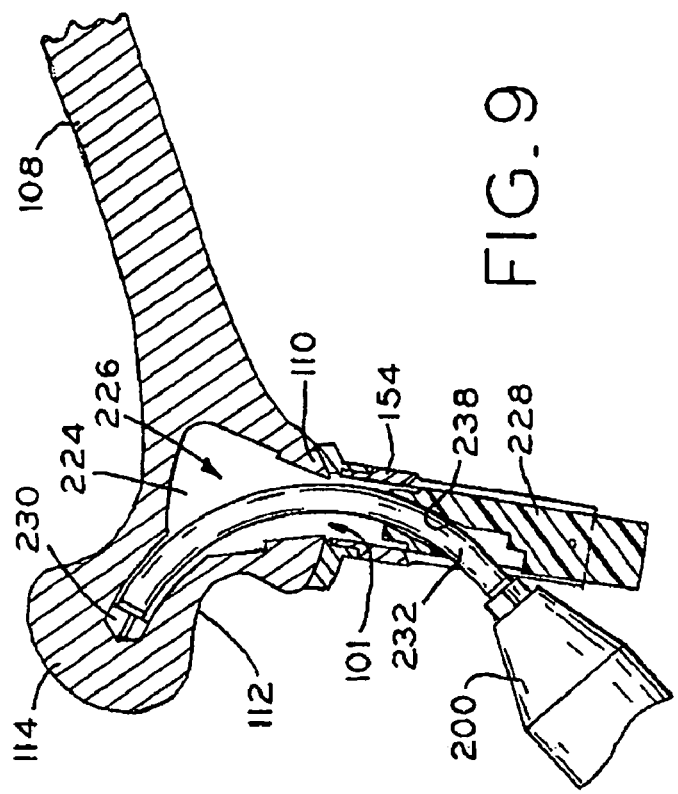
FIG. 9 is a sectional view illustrating the use of a curved femoral head reamer to extend the femoral cavity into the femoral head.
Figure 8:
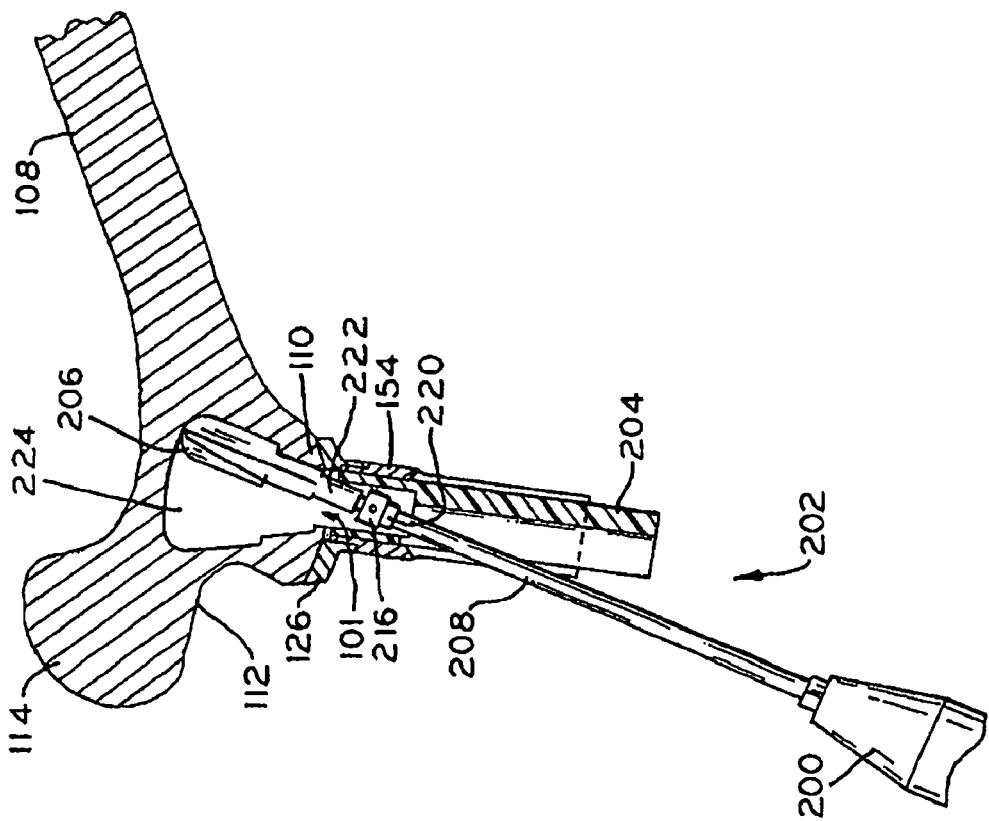
FIG. 8 is a sectional view illustrating further use of the swivel reamer depicted in FIG. 7 to form the femoral cavity.
Figure 10:
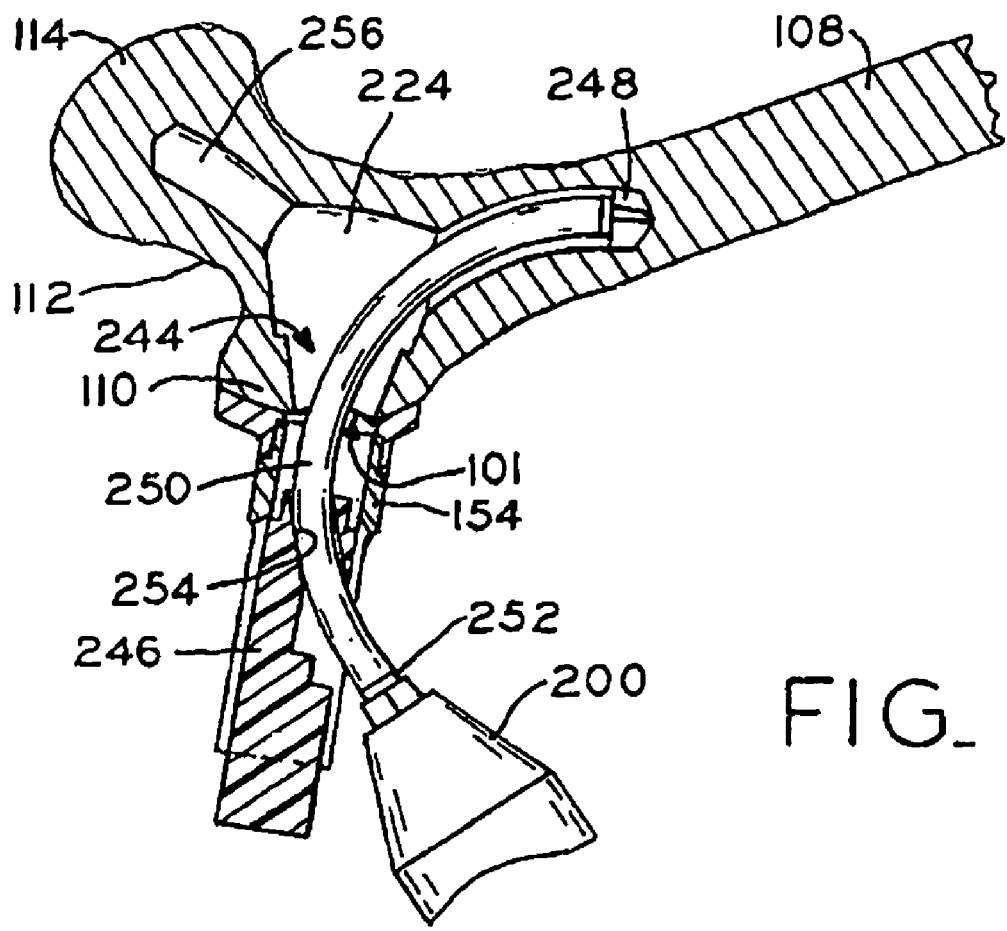
FIG. 10 is a sectional view illustrating the use of a curved femoral reamer to extend the femoral cavity into the intramedullary canal of the femur.

Returning now to the exemplary embodiment utilizing straight or angled guide tube/retractor 296 or 154, once the appropriate guide tube/retractor is chosen and attached to guide plate 126, cavity 224 (FIG. 11) can be formed in femur 108. As illustrated in FIG. 6, straight reamer 186 is first positioned within guide tube/retractor 154 and utilized to create access 101 in greater trochanter 110. In one exemplary embodiment, access 101 has a 1.9 centimeter (0.75 inch) diameter. After creating access 101 in greater trochanter 110, straight reamer 186 is removed from guide tube/retractor 154 and replaced with swivel reamer 202 as illustrated, e.g., in FIG. 7. As illustrated in FIG. 7, swivel reamer 202 is rotatable about pivot 216 and, in the configuration illustrated in FIG. 7, allows for the extension of femoral cavity 224 toward femoral head 114. After femoral cavity 224 is extended as illustrated in FIG. 7, swivel reamer 202 is repositioned to allow for extension of femoral cavity 224 toward the shaft of femur 108 as illustrated in FIG. 8. Swivel reamer 202 is then removed in favor of curved femoral head reamer 226. As illustrated in FIG. 9, curved femoral head reamer 226 is advanced through access 101 into femoral head 114, thus expanding femoral cavity 224 into femoral head 114. Curved femoral head reamer 226 is thereafter removed from guide tube/retractor 154 and replaced with curved femoral shaft reamer 244, as illustrated in FIG. 10. Curved femoral shaft reamer 244 is positioned through access 101 into the intramedullary canal of femur 108, as illustrated in FIG. 7, to extend femoral cavity 224 into the femoral shaft. The reaming process illustrated in FIGS. 6-10 produces femoral cavity 224 as illustrated, e.g., in FIG. 11.

Figure 31:
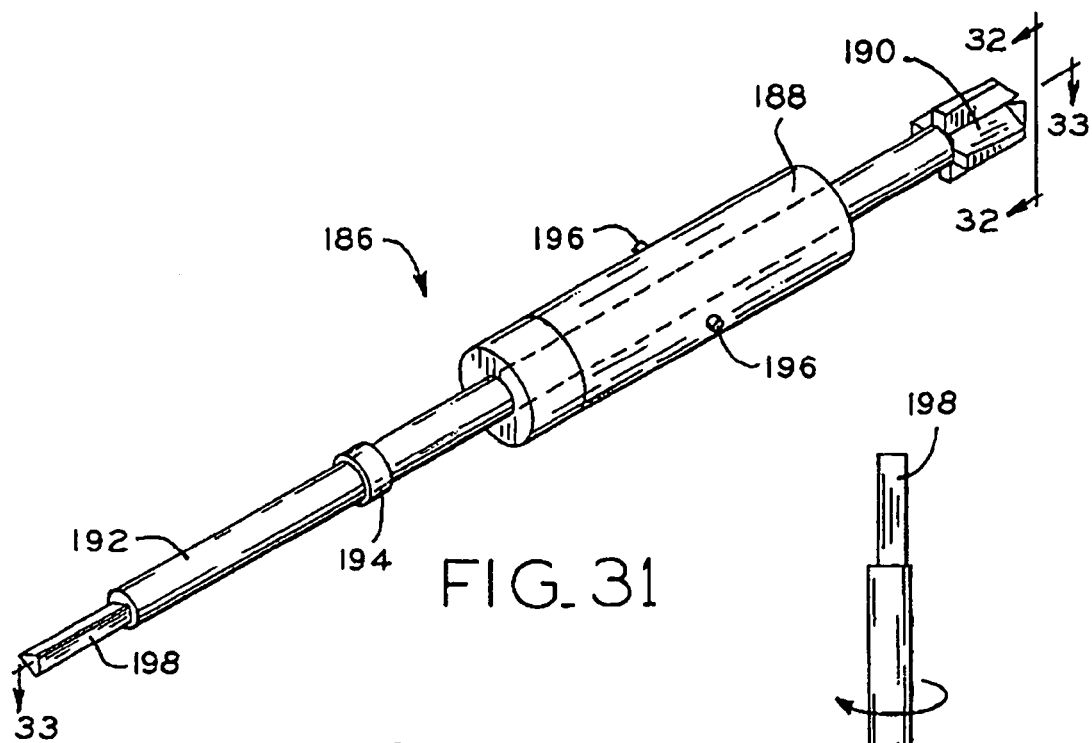
FIG. 31 is a perspective view of a straight reamer of the present invention.
Figure 32:
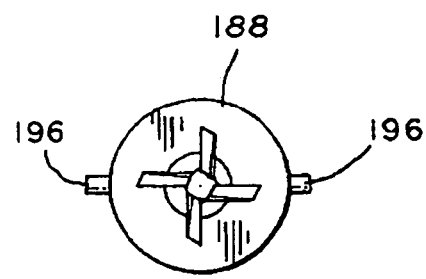
FIG. 32 is a distal axial view thereof.
Figure 33:
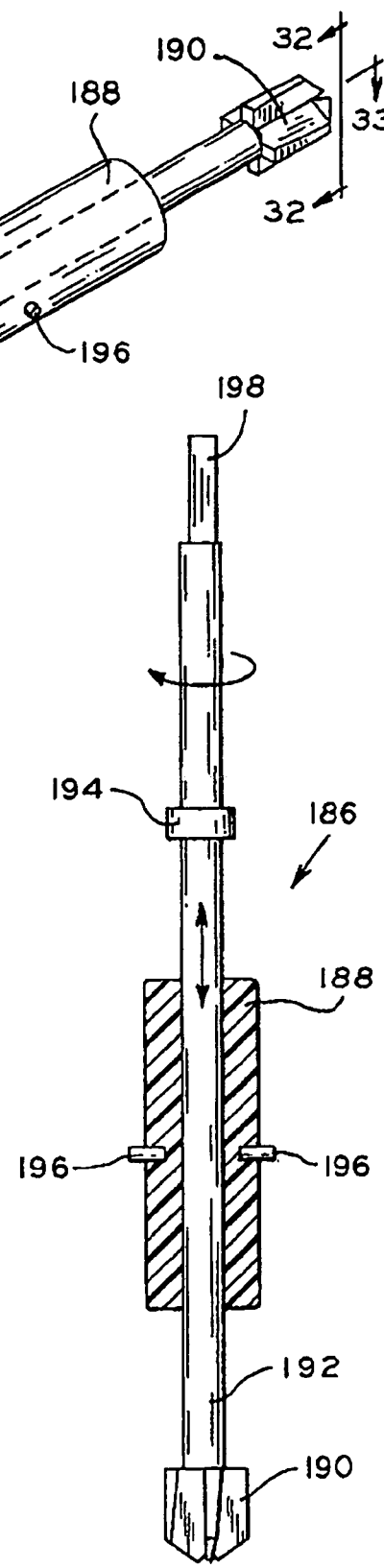
FIG. 33 is a partial sectional, elevational view thereof.
Figure 34:
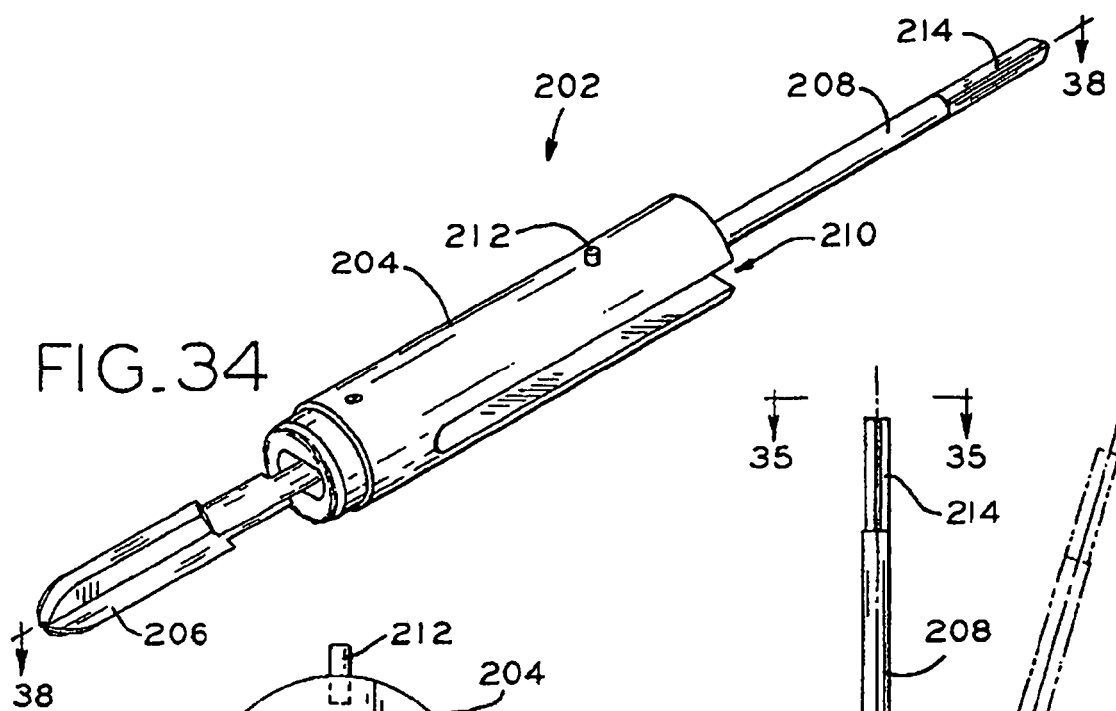
FIG. 34 is a perspective view of a swivel reamer of the present invention.
Figure 35:
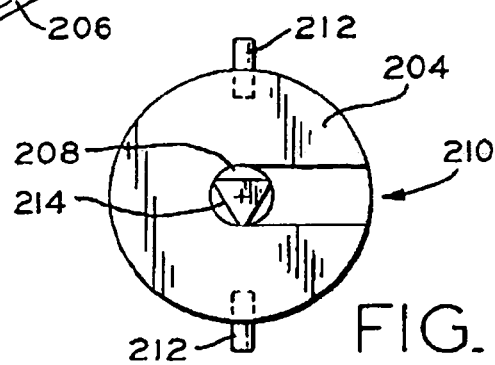
FIG. 35 is a proximal axial elevational view thereof.

Straight reamer 186 is illustrated in detail in FIGS. 31-33. As illustrated in FIGS. 31-33, straight reamer 186 includes straight reamer guide tube 188 surrounding straight reamer shaft 192. Straight reamer guide tube 188 is positioned intermediate straight reamer head 190 and flange 194 and is operable to move along reamer shaft 192 therebetween. Straight reamer guide tube 188 as an exterior geometry cooperating with the internal geometry of straight guide tube/retractor 154 and/or angled guide tube/retractor 296 to provide a solid base for reaming femur 108 as illustrated in FIG. 6. Straight reamer 186 further includes proximal end 198 adapted to be received in chuck 200 (FIG. 6) of any of the well known rotation devices utilized to impart rotational motion to various medical instruments including, e.g., reamers. Straight reamer guide tube 188 includes opposing bosses 196 protruding from the exterior surface thereof. Bosses 196 are engageable in boss channels 304 formed in the proximal end of the guide tube/retractors of the present invention (see, e.g., FIGS. 23, 24, and 28).

In use, straight reamer guide tube 188 is positioned within a guide tube/retractor of the present invention, with bosses 196 entering boss channels 304 formed in a proximal end thereof. Guide tube 188 is then rotated until bosses 196 are positioned beneath the lip formed by the proximal end of straight guide tube/retractor of the present invention covering the radially extending portions of boss channels 304. In this position, guide tube 188 cannot readily be axially displaced relative to the guide tube/retractor into which it is inserted. Proximal end 198 of straight reamer 186 is actuated to provide rotational movement of reamer head 190 to form access 101 in femur 108. After achieving a predetermined reamer depth, flange 194 contacts the proximal end of guide tube 188 to limit axial displacement of reamer head 190. In one exemplary embodiment, straight reamer 186 is configured to provide a reaming depth of 1.9 centimeters (0.75 inches) into femur 108.

Figure 38:
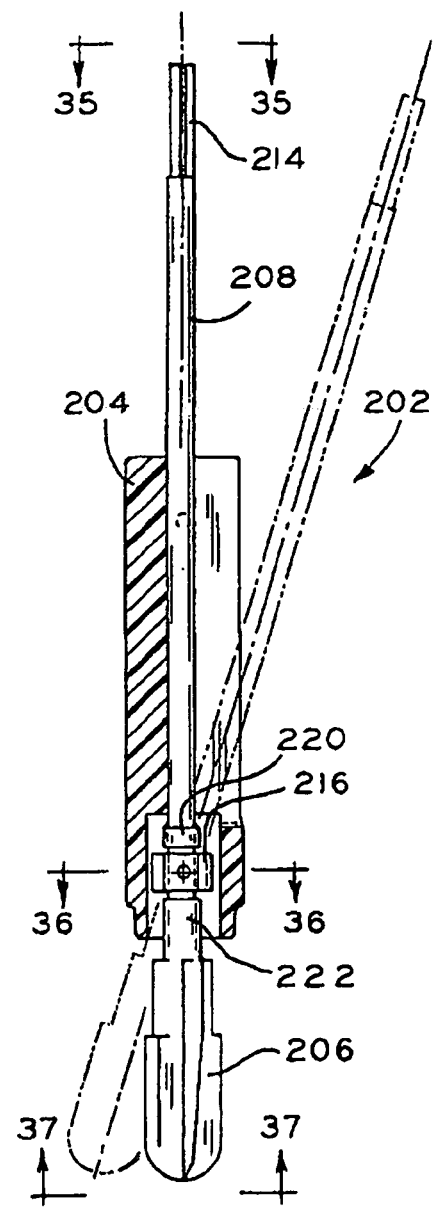
FIG. 38 is a partial sectional, radial elevational view of the swivel reamer of the present invention.

Swivel reamer 202 is illustrated in detail in FIGS. 34-38. As illustrated in FIGS. 34-38, swivel reamer 202 includes swivel reamer guide tube 204 having opposing bosses 212 protruding therefrom. Swivel reamer guide tube 204 includes cutout 210 operable to allow reamer shaft 208 to pivot about swivel reamer pivot 216 as further described below and as illustrated in FIG. 38. Similar to straight reamer 186, swivel reamer 202 includes proximal end 214 operable to connect swivel reamer 202 to chuck 200 (FIG. 7). Bosses 212 are utilized to connect swivel reamer 202 to a guide tube/retractor of the present invention in the same manner as bosses 196 of straight reamer 186.

Figure 36:
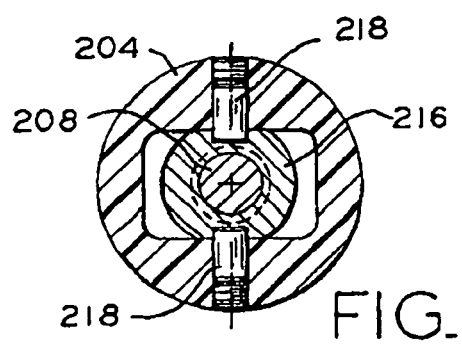
FIG. 36 is a sectional view taken along line 36-36 of FIG. 38.
Figure 37:
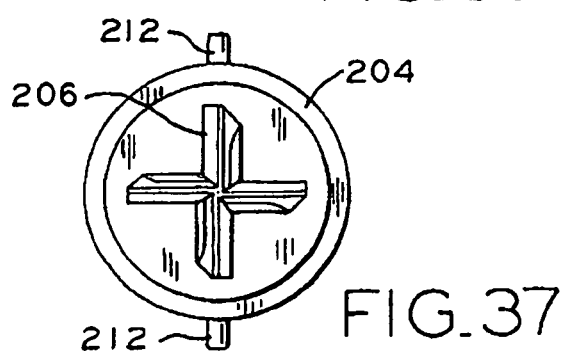
FIG. 37 is a distal axial elevational view thereof.

As illustrated in FIG. 36, swivel reamer pivot 216 is pivotally connected to swivel reamer guide tube 204 via pivot pins 218. As illustrated in FIG. 38, swivel reamer pivot 216 is positioned about reamer shaft 218 and abuts enlarged portion 222 of swivel reamer shaft 208 and flange 220 on opposing axial ends thereof to prevent axial displacement of swivel reamer head 206. As illustrated in FIGS. 7 and 8 and described hereinabove, the orientation of swivel reamer 202 is changed 180 degrees to accommodate swivel reaming toward femoral head 114 as illustrated in FIG. 7 as well as swivel reaming toward the femoral shaft as illustrated in FIG. 8. As illustrated, e.g., in FIGS. 23-25 and 28, the guide tube/retractors of the present invention includes opposing cut-outs 305 to accommodate swivel reaming toward femoral head 114 as illustrated in FIG. 7 as well as swivel reaming toward the femoral shaft as illustrated in FIG. 8, without repositioning the guide tube/retractor.

Figures 39, 40:
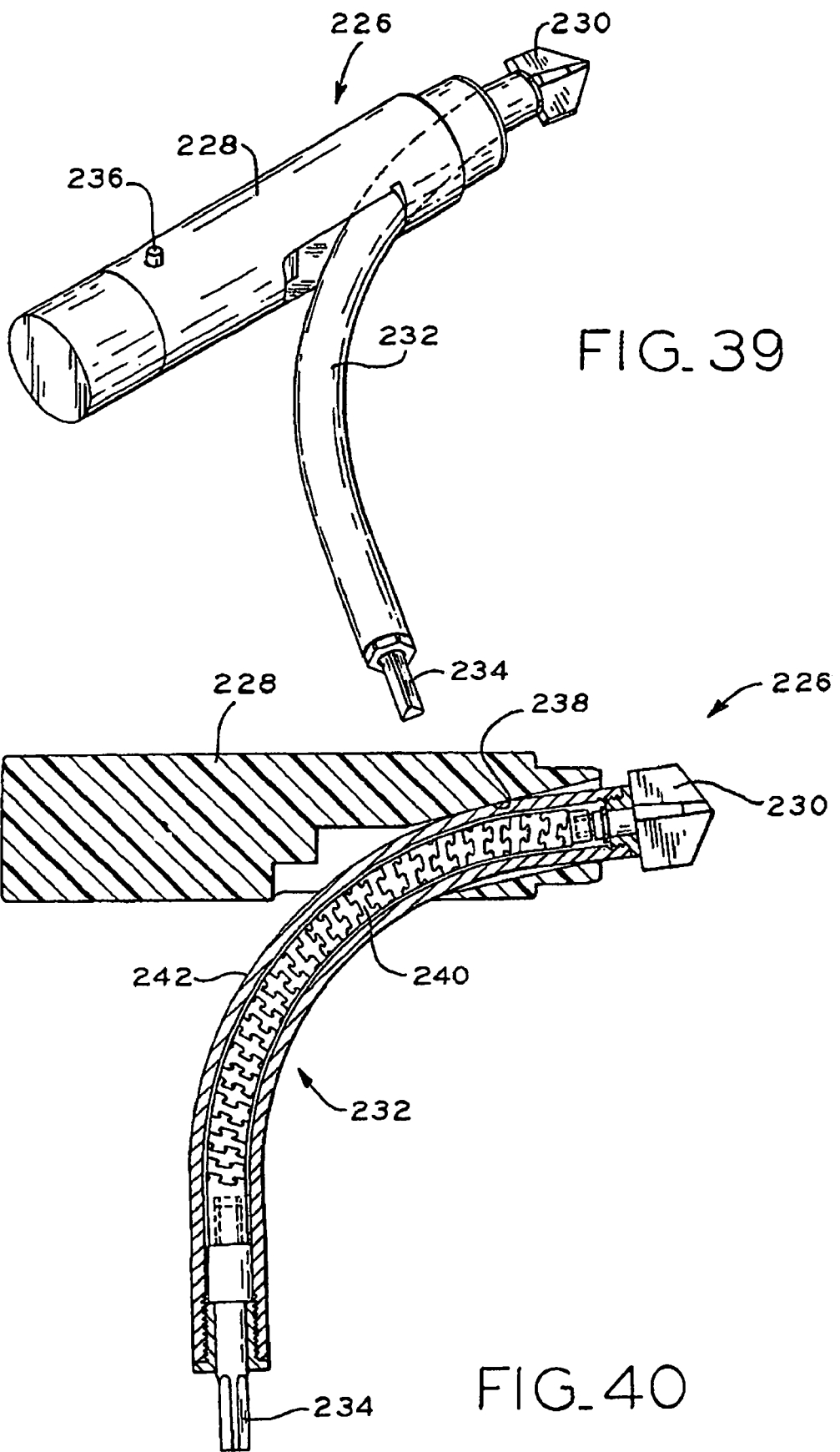
FIG. 39 is a perspective view of a curved femoral head reamer of the present invention.
FIG. 40 is a sectional view thereof.

Curved femoral head reamer 226 is illustrated in detail in FIGS. 39 and 40. As illustrated in FIGS. 39 and 40, curved femoral head reamer 226 includes guide tube 228 having bosses 236 protruding therefrom. Bosses 236 are utilized to position curved femoral head reamer 226 within a guide tube/retractor of the present invention as described above with respect to straight reamer 186 and swivel reamer 202. Curved femoral head reamer 226 includes curved reamer shaft 232 having reamer head 230 operably connected to a distal end thereof. Proximal end 234 of curved reamer shaft 232 is operable to connect curved reamer 226 to chuck 200 of an actuation device as illustrated in FIG. 9. As illustrated in FIG. 40, curved reamer shaft 232 comprises a hollow shaft formed by outer tube 242. Flexible driveshaft 240 is positioned within outer tube 242 and allows for transmission of rotary motion from proximal end 234 of curved reamer 226 to reamer head 230 to effect reaming into femoral head 114 as illustrated in FIG. 9. Flexible driveshaft 240 may include various flexible cuts, including the flexible cuts described in U.S. Pat. No. 6,053,922. Guide tube 228 of curved femoral head reamer 226 includes curved guide channel 238 for guiding movement of outer tube 242 of reamer shaft 232 as reamer head 230 is advanced into femoral head 114 as illustrated in FIG. 9. Curved femoral shaft reamer 242 has an identical structure to curved femoral head reamer 226 and, therefore, is not illustrated in detail for the sake of brevity. In an exemplary embodiment of the present invention, the head of curved femoral shaft reamer 242 is larger than the head of curved femoral head reamer 226. Similarly, the head of curved femoral head reamer 226 may be larger than the head of curved femoral shaft reamer 242. Moreover, the radius of curvature of the reamer shafts may differ between curved femoral head reamer 226 and curved femoral shaft reamer 242. In all cases, a tubular reamer shaft and flexible driveshaft is utilized.

Figure 99:
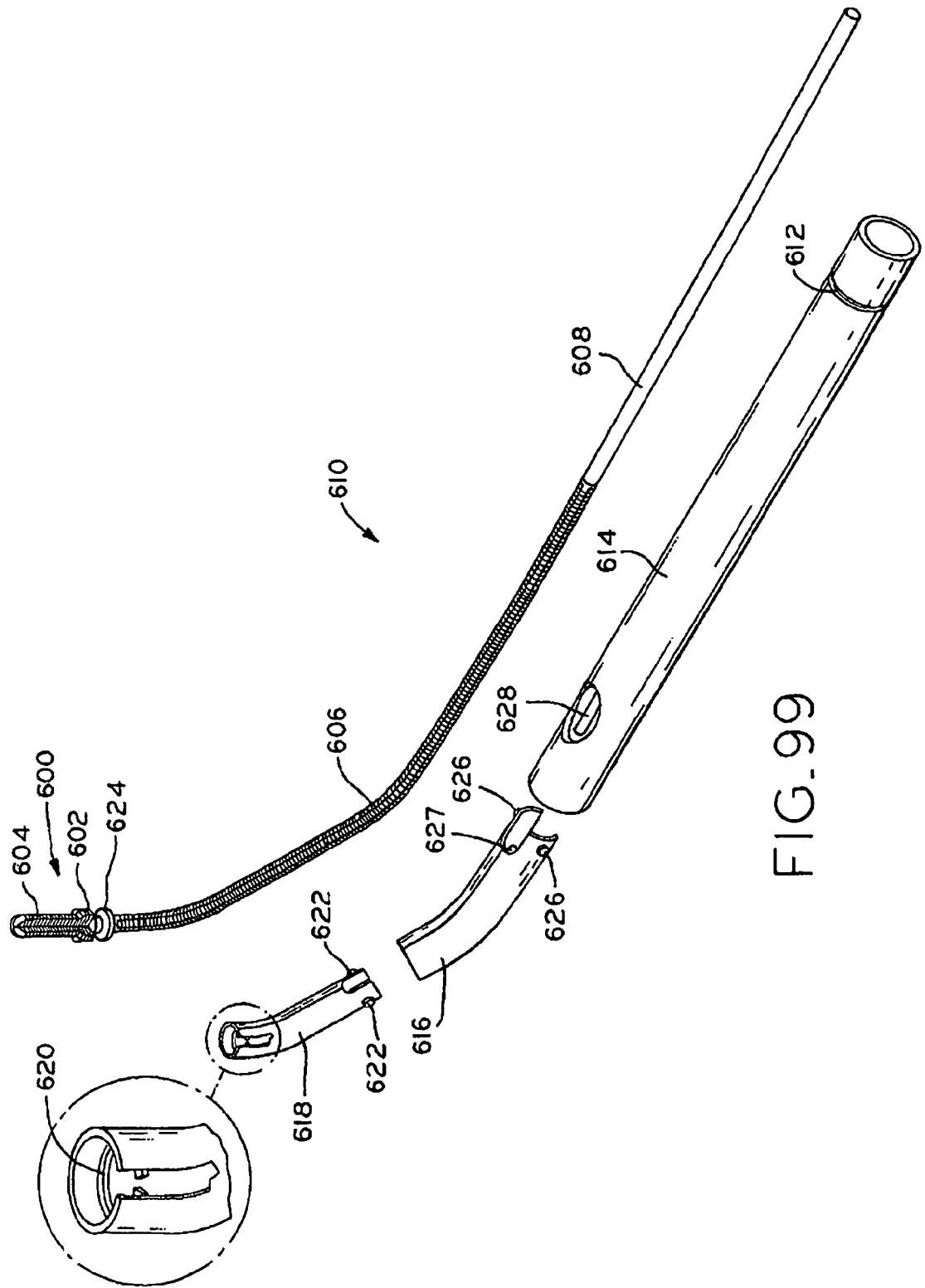
FIG. 99 is an exploded view of the telescoping reamer of FIGS. 97 and 98.

Telescoping reamer 610 illustrated in FIGS. 97-99 may be utilized in lieu of curved femoral head reamer 226 and/or curved femoral shaft reamer 242. While illustrated in FIGS. 97-99 with a flex up reamer head (described below), telescoping reamer 610 may be utilized with other reaming heads including, e.g., a reaming head adapted for extending the implant cavity distally into the intramedullary canal of the femoral shaft. Referring to FIGS. 97-99, telescoping reamer 610 includes body 614 having detent groove 612 formed in an exterior thereof. Detent groove 612 is useful for receiving the ball detent of the ball detent retaining mechanism described below, although body 614 may include any of the mechanisms disclosed herein for positioning and/or locking an instrument into any of the guide tube/retractors of the present invention.

Referring to FIG. 99, in construction, outer extension sleeve 616 is positioned within body 614 of telescoping reamer 610, with exterior bosses 626 of outer extension sleeve 616 positioned within internal channels 628 (only one of which is depicted in FIG. 99) of body 614. Similarly, inner extension sleeve 618 is positioned within outer extension sleeve 616, with exterior bosses 622 of inner extension sleeve 618 positioned within internal channels 627 (only one of which is depicted in FIG. 99) of outer extension sleeve 616. Internal channels 627 and 628 of outer extension sleeve 616, and body 614, respectively, guide the direction and extent of relative movement between inner extension sleeve 618 and outer extension sleeve 616, and outer extension sleeve 616 and body 614, respectively. Both channels 627 and 628 have proximal and distal ends. When bosses 622, and 626 are positioned adjacent the proximal ends of channels 627 and 628, respectively, telescoping reamer 610 maintains the retracted position illustrated in FIG. 98. Similarly, when bosses 622 and 626 abut the distal ends of channels 627 and 628, respectively, telescoping reamer 610 maintains the extended position illustrated in FIG. 97.

As illustrated in FIGS. 97-99, body 614 of telescoping reamer 610 includes a cutout accommodating the proximal end of outer extension sleeve 616 when telescoping reamer 610 maintains the retracted position illustrated in FIG. 98. In construction, flexible reamer shaft 606 is positioned within inner extension sleeve 618 and, consequently, within outer extension sleeve 616 and body 614. The reamer shaft runs the length of body 614, with straight reamer shaft 608 extending from a distal end thereof. As illustrated in FIG. 99, flange 624 is positioned about flexible reamer shaft 606 and spaced from the proximal portion of large diameter portion 602 of flex up reamer 600 (further described below). In construction, interior flange 620 of inner extension sleeve 618 is positioned intermediate large diameter portion 602 of flex up reamer 600 and flange 624 extending from flexible reamer shaft 606.

To extend telescoping reamer 610 from the non-extended position illustrated in FIG. 98 to the extended position illustrated in FIG. 97, force F (FIG. 98) having a vector component parallel to the longitudinal axis of straight reamer shaft 608 is applied to straight reamer shaft 608, placing flange 624 in abutting relationship with interior flange 620 of inner extension sleeve 618. As additional force is applied to straight reamer shaft 608, the abutting relationship of flange 624 and interior flange 620 causes extension of inner extension sleeve 618 outwardly from outer extension sleeve 616 and, consequently, body 614. Inner extension sleeve 618 extends from outer extension sleeve 616 until bosses 622 abut the distal ends of internal channels 627 of outer extension sleeve 616. In this position, additional force applied to straight reamer shaft 608 causes extension of outer extension sleeve 616 out of body 614. Outer extension sleeve 616 extends until exterior bosses 626 abut the distal ends of internal channels 628 of body 614. In this position, telescoping reamer 610 is fully extended as illustrated in FIG. 97. Inner extension sleeve 618 and outer extension sleeve 616 may be formed with various curvatures accommodating reaming from greater trochanter 110 into femoral head 114, as well as reaming from greater trochanter 110 into the intramedullary canal of femur 108.

To retract telescoping reamer 610 from the extended position illustrated in FIG. 97 to the non-extended position illustrated in FIG. 98, straight reamer shaft 608 is pulled in a generally opposite direction to force F illustrated in FIG. 98. When straight reamer shaft 608 is pulled in this manner, the reamer head pulls inner extension sleeve 618 into outer extension sleeve 616 until bosses 622 abut the proximal ends of internal channels 627 of outer extension sleeve 616. In this position, additional pulling of straight reamer shaft 608 pulls outer extension sleeve 616 into body 614 until telescoping reamer 610 achieves the non-extended position illustrated in FIG. 98.

Figure 103:
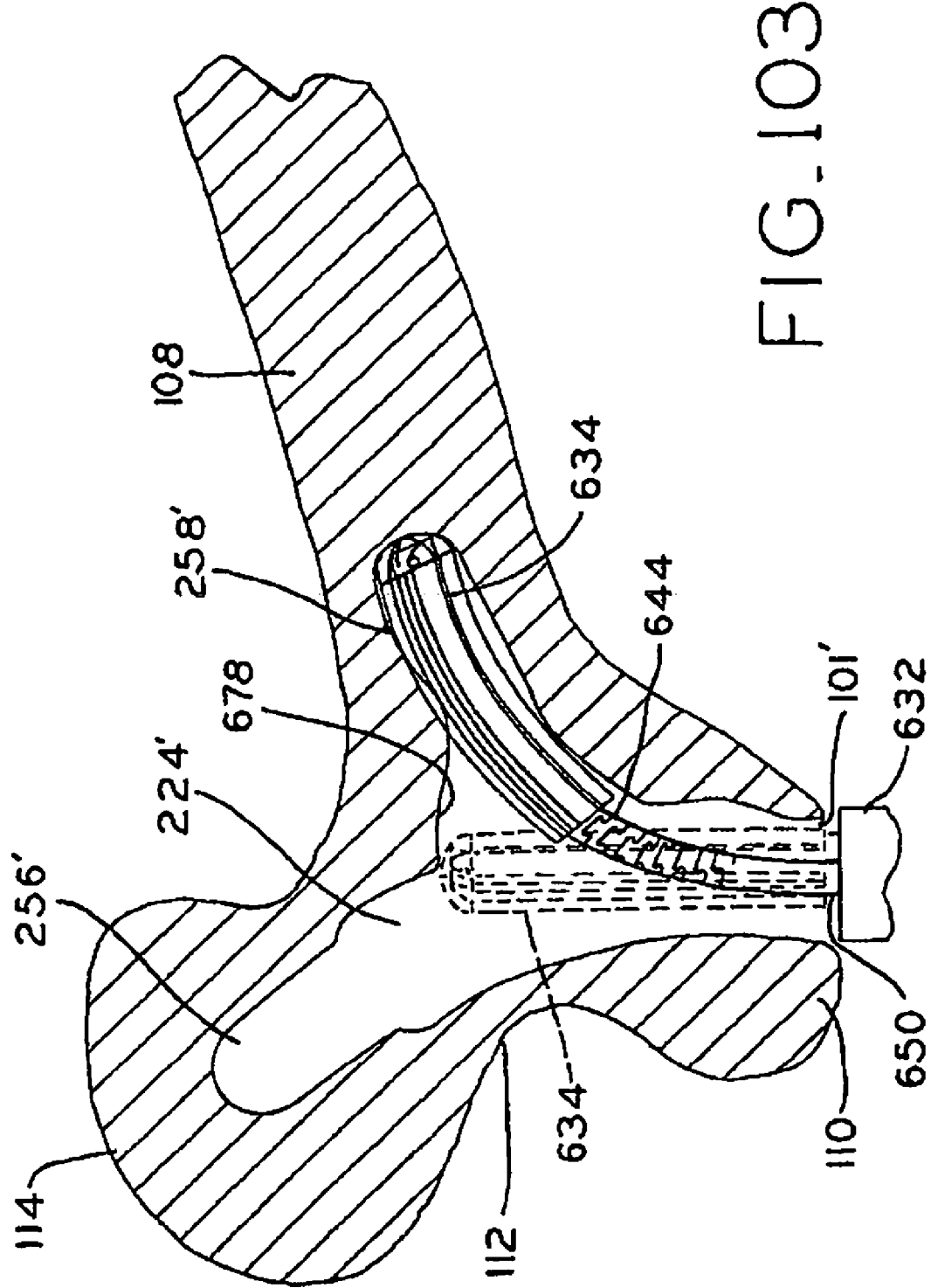
FIG. 103 is a partial elevational view illustrating use of the swivel/down reamer assembly depicted in FIGS. 100-102 to extend the femoral cavity into the intramedullary canal.

In use, telescoping reamer 610 is inserted through incision 106 and secured within a guide tube/retractor of the present invention. Telescoping reamer 610 may be utilized to form access 101 in femur 108 in lieu of straight reamer 186 illustrated in FIG. 6. Alternatively, straight reamer 186 may be utilized to form access 101 in femur 108 prior to insertion of telescoping reamer 610 through incision 106. In any event, after straight reaming is complete and access 101 is formed in femur 108 as illustrated in FIG. 6, telescoping reamer 610 is oriented whereby extension of telescoping reamer 610 from the non-extended position illustrated in FIG. 98 to the extended position illustrated in FIG. 97 extends implant cavity 224' into femoral head 114, forming femoral head arm 256' of implant cavity 224' as illustrated in FIG. 103. In certain embodiments, telescoping reamer may be reoriented to extend from greater trochanter 110 into the intramedullary canal of femur 108 to form femoral shaft arm 258' of implant cavity 224'. In such an embodiment, telescoping reamer 610 will not include a reamer head having a pair of reaming diameters as illustrated in FIGS. 97-99.

Second exemplary telescoping reamer 1044, shown in FIG. 156A is similar to telescoping reamer 610 above and may be similarly used to form femoral head arm 256" of implant cavity 224", as shown in FIGS. 154 and 155. Referring to FIG. 156A, telescoping reamer 1044 generally includes body 1046, driveshaft 1048, flexible shaft 1050, telescoping guide 1051, and reamer head 1052. Body 1046 includes handle 1054 and shaft guide 1056. Handle 1054 is cannulated to receive driveshaft 1048. Telescoping guide 1051 includes clamshell base 1057, distal clamshell cover 1058, proximal clamshell cover 1060, outer extension sleeve 1072, and inner extension sleeve 1077, all of which are cannulated or grooved to receive and arcuately guide flexible shaft 1050. Shaft guide 1056 is also cannulated to receive driveshaft 1048 therethrough.

Reamer head 1052 (FIG. 156C) is fixed to distal end 1062 of flexible shaft 1050 by, for example, pin 1063 and/or welding. Male key 1064 (FIG. 156A) and left hand male thread 1066 are defined at proximal end 1068 of flexible shaft 1050. Body 1046 is designed to be removed from flexible shaft 1050 without removing reamer head 1052 from implant cavity 224", for example, in the event it becomes necessary to dislodge reamer head 1052 from implant cavity 224". In one embodiment, driveshaft 1048 may be removably coupled to flexible shaft 1050 so that driveshaft 1048 can be proximally removed from body 1046 and, subsequently, body 1046 can be proximally removed from flexible shaft 1050.

Telescoping reamer 1044 provides this disassembly feature by means of rotating link 1070. Rotating link 1070 is coupled to distal end 1071 of driveshaft 1048 while allowing relative rotation. For example, rotating link 1070 may include spring clips 1073 so that link 1070 may be coupled to distal end 1071 of driveshaft 1048 while allowing relative rotation. Rotating link 1070 is cannulated and includes an internal left-hand female thread (not shown) for receiving left-hand male thread 1066 of flexible shaft 1050. The threads of rotating link 1070 in flexible shaft 1052 are left-handed so that the connection formed by engagement of the threads does not loosen upon driving driveshaft 1048 in a clockwise direction (as viewed from the proximal end of reamer 1044). Distal end 1071 of driveshaft 1048 defines keyway 1069 for receiving male key 1064 of flexible shaft 1050. Key 1064 and keyway 1069 transmit rotational torque from driveshaft 1048 to flexible shaft 1050, while the threads of rotating link 1070 engaged with threads 1066 of flexible shaft 1050 axially retains flexible shaft 1050 relative to driveshaft 1048 so that key 1064 is held engaged within keyway 1069. Removal of proximal clamshell cover 1060, for example, by removing fasteners 1067, provides access to rotating link 1070 for coupling or uncoupling of driveshaft 1048 from flexible shaft 1050.

Referring to FIGS. 154 and 155, in operation, telescoping guide 1051 guides reamer head 1052 along an earlier selected arc, as described hereinabove, having arc radius 1007 (FIG. 174). Referring to FIGS. 156A-C, in construction, outer extension sleeve 1072 is slidably positioned within base 1057 and distal cover 1058, with exterior boss 1074 of outer extension sleeve 1072 engageable with channel 1076 (FIGS. 156B and 156C) of distal cover 1058. Similarly, inner extension sleeve 1077 is slidably positioned within outer extension sleeve 1072, with interior bosses 1078, located adjacent distal end 1082 of outer extension sleeve 1072, positioned within slot 1080 (FIG. 156A) of inner extension sleeve 1077.

Engagement of channel 1076 with exterior boss 1074, and of slot 1080 with interior bosses 1078, guide the extent of relative movement between outer extension sleeve 1072 and base 1057, and inner extension sleeve 1077 and outer extension sleeve 1072, respectively. The engagement also rotationally fixes inner extension sleeve 1077 and outer extension sleeve 1072 relative to body 1046, thus constraining translation of reamer head 1052 through an arc residing in a single plane of motion, for example coronal femoral plane 1008, or a plane of anteversion based thereon. Specifically, coronal femoral plane 1008 is defined as the plane which centrally intersects greater trochanter 110 and the shaft of femur 108 extends. The plane of anteversion is defined as the plane which centrally intersects greater trochanter 110, femoral neck 112, and femoral head 114. The plane of anteversion is generally rotated about 15° about lateral/medial axis 1010 relative to coronal femoral plane 1008, clockwise for the right femur 108 when viewed from a lateral aspect.

Referring to FIG. 156C, base 1057 and distal cover 1058 each define arcuate channel 1084 and 1086, respectively, for arcuately guiding outer extension sleeve 1072. Additionally, clearance slot 1088 (FIGS. 156B-C) defined by distal cover 1058 provides clearance for nested outer extension sleeve 1072 and inner extension sleeve 1077 in the retracted position shown in FIGS. 154 and 156C. Access 101 and implant cavity 224" are substantially the shape of cutting head 1034. Cylindrical surfaces 1059 and 1061 of distal cover 1058 and base 1057, respectively, are sized and shaped to substantially match access 101, thereby aligning longitudinal axis 1096 of telescoping reamer 1044 relative to femur 108. Additionally, shoulders 1092 and 1094 of clamshell base 1057 and cover 1058 form a surface for abutting greater trochanter 110, facilitating further stabilization and positioning of telescoping reamer 1044 relative to femur 108.

Referring to FIG. 156A, slot 1080 has distal end and proximal end. Channel 1076 (FIGS. 156B-C) has a distal end and also a proximate end defined by the proximal end of clearance slot 1088. Upon bosses 1074 and 1078 abutting the proximate ends of channel 1076 and slot 1080, respectively, telescoping reamer 1044 maintains the retracted position illustrated in FIGS. 154 and 156C. Upon bosses 1074 and 1078 positioned adjacent the distal ends of channel 1076 and slot 1080, respectively, telescoping reamer 1044 maintains the extended position illustrated in FIG. 155. Referring to FIG. 156C, which shows a cross-section of telescoping reamer 1044, flexible shaft 1050 includes a portion having a reduced diameter (as shown) or groove that is located adjacent distal end 1062 and that receives interior flange 1083 of inner extension sleeve 1077, thereby fixing inner extension sleeve 1077 relative to the longitudinal axis of flexible shaft 1050. This engagement also provides for translation of inner extension sleeve 1077 and outer extension sleeve 1072 responsive to axial translation of driveshaft 1048 and flexible driveshaft 1050.

Inner extension sleeve 1077 includes elongate opening 1085 (FIG. 156A) which extends longitudinally along a portion of the length of sleeve 1077 adjacent proximal end 1089 and 180° opposite slot 1080. Similarly, outer extension sleeve 1072 includes elongate opening 1087 (detail of FIG. 156A) extending longitudinally along a portion of the length of sleeve 1072, adjacent proximal end 1091 and 180° opposite boss 1074. In the retracted position shown in FIG. 156C, proximal ends 1089 and 1091 of sleeves 1077 and 1072, respectively, extend upwardly out of arcuate channels 1084 and 1086 and into clearance slot 1088. In this position, both elongate openings 1085 and 1087 provide clearance for flexible shaft 1050 which is substantially axially aligned with driveshaft 1048.

Cylindrical surfaces 1061 and 1059 of base 1057 and distal cover 1058, respectively, and shoulder 1092 and 1094 of base 1057 and distal cover 1058, respectively, provide for accurate, stable positioning of telescoping reamer 1044 in implant cavity 224" and against greater trochanter 110 at access 101, as shown in FIG. 154.

Rotational alignment about longitudinal axis 1096 of telescoping reamer 1044 determines the path of femoral head arm 256" of implant cavity 224" relative to coronal femoral plane 1008 (FIG. 148), and thus relative to femoral neck 112 and head 114. For typical femoral anatomy, approximately 12-18 degrees of anteversion exist for femoral neck 112 and head 114 relative to coronal femoral plane 1008. To accommodate typical anteversion, reference marks 1100 and 1098 (FIG. 156D) indicate 90 degrees and 65 degrees clockwise rotation, respectively, from the plane that reamer head 1052 translates through. Therefore, after insertion of the distal portion of shaft guide 1051 into implant cavity 224", telescoping reamer 1044 is rotated to locate reference mark 1098 at an anterior most position, substantially colinear with anterior/posterior axis 1014 (FIG. 148) and perpendicular relative to coronal femoral plane 1008, thus locating reamer head 1052 approximately 15 degrees anteriorly from coronal femoral plane 1008 in the plane of anteversion defined above, thereby accounting for typical femoral anteversion.

Referring to FIG. 156A and specifically the detail of clamshell base 1057 and distal clamshell cover 1058, an interlock is provided distally to retain cover 1058 to base 1057. Specifically, protrusions 1102 on opposite sides of arcuate channel 1084 of base 1057 engage receptacles 1104 located at opposite sides of channel 1086 of cover 1058. A proximal end of cover 1058 is retained to base 1057 by engagement of flanges 1106 within recesses 1108 upon proximal cover 1060 being coupled to base 1057 by fasteners 1067. Cover 1058 may also include arcuate end 1005 to provide clearance for reamer head 1052.

Referring to FIG. 155, as telescoping reamer 1044 is utilized by driving drive shaft 1048 rotationally and axially to form femoral head arm 256" of implant cavity 224", a fluoroscopic or other suitable image may be used to determine the depth to which femoral head arm 256" of implant cavity 224" is formed relative to femoral head 114. Specifically, fluoroscopy may assist in determining that reamer head 1052 forms femoral head arm 256" of implant cavity 224" into a central portion of femoral head 114, but not into the cortical bone along the circumference of femoral head 114. Length markings 1110 located adjacent flange 1112 of driveshaft 1048 may be used to determine the length of femoral head arm 256" of implant cavity 224" and of the implant length. Alternatively, if an implant length is previously determined, the required reaming depth may be determined by reference to length markings 1110. Each length marking 1110 corresponds with a selected implant length. When reamer head 1052 is fully extended to the desired depth into femoral head 114, the particular one of length markings 1110 which is closest to handle 1054 indicates the appropriate implant for the formed femoral head arm 256" of implant cavity 224" length. Flange 1112 limits the distal extension of reamer head 1052 by contact with a proximal end of handle 1054.

After formation of femoral cavity 224, any remaining guide tube/retractor as well as guide plate 126 is removed and implant 260 is positioned through access 101 to be implanted in femoral cavity 224. During implantation of implant 260, retractors are utilized to provide access from incision 106 to access 101 formed in femur 108. As illustrated in FIG. 12, bag 270 (FIG. 41) is manipulated into a relatively small package positioned adjacent lag screw tube 266 before inserting implant 260 through access 101. In one exemplary embodiment, bag 270 is accordion folded. As further illustrated in FIG. 12, fill tube 262 and reinforcement/expansion bar 268 of femoral implant 260 are positioned adjacent lag screw tube 266 for positioning implant 260 through access 101 and into femoral cavity 224. When femoral implant 260 is fully inserted through access 101, lag screw thread 282 abuts the entry to femoral head arm 256 of implant cavity 224 as illustrated, e.g., in FIG. 13. In this position, fill tube 262 and reinforcement/expansion bar 268 can be manipulated into the operable position illustrated in FIG. 14. In this position, bag 270 extends into femoral shaft arm 258 of implant cavity 224.

Figure 14:
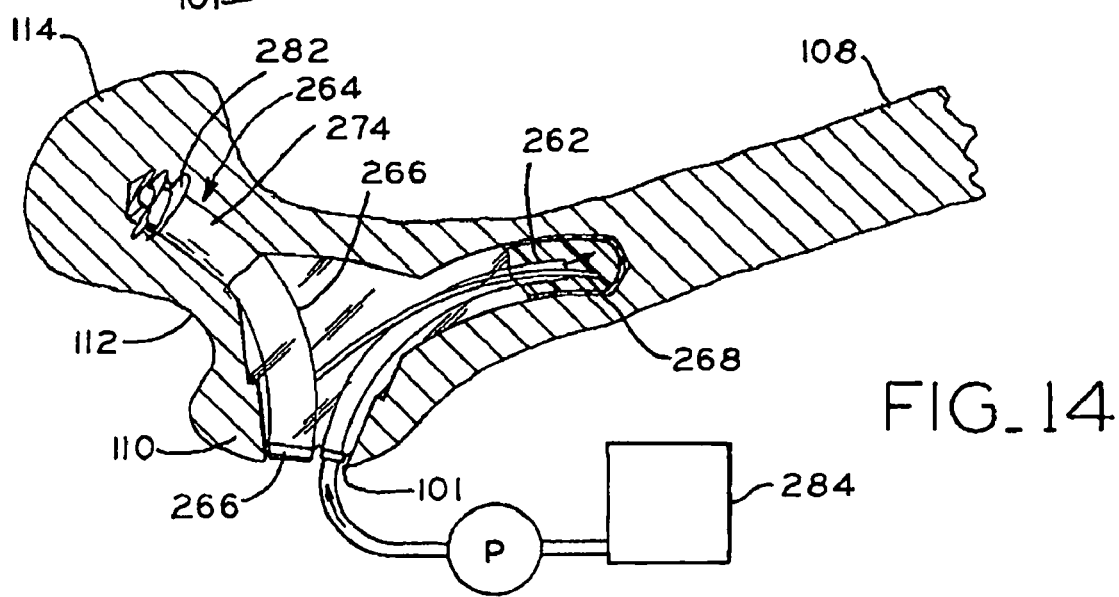
FIG. 14 is a sectional view illustrating extension of a lag screw through the lag screw tube and into the femoral head, as well as a pump and source of bag fill, e.g., bone cement, utilized to fill the bag of the femoral implant of the present invention.

After implant 260 is positioned as illustrated in FIG. 13, a flexible drive device is utilized to advance lag screw 264 into femoral head 114 until reaching the terminal position illustrated in FIG. 14. With lag screw 264 firmly implanted in femoral head 114, pump P is utilized to convey a bag fill material for filling bag 270 from source of bag fill 284 through fill tube 262. In one exemplary embodiment, source of bag fill 284 comprises a source of bone cement. Fill tube 264 is formed to provide for retrograde filling of bag 270. As bag 270 is filled with, e.g., bone cement, it expands to fill femoral cavity 224, including, femoral shaft arm 258 thereof. Once bag 270 is filled, the bone cement injected therein cures and provides intramedullary fixation of femoral implant 260. As indicated above, in a further embodiment of the present invention, the bag structure of the implant of the present comprises a nested bag structure in which an inner bag is filled with a high strength material relative to an outer bag in which the inner bag is placed. The outer bag of this form of the present invention is formed from and filled with a more bioresorbable material relative to the material of construction and fill material of the inner bag.

Implant 260 is illustrated in detail in FIG. 41. As illustrated in FIG. 41, bag 270 is secured to lag screw tube 266 to prevent material inserted into bag 270 from escaping between the contact points formed between bag 270 and lag screw tube 266. As further illustrated in FIG. 41, reinforcement/expansion bar 268 is positioned to facilitate deployment of implant 260 into femoral shaft arm 258 of femoral cavity 224 as described hereinabove. Reinforcement/expansion bar 268 will not be utilized in every embodiment of the present invention. As illustrated in FIG. 43, reinforcement/expansion bar 268 also functions to laterally spread bag 270 to facilitate placement of bone cement therein. As illustrated in FIG. 41, fill tube 262 is positioned within bag 270, with bag 270 securely affixed to a proximal end thereof.

Figure 90:
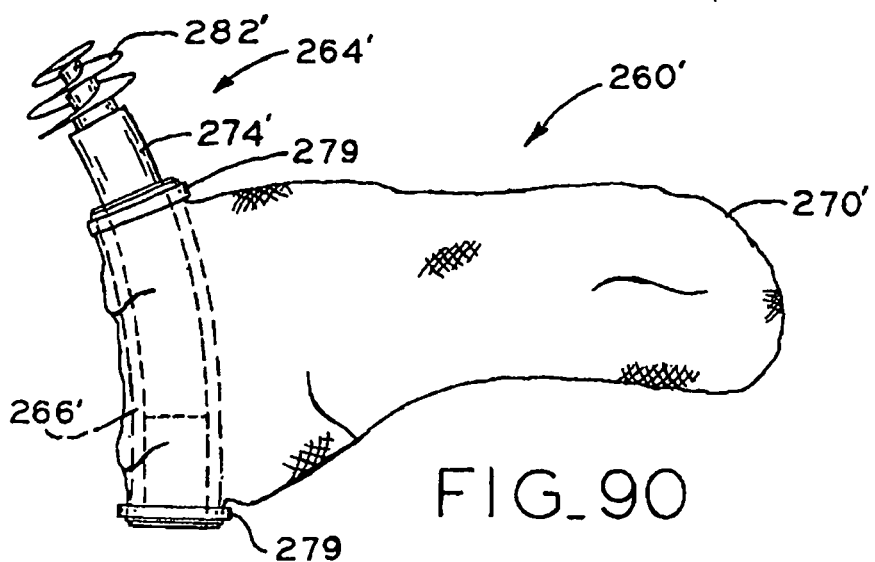
FIG. 90 is an elevational view of an alternative embodiment femoral implant of the present invention.

FIG. 90 illustrates alternative embodiment femoral implant 260'. Femoral implant 260' is generally identical to femoral implant 260 illustrated in FIG. 41 except for the provision of external fasteners 279 utilized to securely affix bag 270' to lag screw tube 266. Although not illustrated in FIG. 90, it is contemplated that femoral implant 260' will include a fill tube 262' for filling bag 270' with bone cement. Bag 270 of femoral implant 260 can be, e.g., formed of various films and fabrics. In one exemplary embodiment, bag 270 is formed from an acrylic material, e.g., a woven acrylic material. Because bone cement is an acrylic, if implant bag 270 is formed of an acrylic material, implant bag 270 and the bone cement will achieve an intimate chemical bond. Implant bag 270 of femoral implant 260 of the present invention generally comprises a containment device and can be constructed of various materials including films such as, e.g., fiber or fabric reinforced films, or fabrics created by processes such as weaving, knitting, braiding, electrospinning, or hydrospinning. Alternative materials contemplated for implant bag 270 include various polymers including, e.g., polymethylmethacrylate, polycarbonate, UHMWPE, LDPE, HDPE, polyamides, polypropylene, polyester, polyaryletherketone, polysulfone, or polyurethane. Further alternative materials contemplated for implant bag 270 include fabrics constructed of fibers formed of glass, ceramics, surgical grade stainless steel (e.g., 316L), titanium, or titanium alloys. Moreover, implant bag materials may be coated with, e.g., calcium phosphate, or a bioactive glass coating. Furthermore, implant bag 270 and the associated filler may be utilized as a delivery mechanism for, e.g., drugs, or growth factors.

Figure 91:
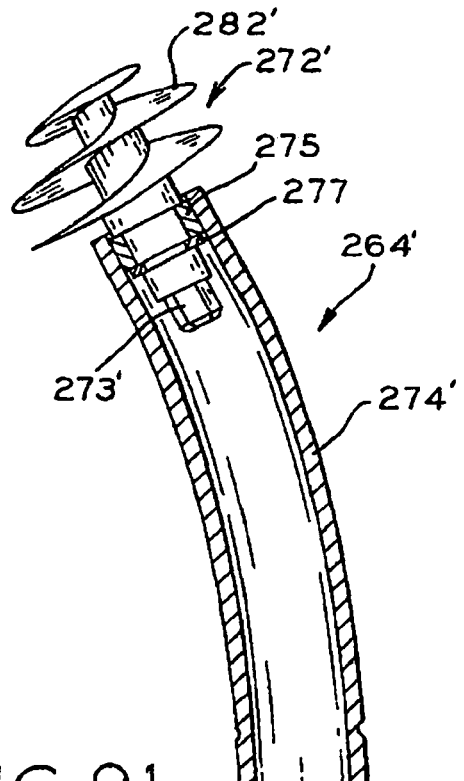
FIG. 91 is a sectional view of an alternative embodiment lag screw of the present invention, illustrating insertion of an actuating device for actuating the lag screw head.
Figure 92:
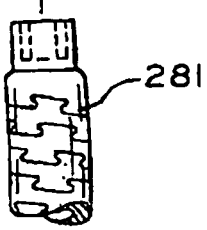
FIG. 92 is a partial sectional view of a further alternative embodiment lag screw of the present invention.

Alternative embodiments of the lag screw of the present invention are illustrated in FIGS. 42, 91, and 92. As illustrated in FIG. 42, lag screw 264 generally comprises curved lag screw shaft 274 rotatably connected to lag screw head 272. In the embodiment illustrated in FIG. 42, lag screw shaft 274 includes distal male threads 276 cooperating with proximal female threads 278 formed in lag screw head 272. Mating threads 276, 278 are left handed threads. Lag screw head 272 includes chamber 280 to accommodate distal threaded end 276 of lag screw shaft 274 when lag screw head 272 is operably positioned on lag screw shaft 274. Lag screw head 272 includes distal lag screw threads 282 for implanting lag screw 264 into femur 108 as described hereinabove. Cooperating threads 276, 278 are left handed threads, while lag screw threads 282 are right handed threads. In this way, lag screw head 272 may be threadedly engaged on lag screw shaft 274 and, rotation of lag screw head 272 in a clockwise fashion to effect implantation of lag screw threads 282 into femur 108 will not cause lag screw head 272 to become separated from lag screw shaft 274.

FIG. 91 illustrates alternative embodiment lag screw 264' in which lag screw head 272 includes flange 277 and lag screw shaft 274 includes bearing protrusion 275. In this embodiment, bearing protrusion 275 is positioned intermediate the most proximal portion of lag screw head 272' and flange 277. In this arrangement, flange 277 cooperates with the most proximal portion of lag screw head 272 and bearing protrusion 275 to prohibit axial displacement of lag screw head 272'. Lag screw head 272' includes male hex 273' operable for connection to flexible drive 281 as illustrated in FIG. 91. In use, flexible drive 281 will be inserted within tubular lag screw shaft 274 and engaged with male hex 273' to rotate lag screw head 272 to effect implantation thereof. In the embodiment illustrated in FIG. 42, lag screw shaft 274 is similarly cannulated to allow a flexible drive to enter lag screw shaft 274 and engage a cooperating protrusion (not shown) formed on lag screw head 272. FIG. 92 illustrates an alternative embodiment of lag screw head 272" wherein male threads 276" are formed on lag screw head 272", and female threads 278' are formed in lag screw shaft 274.

Alternative embodiments of guide plate 126 are illustrated in FIGS. 50-55, and 65-68. Referring now to FIGS. 50-55, guide plate 126' includes screw apertures 286' for use in securing guide plate 126 to femur 108 as described hereinabove with respect to guide plate 126. Guide plate 126' further includes spring pins 318 traversing axially oriented apertures in guide plate 126'. As illustrated in FIG. 55, spring pins 318 engage alternate ends of springs 316 to hold springs 316 in position within guide plate 126'. As illustrated in FIG. 51, guide plate 126' includes circular opening 322 as well as elliptical opening 324, with springs 316 extending into circular opening 322. In one exemplary embodiment, springs 316 are formed from titanium.

Referring now to FIGS. 65-68, guide plate 126" includes axially oriented apertures accommodating spring pins 318" in much the same way as guide plate 126' illustrated in FIGS. 50-55. Spring pins 318" are utilized to hold springs 316" in position within guide plate 126" as illustrated with respect to guide plate 126' in FIG. 55. Guide plate 126" includes circular opening 322" as well as elliptical opening 324" similar to the corresponding openings found in guide plate 126'. The distal end of guide plate 126" includes gripping teeth 404 formed thereon. Additionally, guide plate 126" includes fixation screw shoulder 406 as illustrated, e.g., in FIG. 67. Fixation screw shoulder 406 will be further described below.

In use, guide plate 126' is inserted through incision 106 for affixation to femur 108 in the same manner as guide plate 126 described hereinabove. Insertion member 124' illustrated in FIGS. 83-86 is utilized to position guide plate 126' through incision 106 for placement atop greater trochanter 110. In many respects, insertion instrument 124' is similar to insertion instrument 124 illustrated in FIGS. 19-22 and further described hereinabove. As illustrated in FIGS. 83-86, insertion instrument 124' includes elongate aperture 132' for accommodating stabilization nail 144 (FIG. 2). Insertion member 124' includes release member 134' connected via connecting rods 348, and cylindrical connector 352 to release bars 350. Release bars 350 travel in axially oriented slots formed in the distal end of insertion member 124. The distal end of insertion member 124' includes elliptical protrusion 354 for placement within elliptical aperture 324 of guide plate 126'. Cooperation of elliptical protrusion 354 with elliptical aperture 324 insures proper rotational alignment of insertion member 124' and guide plate 126'. Upon achieving proper rotational alignment, insertion member 124' may be axially displaced into the central aperture of guide plate 126', with springs 316 engaging spring slots 326" formed in opposing sides of the distal end of insertion member 124'. In this way, springs 316 lock guide plate 126' to insertion member 124'. Bevel 317 facilitates positioning of springs 316 in spring slots 326". After guide plate 126' is secured to femur 108 as described hereinabove with respect to guide plate 126, release bars 350 are utilized to actuate springs 316 radially outwardly from their normally biased position to disengage spring slots 326" and allow for removal of insertion member 124' from guide plate 126'.

Release member 134' is utilized to effect axial displacement of release bars 350 from the position illustrated in FIG. 85 in which spring slots 326" are available for engagement with springs 316 to the position illustrated in FIG. 84 in which release bars 350 provide a radially outward force to springs 316 to allow for disengagement of insertion member 124' from locking engagement with guide plate 126' and allow for removal of insertion member 124' through incision 106. As illustrated in FIG. 85, release bars 350 include a distal bevel to facilitate movement from the position illustrated in FIG. 85 to the position illustrated in FIG. 84 to effect release of springs 316 from spring slots 326". Similarly, insertion member 124' can be lockingly engaged with guide plate 126" illustrated in FIGS. 65-68 to effect implantation of guide plate 126" through incision 106 for placement atop greater trochanter 110.

When utilizing guide plate 126" illustrated in FIGS. 65-68, plunge reamer 480 (FIG. 82) must first be utilized to form a cavity in femur 108 extending through greater trochanter 110. Plunge reamer 480 includes reamer head 484 and flange 482. In this embodiment, plunge reamer 480 is inserted through incision 106 and reamer head 484 is placed atop greater trochanter 110. As with initial placement of guide plate 126 and 126', a fluoroscope may be utilized to facilitate proper positioning of reamer head 484 atop greater trochanter 110. Furthermore, a surgeon may rely on tactile feedback for proper positioning of plunge reamer 480. Plunge reamer 480 is actuated and plunge reaming is effected until flange 482 abuts greater trochanter 110. Plunge reamer 480 is thereafter removed through incision 106 to allow for placement of guide plate 126" atop greater trochanter 110. Fixation screw 394 illustrated in FIGS. 61-64 is thereafter utilized to secure guide plate 126" to greater trochanter 110. While insertion instrument 124' may be utilized to initially position guide plate 126" through incision 108, it must be removed prior to implantation of fixation screw 394.

Figures 66, 67:
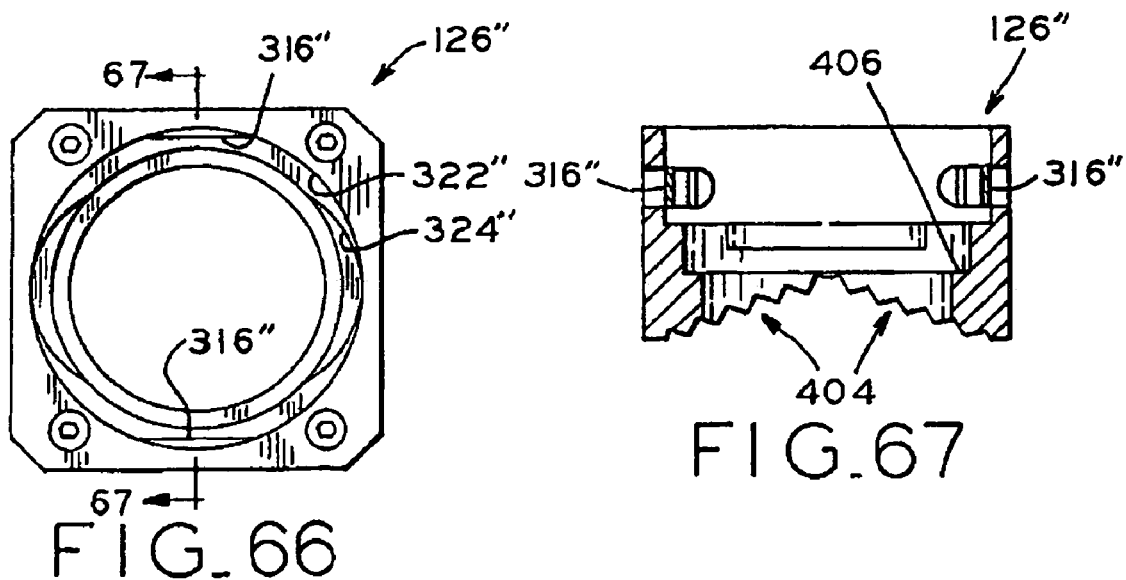
FIG. 66 is a top elevational view thereof.
FIG. 67 is a sectional view thereof taken along line 67-67 of FIG. 66.
Figure 68:
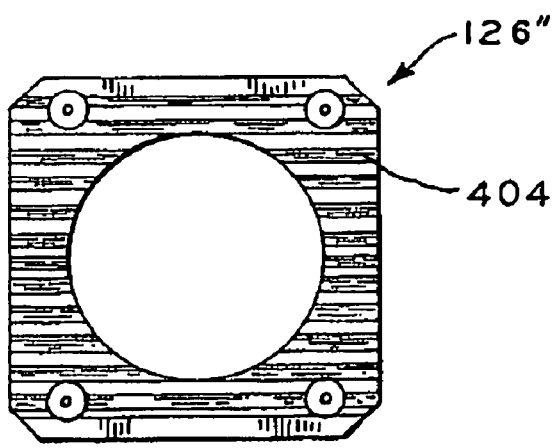
FIG. 68 is a bottom elevational view thereof.

As illustrated in FIGS. 61-64, fixation screw 394 includes fixation screw head 398 with fingers 396 axially depending therefrom. Screw threads 400 are formed on axially extending fingers 396. The proximal end of fixation screw 394 includes locking channel 402, the utility of which will be further described below. Fixation screw head 398 forms a flange engageable with fixation screw shoulder 406 formed in guide plate 126" (FIG. 67). Fixation screw 394 is inserted through the central aperture of guide plate 126" and is screwed into the bore formed through greater trochanter 110 to secure guide plate 126" atop greater trochanter 110. Threads 400 cut into the femoral bone stock to provide fixation of fixation screw 394.

Fixation screw placement instrument 470 as illustrated in FIGS. 80 and 81 is utilized to insert fixation screw 394 through incision 106 and to secure fixation screw 394 within guide plate 126" as described hereinabove. Referring now to FIGS. 80 and 81, fixation screw placement instrument 470 includes a proximal handle as well as a distal end having blades 466 and ball detent 464 formed therein. In use, blades 466 engage locking channels 402 in fixation screw 394, with ball detent 464 engaging a detent (not shown) formed in the inner diameter of locking screw 394. The proximal handle of fixation screw placement instrument 470 may then be utilized to rotate fixation screw 394 and secure the same within femur 108.

When utilizing either guide plate 126' (FIGS. 50-55) or guide plate 126" (FIGS. 65-68), alternative embodiment guide tube/retractor 154' is utilized in lieu of guide tube/retractor 154 described hereinabove with reference to guide plate 126. Guide tube/retractor 154' is illustrated in FIGS. 56, 57, 59, and 60. As illustrated, guide tube/retractor 154' includes a distal end having rounded portion 330 with spring slots 326 formed on opposing sides thereof. Furthermore, distal end of guide tube/retractor 154' includes engagement protrusions 328 having a radius of curvature matching the rounded ends of elliptical openings 324 and 324" in guide plates 126' and 126", respectively. Opposing spring slots 326 formed in the distal end of guide tube/retractor 154' are utilized to selectively affix guide tube/retractor 154' to either guide plate 126' or 126" in the same fashion as described above with respect to insertion member 124'. As illustrated in FIG. 58, angled guide tube/retractor 296' is provided for use with guide plates 126' or 126". Angled guide tube/retractor 296' provides the same functionality as angled guide tube/retractor 296 described hereinabove with respect to guide plate 126 and includes a distal end identical to the distal end of straight guide tube/retractor 154 illustrated in FIGS. 56, 57, 59, and 60. Straight guide tube/retractor 154' and angled guide tube/retractor 296' have a greater axial length than straight guide tube/retractor 154 and angled guide tube/retractor 296 described in the primary embodiment of the present invention. The inventors of the present invention contemplate various guide tube/retractors having differing lengths to accommodate physiological differences in a variety of patients as well as different attaching mechanisms in accordance with the various embodiment of the present invention. As illustrated in FIGS. 56-60, guide tube/retractors 154' and 296' include latch channels 332 and 332', respectively. The utility of latch channels 332 and 332' will be further described below.

Figure 44:
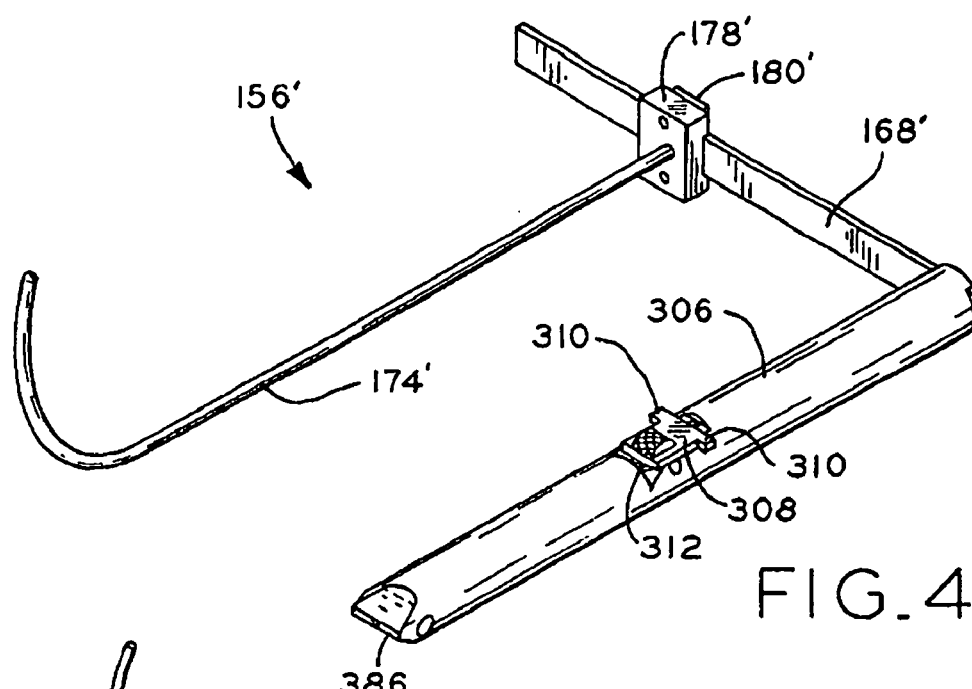
FIG. 44 is a perspective view of an alternative embodiment alignment device of the present invention.
Figure 45:
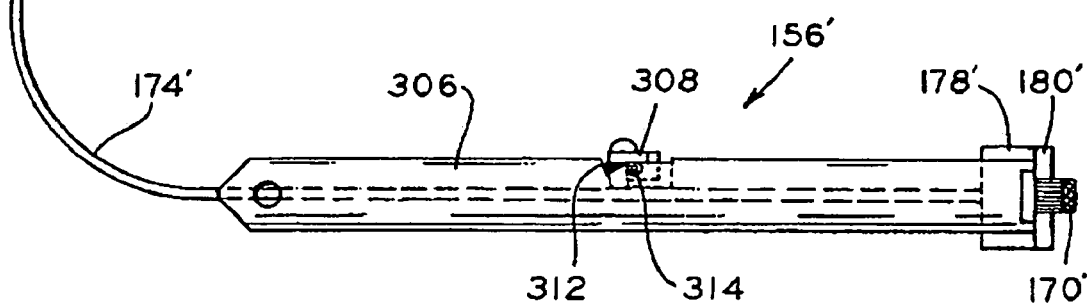
FIG. 45 is an elevational view thereof.
Figure 61:
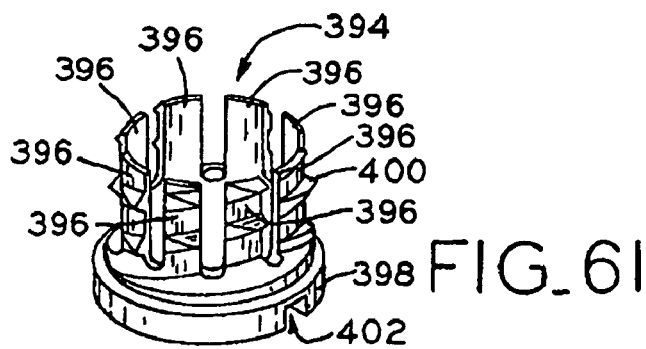
FIG. 61 is a perspective view of a fixation screw in accordance with an alternative embodiment of the present invention.
Figure 62:
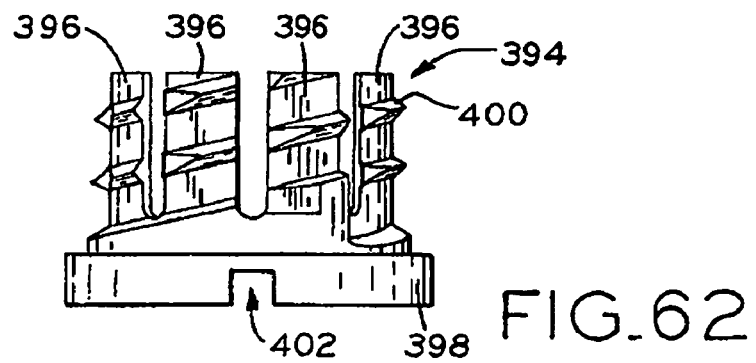
FIG. 62 is a radial elevational view thereof.
Figure 63:
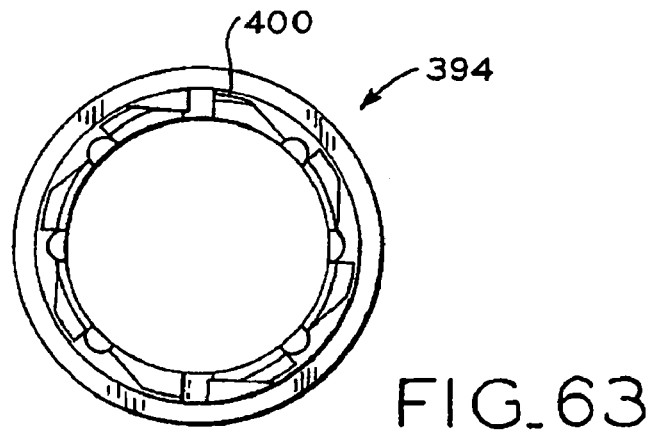
FIG. 63 is a distal axial view thereof.
Figure 64:
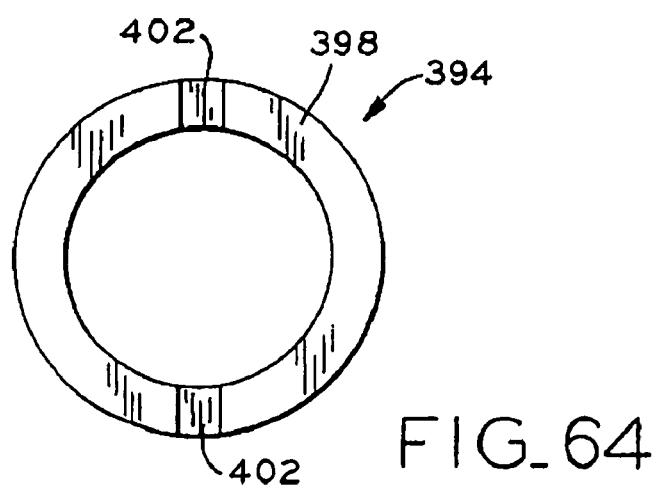
FIG. 64 is a proximal axial view thereof.
Figure 65:
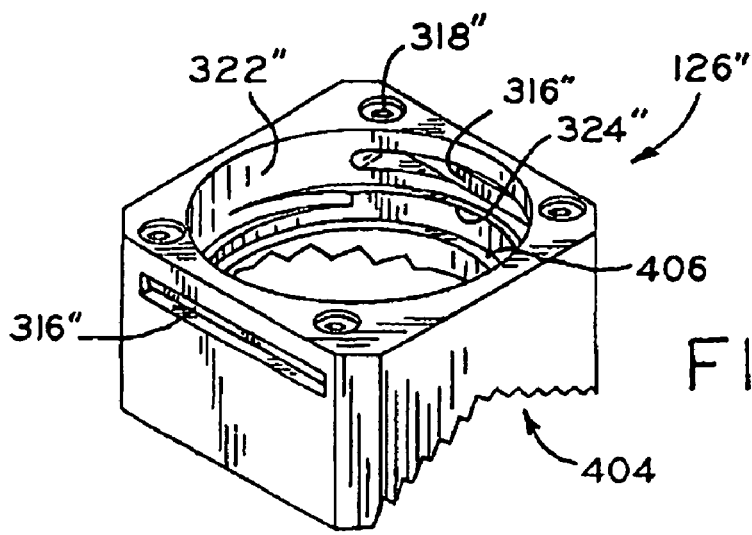
FIG. 65 is a perspective view of a second alternative embodiment guide plate in accordance with the present invention.

Referring now to FIGS. 44 and 45, alignment device 156' is utilized in conjunction with guide tube/retractors 154', 296' to select the appropriate guide tube/retractor as described hereinabove with respect to alignment device 156. Alignment device 156' includes alignment guide tube 306 for positioning within guide tube/retractor 156', or angled guide tube/retractor 296' and providing a stable base for alignment device 156' as described above with respect to insertion portion 160 of alignment device 156 (FIGS. 29 and 30). Alignment guide tube 306 includes latch 308 pivotally connected thereto via pivot pin 314. Additionally, alignment guide tube 306 includes distal flat 386 which, in this exemplary embodiment will bottom out on the shoulder formed between the elliptical aperture and a round aperture in guide plates 126' and 126". Latch 308 includes oppositely depending locking tabs 310 extending from opposing sides thereof. Latch 308 is biased into the position illustrated in FIG. 45 by spring 312. As alignment guide tube 306 is inserted into guide tube/retractor 156' or 296', locking tabs 310 contact the proximal end of guide tube/retractor 154' or 296'. After achieving this position, the distal end of latch 308 is depressed radially inwardly to move locking tabs 310 away from alignment guide tube 306 and allow for further insertion of alignment guide tube 306 into guide tube/retractor 154' or angled guide tube/retractor 296'. As indicated above, distal flat 386 bottoms out on the shoulder formed between the elliptical and the round apertures in guide plates 126' and 126" when alignment guide tube 306 is fully inserted into guide tube/retractor 154' or 296'. In this position, locking tabs 310 align with latch channels 332 (FIGS. 56-58) and latch 308 can return to its normally biased position as illustrated in FIG. 45. In this position, locking tabs 310 engage latch channels 332 to prevent axial displacement of alignment guide tube 306 relative to guide tube/retractor 154' or 296'. Furthermore, when engaged in latch channels 332, locking tabs 310 resist rotational movement of alignment guide tube 306. In all other respects, alignment device 156' is identical to alignment device 156 described above and is utilized in a similar fashion to choose between straight guide tube/retractor 154' and angled guide tube/retractor 296'.

Reaming of femoral cavity 224 is effected with reamers having guide tubes and latches similar to guide tube 306 and latch 308 described above with respect to alignment device 156'. In one alternative embodiment, combination reamer 358 illustrated in FIGS. 46-49 is utilized to effect both plunge, i.e., straight reaming into the femur as well as swivel reaming. In this embodiment, combination reamer 358 is inserted into guide tube/retractor 154' or 296', with orientation plate 384 cooperating with one of the longitudinal channels formed in guide tube/retractor 154' or 296' (see, e.g., FIGS. 56-60) to properly align combination reamer 358 within the guide tube/retractor. As illustrated in FIGS. 46-49, combination reamer 358 includes reamer head 360 connected to the distal end of reamer shaft 362. Reamer shaft 362 includes flange 364 positioned toward the distal end thereof and ratchet teeth 382 formed toward the proximal end thereof. As illustrated in FIG. 49, reamer shaft 362 is positioned within reamer shaft tube 372 having reamer depth lock 374 formed on a proximal end thereof. Reamer depth lock 374 includes ratchet release 376 connected via connecting rod 378 to ratchet head 380 as illustrated in FIG. 49. As illustrated in FIG. 49, a spring is utilized to bias ratchet head 380 into engagement with ratchet teeth 382 on reamer shaft 362. Ratchet release 376 is pivotally connected to reamer depth lock 374 such that actuation of ratchet release 376 causes outward radial movement of ratchet head 380 with respect to reamer shaft 362, thus disengaging the ratchet teeth formed in ratchet head 380 from ratchet teeth 382 and allowing for relative axial movement of reamer shaft tube 372 and reamer shaft 362. In the configuration illustrated in FIG. 49, combination reamer 358 can be utilized to effect plunge reaming, with the terminal reaming depth being reached when the distal end of reamer shaft tube 362 contacts pivot 216. The overall depth of plunge reaming may thus be adjusted by varying the axial displacement of reamer depth lock 374 along reamer shaft 362.

As illustrated in FIG. 46, combination reamer 358 includes combination reamer guide tube 366 having channel 368 formed therein. Swivel/plunge reaming selector 370 is operably connected to a proximal end of combination reamer guide tube 366. As illustrated in FIG. 49, rotation guide pin 388 is fixably secured to combination reamer guide tube 366 and positioned within rotation guide channel 390 of swivel/plunge reaming selector 370. Swivel/plunge reaming selector 370 may be rotated about guide tube 366 of combination reamer 358 between the extremes illustrated in FIGS. 47 and 48, i.e., with rotation guide pin 388 abutting opposite ends of rotation guide channel 390. When swivel/plunge reaming selector 370 is positioned as illustrated in FIG. 47, swivel reaming with combination reamer 358 is not allowed because swivel/plunge reaming selector 370 covers channel 368. To allow for swivel reaming, swivel/plunge reaming selector 370 is rotated into the position illustrated in FIG. 48. In the position illustrated in FIG. 48, channel 392 in swivel/plunge reaming selector 370 aligns with channel 368 in guide tube 366 of combination reamer 358. In this position, swivel reaming can be effected as illustrated in FIG. 48. Reamer shaft 362 is connected to guide tube 366 of combination reamer 358 via pivot 216' and pivot pins 218' to allow for the swivel reaming illustrated in FIG. 48. Combination reamer 358 includes distal flat 386' for signaling complete insertion of combination reamer 358 into reamer/guide tube 154' or 296'. As described above with respect to alignment guide tube 306 of alignment device 156', distal flat 386' bottoms out on the shoulder formed between the elliptical and round apertures in guide plates 126' and 126" when combination reamer 358 is fully inserted into guide tube/retractor 154' or 296'.

Upon completion of femoral reaming, guide tube/retractor 156' or 296' is removed from locked engagement with guide plate 126' or 126" with spring lock release instrument 336 illustrated in FIGS. 87-89. As illustrated in FIGS. 87-89, spring lock release instrument 336 includes a tubular body sized for insertion into guide tube/retractor 156' or 296' with a distal shoulder indicating complete insertion of spring lock release instrument 336 into guide tube/retractor 156' or 296' in the manner described above with respect to alignment guide tube 306 of alignment device 156', and combination reamer 358. Moreover, spring lock release instrument 336 includes latch 308' as described hereinabove with respect to guide tube 306 of alignment device 156'. After insertion of spring lock release instrument 336 into guide tube/retractor 156' or 296', handle 338 is utilized to axially displace actuation rod 342 traversing internal aperture 344 of spring lock release instrument 336 into the position illustrated in FIG. 89. In this position, the distal ramped end of actuation rod 342 contacts the proximal ends of release pins 346 to overcome the biasing force of springs 347 (FIG. 88) and cause release pins 346 to protrude from spring lock release instrument 336 as illustrated in FIG. 89. In this position, release pins 346 traverse apertures 155, 155' and act against springs 316 to disengage springs 316 from spring slots 326 and allow for removal of guide tube/retractor 154' or 296'. In the embodiment illustrated, release pins 346 are spring biased. The inventors of the current invention contemplate that release pins 346 could be linked to actuation rod 346 via a mechanical linkage whereby pulling actuation rod 342 would pull pins 346 into the instrument and, conversely, pushing rod 342 would push the pins outwardly from the instrument. Moreover, while release pins 346 are illustrated as forming an acute angle with the longitudinal axis of spring lock release instrument 336, release pins 346 could be transversely positioned within spring lock release instrument 336.

Figure 69:
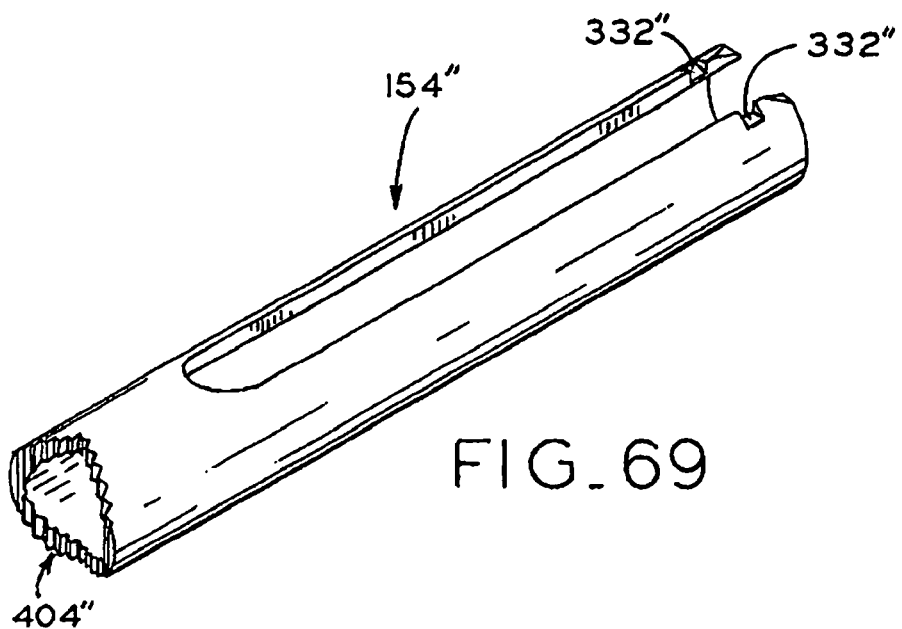
FIG. 69 is a perspective view of a second alternative embodiment guide tube/retractor in accordance with the present invention.
Figure 70:
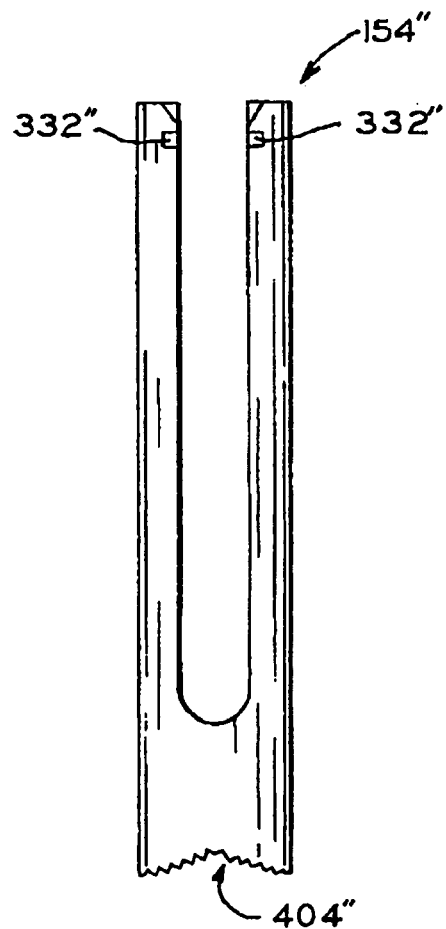
FIG. 70 is a radial elevational view thereof.

Guide tube/retractor 156" in accordance with a further alternative embodiment of the present invention is illustrated in FIGS. 69 and 70. In this embodiment, guide tube/retractor 154" is configured for affixation directly to greater trochanter 110, with guide plate 126 no longer being used. As illustrated in FIGS. 69 and 70, guide tube/retractor 154" includes gripping teeth 404" formed in a distal end thereof. In use, gripping teeth 404" are positioned atop greater trochanter 110 and fixation screw 394 is positioned within guide tube/retractor 154" and utilized to affix guide tube/retractor 154" to femur 108 as described above with reference to guide plate 126". While not illustrated in FIGS. 69 and 70, guide tube/retractor 154" includes a shoulder for engaging screw head 398 of fixation screw 394 to complete fixation of guide tube/retractor 154" to femur 108 in the same manner as described above with respect to guide plate 126".

Figure 108:
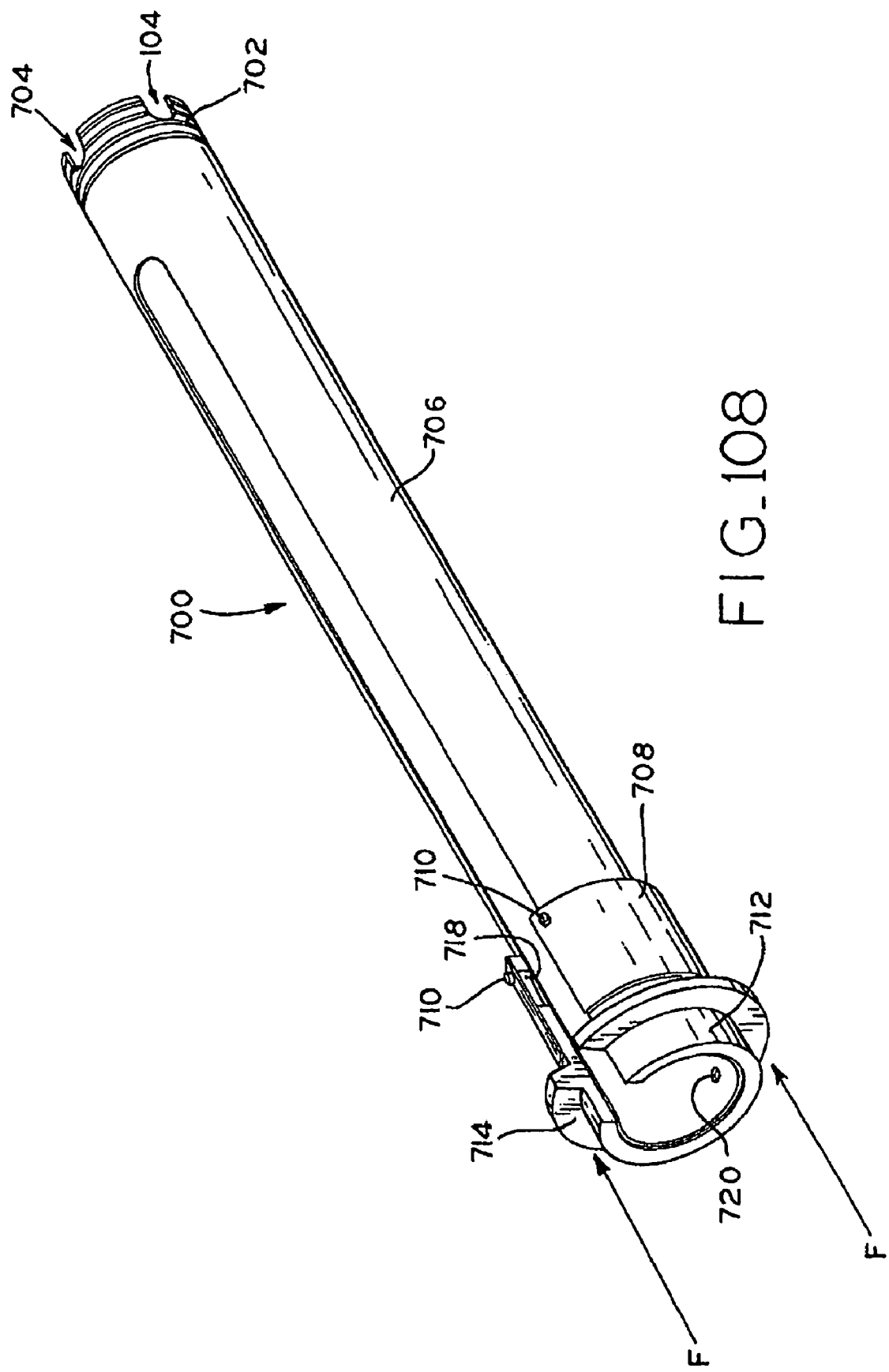
FIG. 108 is a perspective view of the unitube retractor of FIG. 107 illustrating the ball detent retaining mechanism actuated to allow for release of an instrument positioned within the unitube retractor.
Figure 109:
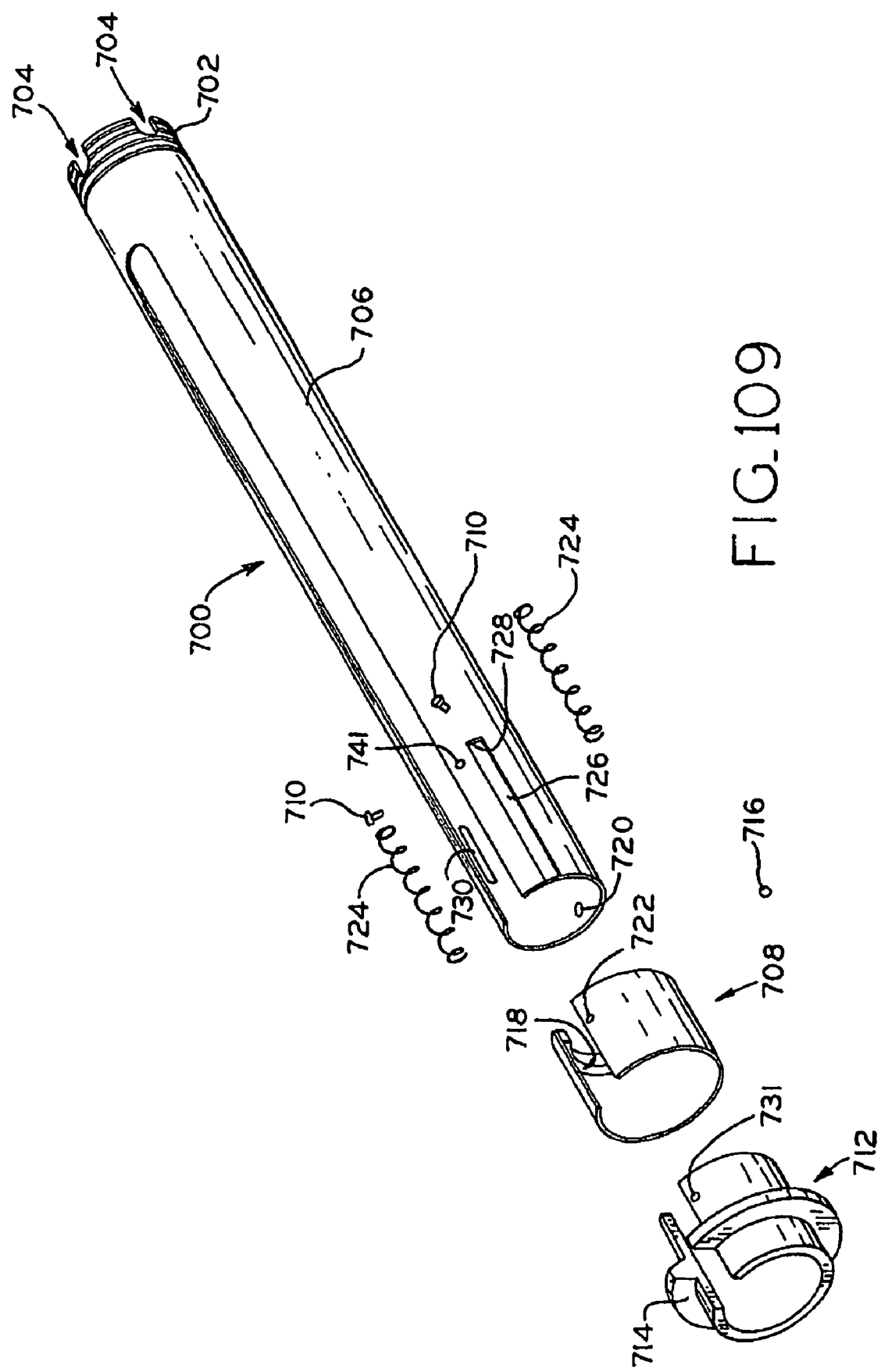
FIG. 109 is an exploded perspective view of the unitube retractor illustrated in FIGS. 107 and 108.

FIGS. 107-109 illustrate another alternative embodiment guide/retractor in accordance with the present invention. Specifically, FIGS. 107-109 illustrate unitube retractor 700. Unitube retractor 700 functions as the guide tube/retractors described above to maintain an access from incision 106 (FIG. 1) made in the epidermis of patient 100 and developed to expose femur 108. Unitube retractor 700 is referred to as a "unitube" retractor because it is designed to be directly secured to femur 108, without use of a discrete guide plate or fixation screw. To effect fixation of unitube retractor 700 to femur 108, unitube retractor 700 includes self-tapping threads 702. Self-tapping threads 702 are formed on the distal end of unitube body 706, with cutouts 704 formed in and spaced about the periphery of the distal end of unitube body 706 to facilitate tapping of threads in femur 108 as unitube retractor 700 is threaded into engagement with femur 108 through access 101 described above. In an alternative embodiment, unitube retractor 700 will not include self-tapping threads, but rather will include threads that do not self-tap. In this embodiment, a discrete tap will be used to thread into access 101 in femur 108 prior to securement of unitube retractor 700 therein.

As illustrated in FIGS. 107-109, unitube body 706 includes a longitudinal slot to cooperate with guide tabs protruding from instruments to be inserted through unitube body 706 to properly align the instruments prior to use. The longitudinal slot formed in unitube body 706 will also accommodate the swivel reaming of certain embodiments of the present invention. In use, unitube retractor 700 will be inserted through incision 106 until the distal end abuts greater trochanter 110. In this position, a surgeon will utilize tactile feedback to position the distal end of unitube retractor 700 in access 101 formed in greater trochanter 110. In one exemplary embodiment, a fluoroscope will be utilized to facilitate positioning of the distal end of unitube retractor 700 in access 101 formed in greater trochanter 110. In this position, unitube retractor 700 will be threaded into access 101 in femur 108, with self-tapping threads 702 threading access 101 to secure unitube retractor 700 therein. Threading of unitube retractor 700 is complete when unitube retractor 700 is secured in access 101 and the longitudinal slot of unitube body 706 is aligned with an appropriate physiological landmark to guide alignment of instruments inserted therein. For example, a central axis of the longitudinal slot of unitube body 706 may be positioned substantially perpendicular to the plane of the greater trochanter and generally aligned with the axis of the femoral shaft.

As illustrated in FIGS. 107-109, unitube retractor 700 includes a ball detent retaining mechanism for retaining instruments inserted therein in a fixed longitudinal position relative to unitube body 706. The ball detent retaining mechanism cooperates with the longitudinal alignment slot of unitube body 706 to fix instruments positioned in unitube retractor 700 and prevent relative rotational and axial displacement of an instrument positioned in unitube retractor 700. Referring to FIGS. 107-109, ball detent 716 is received by counterbored ball detent aperture 720. Counterbored ball detent aperture 720 is formed from the exterior of unitube body 706 to the hollow interior thereof such that the largest diameter portion of counterbored ball detent aperture 720 is formed in the exterior wall of unitube body 706. Counterbored ball detent aperture 720 is sized whereby the smallest diameter portion thereof, i.e., the portion formed in the hollow interior of unitube body 706 is smaller than the equator of ball detent 716. With this structure, ball detent 716 cannot traverse counterbored ball detent aperture.

Ball detent 716 is interposed between plunger 712 and unitube body 706. As illustrated in FIG. 110, plunger 712 includes internal ball detent ramp 713 connecting base flat 711 and peak flat 715. FIG. 107 illustrates the ball detent retaining mechanism of unitube retractor 700 positioned to retain an instrument within unitube retractor 700, with ball detent 716 protruding into the hollow interior of unitube body 706. In this position, ball detent 716 contacts peek flat 715 (FIG. 110) of plunger 712, which forces ball detent 716 to protrude into the hollow interior of unitube body 706. FIG. 108 illustrates the ball detent retaining mechanism of unitube retractor 700 actuated to allow for release of an instrument positioned within unitube retractor 700, with ball detent 716 not protruding into the hollow interior of unitube body 706. In this position, ball detent 716 contacts base flat 711 (FIG. 110) of plunger 712, which allows ball detent 716 to retract from the hollow interior of unitube body 706. As illustrated in FIG. 108, force F is applied to flange 714 of plunger 712 to reposition plunger 712 from its normally biased position illustrated in FIG. 107 to the position illustrated in FIG. 108.

To bias plunger 712 into the position illustrated in FIG. 107, springs 724 (FIG. 109) are positioned intermediate plunger 712 and collar 708. Collar 708 includes internal collar flange 718 as illustrated in FIG. 107-109. In construction, collar 708 is secured to unitube body 706 with set screws 710 positioned through set screw apertures 722 (only one of which is illustrated in FIG. 109) in collar 708 and secured in set screw apertures 741 in unitube body 706. Springs 724 are positioned in spring slots 726 (only one of which is illustrated in FIG. 109) on opposing sides of unitube body 706, with the distal ends of springs 724 abutting internal collar flange 718 and distal end 728 of spring slots 726. Spring slots 726 maintain the position of springs 724 substantially parallel to the longitudinal axis of unitube body 706. In one exemplary embodiment, internal collar flange 718 of collar 708 includes circular cutouts aligned with spring slots 726 to further facilitate alignment of springs substantially parallel to the longitudinal axis of unitube body 706. Plunger 712 is positioned over the proximal end of unitube body 706 such that springs 724 are interposed between internal collar flange 718 of collar 708 and the distal end of plunger 712. Plunger 712 includes at least one set screw aperture 731 and unitube body 706 includes at least one corresponding set screw slot 730. To complete assembly of unitube retractor 700, set screws 732 are threaded into set screw apertures 731 in plunger 712 and extend into set screw slots 730 in unitube body 706. Set screws 732 cooperate with set screw slots 730 to limit displacement of plunger 712 to longitudinal movement only. In the normally biased position illustrated in FIG. 107, set screws 732 abut the proximal end of set screw slots 730. In use, ball detent 716 engages a detent formed in an instrument inserted into unitube retractor 700 to retain the instrument in a fixed position relative to unitube retractor 700.

Referring to FIGS. 111-115, alternative embodiment unitube retractor 700' is illustrated. Unitube retractor 700' includes a ball detent retaining mechanism as described above with respect to unitube retractor 700, with corresponding parts denoted with primed reference numerals. The ball detent retaining mechanism of unitube retractor 700' is structured and operates substantially identical to the ball detent retaining mechanism described above with respect to unitube retractor 700 and, therefore, a detailed description of this mechanism will not now be repeated for the sake of brevity.

Unitube retractor 700' utilizes instrument alignment cutouts in unitube body 706 as opposed to the longer longitudinal slot of unitube body 706. Also, collar 708' and plunger 712' do not include cutouts corresponding to instrument alignment cutouts in unitube body 706, unlike collar 708 and plunger 712 of unitube retractor 700. With this in mind, the instrument alignment tabs associated with the instruments to be positioned in unitube retractor 700' will not protrude past the exterior wall of unitube body 706'. Similar alignment tabs, could be used with unitube retractor 700, allowing use of plunger 712' and collar 708' with unitube 700. Similarly, plunger 712 and collar 708 could be used with unitube retractor 700' if the alignment tabs of the instruments to be inserted in unitube retractor 700' extend past the exterior wall of unitube body 706'. Unitube body 706' includes a pair of opposing instrument alignment cutouts allowing 180° of instrument realignment, which would necessitate a pair of corresponding cutouts in plunger 712 and collar 708, if used with unitube retractor 700'. If a pair of cutouts are required in the plunger and collar, then the plunger and collar will either be constructed in two pieces, or the cutouts will not run the entire length of the plunger and collar as do the cutouts of plunger 712 and collar 708 illustrated in FIGS. 107-109.

Unitube retractor 700' employs lock ring 742 to secure unitube retractor 700' in access 101 formed in femur 108 as described above. Lock ring 742 includes a number of expandable fingers 744 as illustrated in FIGS. 113-115. In use, unitube retractor 700' is inserted through incision 106 until fingers 744 abut greater trochanter 110. In this position, a surgeon will utilize tactile feedback to position the distal end of unitube retractor 700' in access 101 formed in greater trochanter 110. In one exemplary embodiment, a fluoroscope will be utilized to facilitate positioning of the distal end of unitube retractor 700' in access 101 formed in greater trochanter 110. After insertion of unitube retractor 700' into access 101 and alignment of instrument alignment cutouts 756 with an appropriate physiological landmark such as, the longitudinal axis of the femur, fingers 744 are expanded from the position illustrated in FIG. 113 to the position illustrated in FIGS. 114 and 115 to secure unitube retractor 700' in femur 108. FIGS. 111 and 112 illustrate alternative embodiment lock ring 742' having teeth 748 radially extending from fingers 744 to facilitate locking of lock ring 742' in femur 108.

As illustrated in FIG. 112, each finger 744' of lock ring 742' includes internal ramp 749. Although not illustrated, each finger 744 of lock ring 742 similarly includes an internal ramp. As illustrated in FIG. 111, unitube body 706' includes beveled distal end 746. In the unactuated position of unitube retractor 700' as illustrated in FIG. 113, beveled distal end 746 of unitube body 706' abuts internal ramps 749 of fingers 744. To actuate fingers 744 from the position illustrated in FIG. 113 to the position illustrated in FIG. 114 to effect locking of unitube retractor 700' to femur 108, unitube body 706' is longitudinally displaced toward lock ring 742, with beveled distal end 746 of unitube body 706' cooperating with internal ramps 749 of expandable fingers 744 to force expandable fingers 744 to move radially outwardly as illustrated in FIGS. 114 and 115.

A number of mechanisms may be employed to effect the necessary longitudinal displacement of unitube body 706' relative to lock ring 742. FIGS. 111, 113, and 114 illustrate one such mechanism. As illustrated in FIGS. 111, 113, and 114, threaded driver 736 is rotationally connected to unitube body 706' via set screw 738. Specifically, set screw 738 is threaded into set screw aperture 739 of threaded driver 736 and extends into annular threaded driver rotation groove 752 formed in unitube body 706'. In this way, threaded driver 736 may rotate relative to unitube body 706', but may not be longitudinally displaced relative to unitube body 706'. Connector shaft 734 is positioned about unitube body 706' and is threaded to threaded driver 736. After connector shaft 734 is positioned about unitube body 706', a set screw is threaded into set screw aperture 750 of connector shaft 734 and extends into guide slot 754 formed in unitube body 706' to restrict relative movement between connector shaft 734 and unitube body 706' to axial movement only. Connector shaft 734 is further threaded to lock ring 742, although, in an alternative embodiment, lock ring 742 could be secured to connector shaft 734 via any one of a number of connectors including, e.g., one or more set screws. In the position illustrated in FIG. 113, connector shaft 734 is threaded into threaded driver a sufficient distance to place beveled distal end 746 (FIG. 111) of unitube body 706' in abutting relationship with the internal ramps of expandable fingers 744 of lock ring 742. To actuate unitube retractor into the position illustrated in FIG. 114, connector shaft 734 is held stationary, while threaded driver 736 is rotated to continue threading connector shaft 734 into threaded driver 736 and thereby force unitube body 706', which cannot be longitudinally displaced relative to threaded driver 736, further into lock ring 742, whereby beveled distal end 746 of unitube body 706' cooperates with internal ramps 749 of expandable fingers 744 to force expandable fingers 744 into the position illustrated in FIG. 114. Specifically, set screw 738 acts against threaded driver rotation groove 752 to force unitube body 706' further into lock ring 742 as connector shaft 734 is threaded into threaded driver 736.

In an alternative embodiment of the present invention, flexible reamer 428 illustrated in FIGS. 75 and 76 is utilized in lieu of the curved reamers described above to ream into femoral head 114 and into the shaft of femur 108. As illustrated in FIGS. 75 and 76, flexible reamer 428 includes reaming head 432 and flexible reaming shaft 434. As illustrated in FIG. 76, flexible reaming shaft 434 is cannulated, allowing for insertion of flexible reamer shaft 434 over a guide wire to guide reaming into femoral head 114 and into the shaft of the femur 108. Flexible reamer 428 illustrated in FIGS. 75 and 76 utilizes flexible reamer guide tube 430 and a latch member associated with a particular reamer/guide tube of the present invention. However, flexible reamer 428 may include various guide tubes having physical characteristics allowing for use of flexible reamer 428 with the various guide tube/retractors of the present invention. As illustrated in FIGS. 75 and 76, the proximal end of flexible reamer shaft 434 is connected to flange 436 which acts against the proximal end of flexible reamer guide tube 430 to limit the reaming depth of flexible reamer 428.

In one exemplary embodiment, flexible reamer guide 408 (FIGS. 71 and 72) is utilized to position guide wire 410 within the femur to guide flexible reamer 428. As illustrated in FIGS. 71 and 72, flexible reamer guide 408 includes guide 416 having guide shaft fixation channel 412 formed therein. Guide 416 is insertable within guide channel 420 of the main body of flexible reamer guide 408 as illustrated in FIG. 72. Guide pegs 418 depend from guide 416 and are further inserted within guide channel 420 as illustrated in FIG. 72. Flexible reamer guide tube 486 of flexible reamer guide 408 includes advance/retract screw aperture 488 and guide wire aperture 490. With guide 416 inserted in guide channel 420 of flexible reamer guide tube 486, guide wire 410 is inserted in guide wire aperture 490 and positioned within guide shaft fixation channel 412. Set screw 414 is utilized to secure guide wire 410 within guide shaft fixation channel 412. Advance/retract screw 422 traverses a proximal aperture in guide 416 and advance/retract screw aperture 488, and is threadably engaged with receiving block 426 as illustrated in FIG. 72. Advance/retract screw 422 includes flange 424 for abutting the proximal end of guide 416 and for forcing guide 416 to be distally displaced in flexible reamer guide tube 486 in response to distal movement of advance/retract screw 422. Guide wire 410 is formed from a memory metal such as, e.g., nitinol. With this in mind, advance/retract screw 422 may be retracted from receiving block 426 to allow guide wire 410 to retreat into guide wire aperture 490 to completely retract guide wire 410 within flexible reamer guide tube 486 of flexible reamer guide 408, without losing the ability of guide wire 410 to regain the bent shape illustrated in FIG. 71.

In use, flexible reamer guide 408 is inserted within a guide tube/retractor of the present invention with guide wire 410 not protruding from the distal end of guide wire aperture 490. The proximal end of advance retract screw 422 is thereafter actuated to force guide 416 and, consequently, guide wire 410 through flexible reamer guide tube 486 and into femoral head 414 as illustrated in FIG. 73. Once guide wire 410 achieves the position illustrated in FIG. 73, set screw 414 may be removed and flexible reamer guide 408 removed from the guide tube/retractor, leaving guide wire 410 in place within femur 108. Flexible reamer 428 may then be operably inserted in guide tube/retractor 154 as illustrated in FIG. 74 and, with guide wire 410 positioned within the cannula of flexible reamer 428, femoral cavity 224 may be extended into femoral head 114 as illustrated in FIG. 74, with flexible reamer 428 being guided by guide wire 410. A similar technique may be utilized for advancing guide wire 410 into the femoral shaft to extend femoral cavity 224 therein.

Figure 77:
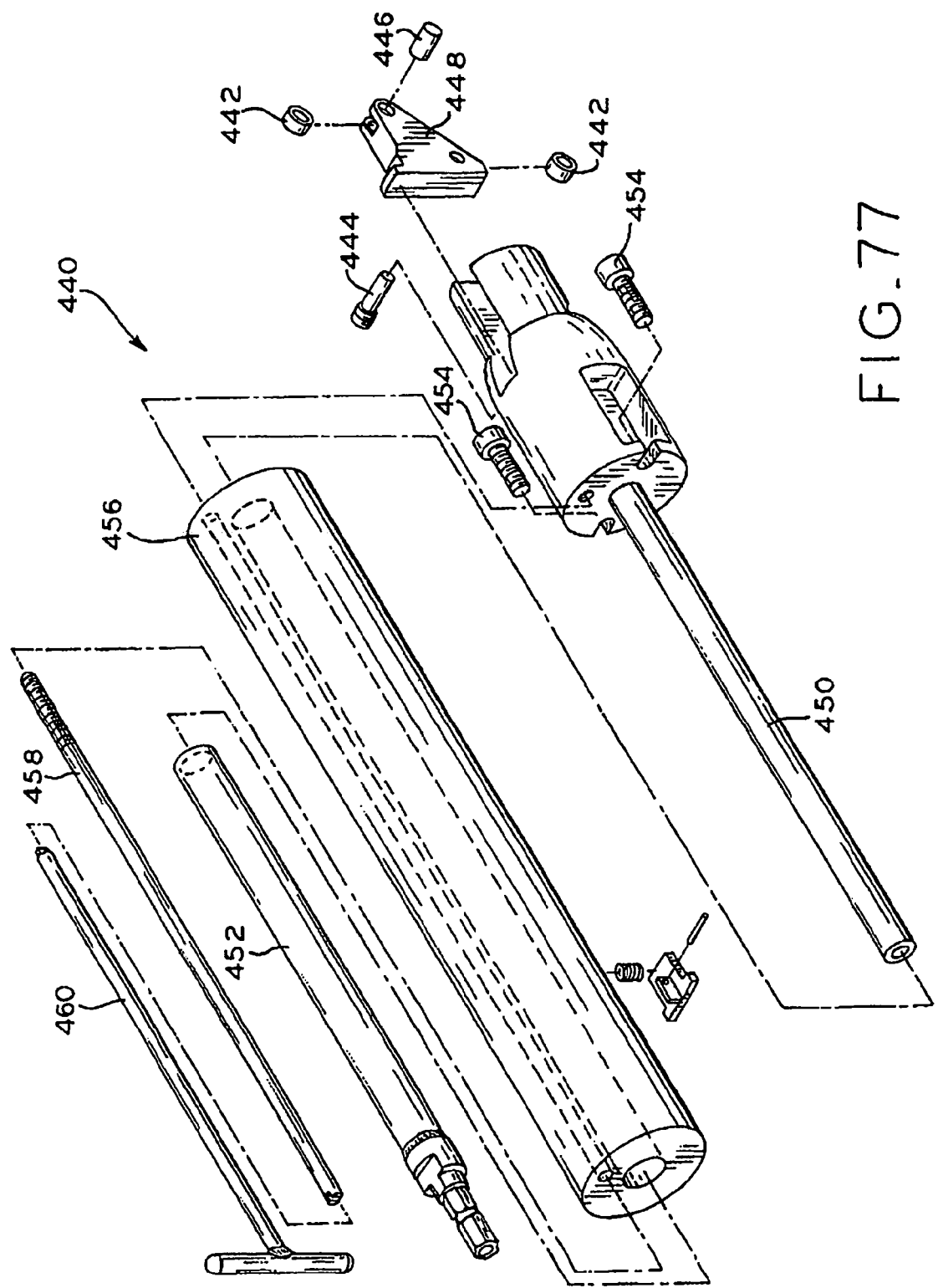
FIG. 77 is an exploded view of a flexible reamer guide wire bender in accordance with the present invention.

In a further alternative embodiment of the present invention, flexible reamer guide wire bender 440 as illustrated in FIGS. 77-79 is utilized to in vivo bend a guide wire to guide reaming into, e.g., femoral head 114 as illustrated, e.g., in FIG. 73. As illustrated in FIGS. 77-79, flexible reamer guide wire bender 440 includes guide tube 456 for insertion into a guide tube/retractor of the present invention. Guide tube 456 includes a pair of elongate apertures. A first of these apertures accommodates inner wire tube 450 and outer wire tube 452 as illustrated, e.g., in FIG. 79. The second of the elongate apertures formed in guide tube 456 accommodates adjustment screw 458 as illustrated, e.g., in FIG. 79. Wire shaping head 448 is pivotally connected via pivot pin 444 to the distal end of flexible reamer guide wire bender 440 as illustrated in FIG. 79. As illustrated in FIGS. 77 and 79, roller 442 is positioned about pivot pin 444. Wire shaping head 448 further includes roller pin 446 for connecting a second roller 442 in a rotatable manner to wire shaping head 448. As illustrated in FIG. 77, screws 454 are utilized to affix the distal end of flexible reamer guide wire bender 440 to guide tube 456. As illustrated in FIG. 79, outer wire tube 452 includes proximal wire extreme 462 against which an end of a guide wire will abut. Outer wire tube 452 is threadably engageable with either guide tube 456 or inner wire tube 450 so that outer wire tube 452 may be advanced into guide tube 456 to force a guide wire positioned against proximal wire extreme 462 through distal aperture 500 of flexible reamer guide wire bender 440. Adjustment screw 458 is utilized to rotate wire shaping head 448 about pivot pin 444 whereby rollers 442 bend a guide wire into the desired shape as it exits distal aperture 500. Shaping of a guide wire in vivo with flexible reamer guide wire bender 440 may be observed with a fluoroscope.

A guide wire bent with flexible reamer guide wire bender 440 will be advanced into, e.g., femoral head 114 as illustrated, e.g., in FIG. 73 with respect to guide wire 410. In this way, a flexible reamer will be utilized to extend femoral cavity 224 toward the femoral head as illustrated in FIG. 74. A similar procedure may be utilized for extending femoral cavity 224 into the shaft of femoral 108.

In yet another alternative embodiment of the present invention, flexible reamers having flexible reaming heads are utilized to form the cavity in femur 108 into which a femoral implant in accordance with the present invention is implanted. As illustrated in FIG. 93, guide wire 590 is inserted into femur 108 and extends from greater trochanter 110, through femoral neck 112, and into femoral head 114. Guide wire 590 can be inserted into femur 108 utilizing flexible reamer guide 408 (FIGS. 71 and 72), or flexible reamer guide wire bender 440 (FIGS. 77-79). After inserting guide wire 590 into femur 108, flex up reamer 600 is used to ream a path from greater trochanter 110, through femoral neck 112, and into femoral head 114 as illustrated in FIG. 94. In one embodiment of the present invention, access 101 is formed in femur 108 prior to using flex up reamer 600 to ream a path from greater trochanter 110, through femoral neck 112, and into femoral head 114. As illustrated in FIG. 96, flex up reamer 600 includes elongate aperture 611. In use, guide wire 590 is positioned through elongate aperture 611 to guide reaming from greater trochanter 110, through femoral neck 112, and into femoral head 114.

As illustrated in FIGS. 94-96, flex up reamer 600 includes a reamer head having large diameter portion 602 and small diameter portion 604, with flexible cuts throughout the length of the flex up reamer head to allow the flex up reamer head to curve along the path defined by guide wire 590. A number of flexible cuts may be utilized along the length of the reamer head of flex up reamer 600, including the flexible cuts described in U.S. Pat. No. 6,053,922 with respect to flexible reamer shafts. Flex up reamer 600 may be inserted through any of the guide tube/retractors of the present invention, and may include a cooperating guide tube matched to the guide tube/retractor utilized. Flex up reamer 600 advantageously includes large diameter portion 602 and small diameter portion 604 sized to form apertures accommodating lag screw tube 266, and lag screw shaft 274, respectively.

Figure 100:
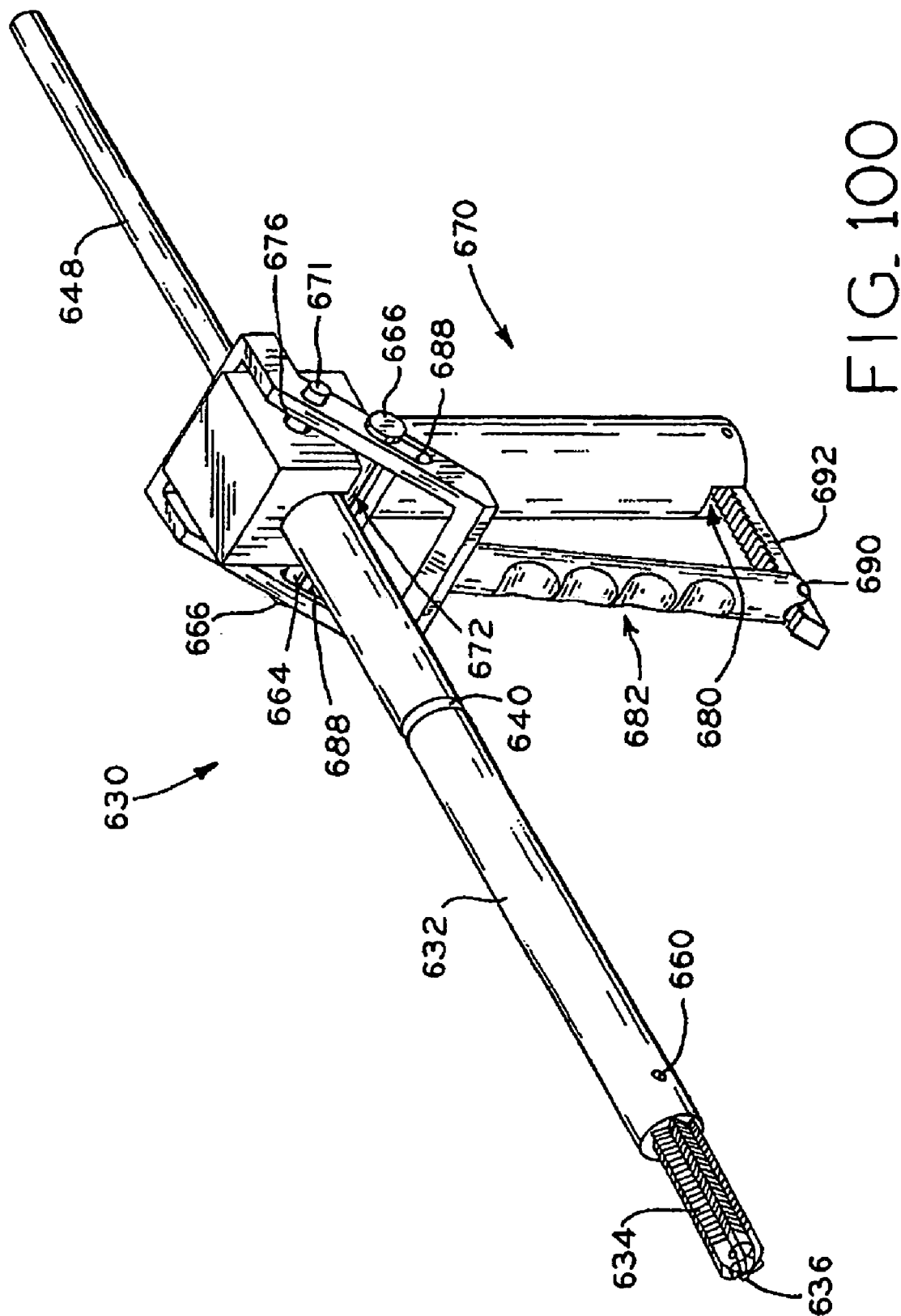
FIG. 100 is a perspective view of a swivel/down reamer assembly shown in unactuated position.
Figure 101:
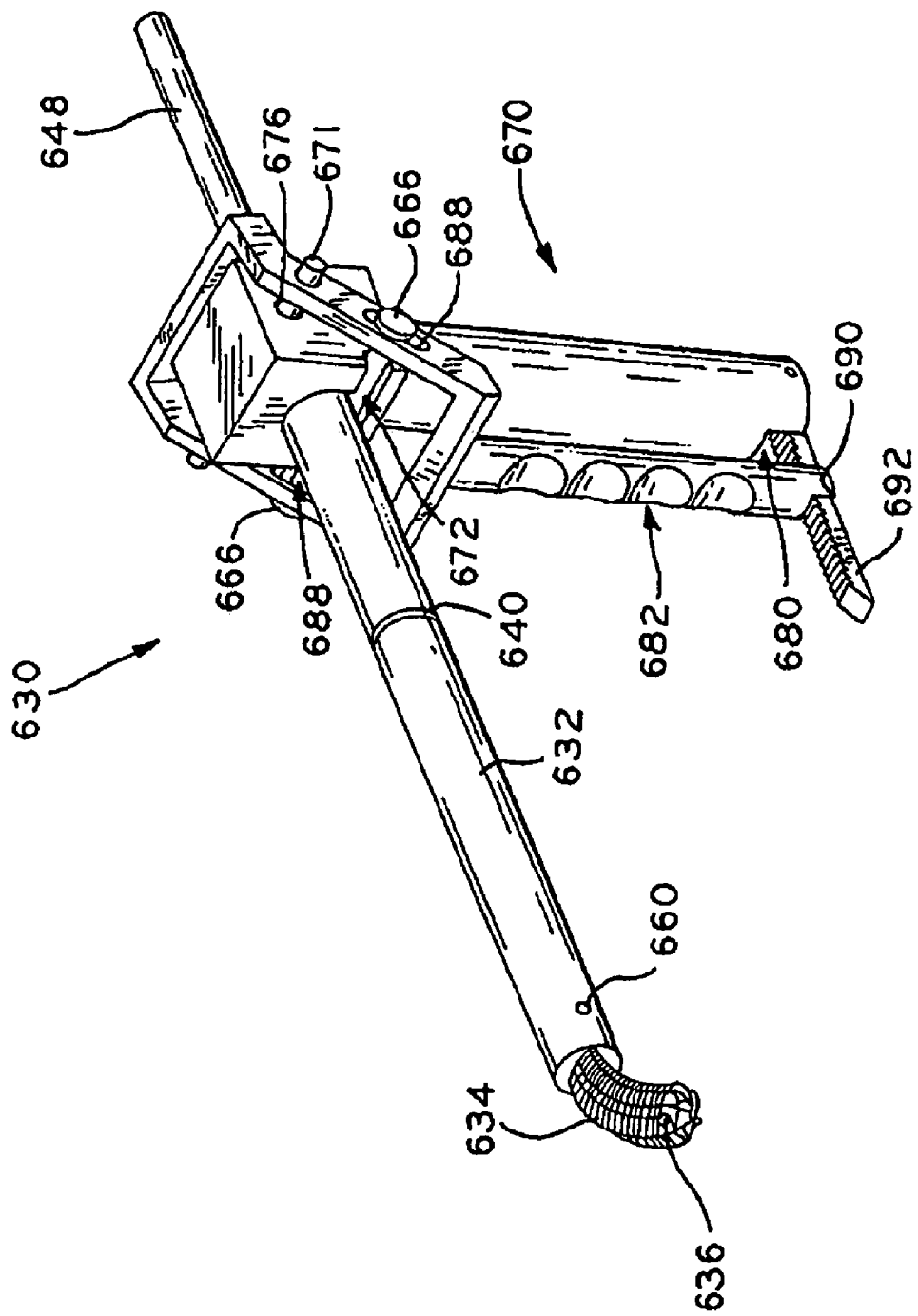
FIG. 101 is a perspective view thereof shown in actuated position.
Figure 102:
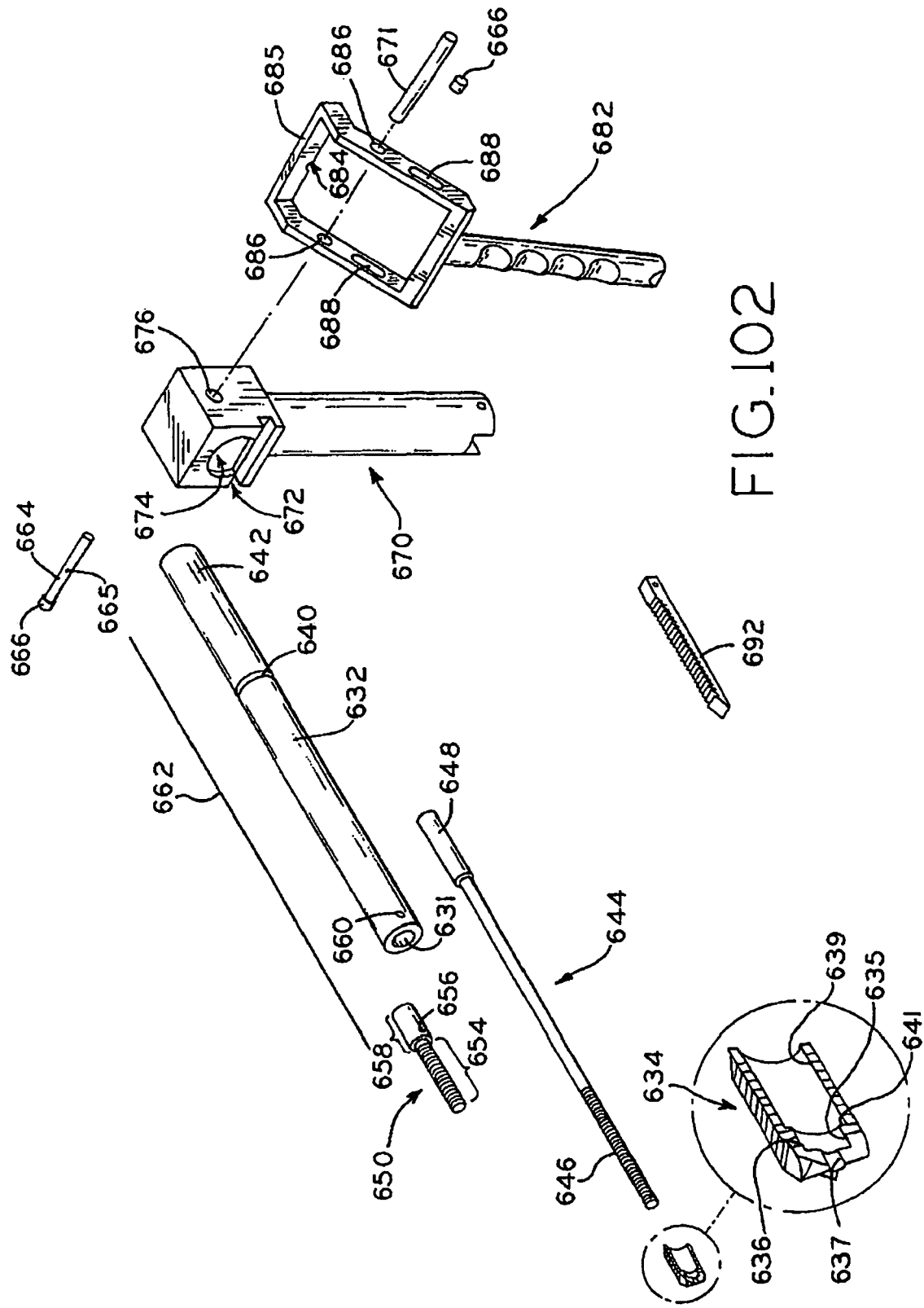
FIG. 102 is an exploded view of the swivel/down reamer assembly illustrated in FIGS. 100 and 101.

After formation of femoral head arm 256' (FIG. 103) of the implant cavity, swivel/down reamer assembly 630 (FIGS. 100-102) is utilized to extend the implant cavity as illustrated in FIG. 103. Referring to FIGS. 100-102, swivel/down reamer assembly 630 includes tool housing 632 having longitudinal aperture 631 running the length thereof as illustrated in FIG. 104. Tool housing 632 includes detent groove 640 for receiving the ball detent of the ball detent retaining mechanism described above. Tool housing 632 further includes set screw aperture 660 for securing flexible guide shaft 650 therein. As illustrated in FIG. 102, flexible guide shaft 650 includes set screw aperture 656 corresponding to set screw aperture 660 in tool housing 632.

As illustrated in FIGS. 102 and 105, flexible guide shaft 650 includes flexible portion 654 and proximal end 658, with set screw aperture 656 formed in proximal end 658. Flexible portion 654 of flexible guide shaft 650 can be formed with a plurality of alternating, substantially semi-circular cuts 668 as illustrated in FIG. 105. Specifically, cuts 668 are alternatively formed from the top and the bottom of flexible portion 654 as illustrated in FIG. 105. As further illustrated in FIG. 105, alternating cuts 668 overlap the center line of flexible guide shaft 650. Using non-continuous cuts as illustrated in FIG. 105 to create flexibility in flexible portion 654 of flexible guide shaft 650 also limits flexibility to a plane perpendicular to the cuts because continuous material remains on either outside edge of flexible portion 654 of flexible guide shaft 650. This additional material at both sides of flexible guide shaft 650 advantageously prevents axial compression of the tube along the longitudinal axis thereof. In an alternative embodiment, cuts 668 are pie shaped, terminating in an apex toward the center of flexible portion 654 of flexible guide shaft 650. In construction, proximal end 658 of flexible guide shaft 650 is positioned within longitudinal aperture 631 of tool housing 632 and secured therein via a set screw. When proximal end 658 of flexible guide shaft 650 is secured within tool housing 632, flexible portion 654 of flexible guide shaft 650 protrudes from tool housing 632. Flexible guide shaft 650 includes reamer shaft aperture 653 (FIG. 106) running the length thereof. Reamer shaft aperture 653 of flexible guide shaft 650 accommodates flex down reamer shaft 644 (FIG. 102). Referring to FIG. 102, to assemble swivel/down reamer assembly 630, flex down reamer shaft 644 is positioned within reamer shaft aperture 635 of flex down reamer head 634 and secured therein with a set screw positioned through set screw aperture 636 in flex down reamer head 634. Flexible guide shaft 650 is inserted through flexible guide shaft aperture 639 of flex down reamer head 634 until end 651 (FIG. 105) of flexible guide shaft 650 abuts shoulder 641 (FIG. 102) of flex down reamer head 634. Flex down reamer shaft 644 is positioned within reamer shaft aperture 653 of flexible guide shaft 650, with flexible guide shaft 650 positioned within flexible guide shaft aperture 639 of flex down reamer head 634. Flex down reamer shaft 644 extends the length of reamer shaft aperture 653 of flexible guide shaft 650 as well as the length of longitudinal aperture 631 of tool housing 632, with chuck end 648 of flex down reamer shaft 644 extending out of tool housing 632 as illustrated in FIGS. 100 and 101.

Prior to securing flexible guide shaft 650 to tool housing 632, and positioning flex down reamer shaft 644 therein, cable 662 is inserted through cable aperture 652, which runs the length of flexible guide shaft 650. After inserting cable 662 through cable aperture 652, a piece of material larger in cross sectional area than cable aperture 652 is secured to the end of cable 662 extending outwardly from end 651 of flexible guide shaft 650 to prevent cable 662 from being pulled out of cable aperture 652 in a distal to proximal direction relative to flexible guide shaft 650. In one exemplary embodiment, a ball of weld material is welded to the end of cable 662. In construction, cable 662 extends from flexible guide shaft 650 through the length of tool housing 632.

As illustrated in FIGS. 100 and 101, cable rod 664 traverses aligned cable rod slots 642 (FIGS. 102 and 104) formed in opposing sides of tool housing 632. Cable rod 664 includes cable aperture 665 for receiving cable 662. After cable 662 is inserted through cable aperture 665 in cable rod 664, the slack in cable 662 is eliminated and cable 662 is secured to cable rod 664. As illustrated in FIGS. 100-102, handle 670 includes cable rod cutout 672 accommodating cable rod 664. Handle 670 further includes tool housing aperture 674 into which tool housing 632 is positioned. Tool housing 632 can be secured to handle 670 via a set screw or other fastener extending through handle 670 into tool housing aperture 674.

As illustrated in FIGS. 100 and 101, lever handle 682 is pivotally connected to handle 670 via pivot shaft 671, with pivot shaft 671 traversing pivot apertures 686 and 676 (FIG. 102) in lever handle 682 and handle 670, respectively. Lever handle 682 includes a pair of elliptical cable rod apertures 688 in opposing arms thereof. Elliptical cable rod apertures 688 accommodate cable rod 664. With cable rod positioned through elliptical cable rod apertures 688 in lever handle 682, cable rod end nuts 666 are secured to opposing ends of cable rod 664 to prevent axial displacement of cable rod 664. To complete assembly of swivel/down reamer assembly 630, ratchet bar 692 is positioned within ratchet cutout 680 of handle 670 and pivotally connected thereto, with a leaf spring interposed between ratchet bar 692 and handle 670 to bias ratchet bar 692 upwardly toward handle 670. As illustrated in FIGS. 100 and 101, lever handle 682 includes pawl end 690 for engaging the ratchet teeth of ratchet bar 692.

In use, swivel/down reamer assembly 630 can be actuated from a straight or unflexed position as illustrated in FIG. 100 to a flexed position as illustrated in FIG. 101. To actuate swivel/down reamer assembly 630 from the straight position illustrated in FIG. 100 to the flexed position illustrated in FIG. 101, force is applied to lever handle 682 to pivot lever handle 682 about pivot shaft 671 toward handle 670. When lever handle 682 is actuated in this manner, cable rod 664 is pulled toward handle 670, causing flexible guide shaft 650 to flex downwardly. Specifically, cable 662 pulls the lower portion of flexible guide shaft inwardly, flexing flexible guide shaft 650 whereby the top portion of flexible guide shaft 650 is placed in tension or stretches, and the bottom portion of flexible guide shaft 650 is compressed. As illustrated in FIGS. 100-102, flex down reamer head 634 includes flexible cuts along its length. When flexible guide shaft 650 flexes as described above, flex down reamer head 634 similarly flexes downwardly, as flex down reamer shaft is positioned within flexible guide shaft aperture 639 of flex down reamer head 634 when swivel/down reamer assembly 630 is actuated from the straight position illustrated in FIG. 100 to the flexed position illustrated in FIG. 101. As illustrated in FIG. 101, pawl end 690 of lever handle 682 engages the teeth of ratchet bar 692 to retain swivel/down reamer assembly 630 in the actuated position of FIG. 100. As described above, ratchet bar 692 is biased toward handle 670 by a leaf spring. To release swivel/down reamer assembly 630 from the actuated position illustrated in FIG. 100, a distal end of ratchet bar 692 may be pushed downwardly, i.e., away from handle 670 to release pawl end 690 of lever handle 682 from engagement with the teeth of ratchet bar 692.

Referring to FIG. 102, lever handle 682 includes radiused cutout 684 sized to accommodate flex down reamer shaft 644. In the straight or unflexed position illustrated in FIG. 100, radiused cutout 684 is positioned about flex down reamer shaft 644 such that cross bar 685 of lever handle 682 abuts the shoulder formed on flex down reamer shaft 644 between chuck end 648 and the remainder of flex down reamer shaft 644. This cooperating shoulder arrangement prevents flex down reamer shaft 644 and, consequently, flex down reamer head 634 from being advanced through and away from tool housing 632. When swivel/down reamer assembly 630 is actuated into the flexed position as illustrated in FIG. 101, lever handle 682 is moved so that flex down reamer shaft 644 is no longer positioned within radiused cutout 684 contacting flex down reamer shaft 644 and the cooperating shoulder arrangement which prevents flex down reamer shaft 644 and flex down reamer head 634 from being advanced through tool housing 632 is eliminated.

In use, flex down reamer head 634 is inserted into access 101' formed in femur 108 as described above. As illustrated in FIG. 103, on initial insertion, flex down reamer head 634 is positioned about flexible guide shaft 650 as illustrated in FIG. 103. As illustrated in FIG. 103, tool housing 632 abuts greater trochanter 110 when swivel/down reamer assembly 630 is utilized to extend implant cavity 224' as illustrated in FIG. 3. Upon insertion of flex down reamer head 634 through access 101' in femur 108, flex down reamer head 634 is actuated by coupling an actuation device to chuck end 648 of flex down reamer shaft 644 and supplying rotational motion thereto. With flex down reamer head 634 rotating to ream bone from femur 108, swivel/down reamer assembly is actuated from the straight or non-flexed positioned illustrated in FIG. 100 to the flexed position illustrated in FIG. 101 to extend implant cavity 224 from femoral head arm 256' formed by flex up reamer 600, as illustrated in FIG. 94, toward the shaft of femur 108. Actuation of swivel/down reamer assembly 630 from the straight or non-flexed position illustrated in FIG. 100 to the flexed position in FIG. 101 generally effects a swivel type reaming as described above. After swivel reaming is complete, chuck end 648 of flex down reamer shaft 644 is advanced through tool housing 632 to advance flex down reamer head 634 into and through the intramedullary canal of femur 108. As flex down reamer head 634 is advanced relative to tool housing 632, flex down reamer head 634 is also advanced relative to flexible guide shaft 650 so that flexible reamer head 634 is eventually moved out of engagement with flexible guide shaft 650, i.e., flexible guide shaft 650 is no longer positioned within flexible guide shaft aperture 639 of flex down reamer head 634 (see FIG. 102). As flex down reamer head 634 is advanced toward the intramedullary canal of femur 108, flex down reamer head 634 will be directed into the intramedullary canal of the femur as it is moved from engagement with flexible guide shaft 650 due to the curvature provided by flexible guide shaft 650 and also due to the softer cancellous bone occupying the intramedullary canal versus the harder cortical bone material of the femur. To facilitate appropriate movement of flex down reamer head 634 into the intramedullary canal of femur 108, flex down reamer head 634 has a generally bullet shape as illustrated, e.g., in FIGS. 100-103. The distal end of bullet shaped flex down reamer head 634 will glance off the harder cortical wall of the femur and be directed into the intramedullary canal as described above.

In an alternative embodiment of the present invention, a guide plate is not secured to the femur as described hereinabove. In this embodiment, alignment guide 760 (FIGS. 116-119) is utilized to facilitate location of greater trochanter 110 and guide reaming of femur 108. As illustrated in FIGS. 116-119, alignment guide 760 includes locating pin 764 extending from the distal end thereof. In use, the distal end of alignment guide 760 is inserted through incision 106 (FIG. 1) and locating pin 764 is utilized to facilitate location of greater trochanter 110 utilizing tactile feedback. A fluoroscopic image can be utilized to identify proper placement of locating pin 764 atop the proximal aspect of greater trochanter 110. In one exemplary embodiment, a series of locating pins 764, each having differing lengths and offsets are used to account for differences in patient physiology. Depending upon preoperative templating, the appropriate locating pin 764 is chosen and secured to alignment guide 760. When inserting alignment guide 760, pin cover 762 is moved into the position illustrated in FIG. 116, covering bone gripping pins 766 to prevent bone gripping pins 766 from irritating soft tissues during insertion of alignment guide 760 through incision 106. After proper positioning of the distal end of alignment guide 760 atop greater trochanter 110, with locating pin 764 positioned atop the proximal aspect of greater trochanter 110, pin cover 762 can be actuated into the position illustrated in FIG. 118 to allow bone gripping pins 766 to be exposed from the distal end of alignment guide 760. Bone gripping pins 766 allow alignment guide 760 to grip greater trochanter 110 and resist movement from its position atop greater trochanter 110. As illustrated in FIG. 118, bone gripping pins 766 extend variable distances from the distal end of alignment guide 760. In one exemplary embodiment, these variable distances are matched to the statistical topology of greater trochanter 110 to allow for better gripping thereof. For the purposes of this document, statistical topology means the topology of the greater trochanter as determined by statistical analysis of a number of femurs. With the distal end of alignment guide 760 properly positioned atop greater trochanter 110, a guide pin such as, e.g., a Steinman pin is positioned through pin aperture 806 of alignment guide 760 and traverses cannulated alignment guide 760 until it is exposed from the distal end thereof and is positioned atop greater trochanter 110. In this position, the guide pin is impacted into greater trochanter 110 to serve as a guide for initial reaming thereof. With the guide pin impacted into greater trochanter 110, a cannulated plunge reamer such as plunge reamer 480 depicted in FIG. 82 can be utilized to form the initial access in greater trochanter 110. The guide pin is then removed and femoral cavity 224 (FIG. 11) can then be prepared in accordance with various embodiments of the present invention.

Alignment guide 760 is illustrated in detail in FIGS. 116-119. Referring to FIGS. 116-119, alignment guide 760 includes central body 770 which is secured via set screws 800 (FIG. 119) to distal body end 768 and proximal body end 798 to form a cannulated body. Bone gripping pins 766 are positioned within apertures 802 (FIG. 119) and secured to distal body end 768 as illustrated in FIG. 118. Locating pin rod 792 is positioned through aperture 816 of central body 770, protruding from either end thereof. Locating pin rod 792 rests in channel 804 of distal body end 768. Pin cover 762 is positioned over distal body end 768 and central body 770 of alignment guide 760, with aperture 796 of pin cover 762 aligned with aperture 794 of locating pin rod 792. In this position, locating pin 764 is positioned through aperture 796 of pin cover 762 and aperture 794 of locating pin rod 792 and secured thereto. Locating pin 764 serves to secure pin cover 762 to locating pin rod 792. Locating pin rod 792 is slidable within central body 770, distal body end 768, and proximal body end 798 of alignment guide 760 to allow for axial movement of pin cover 762 relative to central body 770.

The proximal end of locating pin rod 792 is positioned within aperture 818 of proximal body end 798, with aperture 790 of locating pin rod 792 aligned with set screw channel 788 of proximal body end 798. Plunger 772 is positioned over proximal body end 798, with set screw aperture 820 aligned with set screw channel 788. Set screw 786 is threaded through set screw aperture 820 and extends into set screw channel 788 and aperture 790 of locating pin rod 792. Set screw 786 secures locating pin rod 792 to plunger 772 and, because of its placement in set screw channel 788 prevents rotational movement of both plunger 772 and locating pin rod 792 relative to proximal body end 798, while allowing axial movement of plunger 772 and locating pin rod 792 relative to proximal body end 798. Axial movement of plunger 772 relative to proximal body end 798 causes axial movement of locating pin rod 792 relative to central body 770 and axial movement of pin cover 762 relative to distal body end 768. Axial movement of plunger 772 relative to proximal body end 798 can be used to reposition cover 762 from the covering position illustrated in FIG. 116 to the position illustrated in FIG. 117 and, finally, to the exposing position illustrated in FIG. 118 to allow for distal exposure of bone gripping pins 766.

Figure 119:
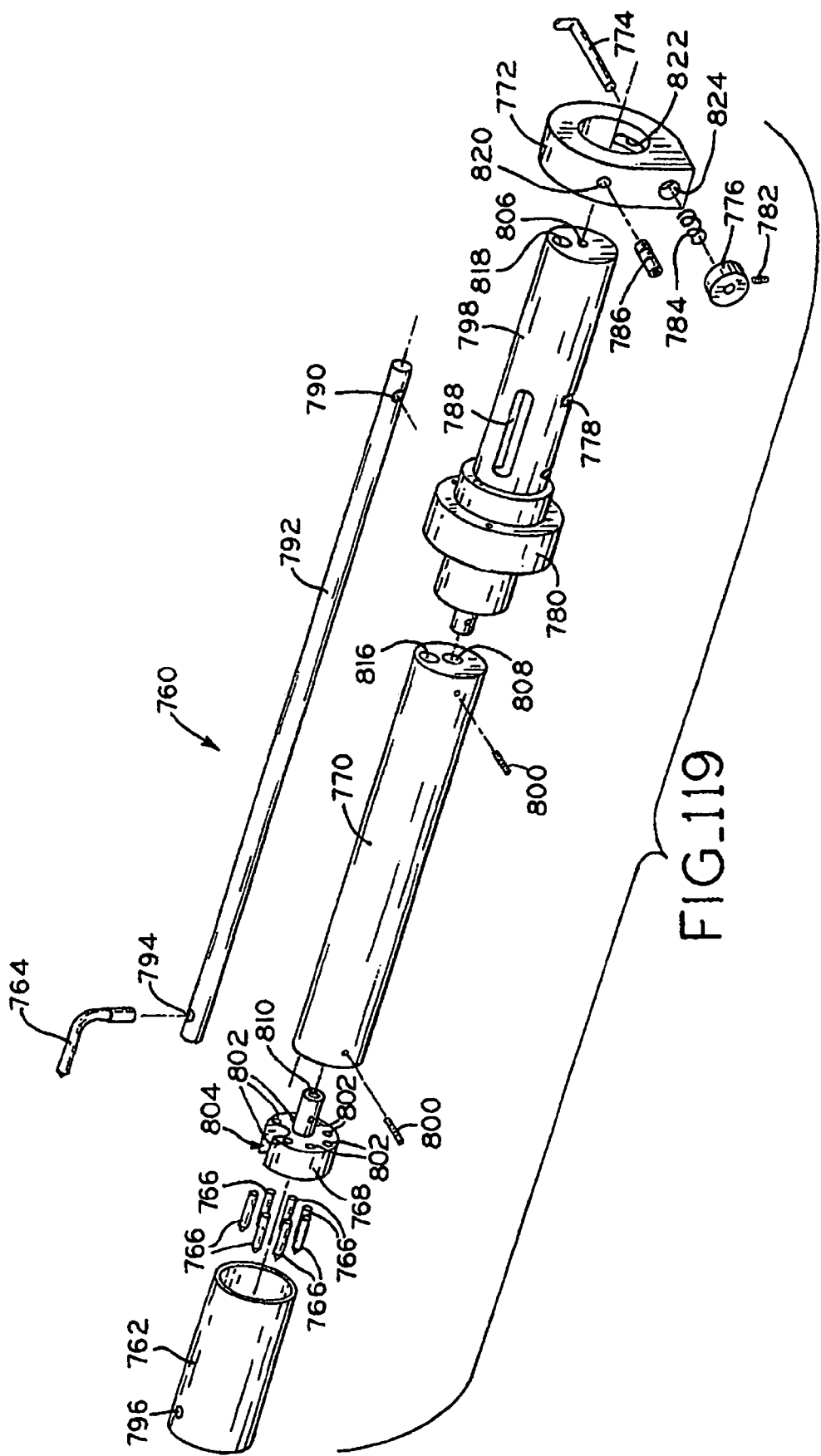
FIG. 119 is an exploded perspective view of the alignment guide of FIGS. 116-118.

As illustrated in FIG. 117, cover 762 includes channel 814 accommodating set screw 812 which works in conjunction with locating pin 764 to resist rotational movement of cover 762 relative to distal body end 768. Movement of plunger 772 between the positions illustrated in FIGS. 116-118 is controlled by plunger push button 776. As illustrated in FIG. 119, plunger 772 includes plunger rod slot 822 and plunger rod aperture 824. In construction, the long leg of plunger rod 774 is positioned through plunger rod aperture 824, with the short leg thereof radially protruding through plunger rod slot 822 of plunger 772 and being positioned within U-shaped plunger rod channel 778 (See, e.g., FIG. 117) of proximal body end 798. The long leg of plunger rod 774 extends through plunger rod aperture 824 and is surrounded by spring 784. Plunger rod aperture 824 includes a counter bore against which spring 784 is positioned. The long leg of plunger rod 774 further extends through the central aperture of plunger push button 776. Set screw 782 is positioned through the body of plunger push button 776 and engages plunger rod 774 to secure plunger push button 776 to plunger rod 774. In use, spring 784 biases plunger push button 776 away from plunger 772 which allows for placement of the short leg of plunger rod 774 in one of the arms of U-shaped plunger rod channel 778. To allow for the short leg of plunger rod 774 to be positioned in the base of U-shaped plunger rod channel 778, plunger push button 776 is actuated against the biasing force of spring 784 as illustrated in FIG. 117. In this position, plunger 772 can be axially displaced relative to proximal body end 798 to allow for movement of pin cover 762 from the covering position illustrated in FIG. 116 to the position illustrated in FIG. 117 and finally to the exposing position illustrated in FIG. 118. After achieving the exposing position illustrated in FIG. 118, the biasing force of spring 784 positions the short leg of plunger rod 774 in the proximal most arm of U-shaped plunger rod channel 778.

Alignment guide 760 includes flange 780 which is useful in manipulating alignment guide 760 through incision 106 and is further useful, in an alternative embodiment, for securing an alignment device having an alignment arm similar to alignment arm 174 of alignment device 156 discussed hereinabove. In this embodiment, the alignment device is utilized to confirm the proper positioning of the distal end of alignment guide 760 atop greater trochanter 110.

In an alternative embodiment, flexible reamer 826 (FIGS. 120-132) is utilized to form implant cavity 224 (FIG. 11). To form implant cavity 224, flexible reamer head 828 is positioned through access 101 formed in femur 108 by plunge reaming. When inserting flexible reamer 826 through access 101, interior extension 838 of distal body end 832 is positioned within access 101, with flange 840 abutting the exterior wall of femur 108. In this position, flexible reamer 826 can be actuated between the flex up position illustrated in FIG. 121 to the flex down position illustrated in FIG. 123 to effect swivel reaming. Furthermore, in the flex up position illustrated in FIG. 121, flexible reamer head 828 can be advanced into femoral head 114 to form femoral head arm 256 of implant cavity 224 (FIG. 11). Similarly, in the flex down position illustrated in FIG. 123, flexible reamer head 828 can be advanced into the intramedullary canal of femur 108 to form femoral shaft arm 258 of implant cavity 224.

Figure 120:
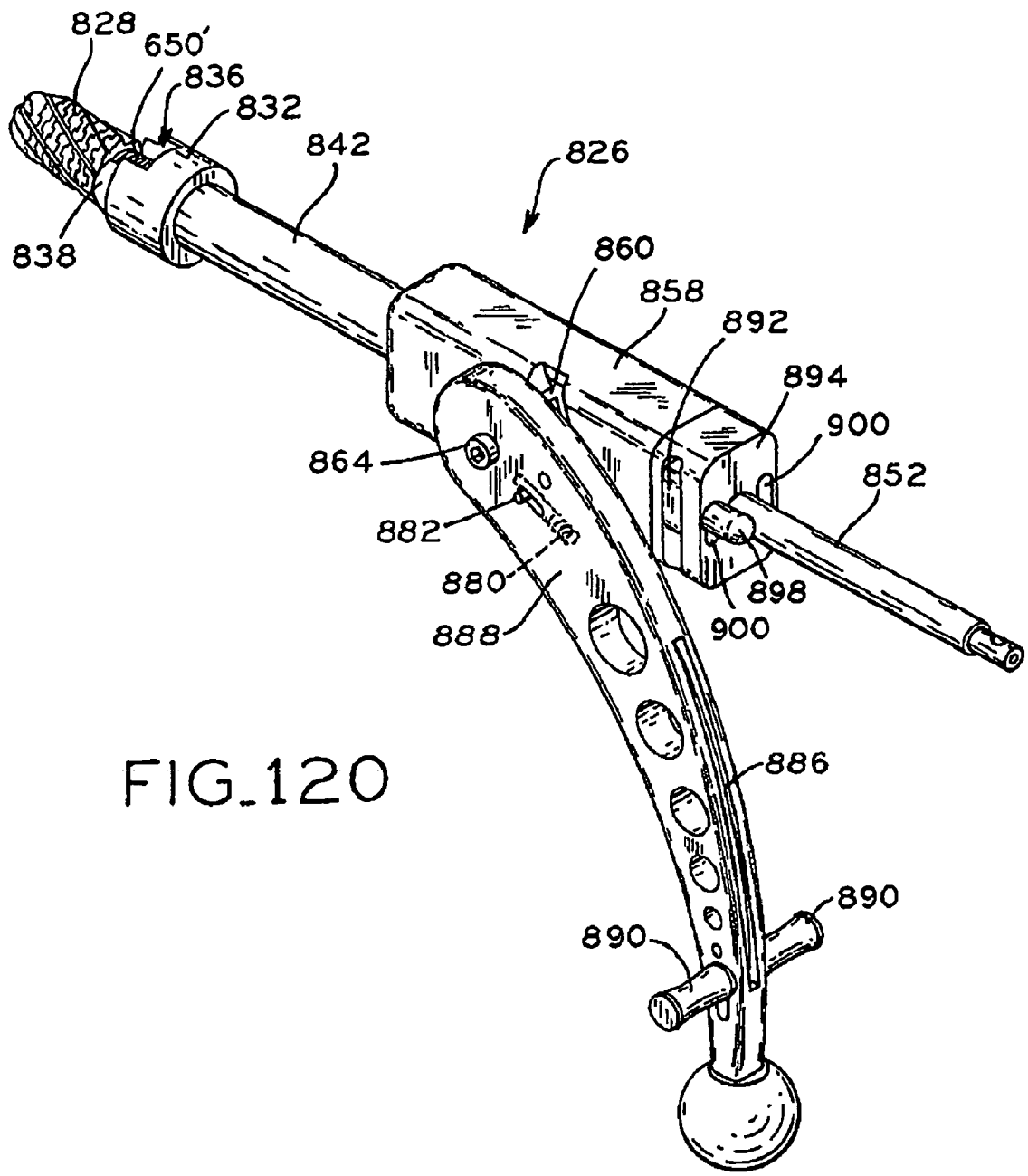
FIG. 120 is a perspective view of a flexible reamer of the present invention.
Figure 121:
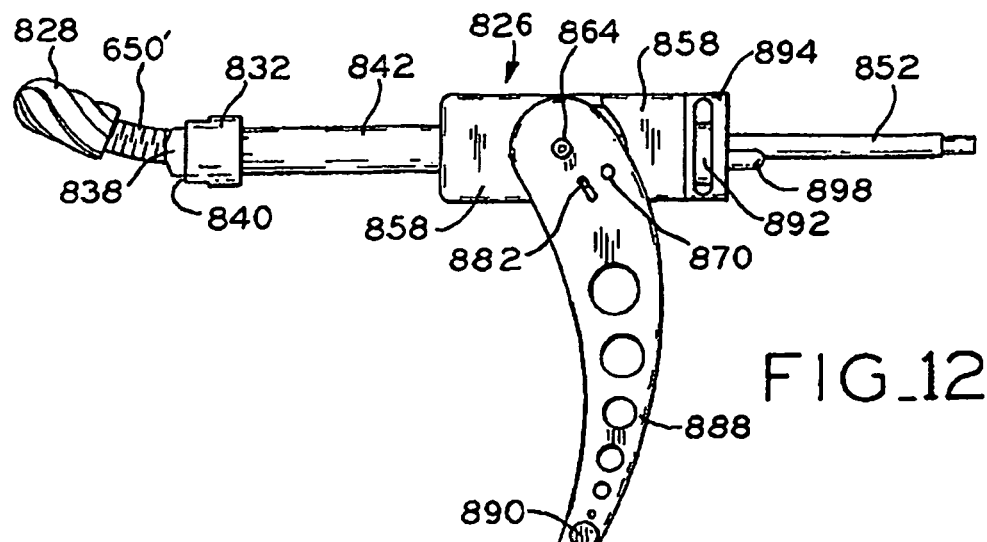
FIG. 121 is a side plan view illustrating actuation of the flexible reamer depicted in FIG. 121 into a flex up position.
Figure 122:
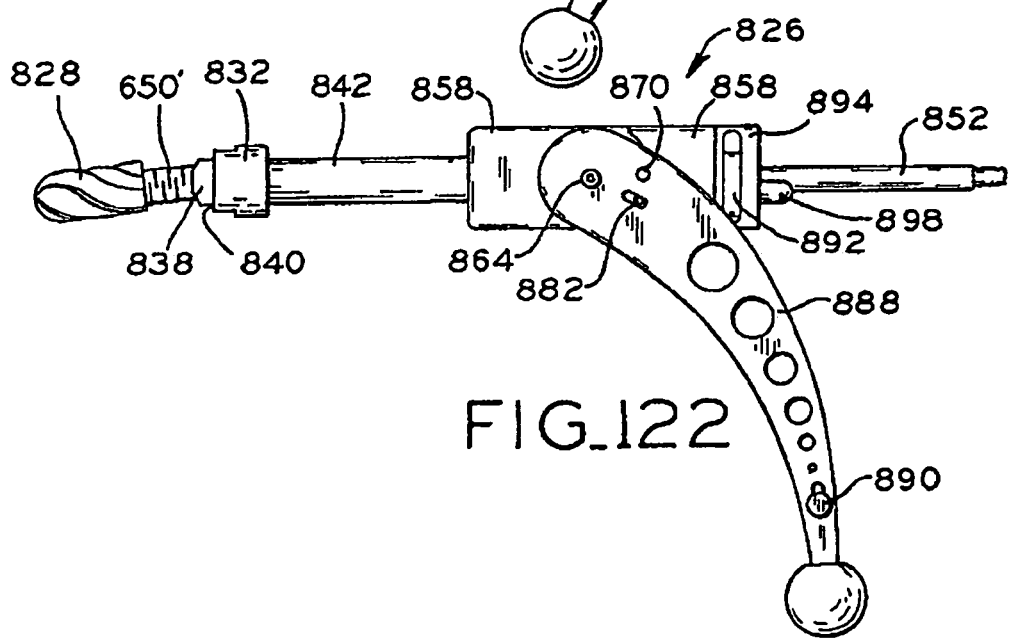
FIG. 122 shows an intermediate step in actuating the flexible reamer depicted in FIGS. 120 and 121 between a straight reaming position and the flex down position.
Figure 123:
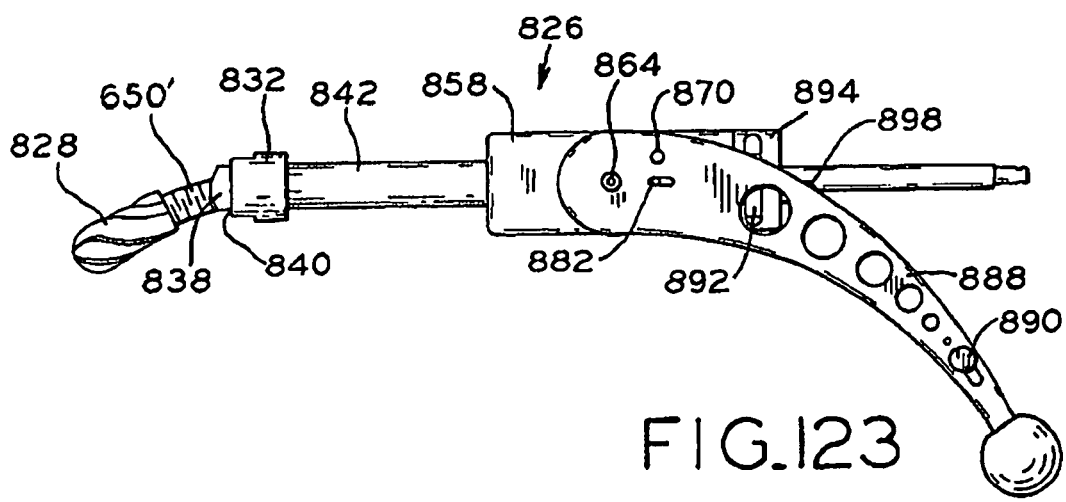
FIG. 123 is a side plan view of the flexible reamer of FIGS. 120-122 shown in the flex down position.
Figure 124:
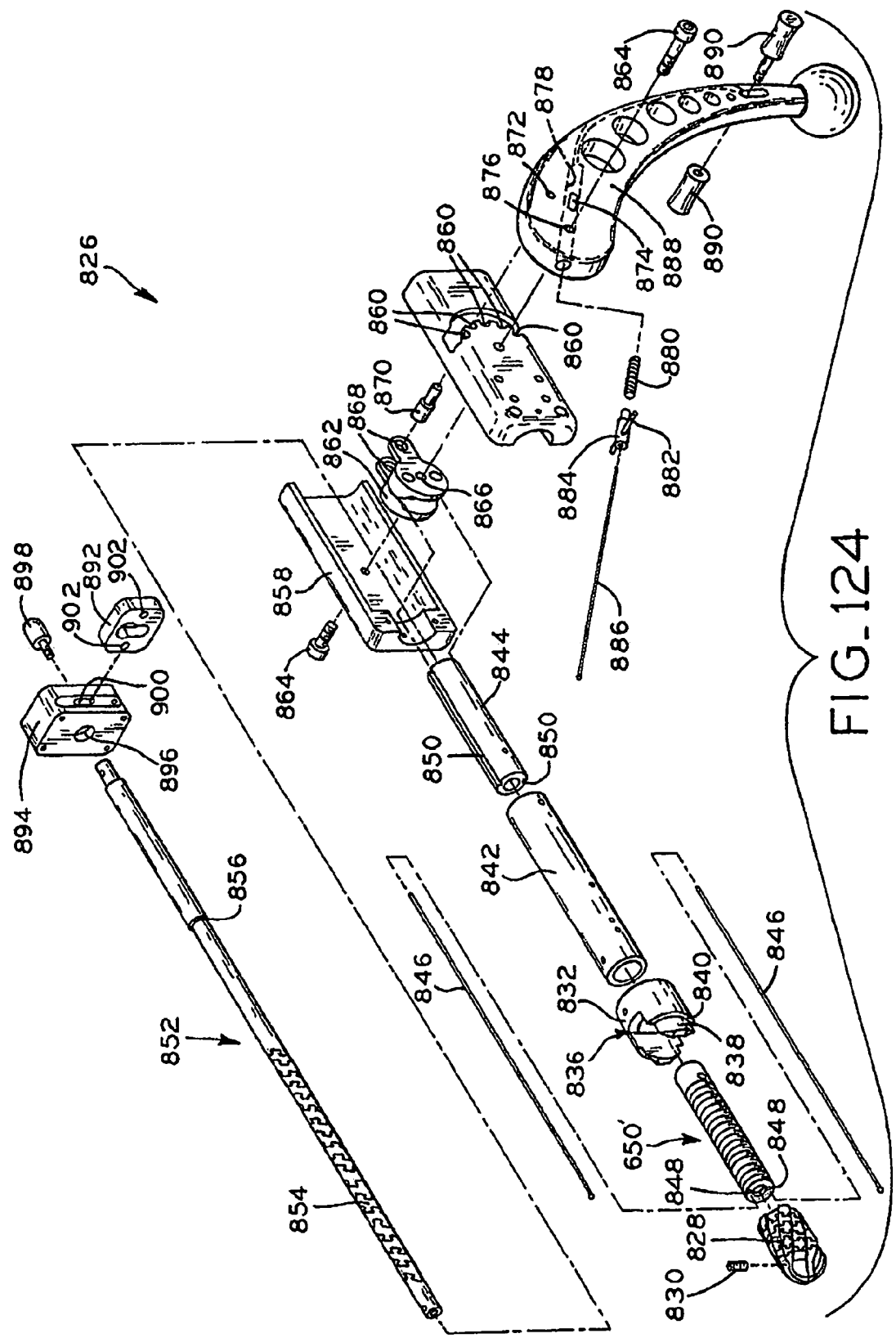
Figure 125:
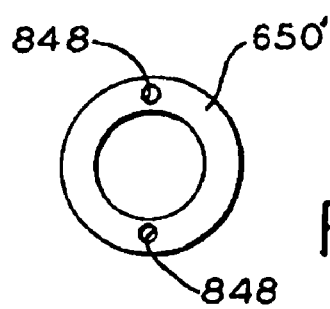

Referring to FIGS. 120-124, flexible reamer 826 includes proximal body end 894 connected to main body housing 858 which is further connected to outer tool shaft 842 and distal body end 832. Flexible driveshaft 852 extends through the cannulated body of flexible reamer 826. Distal body end 832 includes guide tube slot 836 accommodating flexure of flexible guide shaft 650'. As illustrated in FIGS. 121-123, flexible driveshaft 852 includes a proximal end for securing flexible driveshaft 852 to the chuck of a device for imparting rotational motion thereto. Referring to FIG. 124, flexible driveshaft 852 includes a distal end adapted for connection to flexible reamer head 828. As illustrated in FIG. 124, set screw 830 traverses a generally radial aperture in flexible reamer head 828 and is thereafter engaged in a radial aperture positioned at the distal end of flexible driveshaft 852. As illustrated in FIG. 124, flexible driveshaft 852 includes flexible distal end 854. Flexible distal end 854 includes at least one spiral flex cut as described hereinabove with respect to various flexible driveshafts and reamer heads. Similarly, flexible reamer head 828 includes a plurality of spiral cuts allowing for flexure thereof.

With flexible reamer head 828 secured thereto, flexible driveshaft 852, traverses the central apertures of flexible guide shaft 650', inner tool shaft 844, and proximal body end 894 to protrude proximally from flexible reamer 826 as illustrated in FIGS. 121-123. In construction, distal body end 832 is secured about outer tool shaft 842 as illustrated in FIGS. 121-123. Flexible guide shaft 650' is positioned within the distal end of outer tool shaft 842 and is secured thereto with, e.g., a set screw. Similarly, inner tool shaft 844 is positioned within outer tool shaft 842 and is secured thereto with, e.g., a set screw. In construction, inner tool shaft 844 is positioned with its distal end in close proximity to the proximal end of flexible guide shaft 650. In one exemplary embodiment, the distal end of inner tool shaft 844 abuts the proximal end of flexible guide shaft 650'. Flexible guide shaft 650' includes a pair of cable apertures 848 formed in radially opposing sides thereof. With reference to flexible guide shaft 650', "radially opposing sides," and/or "opposing sides" refers to a pair of outer portions of flexible guide shaft 650' separated by 180°. Flexible guide shaft 650' can take many forms, including those in which the transverse cross section is circular or polygonal. Cable apertures 848 accommodate cables 846. Cables 846 include a ball, flange, or otherwise radially expanding structure or protrusion on a distal end thereof to prohibit cables 846 from being pulled through cable apertures 848 in a distal to proximal fashion. When operably positioned through cable apertures 848, the radially expanded distal end of cables 846 abuts the distal end of flexible guide shaft 650'. Cables 846 extend from the proximal end of flexible guide shaft 650' and are positioned in cable channels 850 of inner tool shaft 844. Cables 846 further extend proximally from inner tool shaft 844 and are received by and fixably secured to mandrel 862.

Mandrel 862 is pivotably connected to main body housing 858 whereby rotation of mandrel 862 tensions one of cables 846. Lag screws 864 are utilized to pivotally connect mandrel 862 to main body housing 858. As illustrated in FIG. 124, lag screws 864 are positioned through opposing sides of main body housing 858 to pivotally connect mandrel 862 thereto. One lag screw 864 traverses handle 888 to further pivotally connect handle 888 to main body housing 858. Mandrel 862 is rotationally fixed to handle 888 via pin 870. Pin 870 traverses an aperture formed in at least one pivot arm 868 of mandrel 862 and extends through the arcuate slot formed proximally of detents 860 in main body housing 858 and is engaged in aperture 872 of handle 888. Rotation of handle 888 about lag screw 864 therefore causes rotation of mandrel 862 about lag screw 864. As handle 888 and mandrel 862 are rotated relative to main body housing 858, one cable 846 is tensioned to force flexible guide shaft 650' into a flexed position as illustrated, e.g., in FIG. 128. For example, if handle 888 and, consequently, mandrel 862 are rotated clockwise as illustrated in FIG. 121, then the upper cable 846 is tensioned and flexible guide shaft 650' is curved upward to place flexible reamer 826 in the flex up position illustrated in FIG. 121. Similarly, if handle 888 is rotated counterclockwise as illustrated in FIG. 123, flexible reamer head 828 is positioned in the flex down position as illustrated in FIG. 123.

Tensioning of a cable 846 exerts a distal to proximal force on flexible guide shaft 650' causing compression of one side of flexible guide shaft 650' as illustrated, e.g., in FIG. 128. In an alternative embodiment, a flexible shaft or other device for transmitting force in a non-liner fashion is utilized to push or extend one side or portion of the distal end of flexible guide shaft 650' in a proximal to distal direction and cause compression of the opposing side thereof. Flex cuts 668 provide gaps in radially opposing sides of flexible guide shaft 650' which gaps allow for compression of a side of flexible guide shaft 650' as illustrated, e.g., in FIG. 128. Each flex cut 668 is a discrete cut, i.e., each flex cut 668 does not intersect another flex cut 668. As illustrated in FIGS. 128-130, flexible cuts 668 may take many forms, including triangular cuts 668" illustrated in FIGS. 128 and 129, and straight cuts 668' illustrated in FIG. 130. Other geometrical shapes may be utilized to form flex cuts 668. Importantly, material of flexible guide shaft 650' is removed to allow for compression of a portion of flexible guide shaft 650' to allow for flexure thereof as illustrated in FIG. 128. Further, flex cuts 668 are formed so that flexure in only a single plane (hereinafter the "plane of flexure") is possible, i.e., the longitudinal axis of guide shaft 650' remains in a single plane whether guide shaft 650' is flexed or straight. To accommodate flexure in only the plane of flexure, flex cuts 668 are formed to leave continuous material 669 on radially opposing sides of guide shaft 650' as illustrated in FIGS. 131 and 132. The radially opposing sides having continuous material 669 are 90° from the plane of flexure and prevent flexure in any plane other than the plane of flexure. Continuous material 669 further prevents compression of flexible guide shaft 650' when one of cables 846 is tensioned. Flex cuts 668 are formed through radially opposing sides of flexible guide shaft 650'. Flex cuts 668 each extend from the outer surface of flexible guide shaft 650' to and slightly beyond the longitudinal axis of flexible guide shaft 650'. Advantageously, flexure of guide shaft 650' in a single plane provides for excellent control and predictability in controlling the flexure of flexible driveshaft 852, and flexible reamer head 828. In an alternative embodiment, flex cuts are made through one side only of the flexible guide shaft. In this embodiment, the flex cuts are incomplete flex cuts, but are nearly complete. With reference to flex cuts formed in the flexible guide of the present invention, "incomplete flex cut" means a flex cut that has a transverse directional component and that is not made through the entire body, i.e., they are not made from one opposing side to another. Similarly, "complete flex cut" means a flex cut that has a transverse directional component and is made through the entire body, i.e., they span opposing sides.

Flexible guide shaft 650' cooperates with flexible reamer head 828 as described hereinabove with respect to swivel/down reamer assembly 630. Flexible reamer head 828 includes the same features as flex down reamer head 634 discussed hereinabove. Handle 888 includes a lock mechanism for retaining flexible reamer head 828 in one of the flex up, straight, and flex down positions. As illustrated in FIG. 124, handle 888 includes internal aperture 878 accommodating detent rod body 884. With detent rod body 884 positioned within internal aperture 878 of handle 888, detent rod 882 extends through detent rod slot 874. Cable 886 extends through the central aperture of detent rod body 884 and through internal aperture 878 of handle 888. As illustrated in FIG. 120, cable 886 exits internal aperture 878 and is positioned within an external channel formed in handle 888 until it is secured to cable finger grips 890. As illustrated in FIG. 124, internal aperture 878 includes a counterbore. Spring 880 is positioned against an external shoulder formed in detent rod body 884 and cooperates with counterbored aperture 878 of handle 888 to bias detent rod body 884 into the position illustrated in FIGS. 121 and 123. In this position, detent rod 882 is positioned within one of detents 860 (FIGS. 124 and 127) formed in main body housing 858. To rotate handle 888 to actuate flexible reamer head 828 between the flex up, straight, and flex down positions, cable finger grips 890 are moved from the position illustrated in FIG. 121 to the position illustrated in FIG. 122 against the biasing force of spring 880. This movement of cable finger grips 890 repositions detent rod 882 from the position illustrated in FIG. 121 to the position illustrated in FIG. 122 and moves detent rod 882 from position within one of detents 860 into the arcuate channel adjacent to and proximal of detents 860. In this position, handle 888 can be moved to actuate flexible reamer head 828 between, e.g., the flex up, straight, and flex down position. When the chosen position is achieved, cable finger grips 890 can be released so that the biasing force of spring 888 acts against detent rod body 884 to position detent rod 882 in one of detents 860 and lock handle 888 in position.

Figure 126:
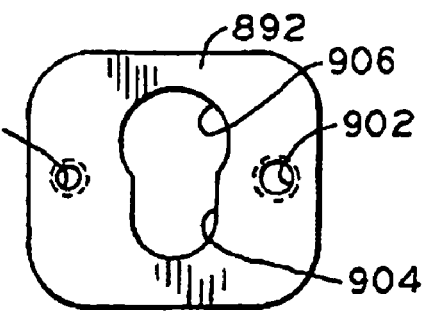
Figure 127:
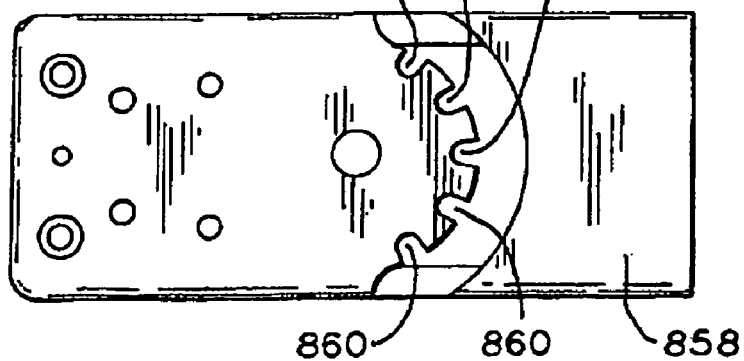

Flexible driveshaft 852 can be advanced through flexible guide shaft 650' as described above with respect to flex down reamer shaft 644 and flexible guide shaft 650. As illustrated in FIG. 124, flexible driveshaft 852 includes shoulder 856. In the retracted position illustrated in FIG. 120, shoulder 856 is positioned within proximal body end 894. As illustrated in FIGS. 120-123, lock plate 892 is positioned within proximal body end 894 of flexible reamer 826. Lock plate 892 is illustrated in detail in FIG. 126. As illustrated in FIG. 126, lock plate 892 includes a central aperture formed by the intersection of release aperture 906 with lock aperture 904. Both lock aperture 904 and release aperture 906 accommodate rotational movement of flexible driveshaft 852. However, only release aperture 906 accommodates passage of shoulder 856 of flexible driveshaft 852. Lock aperture 904 is sized whereby shoulder 856 will not pass therethrough. As illustrated in FIGS. 120-124, lock knob 898 is positioned through lock knob slot 900 of proximal body end 894 and engaged with lock plate 892 via lock knob aperture 902. Lock knob 898 can be moved within lock knob slot 900 of proximal body end 894 to actuate lock plate 892 to allow for distal to proximal advancement of flexible driveshaft 852 by positioning flexible driveshaft 852 within release aperture 906. Lock knob 898 can also be utilized to reposition lock plate 892 so that flexible driveshaft 852 is positioned within lock aperture 904. Achieving the locked position of lock plate 892 is only possible when flexible driveshaft 852 is positioned in the retracted position illustrated in FIG. 120. FIG. 120 illustrates lock knob 892 positioned whereby flexible driveshaft 852 is positioned within lock aperture 904, while FIGS. 121-123 illustrate lock knob 898 positioned whereby flexible driveshaft 852 is positioned within release aperture 906 of lock plate 892 and flexible driveshaft 852 is moved in a proximal to distal direction to advance flexible reamer head 828. In one exemplary embodiment, flexible driveshaft 852 includes a proximal flange limiting the length of advancement of flexible reamer head 828 with respect to the body of flexible reamer 826.

In an alternative embodiment, flexible reamer 1200 (FIGS. 157-160) is utilized to form femoral shaft arm 258" of implant cavity 224" (FIG. 160). After initially forming access 101 with plunge reamer 1020 (FIG. 153) and femoral head arm 256" of implant cavity 224" with telescoping reamer 1044 (FIG. 155), flexible reamer head 1202 is positioned through access 101 formed in femur 108 (FIG. 159). When inserting flexible reamer head 1202 through access 101, interior extension 1204 of distal body end 1206 is positioned within access 101, with flange 1208 (FIG. 158A) abutting the generally planar surface of greater trochanter 110. As shown in FIG. 159, positioned within access 101, flexible reamer head 1202 of flexible reamer 1200 can be actuated between flex up position 1202' (FIG. 159) and flex down position 1202" (FIG. 159) to effect swivel reaming. Furthermore, in either flex position, flexible reamer head 1202 can be advanced, for example, to form femoral head arm 256" of implant cavity 224", or as illustrated in FIG. 160, flexible reamer head 1202 can be advanced into the intramedullary canal 1210 of femur 108 to form femoral shaft arm 258" of implant cavity 224". Advantageously, the generally bullet shape and the flexibility of reamer head 1202 relative to distal body end 1206 is such that flexible reamer head 1202 will be deflected off of cortical bone and will generally only ream and follow the path of less dense cancellous bone, for example of intramedullary canal 1210. Generally, femoral shaft arm 258" of implant cavity 224" will be reamed to remove as much cancellous bone as practical in order to anchor implant 1300 (FIG. 167) in the harder cortical bone.

Intraoperatively, flexible reamer 1200 functions much like flexible reamer 826 as described above and as shown in FIGS. 120-132. Referring to FIGS. 157 and 158A-C, flexible reamer 1200 includes main body housing 1212 which is connected to outer tool shaft 1214, coupling 1216, and distal body end 1206. Flexible driveshaft 1218 (FIGS. 158A and 160) extends through the cannulated bodies of flexible guide shaft 1222, distal body end 1206, coupling 1216, and outer tool shaft 1214. Distal body end 1206 includes guide tube slot 1220, which accommodates flexure of flexible guide shaft 1222 through a single plane, which, for example, may be coplanar with coronal femoral plane 1008 (FIG. 148). Body cover 1292 (FIG. 158A) may be secured to main body housing 1212 by thumb screw 1294.

As illustrated in FIGS. 157 and 158A, flexible driveshaft 1218 includes flexible distal end 1224 and a proximal end having left-hand male thread 1226 and key 1228 protruding proximally from thread 1226. Thread 1226 and key 1228 releasably secure flexible driveshaft 1218 to intermediate driveshaft 1230 and proximal driveshaft 1232. Intermediate shaft 1230 (FIG. 158B) is cannulated for reception of a distal portion of proximal driveshaft 1232 therein. Specifically, distal end 1244 of proximal driveshaft 1232 is received within intermediate driveshaft 1230. Upon driveshafts 1230 and 1232 being fully coupled, distal end 1244 of proximal driveshaft 1232 approximately abuts female threads 1236 located at the interior of distal end 1234 of intermediate driveshaft 1230. Proximate end 1242 of intermediate driveshaft 1230 includes coupling device 1240. Upon driveshafts 1230 and 1232 being fully coupled, circumferential groove 1238 of proximal driveshaft 1232 is located within coupling device 1240. Coupling device 1240 includes interior radial projections (not shown), e.g. pins or spring loaded bearings, for engaging circumferential groove 1238 of proximal driveshaft 1232, thereby longitudinally fixing intermediate driveshaft 1230 to proximal driveshaft 1232 while allowing relative rotation.

Distal end 1234 of intermediate driveshaft 1230 includes female thread 1236 for receiving male thread 1226 of flexible driveshaft 1218. Distal end 1244 of proximal driveshaft 1232 includes keyway 1246, which upon coupling driveshafts 1230 and 1232, is adjacent threads 1236. Flexible driveshaft 1218 is coupled to driveshafts 1230 and 1232. Engagement of key 1228 of flexible driveshaft 1218 in keyway 1246 provides rotational fixation of flexible driveshaft 1218 with proximal driveshaft 1232, thereby enabling driveshaft 1232 to rotationally drive flexible reamer head 1202. Proximal end 1248 of proximal driveshaft 1232 may include flats 1250 for coupling to the chuck of a device capable of imparting rotational motion thereto.

Flexible driveshaft 1218 is longitudinally fixed with proximal driveshaft 1232 by engaging male thread 1226 of flexible driveshaft 1218 with female thread 1236 of intermediate driveshaft 1230. Because male thread 1226 abuts key 1228 and female thread 1236 abuts keyway 1246, engagement of threads 1226 and 1236 secures key 1228 in keyway 1246. Threads 1226 and 1236 are advantageously left handed so that right hand driving of proximal driveshaft 1232, as viewed from the proximal end of flexible reamer 1200, rotates flexible driveshaft 1218 via keyway 1246 and key 1228 without loosening the engagement of threads 1226 and 1236.

Similar to telescoping reamer 1044 described above, releasably coupling driveshafts 1218, 1230, and 1232 in this manner allows removal of housing 1212, flexible guide shaft 1222, distal body end 1206, coupling 1216, and outer tool shaft 1214 from flexible driveshaft 1218 without removing flexible reamer head 1202 from implant cavity 224". While proximal driveshaft 1232 is held to prevent flexible shaft 1218 from rotating, coupling device 1240 and intermediate driveshaft 1230 can be rotated relative to driveshafts 1218 and 1232. Left hand rotation of intermediate driveshaft 1230 disengages flexible driveshafts 1230 and 1232 from flexible driveshaft 1218. Without disengagement of driveshafts 1230 and 1232 from flexible driveshaft 1218, the increased diameter of coupling 1240 prevents housing 1212 and other components from sliding proximally off of driveshafts 1230 and 1232. Disengagement of driveshafts 1230 and 1232 allows housing 1212, flexible guide shaft 1222, distal body end 1206, coupling 1216, and outer tool shaft 1214 to slide proximally off of flexible driveshaft 1218.

Flexible driveshaft 1218 includes a distal end adapted for connection to flexible reamer head 1202, for example by using a set screw or other fastener as is described above and as is illustrated in FIG. 124 for flexible reamer head 828. Flexible distal end 1224 of flexible driveshaft 1218 includes at least one spiral flex cut as described hereinabove with respect to various flexible driveshafts and reamer heads. Similarly, flexible reamer head 1202 includes one or more spiral cuts allowing for flexure thereof.

In construction, flexible guide shaft 1222 is positioned within the distal end of distal body end 1206 and is secured thereto, e.g., with a set screw. Distal body end 1206 is coupled to coupling 1216, e.g., by engaging set screws 1254 (FIG. 158A) radially into circumferential groove 1252 of distal body end 1206, so that coupling 1216 may rotate relative to distal body end 1206 and outer tool shaft 1214. Rotation of coupling 1216 engages or disengages coupling 1216 with threads 1215 of outer tool shaft 1214, thereby allowing assembly and disassembly. Flexible guide shaft 1222 includes a pair of cable apertures (not shown) formed in each of radially opposing sides thereof, separated by 180° and accommodating cables 1256. Cables 1256 are operably positioned through flexible guide shaft 1222 in the same manner as is described hereinabove for flexible guide shaft 650'. Additionally, flexible guide shaft 1222 is formed in accordance with flexible guide shaft 650 described above. Cables 1256 extend through cable channels 1258 of outer tool shaft 1214. Each pair of cables 1256 extend proximally from outer tool shaft 1214 into main body housing 1212 and are fixably secured to one of pins 1260 (detail of FIG. 158A). Pins 1260 are each coupled in radially outwardly extending slots 1264 of drive wheel 1262. Slots 1264 are located 180° apart.

Drive wheel 1262 is rotationally connected to main body housing 1212 whereby rotation of drive wheel 1262 tensions one pair of cables 1256, thus actuating flexible guide shaft 1222 in guide tube slot 1220 as described above with respect to flexible guide shaft 650. Handle 1266 is operably coupled to drive wheel 1262, and is thereby capable of rotationally actuating drive wheel 1262. Hexagonal shaped hub 1268 (detail of FIG. 158A) of drive wheel 1262 protrudes through aperture 1270 in main body housing 1212 and is received by complementary shaped receptacle 1272 defined in handle 1270. Thumb screw 1274 may be used to fasten handle 1266 to drive wheel 1262. Actuating handle 1266 rotationally clockwise or counter-clockwise thus actuates flexible reamer head 1202 to down position 1202" (FIG. 159) or up position 1202', respectively.

Drive wheel 1262 includes teeth 1276 (detail of FIG. 158A) which cooperate with projections 1278, located at opposite ends of locking pawl 1280, to rotationally lock drive wheel 1262. Locking pawl 1280 is pivotably coupled to housing 1212 and is actuated by rotational locking lever 1282 in order to engage one of projections 1278 with teeth 1276 so that drive wheel 1262 is free to rotate clockwise or counter-clockwise, depending upon which projection 1278 is engaged with teeth 1276. Projections 1278 and teeth 1276 are angled upon engagement to function like a ratchet device, allowing engaged projection 1278 to drag over teeth 1276 in a first direction, but to block relative rotation of wheel 1262 in the opposite direction. In one position of rotational locking lever 1282, neither projection 1278 is engaged with teeth 1276 so that drive wheel 1262 is free to be rotated by handle 1266 in either direction. Rotational locking lever 1282 may include a spring detent or other mechanism (not shown) for preventing unintended actuation.

Axial lock member 1284 (FIG. 158A) is pivotably coupled to main body housing 1212 and operably cooperates with flexible driveshaft 1218 and intermediate driveshaft 1230 to prevent or allow axial translation of flexible reamer head 1202. Specifically, slot 1286 (shown in FIG. 158C), defined in face 1285 of axial locking member 1284, is sized to allow translation of a proximal end of flexible driveshaft 1218 therethrough and to not allow translation of distal end 1234 (FIG. 158B) of intermediate driveshaft 1230 therethrough, thus preventing extension of flexible reamer head 1202 from flexible guide tube 1222. However, upon rotation of axial locking member 1284 so that bore 1288 is axially aligned with intermediate driveshaft 1230, intermediate driveshaft 1230 may translate therethrough, because bore 1288 has an inner diameter greater than that of the outer diameter of intermediate driveshaft 1230. Axial locking lever 1290 is operably coupled to axial locking member 1284 and rotationally actuates member 1284 in order to allow or prevent axial extension therethrough of intermediate driveshaft 1230, and therefore allow or prevent extension of flexible reamer head 1202 from flexible guide tube 1222. Axial locking lever 1290 may include a spring detent or other mechanism (not shown) to prevent accidental actuation.

Flexible guide shaft 1222 includes flex cuts such as described above for flexible guide shaft 650" and as illustrated in FIGS. 128-131. Flex cuts provide gaps in radially opposing sides of flexible guide shaft 1222 which allow for compression of a side of flexible guide shaft 1222 so that flexure in only a single plane is possible.

Flexible driveshaft 1218 can be advanced through flexible guide shaft 1222 as described above with respect to flex down reamer shaft 644' and flexible guide shaft 650', thereby providing reaming of femoral shaft arm 258" of implant cavity 224" in femur 108 as shown in FIG. 160. In one exemplary embodiment, proximal intermediate driveshaft 1230 includes a coupling device 1240 limiting the length of advancement of flexible reamer head 1202 with respect to the body of flexible reamer 1200, as shown in FIG. 160. Specifically, distal advancement of flexible reamer head 1202 requires distal advancement of intermediate driveshaft 1230 and proximal driveshaft 1232, which are coupled to flexible reamer head 1202 by flexible driveshaft 1218. However, distal advancement of flexible reamer head 1202 is stopped by coupling device 1240 contacting proximate end of main body housing 1212. Although the shaft of intermediate driveshaft 1230 is sized to translate through main body housing 1212 and bore 1288 (FIG. 158C), coupling 1240 has a larger outer diameter and will not translate therethrough. In one exemplary embodiment, a plurality of distal body ends 1206 are provided, each distal body end 1206 having a different length, thereby selectively limiting the distal extension length of flexible reamer head 1202 relative to flange 1208. Alternatively, a plurality of couplings 1216 may be provided for the same purpose, each coupling 1216 having a different length.

Alternative embodiment femoral implant 260" is illustrated in detail in FIGS. 133-143. FIGS. 144-146 illustrate implantation of femoral implant 260". As illustrated, e.g., in FIGS. 133 and 134, implant 260" includes injection/insertion tube 908, inner lag screw tube 934, bag 270", and outer lag screw tube 910. In construction, inner lag screw tube 934 is positioned within outer lag screw tube 910, bag 270" is positioned over outer lag screw tube 910 and is secured thereto. The distal end of injection/insertion tube 908 is secured to the proximal end of outer lag screw tube 910 as will be further described below. In one exemplary embodiment, inner lag screw tube 934 is a metallic tube, while outer lag screw tube 910 is formed of a biologically compatible material such as an acrylic. Injection/insertion tube 908 is illustrated in detail in FIGS. 135-138. As illustrated, injection/insertion tube 908 includes lag screw channel 912. As illustrated in FIG. 133, lag screw channel 912 is an open channel which allows for insertion of lag screw 264" through injection/insertion tube 908. In an alternative embodiment, lag screw channel 912 is a closed channel having a radius of curvature matching the radius of curvature of lag screw 264".

As illustrated in FIGS. 144 and 145, lag screw 264" is inserted into lag screw channel 912 and traverses inner lag screw tube 934 to be implanted in femoral head 114 as illustrated in FIG. 146. Injection/insertion tube 908 includes coupling aperture 914 for coupling injection/insertion tube 908 to source of bag fill 284 as illustrated in FIG. 146. Coupling aperture 914 is fluidly connected to bag fill passage 916 as illustrated in FIG. 136. Bag fill passage 916 allows for injection of bag fill through injection/insertion tube 908 and into bag 270". Bag 270" is secured about the distal end of injection/insertion tube 908 as illustrated in FIG. 133 and is in fluid communication with bag fill passage. The distal end of injection/insertion tube 908 includes grooves 922 for accommodating tongues 924 of outer lag screw tube 910 and securing injection/insertion tube 908 thereto.

As illustrated, e.g., in FIGS. 139 and 140, outer lag screw tube 910 includes bag channel 926 formed about the periphery of the distal end thereof. In construction, a distal portion of bag 277 is positioned within bag channel 926 and adhered thereto. Bag 270 is positioned over the body of outer lag screw tube 910 and the distal end of injection/insertion tube 908 as previously discussed. With outer lag screw tube 910 positioned over inner lag screw tube 934, no bag fill material directly contacts inner lag screw tube 934, which allows for easy removal thereof if necessary. If desired, transverse apertures can be formed in outer lag screw tube 910 to allow bag fill to contact inner lag screw tube 934 and effect securement thereof. These holes will vary in number and size depending upon the extent of securement desired.

Referring to FIGS. 141-143, lag screw 264" includes a plurality of radially expanding fingers 928 positioned at the distal end thereof. As illustrated in FIG. 143, radially expanding fingers 928 can be deformed to radially expand and engage the femur as illustrated in FIG. 146. To effect deformation of radially expanding fingers 928, threaded end cap 936 is provided. Threaded end cap 936 includes a central threaded aperture into which a deformation tool such as deformation tool 938 illustrated in FIG. 142 can be threaded. As illustrated in FIG. 142, deformation tool 938 includes an internal flexible and threaded shaft which can be advanced into the hollow interior of lag screw 264" and threadedly engaged with end cap 934. Once engaged with end cap 934, distal to proximal movement of the threaded shaft of deformation tool 938 will cause deformation of radially expanding fingers 928 into the position illustrated in FIG. 143. In an alternative embodiment, deformation tool 938 includes a curved shaft having a curvature matching that of lag screw 264". In this embodiment, the curved shaft is inserted through the hollow interior of lag screw 264" and engages end cap 934 to effect deformation of radially expanding fingers 928 as previously described.

As illustrated in FIG. 141, each radially expanding finger 928 of lag screw 264" is defined between outer circumferential grooves 930. Outer circumferential grooves 930 create a hinge point for radially expanding fingers 928 and facilitate deformation into the position illustrated in FIG. 143. Similarly, inner circumferential groove 932 (FIG. 141) is formed in the interior wall of lag screw 264" and creates a hinge point facilitating deformation of radially expanding fingers into the position illustrated in FIG. 143. Finally, the central portion of each radially expanding finger 928 can include a small central cut out on one or opposing side thereof as illustrated, e.g., in FIG. 142. These cut outs further facilitate deformation of radially expanding fingers 928 into the position illustrated in FIG. 143. In one exemplary embodiment, radially expanding fingers 928 are provided with additional hinge points, which allow for radially expanding fingers 928 to be deformed into shapes differing from the triangular shape illustrated in FIG. 143. For example, in one exemplary embodiment, four hinge points are provided such that radially expanding fingers 928 achieve a trapezoidal deformed shape.

In use, implant 260" is positioned through incision 106 and access 101 in femur 108. Bag 270" may be accordion folded during implantation. After insertion through access 101 in femur 110 as illustrated in FIG. 145, bag 270" can be filled with bag fill to provide anchorage in the intramedullary canal of femur 108 either before or after fixation of lag screw 264" in femoral head 114. To secure lag screw 264" to femur 108, lag screw 264" is inserted through injection/insertion tube 908 as discussed hereinabove. Proper placement of lag screw 264" can be confirmed by tactile feedback either alone or in conjunction with a fluoroscopic image. Once the proper position of lag screw 264" is achieved, deformation tool 934 can be inserted through incision 106, into lag screw channel 912, through the internal aperture of inner lag screw tube 934 and the hollow interior of lag screw 264" to engage end cap 936 for deformation of radially expanding fingers 928 as described hereinabove. After implant 270" is fully seated as illustrated in FIG. 146, injection/insertion tube 908 is broken along score mark 916 and removed through incision 106.

FIG. 161A illustrates alternative embodiment femoral implant 1300 of the present invention. Femoral implant 1300 generally includes implant bag 1302, implant tube 1304, lag tube 1306, and lag 1400 (FIG. 168A). Associated instruments include implant sleeve 1308, insertion tube 1310, injection tube 1312, and fill adapter 1314. In one embodiment, the size of femoral implant 1300 is chosen or determined in part by arc length 1305 (FIG. 163A) of a central portion of implant tube 1304 and of lag tube 1306 being approximately equal to medial depth 1042 (FIG. 174), for example, exemplary embodiments may include arc length 1305 of approximately 38 mm (1.5 in.), 48 mm (1.875 in.), or 58 mm (2.25 in.). The length of arc radius 1007 is determined as described hereinabove. Arc radius 1307 (FIG. 163A) of implant tube 1304 and of lag tube 1306 may be selected to be approximately equal to arc radius 1007 (FIG. 174) determined as described hereinabove, for example approximately 51 mm (2.0 in.) or 63 mm (2.5 in.). Lag tube 1306 has a substantially elliptical cross-section, to provide for two fill ports 1365, located 180° apart, which facilitate filling implant bag 1302, while isolating lag tube 1306 and maintaining a small implant cross-section, as is described hereinbelow. Lag 1400 (FIG. 168A) also has an elliptical cross-section sized so that lag 1400 is slidingly received within lag tube 1306.

Insertion tube 1310 may be coupled to assembled implant 1300, as shown in FIG. 161B, to facilitate handling of femoral implant 1300 and insertion of femoral implant 1300 into femoral implant cavity 224", as shown in FIG. 165. Injection tube 1312 and fill adapter 1314 provide for coupling of a filler dispenser and for delivery of bone cement or other filler into implant bag 1302, which subsequent to implantation, fills cavity 224", including femoral shaft arm 258" of femoral cavity 224", in order to anchor and stabilize lag 1400 (FIG. 168A) in femur 108.

Femoral implant 1300 includes many of the same features and characteristics as hereinabove described femoral implant 260". For example, in one exemplary embodiment, lag tube 1306 is a metallic tube, e.g., SST; implant tube 1304 and implant bag 1302 are formed of a biologically compatible material such as an acrylic, e.g., PMMA. Specifically, implant tube 1304 may be molded from PMMA into a rigid form and implant bag 1302 may be flexible and woven of PMMA with a sufficiently tight weave to contain a biologically compatible filler. The filler may be, for example, a curable material, an expandable material, a fibrous or woven material, nitinol, hydrogel, or a known bone cement, e.g., PMMA based bone cement. Bone cement is generally inserted as a liquid, conforming to the shape of cavity 224" and then cures to a solid. Implant bag 1302 may alternatively be a biocompatible material which is expandable after implantation into femur 108, for example, expandable biocompatible fabric or textile, nitinol, or hydrogel. Nitinol has the advantage of being able to compress from a "set" shape to a small shape and temporarily hold that shape; however, upon heating, nitinol will resume to the set shape, thus allowing a dimensionally small implant insertion size which expands upon receiving body or other heat. Hydrogel has the advantage of expanding dramatically in volume when exposed to water; therefore, implant bag 1302 of filler could be expanded using water or an aqueous solution after placement within implant cavity 224".

Referring to FIGS. 163A-163C, femoral implant 1300 is formed by axially inserting lag tube 1306 within central opening 1316 extending axially through implant tube 1304, and securing implant bag 1302 over the length of implant tube 1304 while keeping distal end 1318 and proximal end 1320 of implant tube 1304 uncovered. Advantageously, femoral implant 1300 is designed so that no filler material contacts lag tube 1306 or lag 1400 (FIG. 168A) so that lag 1400 may freely slide within lag tube 1306. Referring again to FIG. 161A, implant bag 1302 includes a substantially cylindrical portion 1322 having distal aperture 1324 and proximal aperture 1326 through which distal end 1318 and proximal end 1320 of implant tube 1304 respectfully protrude. Implant bag 1302 further includes arm portion 1328 which extends radially from cylindrical portion 1322 and is shaped to generally conform to femoral shaft arm 258" of femoral cavity 224". In one embodiment, implant bag 1302 is woven and then shaped on a mandrel (not shown) while applying enough heat to reform the unstressed shape of implant bag 1302.

Opening 1331 (FIG. 162A) in implant bag 1302 at end 1330 may be closed in order to contain filler material, for example, closed by injection molding. For example, referring to FIG. 162B, plug 1333 for sealing opening 1331 includes walls 1334 against which opening 1331 at end 1330 of implant bag 1302 is gathered and against which molding fill 1336 and ring 1332 is injected to securely seal opening 1331 against walls 1334.

FIG. 162A shows approximately a quarter of the circumference of opening 1331 at end 1330 positioned against adjacent walls 1334. Plug 1333 advantageously includes walls 1334, which project radially from a central point 1335, so that opening 1331 may be sealed closed upon a structure having a smaller diameter than if plug 1333 had a circular surface matching the larger diameter of opening 1331. By providing radially projecting walls 1334, the circumference along walls 1334 of plug 1333 is approximately equal to the circumference of opening 1331, even though the diameter of plug 1333 is smaller than the diameter of opening 1331.

As shown in FIG. 162B, after opening 1331 of end 1330 is pressed inward toward central point 1335 so that the entire circumference is in contact with walls 1334, molding fill 1336 and ring 1332, which couples and retains molding fill 1336 securely against opening 1331 and walls 1334, may be provided, for example, by injection molding. Alternatively other cross-sectional shapes may be utilized for plug 1333 so that opening 1331 may be sealed within a small diameter that will fit through access 101 in femur 108.

Referring again to FIGS. 163A-163C, in construction lag tube 1306 is inserted within central opening 1316 of implant tube 1304. Cylindrical portion 1322 (FIG. 161A) of implant bag 1302 is slid over implant tube 1304. Distal end 1318 and proximal end 1320 of implant tube 1304 are subsequently at least partially overmolded, for example, by injection molding. In one embodiment, implant tube 1304 is at least partially overmolded with the same material used to construct implant tube 1304, e.g., PMMA. Overmolding secures cylindrical portion 1322 of implant bag 1302 to implant tube 1304.

Two cylindrical flanges 1338 (FIGS. 161A and 163A) are located adjacent each of distal end 1318 and proximal end 1320 of implant tube 1304. Flanges 1338 facilitate securing cylindrical portion 1322 (FIG. 161A) of implant bag 1302 to implant tube 1304. A retaining ring 1340 (FIG. 163A) is positioned between each pair of cylindrical flanges 1338 to hold cylindrical portion 1322 of implant bag 1302 in position during overmolding and to provide thermal insulation to implant bag 1302 during the molding process so that implant bag 1302 is not heat embrittled other than where contacted by molding material. Subsequent to placement of retaining rings 1340, cylindrical molding fill 1342 is injected adjacent retaining rings 1340 between cylindrical flanges 1338.

In order to retain lag tube 1306 within implant tube 1304, distal overmolding 1344 (FIGS. 163A and 163C) is injected over distal end 1318 of implant tube 1304. In one embodiment, distal overmolding 1344 includes distal tabs 1346 which radially overlap distal end 1348 of lag tube 1306, thereby preventing lag tube 1306 from distal movement out of implant tube 1304. Proximal end 1320 (FIGS. 163A and 163C) of implant tube 1304 may be injection molded with proximal overmolding 1350, including proximal tabs 1352 which radially overlap top and bottom portions of proximal end 1354 of lag tube 1306, thereby preventing lag tube 1306 from sliding proximally out of implant tube 1304.

Proximal end 1320 of implant tube 1304 includes bosses 1356 (FIGS. 163A and 163C) for releasably coupling insertion tube 1310 (FIG. 161A) to implant 1300. Specifically, bosses 1356 are received within arcuate channels 1359 at the interior of proximal end 1358 of insertion tube 1310. Arcuate channels 1359 include a circumferential and a radial component. Upon rotation and slight axial translation of insertion tube 1310 relative to implant 1300, bosses 1356 translate in arcuate channels 1359 until releasably locking within receptacles 1360 defined at ends of arcuate channels 1359 and through the wall of insertion tube 1310; thereby coupling insertion tube 1310 and implant 1300 as shown in FIG. 161B.

Referring to FIGS. 163A and 163C, proximal end 1320 of implant tube 1304 features fill ports 1362 which are isolated from central opening 1316 by walls 1364. Advantageously, fill ports 1362 provide paths for bone cement or other filler to be delivered from proximal end 1320 of implant tube 1304 into the interior of implant bag 1302, without exposing lag tube 1306 or central opening 1316 to the filler. Central opening 1316 has a generally elliptical cross-section and is formed in part by walls 1364. Fill ports 1362 are located outside of walls 1364 which are approximately parallel to the major axis of the generally elliptical cross-section. Fill ports 1362 are defined by flange 1321 (FIG. 163D) and by walls 1364. In construction, the distal end of flange 1321 is located within the interior of bag 1302, thus fill ports 1362 provide paths for filling implant bag 1302.

The isolation of lag tube 1306 from the filler is desired in the event that later removal of the implant is required. If lag tube 1306 is not cemented or otherwise adhered to implant tube 1304, removal of proximal tabs 1352 allows lag tube 1306 to be easily removed from implant 1300 by sliding it out proximal end 1320.

Referring to FIGS. 164A and 164B, distal end 1366 of injection tube 1312 is adapted to couple to proximal end 1320 of implant 1300 while plugging central opening 1316 and diverting filler from adapter 1314 into fill ports 1362 of implant tube 1304. Boss 1368 protrudes distally from injection tube 1312 and is sized to match and extend into the interior of lag tube 1306, thereby preventing filler from contacting or entering lag tube 1306. Shoulders 1370 defined at opposite sides of boss 1368 project axially from distal end 1366 of injection tube 1312. So arranged, and upon coupling of injection tube 1312 and implant 1300, shoulders 1370 overlap the radially interior sides of the distal ends of walls 1364 (FIG. 163C) and abut the portion of proximal end 1354 of lag tube 1306 not covered by proximal tabs 1352. The substantially matching elliptical shape of boss 1368 and the interior of lag tube 1306 generally ensures that diverting apertures 1372 of injection tube 1312 are aligned with fill ports 1362, thereby providing a pathway with lap joints for filler to be conveyed from injection tube 1312 into the interior of implant bag 1302.

Referring to FIG. 161A, raised surface 1374, which extends longitudinally along at least a portion of the length of injection tube 1312, is received by slot 1311 of insertion tube 1310. Engagement of bosses 1356 of implant tube 1304 and receptacles 1360 of insertion tube 1310 fix the rotational alignment of implant 1300 and insertion tube 1310. The combination of the rotational alignment of injection tube 1312 with insertion tube 1310 and of implant 1300 with insertion tube 1310 provides alignment of diverting apertures 1372 with fill ports 1362. Injection tube 1312 is cannulated so that single fill aperture 1376 (FIG. 161A) at the proximal end branches into two diverting apertures 1372 (FIG. 164B) at distal end 1366. Filler material enters fill aperture 1376 (FIG. 161A) and is directed through diverting apertures 1372 (FIG. 164B). Fill adapter 1314 includes arcuate slots 1380 (FIGS. 161A and 161B) for receiving bosses 1378, to thereby releasably couple fill adapter 1314 to insertion tube 1310, capturing injection tube 1312 therebetween. Fill adapter 1314 may include internal threads 1382 (FIG. 161A) for coupling a standard bone cement dispenser thereto.

For the purposes of this document, lag is defined as an anchoring device. Referring to FIGS. 168-170, lag 1400, which is arcuate and cannulated, is anchored within femoral head arm 256" of femoral cavity 224" and includes many of the characteristics and aspects of lag 264" described hereinabove and illustrated in FIGS. 141-143. In contrast, however, lag 1400 has a substantially elliptical cross-section throughout its entire length with the exterior dimensions of lag 1400 being slightly less than the interior dimensions of lag tube 1306 of femoral implant 1300. In one embodiment, major axis 1403 (FIG. 168A) of the elliptical cross-section is coplanar with the arc defined by longitudinal axis 1401 of lag 1400.

Lag 1400 includes a plurality of radially expanding tines or fingers 1402 between body 1404 and distal end 1406. Distal end 1406 defines distal apertures 1408 180° apart. As shown in FIGS. 169 and 171, anchor 1410 may be engaged into distal apertures 1408, enabling compression to be applied to lag 1400, thereby expanding fingers 1402, as shown in FIG. 170.

Referring to FIG. 171, anchor 1410 includes oppositely oriented engagement ears 1476. Oriented so that engagement ears 1476 extend along major axis 1403 (FIG. 168A), anchor 1410 is sized to be inserted from proximal end 1412 of lag 1400 and to be positioned at distal end 1406. Distal apertures 1408 are formed so that rotation of anchor 1410 by 90 degrees makes engagement ears 1476 perpendicular to major axis 1403, thereby allowing engagement ears 1476 to be engaged within apertures 1408. Referring again to FIG. 168A, proximal end 1412 of body portion 1404 may include insertion receptacles 1414 for coupling of an inserting or retracting instrument to insert or retract lag 1400 through lag tube 1306 or into or from femur 108.

Referring to FIGS. 169 and 170, cable 1416, for example, a cable braided from SST wire, is coupled to tension anchor 1410, for example, by swagging. Distal spacer 1418 and proximal spacer 1420 are cannulated and are strung on cable 1416. Distal spacer 1418 is held in position on cable 1416, for example, by crimped beads (not shown) so that distal spacer 1418 is free to rotate on cable 1416 and is held in position adjacent fingers 1402. Because of the arcuate shape of lag 1400 and of fingers 1402, the finger (1402) located on the concave side of lag 1400 may tend to expand inwardly rather than outwardly as shown in FIG. 170. By positioning distal spacer 1418 adjacent fingers 1402, even if one of fingers 1402 initially folds inward, as distal end 1406 is further compressed toward proximal end 1412, fingers 1402 contact distal spacer 1418. As compression of lag 1400 continues, fingers 1402 must expand radially. Because fingers 1402 are prevented by contact with spacer 1418 from expanding radially inward, fingers 1402 are forced to be expanded radially outward. Additionally, in order to radially substantially center cable 1416 and to prevent cable 1416 from damaging inner lag tube surface 1422 of lag tube 1306, proximal spacer 1420 may be positioned near proximal end 1412 of lag 1400.

In one embodiment of lag 1400, notched regions that locate bend points for fingers 1402 have wall thickness 1415 that is a minimum of about 0.46 mm (0.018 in.) and may be a maximum of about 1.02 mm (0.040 in), or preferably of about 0.76 mm (0.030 in), which provides a deformation force of about 227 kg (500 lbs.) and preferably between about 181- 363 kg (400-800 lbs.). The wall thickness of the remaining portions of lag 1400 in one exemplary embodiment is a minimum of about 1.34 mm (0.053 in.). Lag 1400 may be constructed of, for example, SST and be electro-plated or glass bead blasted for a matte finish.

Major axis 1403 of lag 1400 is slightly less than the diameter of reamer head 1052 (FIG. 156A) used to form femoral head arm 256" of cavity 224". In one embodiment, major axis 1403 is approximately 12.7 mm (0.5 in.) and fingers 1402 expand to approximately 25.4 mm (1.0 in.) along major axis 1403 and 21.6 mm (0.85 in.) along minor axis 1405. In one embodiment, available size selections for lag 1400 are arced longitudinally to conform to typical femoral anatomy, for example, an arc radius of approximately 51 mm (2.0 in.) or 63 mm (2.5 in.). Lag 1400 may also be made in a plurality of lengths, therefore accommodating a typical range of sizes of femoral anatomy.

Referring to FIG. 165, insertion of implant 1300 into implant cavity 224" of femur 108 is facilitated by generally cylindrical sleeve 1308 (FIG. 161A), which has openings 1309 at opposite ends and which may be wrapped or slid over the outer surface of implant 1300, compressing implant bag 1302 into a generally cylindrical cross-section (FIG. 161B) suitable for insertion through access 101 defined in greater trochanter 110 of femur 108. Additionally, insertion tube 1310 is coupled to implant 1300, as discussed above, in order to provide easy manipulation of implant 1300. As shown in FIG. 165, implant 1300 may be positioned so that the arc shape of implant 1300 extends toward femoral head arm 256" of implant cavity 224". Once implant 1300 is positioned within implant cavity 224", string 1424 or other protrusion coupled to sleeve 1308 may be tensioned in order to slide sleeve 1308 proximally over insertion tube 1310 and out of implant cavity 224", thereby exposing implant bag 1302 as shown in FIG. 166.

As shown in FIG. 166, lag 1400 may be inserted through lag tube 1306 of femoral implant 1300 so that distal end 1406 of lag 1400 extends into femoral head arm 256" of implant cavity 224", for example, to a central position within femoral head 114, or at least so that lag 1400 and implant 1300 span fracture line 1426 in femur 108.

Referring to FIG. 167, fingers 1402 of lag 1400 may be expanded into cancellous bone adjacent femoral head arm 256" of implant cavity 224", thereby anchoring lag 1400 relative to femoral head 114. Subsequently, implant bag 1302 may be filled with bone cement or other filler, expanding arm portion 1328 of implant bag 1302 into femoral shaft arm 258" of implant cavity 224", thereby anchoring implant 1300 in femur 108, as illustrated by partially filled implant bag 1302 in FIG. 167.

Referring to FIGS. 171 and 172, lag actuator 1440 may be used for applying compression to lag 1400, expanding radially outwardly fingers 1402. Preferably, lag actuator 1440 is capable of compressing lag 1400 to a load of at least about 454 kg (1,000 lbs.) or at least about twice the deformation force of lag 1400. Referring to FIG. 171, lag actuator 1440 includes body 1442, handle 1444, intermediate shaft 1446, flexible guide 1448, wrench 1450, linear screw 1452, gear 1454, compression device 1456, and cable anchor 1458. Body 1442 includes bore 1460 therethrough. Bore 1460 is shaped to axially receive linear screw 1452. Linear screw 1452 may be, for example, an acme screw having at least one flat 1462 longitudinally extending along its length. Bore 1460 correspondingly includes at least one flat (not shown) so that linear screw 1452 may be axially received into bore 1460 while preventing screw 1452 from rotating within body 1442.

Gear 1454 includes external teeth 1464 which may be engaged by corresponding internal teeth 1466 of wrench 1450 for rotational actuation of gear 1454 by wrench 1450. Gear 1454 also includes internal thread 1468 which corresponds to threads 1470 of linear screw 1452. In construction, rotation of handle 1450 on gear 1454 axially translates linear screw 1452 relative to body 1442. Axial rather than rotational translation is provided because of the matching of flat 1462 of linear screw 1452 with the internal flat of bore 1460, preventing relative rotation of screw 1452 and body 1442, but allowing axial translation. Linear screw 1452 is cannulated, by bore 1472, which receives cable 1416 therethrough.

Intermediate shaft 1446 and flexible guide 1448 are also cannulated, receiving cable 1416 through bore 1474. Flexible guide 1448 includes a substantially elliptical cross-section shaped to be slidingly received into lag tube 1306 as shown in FIG. 172. Flexible guide 1448 may also be cut as described hereinabove in order to provide flexibility in a single plane, thereby facilitating extension into the interior of lag tube 1306, which defines a longitudinal arc, until butted against proximal end 1412 of lag 1400.

Compression device 1456 includes cable 1416, anchor 1410, distal spacer 1418, and proximal spacer 1420 as described above. Anchor 1410 may be T-shaped having engagement ears 1476 for engaging distal apertures 1408 of lag 1400. Anchor 1410 may be swagged or otherwise coupled to cable 1416 in order to withstand a tension of at least approximately 454 kg (1,000 pounds). Proximal end 1478 of cable 1416 is coupled to threaded shaft 1480. Threaded shaft 1480 may be received through bore 1474 of flexible guide 1448, bore 1460 of body 1442, bore 1472 of linear screw 1452, internal thread 1468 of gear 1454, internal teeth 1466 of wrench 1450, and engaged with internal thread 1482 of cable anchor 1458, thereby coupling together the assembly of lag actuator 1440 shown in FIG. 172. As wrench 1450 is rotated, linear screw 1452 translates in a proximal axial direction, displacing cable anchor 1458 and therefore cable 1416 proximally relative to flexible guide 1448. Proximal displacement of cable 1416 compresses distal end 1408 of lag 1400, against flexible guide 1448, expanding fingers 1402 radially outwardly as described above and as shown in FIG. 170.

Referring to FIG. 173, implant bag 1302 of implant 1300 is filled with bone cement or other filler until implant bag 1302 substantially fills cavity 224". Insertion tube 1310 may be then uncoupled from implant 1300 for closure of incision 106. In order to aid determination of implant bag 1302 location within cavity 224", plug 1333 may be at least partially radiopaque for locating end 1330 on a fluoroscopic image.

Referring to FIGS. 175A and 175B, retractor 1500 may be constructed of a rigid substantially radiolucent material, e.g., polyphenylsulfone resin or another polymer or other material that is radiolucent, rigid, and suitable for surgical use, e.g., autoclavable and chemically stable. While the shape of retractor 1500 generally resembles known metallic retractors, tip 1502 may be more blunt and differently shaped to prevent breakage and to accommodate the lower strength of polymers as compared to some metals. In one embodiment, retractor 1500 includes an arcuately shaped elongate member 1504 having apertures 1506 defined adjacent one end and oppositely radiused arcuate tip 1502 at an opposite end. Tip 1502 is suitable for anchoring against a bone or other hard tissue while arcuate elongate member 1504 is used to displace soft tissue, for example, around greater trochanter 110 to form access 101. Because retractor 1500 is constructed from a radiolucent material, retractor 1500 may be positioned with less regard to the line of sight of fluoroscopic or other anatomical imaging systems than as is required for typical metal retractors.

While this invention has been described as having exemplary designs, the present invention may be further modified with the spirit and scope of this disclosure. This application is therefore intended to cover any variations, uses, or adaptations of the invention utilizing its general principles. Further, this application is intended to cover such departures from the present disclosure as come within known or customary practice in the art to which this invention pertains.

What is claimed is:

1. An alignment guide and implant combination, comprising:
    an implant having a curved geometry allowing said implant to be positioned along a path from a femoral greater trochanter through a femoral neck and into a femoral head;
    a plurality of pattern arms, each said pattern arm having a geometry tracking the curved geometry of the implant, each said pattern arm including a radiopaque alignment marker, each said alignment marker having a perceivable aligned position indicative of a proper alignment of said pattern arm relative to the anatomical structure and a perceivable non-aligned position indicative of an improper alignment of said pattern arm relative to the anatomical structure;
    an alignment arm, said plurality of pattern arms connected to said alignment arm at a first end of said alignment arm, said alignment arm including a first alignment identifier; and
    a reference element insertion guide, said reference element insertion guide connected to said alignment arm at a second end of said alignment arm, said second end of said alignment arm opposite said first end of said alignment arm, said reference element insertion guide including a second alignment identifier alignable with said first alignment identifier.

2. The alignment guide and implant combination of claim 1, wherein said plurality of pattern arms comprise a first and a second pair of pattern arms, said first pair of pattern arms comprising opposing pattern arms, said second pair of pattern arms comprising opposing pattern arms, said first pair of pattern arms corresponding to a first implant geometry, said second pair of pattern arms corresponding to a second implant geometry.

3. The alignment guide and implant combination of claim 2, wherein said first pair of pattern arms define a predefined distance corresponding to a size of an instrument, wherein said instrument is usable in combination with said reference element.

4. The alignment guide and implant combination of claim 1, wherein said pattern arms comprising opposing pattern arms.

5. The alignment guide and implant combination of claim 1, wherein said second alignment identifier comprises an alignment pin.

6. The alignment guide and implant combination of claim 1, wherein said radiopaque alignment marker comprises a radiopaque ring.

7. The alignment guide and implant combination of claim 1, wherein said first alignment identifier comprises a radiopaque substantially planar surface on said alignment arm and said second alignment identifier comprises a radiopaque substantially planar surface on said reference element insertion guide.

8. The alignment guide and implant combination of claim 1, wherein said reference element insertion guide comprises a cannulated body having a longitudinal aperture, wherein said first alignment identifier comprises a radiopaque pin in said alignment arm and said second alignment identifier comprises an elongate reference element positioned in said longitudinal aperture.

9. The alignment guide and implant combination of claim 1, wherein said reference element insertion guide comprises a cannulated body having a longitudinal aperture, wherein a portion of said alignment arm is substantially parallel with said body, said alignment arm including an elongate radiopaque member substantially aligned with said longitudinal aperture.

10. The alignment guide and implant combination of claim 1, further comprising an alignment arm extender portion, said alignment arm extender portion connecting said alignment arm and said body, wherein said alignment arm extender portion increases a distance between said body and said portion of said alignment arm substantially parallel with said body.

11. An alignment guide for alignment with an anatomical structure, comprising:
    a plurality of pattern arms, each said pattern arm having a geometry tracking the anatomical structure, each said pattern arm including a radiopaque alignment marker, each said alignment marker having a perceivable aligned position indicative of a proper alignment of said pattern arm relative to the anatomical structure and a perceivable non-aligned geometry indicative of an improper alignment of said pattern arm relative to the anatomical structure;
    an alignment arm, said plurality of pattern arms connected to said alignment arm at a first end of said alignment arm, said alignment arm including a first alignment identifier;
    a reference element insertion guide, said reference element insertion guide connected to said alignment arm at a second end of said alignment arm, said second end of said alignment arm opposite said first end of said alignment arm, said reference element insertion guide including a second alignment identifier alignable with said first alignment identifier;
    wherein said reference element insertion guide comprises a cannulated body having a longitudinal aperture, wherein a portion of said alignment arm is substantially parallel with said body, said alignment arm including an elongate radiopaque member substantially aligned with said longitudinal aperture; and
    an alignment arm extender portion, said alignment arm extender portion connecting said alignment arm and said body, wherein said alignment arm extender portion increases a distance between said body and said portion of said alignment arm substantially parallel with said body.

* * * * *